(12) United States Patent
Milich et al.

(10) Patent No.: US 7,883,843 B2
(45) Date of Patent: *Feb. 8, 2011

(54) HEPATITIS VIRUS CORE PROTEINS AS VACCINE PLATFORMS AND METHODS OF USE THEREOF

(75) Inventors: David R. Milich, Escondido, CA (US); Jean-Noel Billaud, San Diego, CA (US)

(73) Assignee: Vaccine Research Institute of San Diego, San Diego, CA (US)

( * ) Notice: Subject to any disclaimer, the term of this patent is extended or adjusted under 35 U.S.C. 154(b) by 464 days.

This patent is subject to a terminal disclaimer.

(21) Appl. No.: 10/566,322

(22) PCT Filed: Jul. 19, 2004

(86) PCT No.: PCT/US2004/023391
§ 371 (c)(1),
(2), (4) Date: Oct. 18, 2007

(87) PCT Pub. No.: WO2005/011571
PCT Pub. Date: Feb. 10, 2005

(65) Prior Publication Data
US 2008/0131452 A1 Jun. 5, 2008

Related U.S. Application Data

(63) Continuation-in-part of application No. 10/630,070, filed on Jul. 30, 2003, now Pat. No. 7,320,795, and a continuation-in-part of application No. 10/630,074, filed on Jul. 30, 2003, now Pat. No. 7,144,712.

(51) Int. Cl.
C12Q 1/70 (2006.01)
A61K 39/12 (2006.01)
A61K 39/29 (2006.01)
(52) U.S. Cl. ............ 435/5; 424/199.1; 424/228.1
(58) Field of Classification Search ............ None
See application file for complete search history.

(56) References Cited

U.S. PATENT DOCUMENTS

| | | | |
|---|---|---|---|
| 4,599,230 | A | 7/1986 | Milich et al. |
| 4,599,231 | A | 7/1986 | Milich et al. |
| 4,683,136 | A | 7/1987 | Milich et al. |
| 4,818,527 | A | 4/1989 | Thornton et al. |
| 4,882,145 | A | 11/1989 | Thornton et al. |
| 5,143,726 | A | 9/1992 | Thornton et al. |
| 5,726,011 | A | 3/1998 | Milich et al. |
| 5,990,085 | A | 11/1999 | Ireland et al. |
| 6,231,864 | B1 | 5/2001 | Birkett |
| 6,406,705 | B1 | 6/2002 | Davis et al. |
| 6,518,014 | B1 | 2/2003 | Seifer et al. |
| 6,602,705 | B1 | 8/2003 | Barnett et al. |
| 6,887,464 | B1 | 5/2005 | Coleman et al. |
| 7,320,795 | B2 * | 1/2008 | Milich et al. ............ 424/189.1 |
| 2003/0054337 | A1 | 3/2003 | Birkett |
| 2003/0099668 | A1 | 5/2003 | Bachmann et al. |
| 2003/0138769 | A1 | 7/2003 | Birkett |
| 2003/0175296 | A1 | 9/2003 | Brown |
| 2003/0175863 | A1 | 9/2003 | Birkett |
| 2003/0185854 | A1 | 10/2003 | Birkett |
| 2003/0185858 | A1 | 10/2003 | Birkett |
| 2003/0198645 | A1 | 10/2003 | Page |
| 2003/0202982 | A1 | 10/2003 | Birkett |
| 2004/0054139 | A1 | 3/2004 | Page et al. |
| 2004/0146524 | A1 | 7/2004 | Lyons et al. |
| 2004/0152876 | A1 | 8/2004 | Birkett |
| 2004/0156864 | A1 | 8/2004 | Birkett |
| 2004/0219164 | A1 | 11/2004 | Coleman et al. |

FOREIGN PATENT DOCUMENTS

| | | |
|---|---|---|
| JP | 7252300 | 10/1995 |
| WO | WO 95/27083 | 10/1995 |
| WO | WO 99/40934 | 8/1999 |
| WO | WO 00/46365 | 8/2000 |
| WO | WO 01/98333 | 12/2001 |
| WO | WO 02/013765 | 12/2002 |

OTHER PUBLICATIONS

Maruyama et al., "Distinguishing between acute and symptomatic chronic hepatitis B virus infection," Gastroenterology, vol. 106 No. 4, pp. 1006-1015 (Apr. 1994).*
Schodel et al. (1994) "Immunity to Malaria Elicited by Hybrid Hepatitis B Virus Core Particles Carrying Circumsporozoite Protein Epitopes," J Exp Med. 180:1037-1046.
Schodel et al. (1997) "Immunization with Hybrid Hepatitis B Virus Core Particles Carrying Circumsporozoite Antigen Epitopes Protects Mice Against *Plasmodium yoelii* Challenge," Behring Inst Mitt. 114-119.
Milich et al. (1997) "Role of B cells in antigen presentation of the hepatitis B core," Proc Natl Acad Sci USA 94:14648-14653.
Kratz et al. (1999) "Native display of complete foreign protein domains on the surface of hepatitis B virus capsids," Proc Natl Acad Sci USA 96:1915-1920.
Chen et al. (2000) "Nondeletional T-Cell Receptor Transgenic Mice: Model for the CD4+ T-Cell Repertoire in Chronic Hepatitis B Virus Infection," J. Virol. 74:7587-7599.
Lazdina et al. (2001) "Molecular Basis for the Interaction of the Hepatitis B Virus Core Antigen with the Surface Immunoglobulin Receptor on Naive B Cells," J Virol. 75:6367-6374.
Cao et al. (2001) "Hepatitis B Virus Core Antigen Binds and Activates Naive Human B Cells In Vivo: Studies with a Human PBL-NOD/SCID Mouse Model," J Virol. 75:6359-6366.

(Continued)

Primary Examiner—Stacy B Chen
(74) Attorney, Agent, or Firm—Morrison & Foerster LLP

(57) ABSTRACT

The present invention relates to hepatitis virus core proteins and nucleic acids. In particular, the present invention provides compositions and methods comprising recombinant hepatitis virus core proteins or nucleic acids for use in vaccine formulations.

6 Claims, 48 Drawing Sheets

OTHER PUBLICATIONS

Anttila et al. (1998) "Avidity of IgG for *Streptococcus pneumoniae* Type 6B and 23F Polysaccharides in Infants Primed with Pneumococcal Conjugates and Boosted with Polysaccharide or Conjugate Vaccines," J Infect Dis. 177:1614-1621.

Arad et al. (2000) "Superantigen antagonist protects against lethal shock and defines a new domain for T-cell activation," Nat Med. 6:414-421.

Visvanathan et al. (2001) "Inhibition of Bacterial Superantigens by Peptides and Antibodies," Infect Immunol. 69:875-884.

DeVelasco et al. (1994) "Adjuvant Quil A improves protection in mice and enhaces opsonic capacity of antisera induced by pneumococcal polysaccharide conjugate vaccines," Vaccine 12:1419-1422.

Koletzki et al. (1997) "Mosaic hepatitis B virus core particles allow insertion of extended foreign protein segments," J Gen Virol. 78:2049-2053.

Smiley and Minion (1993) "Enhanced readthrough of opal (UGA) stop codons and production of *Mycoplasma pneumoniae* P1 epitopes in *Escherichia coli*," Gene 134:33-40.

GenBank Accession No. NM 009778 printed Apr. 2003.

Dempsey et al. (1996) "C3d of Complement as a Molecular Adjuvant: Bridging Innate and Acquired Immunity," Science 271:348-350.

Tedder et al. (1994) "The CD19/CD21 signal transduction complex of B lymphocytes," Immunol Today 15:437-442.

GenBank Accession No. X65453 printed Apr. 2001.

Morris et al. (1999) "Incorporation of an Isoleucine Zipper Motif Enhances the Biological Activity of Soluble CD40L (CD154)," J. Biol. Chem. 274:418-423.

Mackay and Browning (2002) "Baff: A Fundamental Survival Factor for B Cells," Nature Reviews Immunology 2:465-475.

GenBank Accession No. NM 008479 printed Apr. 2003.

El mir and Triebel (2000) "A Soluble Lymphocyte Activation Gene-3 Molecule Used as a Vaccine Adjuvant Elicits Greater Humoral and Cellular Immune Responses to Both Particulate and Soluble Antigens," J. Immunol 164:5583-5589.

Krieg et al. (1995) "CpG motifs in bacterial DNA trigger direct B-cell activation," Nature 374:546-549.

Davis et al. (1998) "CpG DNA is a Potent Enhancer of Specific Immunity in Mice Immunized with Recombinant Hepatitis B Surface Antigen," J. Immunol. 160:870-876.

Fouet et al. (1999) "*Bacillus anthracis* surface: capsule and S-layer," J Appl Microbiol. 87:251-255.

Paoletti et al. (2002) "Preclinical evaluation of group B streptococcal polysaccharide conjugate vaccines prepared with a modified diphtheria toxin and a recombinant duck hepatitis B core antigen," Vaccine 20:370-376.

Wang et al. (2003) "Construction of designer glycoconjugate vaccines with size-specific oligosaccharide antigens and site-controlled coupling," Vaccine 21:1112-1117.

Bittle et al. (1982) "Protection against foot-and-mouth disease by immunization with a chemically synthesized peptide predicted from the viral nucleotide sequence," Nature 298:30-33.

Van Lierop et al. (1992) "Proliferative lymphocyte responses to foot-and-mouth disease virus and three FMDV peptides after vaccination and immunization with these peptides in cattle," Immunol. 75:406-413.

Wong et al. (2000) "Plasmids Encoding Foot-and-Mouth Disease Virus VPI Epitopes Elicited Immune Responses in Mice and Swine and protected Swine against Viral Infection," Virol. 278:27-35.

Neirynck et al. (1999) "A universal influenza A vaccine based on the extracellular domain of the M2 protein," Nat Med. 5:1157-1163.

Heinen et al. (2002) "Vaccination of pigs with a DNA construct expressing an influenza virus M2-nucleotprotein fusion protein exacerbates disease after challenge with influenza A virus," J. Gen. Virol. 83:1851-1859.

Pekosz and Lamb (1999) "Cell Surface Expression of Biologically Active Influenza C Virus HEF Glycoprotein Expressed from cDNA," J Virol. 73:8808-8812.

Hughey et al. (1995) "Effects of Antibody to the Influenza A Virus M2 Protein on M2 Surface Expression and Virus Assembly," Virol. 212:411-421.

Zebedee and Lamb (1989) "Growth restriction of influenza A virus by $M_2$ protein antibody is genetically linked to the $M_1$ protein," Proc Natl Acad Sci USA 86:1061-1065.

Pegram and Slamon (2000) "Biological Rationale for HER2/*neu* (c-*erb*B2) as a Target for Monoclonal Antibody Therapy," Semin Oncol. 27:13-19.

Schenk et al. (1999) "Immunization with amyloid-β attenuates Alzheimer-disease-like pathology in the PDAPP mouse," Nature 400:173-177.

Chang (2000) "The pharmacological basis of anti-IgE therapy," Nat Biotechnol. 18:157-162.

Maini and Taylor (2000) "Anti-Cytokine Therapy for Rheumatoid Arthritis," Annu Rev Med. 51:207-229.

Chackerian et al. (2001) "Conjugation of a self-antigen to papillomavirus-like particles allows for efficient induction of protective autoantibodies," J Clin Invest. 108:415-423.

Chackerian et al. (1999) "Induction of autoantibodies to mouse CCR5 with recombinant papillomavirus particles," Proc Natl Acad Sci USA 96:2373-2378.

Tall (1993) "Plasma cholesteryl ester transfer protein," Lipid Res. 34:1255-1274.

Barter et al. (1982) "Trasfers and exchanges of esterified cholesterol between plasma lipoproteins," Biochem J. 208:1-7.

Whitlock et al. (1989) "Monoclonal Antibody Inhibition of Cholesteryl Ester Transfer Protein Activity in the Rabbit," J Clin Invest. 84:129-137.

Kothari et al. (1997) "Inhibition of cholesterol ester transfer protein by CGS 25159 and changes in lipoproteins in hamsters," Atherosclerosis 128:59-66.

Sugano and Makino (1996) "Changes in Plasma Lipoprotein Cholesterol Levels by Antisense Oligodeoxynucleotides against Cholesteryl Ester Transfer Protein in Cholesterol-fed Rabbits," J Biol Chem. 271:19080-19083.

Sugano et al. (1998) "Effect of Antisense Oligonucleotides against Cholesteryl Ester Transfer Protein on the Development of Atherosclerosis in Cholesterol-fed Rabbits," J. Biol. Chem. 273:5033-5036.

Agellon et al. (1991) "Reduced High Density Lipoprotein Cholesterol in Human Cholesteryl Ester Transfer Protein Transgenic Mice," J Biol Chem. 266:10796-10801.

Herrera et al. (1999) "Spontaneous combined hyperlipidemia, coronary heart disease and decreased survival in Dahl salt-sensitive hypertensive rats transgenic for human cholesteryl ester transfer protein," Nat Med. 5:1383-1389.

Koizumi et al. (1985) "Deficiency of Serum Cholesteryl-Ester Transfer Activity in Patients with Familial Hyperalphalipoproteinaemia," Atherosclerosis 58:175-186.

Rittershaus et al. (2000) "Vaccine-Induced Antibodies Inhibit CETP Activity In Vivo and Reduce Aortic Lesions in a Rabbit Model of Atherosclerosis," Arterioscler Thromb Vasc Biol. 20:2106-2112.

Milich et al. (1998) "The Secreted Hepatitis B Precore Antigen Can Modulate the Immune Response to the Nucleocapsid: A Mechanism for Persistence," J. Immunol. 160:2013-2021.

Morgan et al. (2000) "Aβ peptide vaccination prevents memory loss in an animal model of Alzheimer's disease," Nature 408:982-985.

Smith et al. (2002) "Predicting the failure of amyloid-β vaccine," Lancet 359:1864-1865.

Hock et al. (2002) "Generation of antibodies specific for β-amyloid by vaccination of patients with Alzheimer disease," Nat Med. 8:1270-1275.

McLaurin et al. (2002) "Therapeutically effective antibodies against amyloid-β peptide target amyloid-β residues 4-10 and inhibit cytotoxicity and fibrillogenesis," Nat Med. 8:1263-1269.

Rabjohn et al. (2002) "Modification of Peanut Allergen Ara h 3: Effects on IgE Binding and T Cell Stimulation," Int Arch Allergy Immunol. 128:15-23.

Beezhold et al. (2001) "Mutational analysis of the IgE epitopes in the latex allergen Hev b 5," J Allergy Clin Immunol. 107:1069-1076.

Reese et al. (2001) "Characterization and identification of allergen epitopes: recombinant peptide libraries and synthetic, overlapping peptides," J Chromatogr B Biomed Sci Appl. 756:157-163.

Suphioglu et al. (2001) "A novel grass pollen allergen mimotope identified by phage display peptide library inhibits allergen-human IgE antibody interaction," FEBS Lett. 502:46-52.

Focke et al. (2001) "Nonanaphylactic synthetic peptides derived from B cell epitopes of the major grass pollen allergen, Phl p 1, for allergy vaccination," FASEB J. 15:2042-2044.

Karpenko, et. al. (2000) "Insertion of foreign epitopes in HBcAg: how to make the chimeric particle assemble," Amino Acids 18:329-337.

Casal et al. (1999) "Parvovirus-Like Particles as Vaccine Vectors," Methods 19:174-186.

Sadeyen et al. (2003) "Insertion of a foreign sequence on capsid surface loops of human papillomavirus type 16 virus-like particles reduced their capacity to induce neutralizing antibodies and delineates a conformational neutralizing epitope," Virology 309:32-40.
Varsani et al. (2003) "Chimeric Human Papillomavirus Type 16 (HPV-16) L1 Particles Presenting the Common Neutralizing Epitope for the L2 Minor Capsid Protein of HPV-6 and HPV-16," J. Virol., 77:8386-8393.
Rose et al. (1993) "Expression of Human Papillomavirus Type 11 L1 Protein in Insect Cells: In Vivo and In Vitro Assembly of Viruslike Particles," J Virol. 67:1936-1944.
Gedvilaite et al. (2000) "Formation of Immunogenic Virus-like Particles by Inserting Epitopes into Surface-Exposed Regions of Hamster Polyomavirus Major Capsid Protein," Virol. 20:21-35.
Pumpens et al. (2002) "Evaluation of HBs, HBc, and frCP Virus-Like Particles for Expression of Human Papillomavirus 16E7 Oncoprotein Epitopes," Intervirol. 45:24-32.
Roth (2000) "The yeast Ty virus-like particles," Yeast 16:785-795.
Wagner et al. (1996) "Safety and Immunogenicity of Recombinant Human Immunodeficiency Virus-Like Particles in Rodents and Rhesus Macaques," Intervirol. 39:93-103.
Baumert et al. (1999) "Hepatitis C Virus-like Particles Synthesized in Insect Cells as a Potential Vaccine Candidate," Gastroenterology 117:1397-1407.
Sabara et al. (1991) "Assembly of Double-Shelled Rotaviruslike Particles by Simultaneous Expression of Recombinant VP6 and VP7 Proteins," J. Virol. 65:6994-6997.
Ball et al. (1999) "Recombinant Norwalk Virus-like Particles given Orally to Volunteers" Phase 1 Study, Gastroenterology 117:40-48.
Brown et al. (1991) "Assembly of Empty Capsids by Using Baculovirus Recombinants Expressing Human Parvovirus B19 Structural Proteins," J. Virol. 65:2702-2706.
Thomsen el al. (1994) "Assembly of Herpes Simplex Virus (HSV) Intermediate Capsids in Insect Cells Infected with Recombinant Baculoviruses Expressing HSV Capsid Proteins," J. Virol. 68:2442-2457.
Urakawa et al. (1989) "Synthesis of Immunogenic, but Non-infectious, Poliovirus Particles in Insect Cells by a Baculovirus Expression Vector," J. Gen. Virol. 70:1453-1463.
Brown et al. (2002) "RNA Bacteriophage Capsid-Mediated Drug Delivery and Epitope Presentation," Intervirol. 45:371-380.
French et al. (1990) "Assembly of Double-Shelled, Viruslike Particles of Bluetongue Virus by the Simultaneous Expression of Four Structural Proteins," J. Virol. 64:5695-5700.
Yamshchikov et al. (1995) "Assembly of SIV Virus-like Particles Containing Envelope Proteins Using a Baculovirus Expression System," Virol. 214:50-58.
Plana-Duran et al. (1996) "Oral immunization of rabbits with VP60 particles confers protection against rabbit hemorrhagic disease," Arch. Virol. 141:1423-1436.
Nikura et al. (2002) "Chimeric Recombinant Hepatitis E Virus-like Particles as an Oral Vaccine Vehicle Presenting Foreign Epitopes," Virol. 293:273-280.
Yao (2003) "Enhancement of mucosal immune responses by chimeric influenza HA/SHIV virus-like particles,"Res. Initiat. Treat Action 8:20-21.
Kakker et al. (1999) "Bovine Leukemia Virus Gag Particle Assembly in Insect Cells: Formation of Chimeric Particles by Domain-Switched Leukemia/Lentivirus Gag Polyprotein," Virol. 265:308-318.
Milich et al. (1994) "Extrathymic Expression of the Intracellular Hepatitis B Core Antigen Results in T Cell Tolerance in Transgenic Mice," J. Immunol. 152:455-466.
Milich and McLachlan (1986) "The Nucleocapsid of Heptatitis B Virus Is Both a T-Cell-Independent and a T-Cell-Dependent Antigen," Science 234:1398-1401.
Takashi et al. (1983) "Immunochemical Structure of Hepatitis B e Antigen in the Serum," J Immunol. 130:2903-2911.
Ferrari et al. (1990) "Cellular Immune Response to Hepatitis B Virus-Encoded Antigens in Acute and Chronic Hepatitis B Virus Infection," J Immunol. 145:3442-3449.
Milich et al. (1990) "Is a function of the secreted hepatitis B e antigen to induce immunologic tolerance in utero," Proc. Natl. Acad. Sci. USA 87:6599-6603.
Calvo-Calle et al. (1997) "Binding of Malaria T Cell Epitopes to DR and DQ Molecules In Vitro Correlates with Immunogenicity In Vivo," J Immunol. 159:1362-1373.
Genbank Accession No. NP_671816 printed 1993.
Genbank Accession No. NKVLC printed 1999.
Genbank Accession No. NP_043683 printed 2002.
Milich et al. (2002) "Conversion of poorly immunogenic malaria repeat sequences into a highly immunogenic vaccine candidate," Vaccine 20:771-788.
Wynne et al. (1999) "The Crystal Structure of the Human Hepatitis B Virus Capsid," Mol. Cell. 3:771-780.
Hollinger and Dienstag, Chapter 82, Hepatitis B and D Viruses, in *Manual of Clinical Microbiology*, 7th ed., ASM Press, Washington, D.C., 1999.
Dubovsky, "Creating a Vaccine against Malaria," The Maralaria Vaccine Initiative, PATH (Program for Appropriate Technology in Health), Jan. 2001.
Falciparum Malaria MSPI Workshop, Progress toward MSPI Vaccine Development and Testing, The Maralaria Vaccine Initiative, PATH (Program for Appropriate Technology in Health), Dec. 2000.
Lu et al. (1999) "Immunization of Woodchucks with Plasmids Expressing Woodchuck Hepatitis Virus (WHV) Core Antigen and Surface Antigen Suppresses WHV Infection," J. Virol. 73:281-289.
Menne et al. (1997) "Characterization of T-Cell Response to Woodchuck Hepatitis Virus Core Protein and Protection of Woodchucks from Infection by Immunization with Peptides Containing a T-Cell Epitope," J. Virol. 71:65-74.
Lew et al. (2001) "In Vitro and In Vivo Infectivity and Pathogenicity of the Lymphoid Cell-Derived Woodchuck Hepatitis Virus," J. Virol. 75:1770-1782.
Siegel et al. (2001) "Coadministration of Gamma Interferon with DNA Vaccine Expressing Woodchuck Hepatitis Virus (WHV) Core Antigen Enhances the Specific Immune Response and Protects against WHV Infection," J. Virol. 75:5036-5042.
Pumpens and Grens (2001) "HBV Core Particles as a Carrier for B Cell/T Cell Epitopes," Intervirology 44:98-114.
Jegerlehner et al. "A molecular assembly system that renders antigens of choice highly repetitive for induction of protective B cell responses," (2002) Vaccine 20:3104.
GenBank Accession No. NKVLC2 printed (1999).
GenBank Accession No. NP_040993 printed (2002).
Böttcher et al. (1997) "Determination of the fold of the core protein of hepatitis B virus by electron cryomicroscopy," Nature 386:88-91.
Conway et al. (1997) "Visualization of a 4-helix bundle in the hepatitis B virus capsid by cryo-electron microscopy," Nature 386:91-94.
Salfeld et al. (1989) "Antigenic Determinants and Functional Domains in Core Antigen and e Antigen from Hepatitis B Virus," J Virol. 63:798-808.
Schodel et al. (1992) "The Position of Heterologous Epitopes Inserted in Hepatitis B Virus Core Particles Determines Their Immunogenicity," J Virol. 66:106-114.
Milich et al. (1995) "The Hepatitis Nucleocapsid as a Vaccine Carrier Moiety," Ann NY Acad Sci. 754:187-201.
Pumpens et al. (1995) "Hepatitis B Virus Core Particles as Epitope Carriers," Intervirology 38:63-74.
Clarke et al. (1987) "Improved immunogenicity of a peptide epitope after fusion to hepatitis B core protein," Nature 330:381-384.

Chang et al., (1994) "Phenotypic mixing between different hepadnavirus nucleocapsid proteins reveals c protein dimerization to be cis preferential," J Virol, 5225-5231.

Belnap et al., "Diversity of core antigen epitopes of hepatitis B virus," Proc Natl Acad Sci USA, 100:10884-10889 (2003).

Fietelson et al., "Core particles of hepatitis B virus and ground squirrel hepatitis virus," J Virol, 43:687-696 (1982).

Fietelson et al., "Monoclonal antibodies raised to purified woodchuck hepatitis virus core antigen particles demonstrate X antigen reactivity," Virology, 177:357-366 (1990).

Galibert et al., "Nucleotide sequence of a cloned woodchuck hepatitis virus genome: Comparison with the hepatitis B virus sequence," J Virol, 41:51-65 (1982).

Gallina et al., "A recombinant hepatitis B core antigen polypeptide with the protamine-like domain deleted self-assembles into capsid particles but fails to bind nucleic acids," J Virol, 63:4645-4652 (1989).

Kidd-Ljunggren et al., "Genetic variability in hepatitis B viruses," J Gen Virol, 83:1267-1280 (2002).

Koschel et al., "Extensive mutagenesis of the hepatitis B virus core gene and mapping of mutations that allow capsid formation," J Virol, 73:2153-2160 (1999).

Marion et al., "A virus in Beechey ground squirrels that is related to hepatitis B virus of humans," Proc Natl Acad Sci USA, 77:241-2945 (1980).

Mason et al., "Virus of Pekin ducks with structural and biological relatedness to human hepatitis B virus," J Virol, 36:829-836 (1980).

Milich et al., "Immune response to hepatitis B virus core antigen (HBcAg): Localization of T cell recognition site within HBcAg/HBeAg," J Immunol, 139:1223-1231 (1987).

Milich et al., "Antibody production to the nucleocapsid and envelope of the hepatitis B virus primed by a single synthetic T cell site," Nature, 329:547-549 (1987).

Milich et al., "Comparative immunogenicity of hepatitis B virus core and E antigens" J Immunol, 141:3617-3624 (1988).

Millman et al., "Immunological Cross-reactivities of woodchuck and hepatitis B viral antigens," Infect Immun, 35:752-757 (1982).

Ponzetto et al., "Core antigen and antibody in woodchucks after infection with woodchuck hepatitis virus," J Virol, 52:70-76 (1984).

Ponzetto et al., "Radioimmunoassay and characterization of woodchuck hepatitis virus core antigen and antibody," Virus Res, 2:301-315 (1985).

Pumpens and Grens, "Hepatitis B core particles as a universal display model: A structure-function basis for development," FEBS Letters, 442:1-6 (1999).

Schodel et al., "Immunization with recombinant woodchuck hepatitis virus nucleocapsid antigen or hepatitis B virus nucleocapsid antigen protects woodchucks from woodchuck hepatitis virus infection," Vaccine, 11:624-628 (1993).

Shanmuganathan et al., "Mapping of the cellular immune responses to woodchuck hepatitis core antigen epitopes in chronically infected woodchucks," J Med Virol, 52:128-135 (1997).

Stannard et al., "Antigenic cross-reactions between woodchuck hepatitis virus and human hepatitis B virus shown by immune electron microscopy," J Gen Virol, 64:975-980 (1983).

Tarar et al., "Expression of a human cytomegalovirus gp58 antigenic domain fused to the hepatitis B virus nucleocapsid protein," FEMS Immunol Med Microbiol, 16:183-192 (1996).

Ulrich et al., "Core particles of hepatitis B virus as carrier for foreign epitopes," Advances in Virus Research, 50:141-182 (1998).

Werner et al., "Serological relationship of woodchuck hepatitis virus to human hepatitis B virus," J Virol, 32:314-322 (1979).

Zheng et al., "The structure of hepadnaviral core antigens," J Biol Chem, 267:9422-9429 (1992).

Zlotnick et al., "Localization of the C terminus of the assembly domain of hepatitis B virus capsid protein: Implications for morphogenesis and organization of encapsidated RNA," Proc Natl Acad Sci USA, 94:9556-9561 (1997).

* cited by examiner

Fig. 23

| | M | S | L | L | T | E | V | E | T | P | I | R | N | E | W | G | C | R | C | N | D | S | S | D | mAb 14C2 | Polyclonal Anti-HyW-IM2(-)78 |
|---|---|---|---|---|---|---|---|---|---|---|---|---|---|---|---|---|---|---|---|---|---|---|---|---|---|---|
| WtM2e | M | S | L | L | T | E | V | E | T | P | I | R | N | E | W | G | C | R | C | N | D | S | S | D | | |
| P1 | - | - | - | - | - | - | - | - | - | - | - | - | - | - | - | - | - | - | - | - | - | - | - | - | 51200 | 625000 |
| P2 | - | - | - | - | - | - | A | - | - | - | - | - | - | - | - | - | - | - | - | - | - | - | - | - | 25600 | 125000 |
| P3 | - | - | - | - | - | - | - | - | - | - | - | - | - | - | A | - | - | - | - | - | - | - | - | - | 12800 | 125000 |
| P4 | - | - | - | - | - | - | - | - | - | - | - | - | - | - | - | - | - | - | - | - | - | - | - | - | 25600 | $3 \times 10^6$ |
| P5 | - | - | - | - | - | - | - | - | - | - | - | - | - | - | - | - | - | - | - | - | - | - | - | - | 6400 | 625000 |
| P6 | - | - | - | - | - | - | - | - | - | - | - | - | - | - | - | - | - | - | - | - | - | - | - | - | 1600 | 625000 |
| P7 | - | - | - | - | - | - | - | - | - | - | - | - | - | - | - | - | A | - | - | - | - | - | - | - | 12800 | $3 \times 10^6$ |
| P8 | - | - | - | - | - | - | - | - | - | - | - | - | - | - | - | - | - | - | A | - | - | - | - | - | 25600 | 625000 |
| P9 | - | - | - | - | - | - | - | - | - | - | - | - | - | - | - | - | A | - | A | - | - | - | - | - | 102400 | $3 \times 10^6$ |

Core-IM2(-) Particle: 625000, $15 \times 10$

Core-M78 Particle: 0

HyW-IM2(-)78

(Dilution=0.5 OD$_{492}$)   (1/Dilution)

Fig. 28

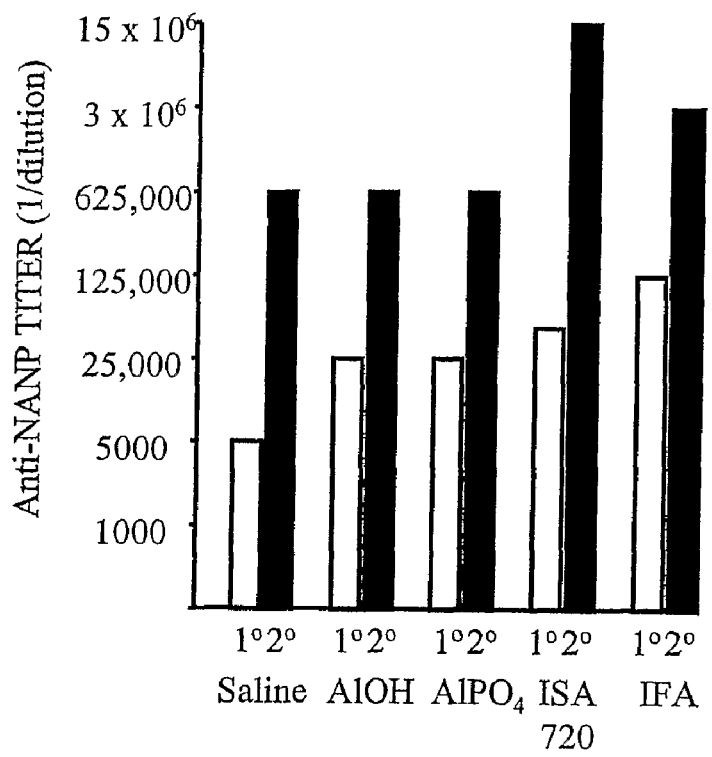
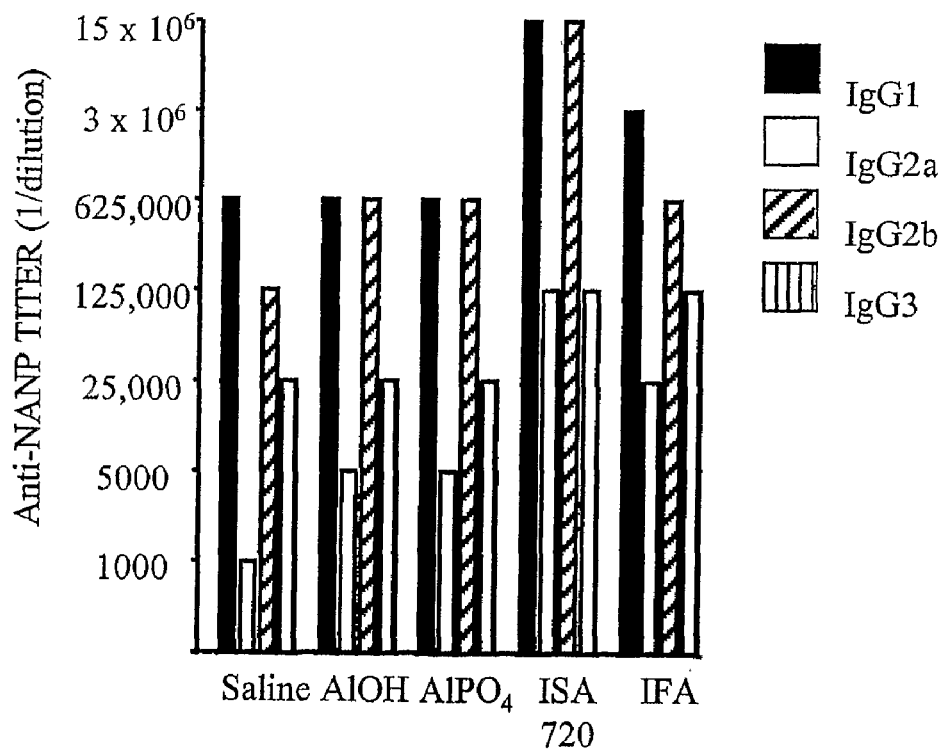
Fig. 30

Fig. 40

A    Wild Type WHcAg DNA (SEQ ID NO:37)

ATGGACATAGATCCCTATAAAGAATTTGGTTCATCTTATCAGTTGTTGAATTTTCTTCC
TTTGGACTTCTTTCCTGACCTTAATGCTTTGGTGGACACTGCTACTGCCTTGTATGAAG
AAGAGCTAACAGGTAGGGAACATTGCTCTCCGCACCATACAGCTATTAGACAAGCTTTA
GTATGCTGGGATGAATTAACTAAATTGATAGCTTGGATGAGCTCTAACATAACTTCTGA
ACAAGTAAGAACAATCATTGTAAATCATGTCAATGATACCTGGGGACTTAAGGTGAGAC
AAAGTTTATGGTTTCATTTGTCATGTCTCACTTTCGGACAACATACAGTTCAAGAATTT
TTAGTAAGTTTTGGAGTATGGATCAGGACTCCAGCTCCATATAGACCTCCTAATGCACC
CATTCTCTCGACTCTTCCGGAACATACAGTCATTAGGAGAAGAGGAGGTGCAAGAGCTT
CTAGGTCCCCCAGAAGACGCACTCCCTCTCCTCGCAGGAGAAGATCTCAATCACCGCGT
CGCAGACGCTCTCAATCTCCATCTGCCAACTGCTGA

B    Wild Type WHcAg (SEQ ID NO:1)

MDIDPYKEFGSSYQLLNFLPLDFFPDLNALVDTATALYEEELTGREHCSPHHTAIRQAL
VCWDELTKLIAWMSSNITSEQVRTIIVNHVNDTWGLKVRQSLWFHLSCLTFGQHTVQEF
LVSFGVWIRTPAPYRPPNAPILSTLPEHTVIRRRGGARASRSPRRRTPSPRRRSQSPR
RRRSQSPSANC

C    Truncated WHcAg (SEQ ID NO:38)

MDIDPYKEFGSSYQLLNFLPLDFFPDLNALVDTATALYEEELTGREHCSPHHTAIRQAL
VCWDELTKLIAWMSSNITSEQVRTIIVNHVNDTWGLKVRQSLWFHLSCLTFGQHTVQEF
LVSFGVWIRTPAPYRPPNAPILSTLPEHTVI

Fig. 41

A  Wild Type GSHcAg DNA (SEQ ID NO:39)

ATGGACATAGATCCCTATAAAGAATTTGGTTCTTCTTATCAGTTGTTGAATTTTCTTCC
TTTGGACTTTTTTCCTGATCTCAATGCATTGGTGGACACTGCTGCTGCTCTTTATGAAG
AAGAATTAACAGGTAGGGAGCATTGTTCTCCTCATCATACTGCTATTAGACAGGCCTTA
GTGTGTTGGGAAGAATTAACTAGATTAATTACATGGATGAGTGAAAATACAACAGAAGA
AGTTAGAAGAATTATTGTTGATCATGTCAATAATACTTGGGGACTTAAAGTAAGACAGA
CTTTATGGTTTCATTTATCATGTCTTACTTTTGGACAACACACAGTTCAAGAATTTTTG
GTTAGTTTTGGAGTATGGATTAGAACTCCAGCTCCTTATAGACCACCTAATGCACCCAT
TTTATCAACTCTTCCGGAACATACAGTCATTAGGAGAAGAGGAGGTTCAAGAGCTGCTA
GGTCCCCCCGAAGACGCACTCCCTCTCCTCGCAGGAGAAGGTCTCAATCACCGCGTCGC
AGACGCTCTCAATCTCCAGCTTCCAACTGCTGA

B  Wild Type GSHcAg (SEQ ID NO:21)

MDIDPYKEFGSSYQLLNFLPLDFFPDLNALVDTAAALYEEELTGREHCSPHHTAIRQAL
VCWEELTRLITWMSENTTEEVRRIIVDHVNNTWGLKVRQTLWFHLSCLTFGQHTVQEFL
VSFGVWIRTPAPYRPPNAPILSTLPEHTVIRRRGGSRAARSPRRRTPSPRRRRSQSPRR
RRSQSPASNC

C  Truncated GSHcAg (SEQ ID NO:40)

MDIDPYKEFGSSYQLLNFLPLDFFPDLNALVDTAAALYEEELTGREHCSPHHTAIRQAL
VCWEELTRLITWMSENTTEEVRRIIVDHVNNTWGLKVRQTLWFHLSCLTFGQHTVQEFL
VSFGVWIRTPAPYRPPNAPILSTLPEHTVI

Fig. 42

A    Wild Type HBcAg DNA (SEQ ID NO:57)

ATGGACATCGACCCTTATAAAGAATTTGGAGCTACTGTGGAGTTACTCTCGTTTTTGCC
TTCTGACTTCTTTCCTTCAGTACGAGATCTTCTAGATACCGCCTCAGCTCTGTATCGGG
AAGCCTTAGAGTCTCCTGAGCATTGTTCACCTCACCATACTGCACTCAGGCAAGCAATT
CTTTGCTGGGGGGAACTAATGACTCTAGCTACCTGGGTGGGTGTTAATTTGGAAGATCC
AGCATCCAGAGACCTAGTAGTCAGTTATGTCAACACTAATATGGGCCTAAAGTTCAGGC
AACTCTTGTGGTTTCACATTTCTTGTCTCACTTTTGGAAGAGAAACCGTTATAGAGTAT
TTGGTGTCTTTCGGAGTGTGGATTCGCACTCCTCCAGCTTATAGACCACCAAATGCCCC
TATCCTATCAACACTTCCGGAAACTACTGTTGTTAGACGACGAGGCAGGTCCCCTAGAA
GAAGAACTCCCTCGCCTCGCAGACGAAGGTCTCAATCGCCGCGTCGCAGAAGATCTCAA
TCTCGGGAATCTCAATGTTGA

B    Wild Type HBcAg (SEQ ID NO:41)

MDIDPYKEFGATVELLSFLPSDFFPSVRDLLDTASALYREALESPEHCSPHHTALRQAI
LCWGELMTLATWVGVNLEDPASRDLVVSYVNTNMGLKFRQLLWFHISCLTFGRETVIEY
LVSFGVWIRTPPAYRPPNAPILSTLPETTVVRRRGRSPRRRTPSPRRRRSQSPRRRRSQ
SRESQC

C    Truncated HBcAg (SEQ ID NO:58)

MDIDPYKEFGATVELLSFLPSDFFPSVRDLLDTASALYREALESPEHCSPHHTALRQAI
LCWGELMTLATWVGVNLEDPASRDLVVSYVNTNMGLKFRQLLWFHISCLTFGRETVIEY
LVSFGVWIRTPPAYRPPNAPILSTLPETTVV

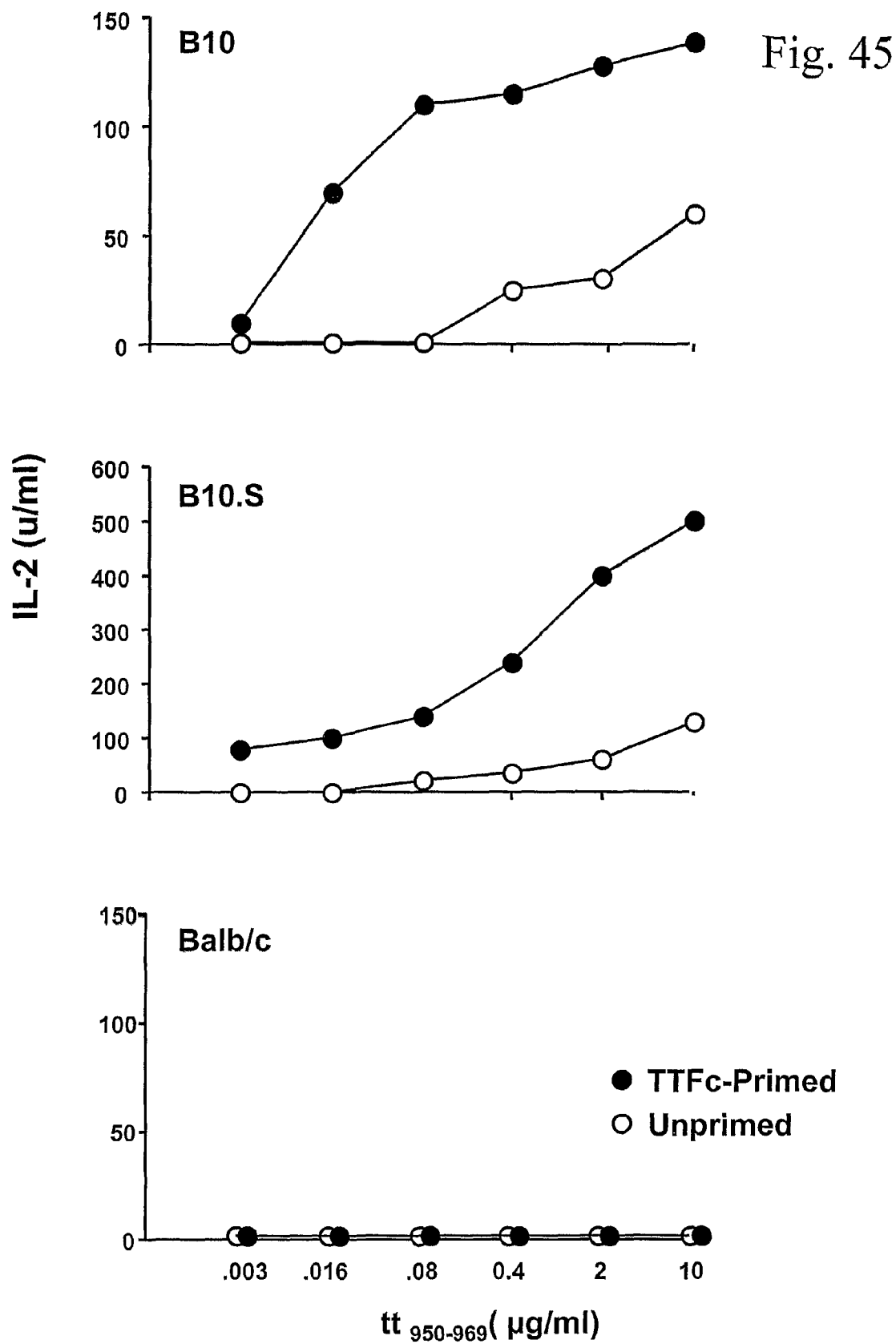

```
                                     10              20              30
DHBV-S31 M32991        M D I N A S R A L A N V Y D - - - - L P D D F F P K I D D L
HHBV M22056            M D V N A S R A L A N V Y D - - - - L P D D F F P Q I D D L
DHBV NC_001344         M D I N A S R A L A N V Y D - - - - L P D D F F P K I D D L
HBV ayw X65257         M D I D P Y K E F G A T V E L L S F L P S D F F P S V R D L
Chimp.HBV AF222323     M D I D P Y K E F G A T V E L L S F L P S D F F P S V R D L
Gibbon HBV AY077735    M D I D P Y K E F G A T V E L L S F L P S D F F P S V R D L
Ross'gooseHBV M95589   M D I N A S R A L A N V Y D - - - - L P D D F F P K I D D L
Orangutan HV NC_002168 M D I D P Y K E F G A T V E L L S F L P S D F F P S V R D L
WMHBV AF046996         M D I D P Y K E F G A T V E L L S F L P A D F F P S V R D L
GSHV K02715            M D I D P Y K E F G S S Y Q L L N F L P L D F F P D L N A L
WHV J02442             M D I D P Y K E F G S S Y Q L L N F L P L D F F P D L N A L
AGSH NC_001719         M D I D P Y K E F G S S Y Q L L N F L P L D F F P E L N A L
                       M D I D P Y K E F G . . Y . L L   F L P   D F F P   . D L 40              50              60
DHBV-S31 M32991        V R D A K D A L E P Y W K S D S I K K H V L I A T H F V D L
HHBV M22056            V R D A K D A L E P Y W K A E T I K K H V L I A T H F V D L
DHBV NC_001344         V R D A K D A L E P Y W K S D S I K K H V L I A T H F V D L
HBV ayw X65257         L D T A S A L Y R D A L E S - - - P E H C S P H H T A L R Q
Chimp.HBV AF222323     L D T A S A L Y R E A L E S - - - P E H C S P N H T A L R Q
Gibbon HBV AY077735    L D T A S A L Y R E A L E S - - - P E H C S P N H T A L R Q
Ross'gooseHBV M95589   V R D A K D A L E P Y W R N D S I K K H V L I A T H F V D L
Orangutan HV NC_002168 L D T A S A L Y R E A L E S - - - P E H C S P N H T A L R Q
WMHBV AF046996         L D T A S A L Y R E A L E S - - - S D H C S P H H T A L R Q
GSHV K02715            V D T A A A L Y E E E L T G - - - R E H C S P H H T A I R Q
WHV J02442             V D T A T A L Y E E E L T G - - - R E H C S P H H T A I R Q
AGSH NC_001719         V D T A T A L Y E E E L T G - - - R E H C S P H H T A I R Q
                       V D T A . A L Y E E   L   S       . E H C S P . H T A . R Q 70              80              90
DHBV-S31 M32991        I E D F W Q T T Q G M H E I A E S L R A V I P P T T A P V P
HHBV M22056            I E D F W Q T T Q G M S Q I A D A L R A V I P P T T V P V P
DHBV NC_001344         I E D F W Q T T Q G M H E I A E S L R A V I P P T T A P V P
HBV ayw X65257         A I L C W G - - - - - - - - - - - - - - E L M T L A T W
Chimp.HBV AF222323     A I L C W G - - - - - - - - - - - - - - E L M T L A S W
Gibbon HBV AY077735    A V L C W G - - - - - - - - - - - - - - E L M T L A S W
Ross'gooseHBV M95589   I E D F W Q T T Q G M H E I A E A L R A I P A T T A P V P
Orangutan HV NC_002168 A V L C W G - - - - - - - - - - - - - - E L M T L A S W
WMHBV AF046996         T V L C W G - - - - - - - - - - - - - - E L M S L A S W
GSHV K02715            A L V C W E - - - - - - - - - - - - - - E L T R L I T W
WHV J02442             A L V C W D - - - - - - - - - - - - - - E L T K L I A W
AGSH NC_001719         A L V C W E - - - - - - - - - - - - - - E L T R L I A W
                       A . . C W                                E L T T L   . W
```

Fig. 46A

```
                              100              110              120
DHBV-S31 M32991      T G Y L I Q H E E A E E I  P L G D L F K H Q E E R I V S F Q
HHBV M22056          E G F L I T H S E A E E I  P L N D L F S N Q E E R I V N F Q
DHBV NC_001344       T G Y L I Q H E E A E E I  P L G D L F K H Q E E R I V S F Q
HBV ayw X65257       V G V N L E D P A S R D L  - - - - - - - - - - - - - - - -
Chimp.HBV AF222323   V G N N L E D P A S R E Q  - - - - - - - - - - - - - - - -
Gibbon HBV AY077735  V G N N L E D P A S R E L  - - - - - - - - - - - - - - - -
Ross'gooseHBV M95589 Q G F L V Q H E E A E E I  P L G E L F R Y Q E E R L T N F Q
Orangutan HV NC_002168 V G N N L E D P A S R E L  - - - - - - - - - - - - - - - -
WMHBV AF046996       V G T N L E D P A A R E L  - - - - - - - - - - - - - - - -
GSHV K02715          M S E N T - E E V R R I    - - - - - - - - - - - - - - - -
WHV J02442           M S S N I T S E Q V R T I  - - - - - - - - - - - - - - - -
AGSH NC_001719       M S A N I N S E E V R R V  - - - - - - - - - - - - - - - -
                     . G   N . .   . . R E .

130              140              150
DHBV-S31 M32991      P D Y P I T A R I H A H L K A Y A K I N E E S L D R A R R L
HHBV M22056          P D Y P I T A R I H T H L R V Y T K L N E Q A L D K A R R L
DHBV NC_001344       P D Y P I T A R I H A H L K A Y A K I N E E S L D R A R R L
HBV ayw X65257       - - - - - - - - - - - - - V V S Y V N T N M G L K F R Q L
Chimp.HBV AF222323   - - - - - - - - - - - - - V V N Y V N T N M G L K I R Q L
Gibbon HBV AY077735  - - - - - - - - - - - - - V V S Y V N N N M G L K I R Q L
Ross'gooseHBV M95589 P D Y P V T A R I H A H L K A Y A K I N E E S L D R A R R L
Orangutan HV NC_002168 - - - - - - - - - - - - - V V N Y V N N M G L K I R Q L
WMHBV AF046996       - - - - - - - - - - - - - V V S Y V N D N M G L K V R Q L
GSHV K02715          - - - - - - - - - - - - - I V D H V N N T W G L K V R Q T
WHV J02442           - - - - - - - - - - - - - I V N H V N D T W G L K V R Q S
AGSH NC_001719       - - - - - - - - - - - - - I V A H V N D T W G L K V R Q N
                                               . V . . V N . . G L K . R Q L 160              170              180
DHBV-S31 M32991      L W W H Y N C L L W G E A N V T N Y I S R L R T W L S T P E
HHBV M22056          L W W H Y N C L L W G E A N V T N Y I S R L R T W L S T P E
DHBV NC_001344       L W W H Y N C L L W G E A N V T N Y I S R L R T W L S T P E
HBV ayw X65257       L W F H I S C L L F G R E T V I E Y L V S F G V W I R T P P
Chimp.HBV AF222323   L W F H I S C L T F G R E T V L E Y L V S F G V W I R T P P
Gibbon HBV AY077735  L W F H I S C L T F G R E T V L E Y L V S F G V W I R T P P
Ross'gooseHBV M95589 L W W H Y N C L L W G E P N V T N Y I S R L R T W L S T P E
Orangutan HV NC_002168 L W F H I S C L T F G R E T V L E Y L V S F G V W I R T P P
WMHBV AF046996       L W F H I S C L T F G R E T V L E Y L V S F W V W I R T P P
GSHV K02715          L W F H L S C L T F G Q H T V Q E F L V S F G V W I R T P A
WHV J02442           L W F H L S C L T F G Q H T V Q E F L V S F G V W I R T P A
AGSH NC_001719       L W F H L S C L T F G Q H T V Q E F L V S F G V R I R T P A
                     L W F H . S C L T F G .   T V   E Y L V S F G V W I R T P
```

Fig. 46B

```
                            190              200              210
DHBV-S31 M32991       K Y R G R D A P T I E A I T R P I Q V A Q G G R K T S S G T
HHBV M22056           K Y R G K D A P T I E A I T R P I Q V A Q G G R N Q T K G T
DHBV NC_001344        K Y R G R D A P T I E A I T R P I Q A A Q G G R K T S S G T
HBV ayw X65257        A Y R P P N A P I L S T L P E T T V V R R R G - - - - - - -
Chimp.HBV AF222323    A Y R P P N A P I L S T L P E T T V V R R R G - - - - - - -
Gibbon HBV AY077735   A Y R P P N A P I L S T L P E T T V V R R R G - - - - - - -
Ross'gooseHBV M95589  K Y R G K D A P T I E A I T R P I Q V A Q G G R N K T Q G V
Orangutan HV NC_002168 A Y R P P N A P I L S T L P E T T V V R R R G - - - - - - -
WMHBV AF046996        A Y R P P N A P I L S T L P E T T V V R R R - - - - - - - -
GSHV K02715           P Y R P P N A P I L S T L P E H T V I R R R G G - - S R A A
WHV J02442            P Y R P P N A P I L S T L P E H T V I R R R G G - - A R A S
AGSH NC_001719        P Y R P P N A P I L S T L P E H T V I R R R G S - - A R V V
                      Y R P P N A P I L S T L P E   T V V R R R G 220              230              240
DHBV-S31 M32991       R K P R G L E P R R R K V K T T F V Y G R R R S K S R E R R
HHBV M22056           R K P R G L E P R R R K V K T T V V Y G R R R S K S R G R R
DHBV NC_001344        R K P R G L E P R R R K V K T T V V Y G R R R S K S R E R R
HBV ayw X65257        R S P R R R T P S P R - - - - - - - - - R R R S Q S P R R R
Chimp.HBV AF222323    R S P R R R T P S P R - - - - - - - - - R R R S Q S P R R R
Gibbon HBV AY077735   R S P R R R T P S P R - - - - - - - - - R R R S Q S P R R R
Ross'gooseHBV M95589  R K S R G L E P R R R V K T T I V Y G R R R S K S R E R R
Orangutan HV NC_002168 R S P R R R T P S P R - - - - - - - - - R R R S Q S P R R R
WMHBV AF046996        R P S G R R T P S P R - - - - - - - - - R R R S Q S P R R R
GSHV K02715           R S P R R R T P S P R - - - - - - - - - R R R S Q S P R R R
WHV J02442            R S P R R R T P S P R - - - - - - - - - R R R S Q S P R R R
AGSH NC_001719        R S P R R R T P S P R - - - - - - - - - R R R S Q S P R R R
                      R S P R R R T P S P R                     R R R S Q S P R R R 250              260              270
DHBV-S31 M32991       A P S P Q R A G S P L P R S S S H H R S P S P R K
HHBV M22056           S S P S Q R A G S P L P R N R G N Q T R S P S P R E
DHBV NC_001344        A P S P Q R A G S P L P R S S S H H R S P S P R K
HBV ayw X65257        R - - - - - - - - - - - - - - - - - S Q S R E S Q C
Chimp.HBV AF222323    R - - - - - - - - - - - - - - - - - S Q S P A S Q C
Gibbon HBV AY077735   R - - - - - - - - - - - - - - - - - S Q S P A S Q C
Ross'gooseHBV M95589  A P T P Q R A G S P L P R T S R D H H R S P S P R E
Orangutan HV NC_002168 R - - - - - - - - - - - - - - - - - S Q S P A S Q C
WMHBV AF046996        R - - - - - - - - - - - - - - - - - S Q S P A S S C
GSHV K02715           R - - - - - - - - - - - - - - - - - S Q S P A S N C
WHV J02442            R - - - - - - - - - - - - - - - - - S Q S P S A N C
AGSH NC_001719        - - - - - - - - - - - - - - - - - - P Q S P A S N C
                      R                                   S Q S P . S . C
```

HEPATITIS VIRUS CORE PROTEINS AS VACCINE PLATFORMS AND METHODS OF USE THEREOF

This application is a U.S. national entry of International Application No. PCT/US2004/023391, filed on Jul. 19, 2004, which is a continuation-in-part of, and claims priority to, application Ser. No. 10/630,070, filed Jul. 30, 2003, now U.S. Pat. No. 7,320,795, and application Ser. No. 10/630,074, filed Jul. 30, 2003, now U.S. Pat. No. 7,144,712.

The invention was made in part with Government support by the National Institutes of Health, Grants RO1 AI020720 and RO1 AI049730. As such, the Government has certain rights in the invention.

FIELD OF THE INVENTION

The present invention relates to hepatitis virus core proteins and nucleic acids. In particular, the present invention provides compositions and methods comprising recombinant hepatitis virus core proteins or nucleic acids for use in vaccine formulations.

BACKGROUND OF THE INVENTION

The ability to map neutralizing B cell epitopes on protein and carbohydrate antigens has created much interest in the potential use of these hapten-like antigens in vaccine development. There are a number of advantages to the use of peptides and small well-defined oligosaccharides (OS) for subunit vaccine design, including for example, chemical purity and safety, ease of production, cost, stability, defined and targeted B and/or T cell epitopes and mutability. The promise of the hapten-like technology hasn't been fully realized because efficient and reproducible methods for the delivery of these small epitopes to the immune system are lacking. Peptidic and OS antigens often require conjugation to an immunogenic carrier in order to provide efficient T cell help for antibody producing B cells, as peptide antigens often do not contain helper T (Th) cell epitopes and carbohydrate antigens are not recognized by T cells.

The particulate human hepatitis B virus (HBV) core protein (HBcAg) has been utilized as a carrier platform as it possesses many of the characteristics uniquely required for the delivery of weak immunogens to the immune system (See, Pumpens and Grens, Intervirology, 44:98-114, 2001). Although the HBcAg is highly immunogenic, the existing HBcAg-based platform technology has a number of serious theoretical and practical limitations. For example, less than 50% of foreign epitopes can be accommodated by the HBcAg platform because of adverse effects on particle assembly (Jegerlehner et al., Vaccine, 20:3104, 2002 and PCT/US01/25625); use of the HBcAg compromises the use of the anti-HBc diagnostic assay; pre-existing anti-HBc antibody is present in all HBV chronically infected patients and in most previously infected and recovered patients, which may limit the effectiveness of the HBcAg as a vaccine carrier; and immune tolerance to HBcAg in individuals chronically infected with HBV (300-400 million worldwide) limits immunogenicity in this population. Thus, there is a profound need in the art for particulate carrier platforms capable of delivering a wide variety of heterologous peptide and oligosaccharide epitopes in an immunogenic form. This need is particularly acute in the event the vaccine recipient is chronically infected with or suspected to be infected with HBV.

SUMMARY OF THE INVENTION

The present invention relates to hepatitis virus core proteins and nucleic acids. In particular, the present invention provides compositions and methods comprising recombinant hepatitis virus core proteins or nucleic acids for use in raising antibodies in vivo and in vitro against antigens of interest, including use in vaccine formulations.

The invention provides a composition comprising a heterologous antigen linked to one or more non-primate hepadnavirus core antigen sequence that comprises a loop region. Without limiting the particular location of the insertion, in one embodiment, the heterologous antigen is inserted in the hepadnavirus core antigen (e.g., Tables 7-2 and 9), such as inside the loop region and/or outside the loop region. Without limiting the particular type of C-terminal modification, in one embodiment, the C-terminal sequence of the hepadnavirus core antigen sequence is replaced by from 1 to 100 amino acids (e.g., Tables 7-2 and 9). In an alternative embodiment, the heterologous antigen and/or the hepadnavirus core antigen comprises one or more of 1) substitution of an amino acid that is not an acidic amino acid with at least one acidic amino acid, and 2) insertion of at least one acidic amino acid compared to the wild type hepadnavirus core antigen sequence (e.g., Tables 7-2, 17, 18). While not intending to limit the type or source of heterologous antigen, in one embodiment, the heterologous antigen comprises at least one B cell epitope, at least one T cell epitope, and/or at least one CD4+ T cell epitope. In a preferred embodiment, the CD4+ T cell epitope comprises a sequence chosen from one or more of SEQ ID NOs:239-244 (derived from Tetanus Toxin), SEQ ID NOs:245-250 (derived from Diphtheria toxin), SEQ ID NOs:251-252 (derived from *Plasmodium falciparum* circumsporozoite), SEQ ID NO:253 (derived from hepatitis B virus antigen (HbsAg)), SEQ ID No:254 (derived from Influenza hemagglutinin), SEQ ID NO:255 (derived from Influenza matrix), and SEQ ID NO:256 (derived from measles virus fusion protein) (see FIG. 43). In one embodiment, the composition further comprises at least one immune enhancer sequence linked to one or more of the heterologous antigen and to the hepadnavirus core antigen sequence. In an alternative embodiment, the composition further comprises one or more of 1) wild type non-primate hepadnavirus core antigen, and 2) modified non-primate hepadnavirus core antigen lacking a heterologous antigen.

In a further embodiment, the non-primate hepadnavirus core antigen sequence is a rodent hepadnavirus core antigen sequence, such as one or more of woodchuck hepatitis virus core antigen (e.g., SEQ ID NO:1, 103-107), arctic ground squirrel hepatitis virus core antigen (e.g., SEQ ID NO:102), and ground squirrel hepatitis virus core antigen (e.g., SEQ ID NO:21 and 108). In one embodiment, the heterologous antigen is inserted inside the loop region. (e.g., Tables 7-2 and 9), such as amino acid residues 76, 77, 78, 81, and/or 82. In another embodiment, the heterologous antigen is inserted at a position outside the loop region, such as amino acid residues 44, 71, 72, 73, 74, 75, 83, 84, 85, 92, N-terminal and/or C-terminal. In a further embodiment, the heterologous antigen is inserted at a position inside the loop region and in a position outside the loop region. In one embodiment, the C-terminal sequence of the rodent hepadnavirus core antigen sequence is replaced by from 1 to 100 amino acids (e.g., Tables 7-2 and 9). In a preferred embodiment, the 1 to 100 amino acids is chosen from R, C, K, A, RRC, and SEQ ID NOs:2-20, 22-36, 42-56, 153, 155, 157, 159, 161, 163, 165, 167, 169, 171, 173, 175, 177, 179, 181, 183-238 (i.e., C-terminal modifications from all rodent hepadnaviruses (Tables 1, 3-1, 3-2), all primate hepadnaviruses (Tables 4-1, 4-2, 4-3), and all avihepadnaviruses (Table 3-3)). More preferably, the hepadnavirus core antigen sequence is a woodchuck hepadnavirus core antigen sequence, and the 1 to 100 amino acids does not consist of the wild type C-terminal sequence of the woodchuck hepadnavirus core antigen (e.g., SEQ ID NO:2).

In one embodiment, the hepadnavirus core antigen sequence is a ground squirrel hepadnavirus core antigen sequence, and the 1 to 100 amino acids does not consist of the wild type C-terminal sequence of the ground squirrel hepadnavirus core antigen (e.g., SEQ ID NO:22). In another embodiment, the hepadnavirus core antigen sequence is arctic ground squirrel hepadnavirus core antigen sequence, and the 1 to 100 amino acids does not consist of the wild type C-terminal sequence of the arctic ground squirrel hepadnavirus core antigen (e.g., SEQ ID NO:153).

In a further embodiment, the 1 to 100 amino acids is chosen from R, C, K, A, RRC, SEQ ID NOS:2-20 (i.e., woodchuck core antigen modification on any core antigen, Table 1), SEQ ID NOS:22-36 (i.e., ground squirrel core antigen modification on any core antigen, Table 3-1), SEQ ID NOS:153, 183-196 (i.e., arctic ground squirrel core antigen modification on any core antigen, Table 3-2), SEQ ID NOS:42-56 (i.e., human core antigen modification on any core antigen, Table 4-1), SEQ ID NOS:157, 159, 161, 211-224 (i.e., orangutan/gibbon/chimpanzee core antigen modification on any core antigen, Table 4-3), SEQ ID NO:155, 197-210 (i.e., woolly monkey core antigen modification on any core antigen, Table 4-2), SEQ ID NOS:163, 165, 167, 169, 171, 173, 175, 177, 179, 181, and 230-238 (i.e., avian core antigen modification on any core antigen, Table 3-3). In an alternative embodiment, the heterologous antigen and/or the hepadnavirus core antigen comprises one or more of 1) substitution of an amino acid that is not an acidic amino acid with at least one acidic amino acid, and 2) insertion of at least one acidic amino acid compared to the wild type hepadnavirus core antigen sequence (e.g., Tables 7-2, 17, 18). Alternatively, the heterologous antigen comprises at least one B cell epitope, at least one T cell epitope, and/or at least one CD4+ T cell epitope. In a further embodiment, the composition further comprises at least one immune enhancer sequence linked to one or more of the heterologous antigen and to the hepadnavirus core antigen sequence. In further embodiment, the composition further comprises one or more of 1) wild type rodent hepadnavirus core antigen, and 2) modified rodent hepadnavirus core antigen lacking a heterologous antigen.

In yet another embodiment, the non-primate hepadnavirus core antigen sequence is an avihepadnavirus core antigen sequence. In one embodiment, the avihepadnavirus core antigen sequence is chosen from one or more of duck avihepadnavirus core antigen sequence, Ross' goose avihepadnavirus core antigen sequence, heron avihepadnavirus core antigen sequence, Sheldgoose avihepadnavirus core antigen sequence, and stork avihepadnavirus core antigen sequence. In a further embodiment, the heterologous antigen is inserted at a position within the loop region (e.g., Table 7-2), such as amino acid residues 91, 92, 93, 96, and/or 97. Alternatively, the heterologous antigen is inserted at a position outside of the loop region, such as amino acid residues 40, 86, 87, 88, 89, 90, 98, 99, 131, 138, N-terminal and/or C-terminal. In one embodiment the heterologous antigen is inserted at a position within the loop region and in a position outside the loop region. In a further embodiment, the C-terminal sequence of the avihepadnavirus core antigen sequence is replaced by from 1 to 100 amino acids (e.g., Tables 7-2), such as R, C, K, A, RRC, and SEQ ID NOs:2-20, 22-36, 42-56, 153, 155, 157, 159, 161, 163, 165, 167, 169, 171, 173, 175, 177, 179, 181, 183-238 (Tables 1, 3-1, 3-2, 3-3, 4-1, 4-2, 4-3). In one preferred embodiment, the avihepadnavirus core antigen sequence is a duck avihepadnavirus core antigen sequence, and the 1 to 100 amino acids does not consist of the wild type C-terminal sequence of the duck avihepadnavirus core antigen. In another preferred embodiment, the avihepadnavirus core antigen sequence is a Ross' goose avihepadnavirus core antigen sequence, and the 1 to 100 amino acids does not consist of the wild type C-terminal sequence of the Ross' goose avihepadnavirus core antigen (e.g., SEQ ID NOS:175). In a further preferred embodiment, the avihepadnavirus core antigen sequence is a heron avihepadnavirus core antigen sequence, and the 1 to 100 amino acids does not consist of the wild type C-terminal sequence of the heron avihepadnavirus core antigen (e.g., SEQ ID NO: 179). In yet another preferred embodiment, the avihepadnavirus core antigen sequence is a Sheldgoose avihepadnavirus core antigen sequence, and the 1 to 100 amino acids does not consist of the wild type C-terminal sequence of the Sheldgoose avihepadnavirus core antigen. (e.g., SEQ ID NO:177). In another preferred embodiment, the avihepadnavirus core antigen sequence is a stork avihepadnavirus core antigen sequence, and the 1 to 100 amino acids does not consist of the wild type C-terminal sequence of the stork avihepadnavirus core antigen. (such as SEQ IID NO:181). In a particular embodiment, the 1 to 100 amino acids is chosen from R, C, K, A, RRC, SEQ ID NOS: 2-20 (i.e., woodchuck core antigen modification on any core antigen, Table 1), SEQ ID NOS:22-36 (i.e., ground squirrel core antigen modification on any core antigen, Table 3-1), SEQ ID NOS:153, 183-196 (i.e., arctic ground squirrel core antigen modification on any core antigen, Table 3-2), SEQ ID NOS:42-56 (i.e., human core antigen modification on any core antigen, Table 4-1), SEQ ID NOS:157, 159, 161, 211-224 (i.e., orangutan/gibbon/chimpanzee core antigen modification on any core antigen, Table 4-3), SEQ ID NO:155, 197-210 (i.e., woolly monkey core antigen modification on any core antigen, Table 4-2), SEQ ID NOS:163, 165, 167, 169, 171, 173, 175, 177, 179, 181, 225-238 (i.e., avian core antigen modification on any core antigen, Table 3-3). In a further embodiment, the heterologous antigen and/or the hepadnavirus core antigen comprises one or more of 1) substitution of an amino acid that is not an acidic amino acid with at least one acidic amino acid, and 2) insertion of at least one acidic amino acid compared to the wild type hepadnavirus core antigen sequence (e.g., Tables 7-2, 17, 18). In another embodiment, the heterologous antigen comprises at least one B cell epitope, at least one T cell epitope, and/or at least one CD4+ T cell epitope. In a further embodiment, the composition further comprises at least one immune enhancer sequence linked to one or more of the heterologous antigen and to the hepadnavirus core antigen sequence. Alternatively, the composition further comprises one or more of 1) wild type avihepadnavirus core antigen, and 2) modified avihepadnavirus core antigen lacking a heterologous antigen. In another embodiment, the avihepadnavirus core antigen sequence comprises a deletion of the loop region or of a portion thereof, such as deletion of from 1 to 40 amino acids of the loop region.

The invention further provides a composition comprising a heterologous antigen linked to one or more primate hepadnavirus core antigen sequence that comprises a loop region, wherein the C-terminal sequence of the hepadnavirus core antigen sequence is replaced by from 1 to 100 amino acids, and wherein the 1 to 100 amino acids does not consist of cysteine or of the wild type C-terminal sequence of the hepadnavirus core antigen. In one embodiment, the 1 to 100 amino acids is chosen from R, K, A, RRC, and SEQ ID NOs:2-20, 22-36, 43-56, 153, 163, 165, 167, 169, 171, 173, 175, 177, 179, 181, 183-238 (Tables 1, 3-1, 3-2, 3-3, 4-1, 4-2, 4-3, 9 and 7-2). In one embodiment, the 1 to 100 amino acids is chosen from R, C, K, A, RRC, SEQ ID NOS:2-20 (i.e., woodchuck core antigen modification on any core antigen, Table 1), SEQ ID NOS:22-36 (i.e., ground squirrel core antigen modification on any core antigen, Table 3-1), SEQ ID NOS:153, 183-196 (i.e., arctic ground squirrel core antigen modification on any core antigen, Table 3-2), SEQ ID NOS: 43-56 (i.e., human core antigen modification on any core antigen, Table 4-1), SEQ ID NOS:211-224 (i.e., orangutan/gibbon/chimpanzee core antigen modification on any core antigen, Table 4-3), SEQ ID NO:197-210 (i.e., woolly monkey core antigen modification on any core antigen, Table 4-2), SEQ ID NOS:163, 165, 167, 169, 171, 173, 175, 177, 179, 181, 225-238 (i.e., avian hepadnavirus core antigen modification on any core antigen, Table 3-3). In a further embodiment, the heterologous antigen is inserted in the hepadnavirus core antigen inside and/or outside the loop region. In an alternative embodiment, the heterologous antigen and/or the hepadnavirus core antigen comprises one or more of 1) substitution of an amino acid that is not an acidic amino acid with at least one acidic amino acid, and 2) insertion of at least one acidic amino acid compared to the wild type hepadnavirus core antigen sequence (e.g., Tables 7-2, 17, 18). In a further embodiment, the heterologous antigen comprises at least one B cell epitope, at least one T cell epitope, and/or at least one CD4+ T cell epitope. In another embodiment, the composition further comprises at least one immune enhancer sequence linked to one or more of the heterologous antigen and to the hepadnavirus core antigen sequence. In a further embodiment, the composition further comprises one or more of 1) wild type primate hepadnavirus core antigen, and 2) modified primate hepadnavirus core antigen lacking a heterologous antigen.

In a preferred embodiment, the primate hepadnavirus core antigen sequence is a human hepatitis B virus core antigen sequence. In a more preferred embodiment, the human hepatitis B virus core antigen sequence is chosen from one or more of SEQ ID NOS:41, and 109-114. Alternatively, the heterologous antigen is inserted inside the loop region such as at amino acid residues 76, 77, 78, 81, and 82 (e.g., Tables 7-2 and 9). In another alternative, the heterologous antigen is inserted at a position outside the loop region, such as at amino acid residues 44, 71, 72, 73, 74, 75, 83, 84, 85, 92, N-terminal and C-terminal. In a further embodiment, the heterologous antigen is inserted at a position inside and outside the loop region. In a further embodiment, the heterologous antigen and/or the hepadnavirus core antigen comprises one or more of 1) substitution of an amino acid that is not an acidic amino acid with at least one acidic amino acid, and 2) insertion of at least one acidic amino acid compared to the wild type hepadnavirus core antigen sequence (e.g., Tables 7-2, 17, 18). In a further embodiment, the heterologous antigen comprises at least one B cell epitope, at least one T cell epitope, and/or at least one CD4+ T cell epitope. In preferred embodiment, the composition further comprises at least one immune enhancer sequence linked to one or more of the heterologous antigen and to the hepadnavirus core antigen sequence. In yet another embodiment, the composition further comprises one or more of 1) wild type human hepatitis B virus core antigen, and 2) modified human hepatitis B virus core antigen lacking a heterologous antigen.

In another preferred embodiment, the primate hepadnavirus core antigen sequence is a non-human primate hepadnavirus core antigen sequence, such as chimpanzee hepatitis B virus (e.g., SEQ ID NO:115), gibbon hepatitis B virus (e.g., SEQ ID NO:116), orangutan hepatitis virus (e.g., SEQ ID NO:117), and woolly monkey hepatitis virus (e.g., SEQ ID NO:118). In one embodiment, the heterologous antigen is inserted at a position within the loop region such as amino acid residues 76, 77, 78, 81, and/or 82 (e.g., Tables 7-2 and 9). In another embodiment, the heterologous antigen is inserted at a position outside of the loop region, e.g., at amino acid residues 44, 71, 72, 73, 74, 75, 83, 84, 85, 92, N-terminal and/or C-terminal. In yet a further embodiment, the heterologous antigen is inserted at a position within and outside the loop region. In another embodiment, the C-terminal sequence of the non-human primate hepadnavirus core antigen sequence is replaced by from 1 to 100 amino acids (e.g., Tables 7-2 and 9), such as R, K, A, RRC, and SEQ ID NOs: 2-20, 22-36, 43-56, 153, 163, 165, 167, 169, 171, 173, 175, 177, 179, 181, 183-238 (Tables 1, 3-1, 3-2, 3-3, 4-1, 4-2, 4-3). In a further embodiment, the 1 to 100 amino acids is chosen from R, C, K, A, RRC, SEQ ID NOS:2-20 (i.e., woodchuck core antigen modification on any core antigen, Table 1), SEQ ID NOS:22-36 (i.e., ground squirrel core antigen modification on any core antigen, Table 3-1), SEQ ID NOS:153, 183-196 (i.e., arctic ground squirrel core antigen modification on any core antigen, Table 3-2), SEQ ID NOS:43-56 (i.e., human core antigen modification on any core antigen, Table 4-1), SEQ ID NOS:211-224 (i.e., orangutan/gibbon/chimpanzee core antigen modification on any core antigen, Table 4-3), SEQ ID NO:197-210 (i.e., woolly monkey core antigen modification on any core antigen, Table 4-2), SEQ ID NOS: 163, 165, 167, 169, 171, 173, 175, 177, 179, 181, and 225-238 (i.e., avian core antigen modification on any core antigen, Table 3-3). In a particular embodiment, the heterologous antigen and/or hepadnavirus core antigen sequence comprises one or more of 1) substitution of an amino acid that is not an acidic amino acid with at least one acidic amino acid, and 2) insertion of at least one acidic amino acid compared to the wild type hepadnavirus core antigen sequence (e.g., Tables 7-2, 17, 18). In another embodiment, the heterologous antigen comprises at least one B cell epitope, at least one T cell epitope, and/or at least one CD4+ T cell epitope. In a further embodiment, the composition further comprises at least one immune enhancer sequence linked to one or more of the heterologous antigen and to the hepadnavirus core antigen sequence. In yet another embodiment, the composition further comprises one or more of 1) wild type non-human primate hepadnavirus core antigen, and 2) modified non-human primate hepadnavirus core antigen lacking a heterologous antigen.

Also provided by the invention is a composition comprising one or more non-primate hepadnavirus core antigen sequence that comprises a loop region, wherein the C-terminal sequence of the hepadnavirus core antigen sequence is replaced by from 1 to 100 amino acids (e.g., Tables 7-2 and 9).

The invention also provides a composition comprising one or more primate hepadnavirus core antigen sequence that comprises a loop region, wherein the C-terminal sequence of the hepadnavirus core antigen sequence is replaced by from 1 to 100 amino acids, and wherein the 1 to 100 amino acids does not consist of cysteine or of the wild type C-terminal sequence of the hepadnavirus core antigen (e.g., Tables 7-2 and 9).

Also provided herein is a method for modifying a non-primate hepadnavirus core antigen, comprising: a) providing: i) a non-primate hepadnavirus core antigen comprising a loop region; and ii) antigen that is heterologous to the non-primate hepadnavirus; and b) inserting the antigen in the non-primate hepadnavirus core antigen (e.g., Tables 7-2 and 9). In one embodiment, the method further comprises determining antigenicity, in vitro and/or in vivo in an animal, of the non-primate hepadnavirus core antigen produced by the method, wherein the mammal is chosen from mouse, non-human primate, and human. In another embodiment, the method further comprises expressing the modified antigen in any organism, including plant. This may be useful in producing food based vaccines, testing antigenicity, immunogenicity, etc. In one embodiment, the non-primate hepadnavirus is a rodent hepadnavirus, such as arctic ground squirrel hepatitis virus (AGSHV), ground squirrel hepatitis virus (GSHV), and woodchuck hepatitis virus (WHV). In one embodiment, the arctic ground squirrel hepatitis virus (AGSHV) core antigen comprises SEQ ID NO:102 (Genbank# NC_001719), or is encoded by a nucleic acid sequence comprising SEQ ID NO:127 (Genbank #U29144). In another embodiment, the ground squirrel hepatitis virus (GSHV) core antigen comprises one or more of SEQ ID NO:21 and 108 or is encoded by a nucleic acid sequence comprising one or more of SEQ ID NO:39 and 128 (Genbank #NP_040993, #K02715). In a further embodiment, the woodchuck hepatitis virus (WHV) core antigen comprises one or more of SEQ ID NO:1, and 103-107 and/or is encoded by a nucleic acid sequence comprising one or more of SEQ ID NOs:37 and 129-133 (Genbank #NKVLC2, #M90520, #M18752, #M11082, #J04514, and #J02442).

In a further embodiment, the non-primate hepadnavirus is an avihepadnavirus, such as Ross' goose hepatitis virus, heron hepatitis virus, duck hepatitis virus, sheldgoose hepatitis virus, and stork hepatitis virus. In one embodiment, the Ross' goose hepatitis virus core antigen comprises SEQ ID NO:125 (Genbank #NC_005888) and/or is encoded by a nucleic acid sequence comprising SEQ ID NO:143 (Genbank #NC_005888). In a further embodiment, the heron hepatitis virus core antigen comprises SEQ ID NO:126 and/or is encoded by a nucleic acid sequence comprising SEQ ID NO:144 (Genbank #M22056). In yet another embodiment, the duck hepatitis virus core antigen comprises one or more of SEQ ID NO:119-124 and/or is encoded by a nucleic acid sequence comprising one or more of SEQ ID NOs:145-150 (Genbank #M32991, # M60677, #M32990, #M21953, #NC_001344, #X60213). In a further embodiment, the sheldgoose hepatitis virus core antigen comprises SEQ ID NO:151 and/or is encoded by a nucleic acid sequence comprising SEQ ID NO:124 (Genbank #AY494853). In another embodiment, the stork hepatitis virus core antigen comprises SEQ ID NO:152, and/or is encoded by a nucleic acid sequence comprising SEQ ID NO:126 (Genbank #AJ251934). In one embodiment, the inserting of the antigen is inside and/or outside the loop region. In a further embodiment, the method further comprises c) replacing the C-terminal sequence of the hepadnavirus core antigen sequence with from 1 to 100 amino acids (e.g., Tables 7-2 and 9), wherein steps b) and c) are carried out in any order or are concomitant. In a further embodiment, the antigen comprises a polypeptide, and wherein the method further comprises c) modifying one or more of the non-primate hepadnavirus core antigen and the heterologous antigen, by one or more of (i) inserting at least one acidic amino acid, and (ii) substituting at least one amino acid that is not an acidic amino acid with one or more acidic amino acid (e.g., Tables 7-2, 17, 18), wherein steps b) and c) are carried out in any order or are concomitant. In a preferred embodiment, the modified heterologous antigen comprises a sequence chosen from one or more of SEQ ID no: 73, 74, 75, 77, 78, 79, 80, 81, 83, 98 (Table 17), 99, 100, and 101 (Table 18) (see also Table 7-2). In an alternative embodiment, the method further comprises c) linking at least one immune enhancer sequence to one or more of the heterologous antigen and to the non-primate hepadnavirus core antigen sequence, wherein steps b) and c) are carried out in any order or are concomitant. In yet another embodiment, the antigen comprises one or more of SEQ ID NOs:70-92 (Table 10). In one embodiment, the hepadnavirus is an avihepadnavirus, and the method further comprises c) deleting at least a portion of the loop region in the avihepadnavirus core antigen, wherein steps b) and c) are carried out in any order or are concomitant, and wherein the deleting comprises deleting the loop region or a portion thereof.

The invention additionally provides a method for modifying a primate hepadnavirus core antigen, comprising: a) providing: i) a primate hepadnavirus core antigen comprising a loop region; and ii) antigen that is heterologous to the primate hepadnavirus; b) inserting the antigen in the primate hepadnavirus core antigen (e.g., Tables 7-2 and 9); and c) replacing the C-terminal sequence of the hepadnavirus core antigen sequence with from 1 to 100 amino acids, wherein the 1 to 100 amino acids does not consist of cysteine or of the wild type C-terminal sequence of the hepadnavirus core antigen (e.g., Tables 7-2 and 9), wherein steps b) and c) are carried out in any order or are concomitant. In one embodiment, the method further comprises determining antigenicity in vitro and/or in vivo in an animal of the primate hepadnavirus core antigen produced by the method. In one embodiment, the mammal is chosen from mouse, non-human primate, and human. In a preferred embodiment, the primate hepadnavirus is a human hepatitis B virus, such as one that comprises one or more of SEQ ID NOs:41, 109-114 or that is encoded by a nucleic acid sequence comprising one or more of SEQ ID NOs:138-142 (Genbank #X65257, #X02763, #X01587, #J02202, #AY123041). In an alternative embodiment, the primate hepadnavirus is a non-human primate hepadnavirus, such as one chosen from orangutan hepatitis virus, woolly monkey hepatitis virus, gibbon hepatitis B virus, and chimpanzee hepatitis B virus. In one embodiment, the orangutan hepatitis virus core antigen comprises SEQ ID NO:117 or is encoded by a nucleic acid sequence comprising SEQ ID NO:134 (Genbank # NC_002168). In a further embodiment, the woolly monkey hepatitis virus core antigen comprises SEQ ID NO:118 or is encoded by a nucleic acid sequence comprising SEQ ID NO:135 (Genbank #AF046996). In yet another embodiment, the gibbon hepatitis B virus core antigen comprises SEQ ID NO:116 or is encoded by a nucleic acid sequence comprising SEQ ID NO:136 (Genbank #AY077735). In one embodiment, the chimpanzee hepatitis B virus core antigen comprises SEQ ID NO:115 or is encoded by a nucleic acid sequence comprising SEQ ID NO:137 (Genbank # AF222323). In a further embodiment, the inserting of the antigen is inside and/or outside the loop region. In yet another embodiment, the antigen comprises a polypeptide, and wherein the method further comprises c) modifying one or more of the primate hepadnavirus core antigen and the heterologous antigen, by one or more of (i) inserting at least one acidic amino acid, and (ii) substituting at least one amino acid that is not an acidic amino acid with one or more acidic amino acid (e.g., Tables 7-2, 17, 18), wherein steps b) and c) are carried out in any order or are concomitant. In a further embodiment, the modified heterologous antigen comprises a sequence chosen from one or more of SEQ ID NOs:73, 74, 75, 77, 78, 79, 80, 81, 83, 98 (e.g., Table 17), 99, 100, and 101 (e.g., Tables 7-2, 17, 18). In yet a further embodiment, the method further comprises c) linking at least one immune enhancer sequence to one or more of the heterologous antigen and to the primate hepadnavirus core antigen sequence, wherein steps b) and c) are carried out in any order or are concomitant. In one embodiment, the antigen comprises one or more of SEQ ID NOs:70-92 (Table 10).

Also provided herein is a method for producing an immunogenic composition, comprising: a) providing: i) a non-primate hepadnavirus core antigen sequence comprising a loop region; and ii) an antigen that is heterologous to the hepadnavirus core antigen; b) altering at least one of the heterologous antigen and the hepadnavirus core antigen with a modification chosen from one or more of: i) insertion of at least one acidic amino acid; and ii) substitution of an amino acid that is not an acidic amino acid with at least one acidic amino acid; c) producing a modified hepadnavirus core antigen by inserting one or more of: i) the altered heterologous antigen of step b into the hepadnavirus core antigen of step a; ii) the heterologous antigen of step a into the altered hepadnavirus core antigen of step b; and iii) the altered heterologous antigen of step b into the altered hepadnavirus core antigen of step b; and d) expressing the modified hepadnavirus core antigen under conditions suitable for producing hepadnavirus particles having a diameter of 25 to 35 nm, wherein steps b) and c) are in any order or are concomitant. In one embodiment, in the absence of the altering, expression of the modified hepadnavirus core antigen yields 25 fold less hepadnavirus particles than does expression of a wild type hepadnavirus core antigen. In a further embodiment, the at least one acidic amino acid residue comprises one or more of at least one aspartic acid residue, and/or at least one glutamic acid residue. Alternatively, the insertion of acidic amino acid is in at least one position chosen from the N-terminus and the C-terminus of the heterologous antigen. In another alternative, the substitution with acidic amino acid comprises replacement of at least one amino acid that is not an acidic amino acid of the heterologous antigen with at least one acidic amino acid residue. In yet a further embodiment, the altering produces a modified heterologous antigen having an isoelectric point in the range of 3.0 to 6.0.

The invention also provides a method for producing an immune response, comprising: a) providing: i) an animal (e.g., mammalian subject); and ii) a composition comprising one or more of: 1) a polypeptide comprising a non-primate hepadnavirus core antigen amino acid sequence linked to a heterologous antigen, wherein the hepadnavirus core antigen comprises a loop region, and 2) an expression vector encoding the polypeptide; and b) administering the composition to the animal under conditions such that an immune response is generated to the heterologous antigen. In one embodiment, the immune response comprises one or more of lymphocyte proliferative response, cytokine response and antibody response. Preferably, the antibody response comprises production of IgG antibodies, and more preferably the IgG antibodies comprise an autoantibody. In another embodiment, the non-primate hepadnavirus core antigen sequence is chosen from a rodent hepadnavirus core antigen sequence and an avihepadnavirus core antigen sequence.

Also provided by the invention is a method for producing an immune response, comprising: a) providing: i) an animal (e.g., mammalian subject); and ii) a composition comprising one or more of: 1) a polypeptide comprising a heterologous antigen linked to one or more primate hepadnavirus core antigen sequence that comprises a loop region, wherein the C-terminal sequence of the hepadnavirus core antigen sequence is replaced by from 1 to 100 amino acids, and wherein the 1 to 100 amino acids does not consist of cysteine or of the wild type C-terminal sequence of the hepadnavirus core antigen; and 2) an expression vector encoding the polypeptide; and b) administering the composition to the animal under conditions such that an immune response is generated to the heterologous antigen. In one embodiment, the immune response comprises one or more of lymphocyte proliferative response, cytokine response and antibody response. Preferably, the antibody response comprises production of IgG antibodies. More preferably, the IgG antibodies comprise an autoantibody. In one embodiment, the primate hepadnavirus core antigen sequence is chosen from human hepatitis B virus core antigen sequence and a non-human primate hepadnavirus core antigen sequence.

The invention also provides a method for producing an immunogenic composition, comprising: a) providing: i) a primate hepadnavirus core antigen sequence comprising a loop region; and ii) an antigen that is heterologous to the hepadnavirus core antigen; b) altering at least one of the heterologous antigen and the hepadnavirus core antigen with a modification chosen from one or more of: i) insertion of at least one acidic amino acid; and ii) substitution of an amino acid that is not an acidic amino acid with at least one acidic amino acid; c) producing a modified hepadnavirus core antigen by inserting one or more of: i) the altered heterologous antigen of step b into the hepadnavirus core antigen of step a; ii) the heterologous antigen of step a into the altered hepadnavirus core antigen of step b; and iii) the altered heterologous antigen of step b into the altered hepadnavirus core antigen of step b; and d) expressing the modified hepadnavirus core antigen under conditions suitable for producing hepadnavirus particles having a diameter of 25 to 35 nm, wherein steps b) and c) are in any order or are concomitant. In one embodiment, in the absence of the altering, expression of the modified hepadnavirus core antigen yields 25 fold less hepadnavirus particles than does expression of a wild type hepadnavirus core antigen. In another embodiment, the at least one acidic amino acid residue comprises one or more of at least one aspartic acid residue, and/or at least one glutamic acid residue. In an alternative embodiment, the insertion of acidic amino acid is in at least one position chosen from the N-terminus and the C-terminus of the heterologous antigen. In yet a further embodiment, the substitution with acidic amino acid comprises replacement of at least one amino acid that is not an acidic amino acid of the heterologous antigen with at least one acidic amino acid residue. In an alternative embodiment, the altering produces a modified heterologous antigen having an isoelectric point in the range of 3.0 to 6.0.

The invention also provides a nucleic acid sequence encoding any one or more of the herein disclosed heterologous antigen linked to a hepadnavirus core antigen sequence. Also provided is an expression vector comprising the herein described nucleic acid sequences. The invention additionally provides a cell comprising the herein described nucleic acid sequences. The invention also provides a vaccine comprising any one or more of the polypeptide and/or nucleic acid sequences disclosed herein.

In particular, the present invention provides compositions comprising a heterologous antigen linked to the amino acid sequence set forth in SEQ ID NO:38, the amino acid sequence comprising a loop region. In some embodiments, the heterologous antigen is inserted at a position within the loop region. In preferred embodiments, the position within the loop region is chosen from amino acid residues 77, 78, 81, and 82. In another embodiment, the position within the loop region is at amino acid residue 76. In further embodiments, the heterologous antigen is inserted at a position outside of the loop region. In preferred embodiments, the position outside the loop region is chosen from amino acid residues 71, 72, 73, 74, 75, 83, 84, 85, 92, N-terminal and C-terminal. In another embodiment, the position outside the loop region is at amino acid residue 44. In still further embodiments, the heterologous antigen is inserted at a position within the loop region, and in a position outside the loop region. The present invention also provides composition in which the heterologous antigen is conjugated to the amino acid sequence. In preferred embodiments, the heterologous antigen comprises at least one B cell epitope. In further preferred embodiments, the heterologous antigen comprises at least one T helper cell epitope. In exemplary embodiments, the heterologous antigen is chosen from but not limited to human immunodeficiency virus antigen, feline immunodeficiency virus antigen, *Plasmodium* parasite antigen, influenza virus antigen, *Staphylococcus* bacterium antigen, cholesteryl ester transfer protein antigen, major histocompatibility complex antigen, cytokine antigen, amyloid P-peptide antigen, peanut allergen antigen, latex allergen hevein antigen, brown shrimp allergen antigen and major grass pollen allergen antigen.

The present invention also provides compositions comprising a heterologous antigen linked to the amino acid sequence set forth in SEQ ID NO:38, the amino acid sequence comprising a loop region and further comprising from 1 to 100 amino acids at the carboxy end of residue $U^{149}$. In some preferred embodiments, the 1 to 100 amino acids is chosen from $R^{150}$, $C^{150}$, $K^{150}$, $A^{150}$, $R^{150}R^{151}C^{152}$, and SEQ ID NOS:2-20. In other preferred embodiments, the 1 to 100 amino acids is chosen from SEQ ID NOS:22-36. In still further preferred embodiments, the 1 to 100 amino acids is chosen from SEQ ID NOS:42-56. Additionally, in particularly preferred embodiments, the heterologous antigen linked to the amino acid sequence set forth in SEQ ID NO:38, comprises a particle having a diameter of 25 to 35 nm. In some embodiments, the amino acid sequence further comprises at least one immune enhancer sequence. The immune enhancer sequence is operably linked to the C-terminus of the amino acid sequence in some embodiments. In exemplary embodiments, the immune enhancer sequence is chosen from but not limited to unmethylated CpG dinucleotides, CD40 ligand, complement C3d fragment, B cell activating factor, and soluble gene product of lymphocyte activation gene-3 and universal human CD4+ T cell epitopes to which the human population has been frequently exposed (e.g., tetanus toxoid epitopes). Also provided are embodiments further comprising woodchuck hepatitis virus core antigen chosen from wild type woodchuck hepatitis virus core antigen and modified woodchuck hepatitis virus core antigen lacking a heterologous antigen. In some embodiments, the composition further comprises one or more compounds chosen from adjuvant, diluent and carrier. In related embodiments, the adjuvant is chosen from but not limited to aluminum hydroxide, aluminum phosphate, squalene and mineral oil. Moreover, the present invention provides a nucleic acid sequence encoding a heterologous antigen linked to the amino acid sequence set forth in SEQ ID NO:38. Related embodiments provide an expression vector comprising a nucleic acid sequence encoding a heterologous antigen linked to the amino acid sequence set forth in SEQ ID NO:38.

Additionally, the present invention provides compositions comprising a heterologous antigen linked to an amino acid sequence which is at least 95% identical to the sequence set forth in SEQ ID NO:38, the amino acid sequence comprising a loop region and forming a particle having a diameter of 25 to 35 μm. In some embodiments, the heterologous antigen comprises at least one modification chosen from insertion of at least one acidic amino acid residue, and substitution of at least one acidic amino acid residue. In some preferred embodiments, the at least one acidic amino acid residue comprises from 1 to 10 residues of one or both of aspartic acid and glutamic acid. In other preferred embodiments, the amino acid sequence comprises at least one modification chosen from insertion of at least one acidic amino acid residue, and substitution of at least one acidic amino acid residue. In some preferred embodiments, the at least one acidic amino acid residue comprises from 1 to 10 residues of one or both of aspartic acid and glutamic acid.

Also provided by the present invention are compositions comprising the amino acid sequence set forth in SEQ ID NO:38, the amino acid sequence comprising a loop region. In some embodiments, the amino acid sequence further comprises from 1 to 100 amino acids (excluding the wild type C-terminus set forth in SEQ ID NO:2) at the carboxy end of residue 1149. In some preferred embodiments, the 1 to 100 amino acids is chosen from $R^{50}$, $C^{150}$, $K^{150}$, $A^{150}$, $R^{150}R^{151}C^{152}$, and SEQ ID NOS:3-20. In other preferred embodiments, the 1 to 100 amino acids is chosen from SEQ ID NOS:22-36. In still further preferred embodiments, the 1 to 100 amino acids is chosen from SEQ ID NOS:42-56. Additionally, in some embodiments, the amino acid sequence further comprises at least one immune enhancer sequence. In preferred embodiments, the immune enhancer sequence is operably linked to the C-terminus of the amino acid sequence. In exemplary embodiments, the immune enhancer sequence is chosen from but not limited to unmethylated CpG dinucleotides, CD40 ligand, complement C3d fragment, B cell activating factor, and soluble gene product of lymphocyte activation gene-3 and universal human CD4+ T cell epitopes to which the human population has been frequently exposed (e.g., tetanus toxoid epitopes). Also provided is a nucleic acid sequence encoding the amino acid sequence set forth in SEQ ID NO:38, the amino acid sequence comprising a loop region. Related embodiments provide an expression vector comprising the nucleic acid sequence encoding the amino acid sequence set forth in SEQ ID NO:38. Additionally, compositions further comprising a modified woodchuck hepatitis virus core antigen comprising a heterologous antigen are provided. In some particularly preferred embodiments, compositions are provided comprising an amino acid sequence which is at least 95% identical to SEQ ID NO:38, the amino acid sequence comprising a loop region and forming a particle having a diameter of 25 to 35 nm.

Importantly, the present invention provides methods, comprising: providing: an animal (e.g., mammalian subject); and a composition comprising one or more of a polypeptide comprising a heterologous antigen linked to the amino acid sequence set forth in SEQ ID NO:38, the amino acid sequence comprising a loop region, and an expression vector encoding the polypeptide; and administering the composition to the animal under conditions such that an immune response is generated. In some embodiments, the immune response comprises one or more of lymphocyte proliferative response, cytokine response and antibody response. In some preferred embodiments, the cytokine response comprises IL-2 production. In further embodiments, the antibody response comprises at least three fold higher levels of antibody than that observed before administration of the at least one composition. In particularly preferred embodiments, the antibody response comprises production of IgG antibodies. In related embodiments, the IgG antibodies comprise an autoantibody. In some preferred embodiments, the composition further comprises one or more compounds chosen from adjuvant, diluent and carrier. In related embodiments, the adjuvant is chosen from but not limited to aluminum hydroxide, aluminum phosphate, squalene and mineral oil.

Also provided by the present invention are methods for producing an immunogenic composition, comprising: providing: a heterologous antigen; and a hepatitis virus core antigen; altering at least one of the heterologous antigen and the hepatitis virus core antigen, with a modification chosen from insertion of at least one acidic amino acid residue and substitution of at least one amino acid residue; and inserting the heterologous antigen of step b within the hepatitis virus core antigen of step b to produce a modified hepatitis virus core antigen; expressing the modified hepatitis virus core antigen under conditions suitable for producing particles having a diameter of 25 to 35 nm. In some embodiments, in the absence of the altering, expression of the modified hepatitis virus core antigen yields aggregates rather than particles. In other embodiments, in the absence of the altering, expression of the modified hepatitis virus core antigen yields 25 fold less particles than does expression of a wild type hepatitis virus core antigen. In some preferred embodiments, the at least one acidic amino acid residue comprises from 1 to 10 aspartic acid residues. In other preferred embodiments, the at least one acidic amino acid residue comprises from 1 to 10 glutamic acid residues. In related embodiments, the at least one acidic amino acid residue comprises at least one aspartic acid residue and at least one glutamic acid residue. In some embodiments, the insertion is in at least one position chosen from the N-terminus and the C-terminus of the heterologous antigen. In other embodiments, the substitution comprises a replacement of at least one non-acidic amino acid residue within the heterologous antigen, with the at least one acidic amino acid residue. In preferred embodiments, the altering produces a modified heterologous antigen with an isoelectric point in the range of 2.0 to 7.0. In a subset of these embodiments, the altering produces a modified heterologous antigen with an isoelectric point more preferably in the range of 3.0 to 6.0, and most preferably in the range of 4.0 to 5.0. In a preferred embodiment, the hepatitis virus core antigen is a woodchuck hepatitis virus core antigen.

Additionally, the present invention provides compositions comprising a heterologous antigen linked to the amino acid sequence set forth in SEQ ID NO:40, the amino acid sequence comprising a loop region. In some embodiments, the heterologous antigen is inserted at a position within the loop region. In preferred embodiments, the position within the loop region is chosen from amino acid residues 77, 80, and 81. In another embodiment, the position within the loop region is at amino acid residue 76. In further embodiments, the heterologous antigen is inserted at a position outside of the loop region. In preferred embodiments, the position outside the loop region is chosen from amino acid residues 71, 72, 73, 74, 75, 82, 83, 84, 91, N-terminal and C-terminal. In another embodiment, the position outside the loop region is at amino acid residue 44. In still further embodiments, the heterologous antigen is inserted at a position within the loop region, and in a position outside the loop region. The present invention also provides composition in which the heterologous antigen is conjugated to the amino acid sequence. In preferred embodiments, the heterologous antigen comprises at least one B cell epitope. In further preferred embodiments, the heterologous antigen comprises at least one T helper cell epitope. In exemplary embodiments, the heterologous antigen is chosen from but not limited to human immunodeficiency virus antigen, feline immunodeficiency virus antigen, *Plasmodium* parasite antigen, influenza virus antigen, *Staphylococcus* bacterium antigen, cholesteryl ester transfer protein antigen, major histocompatibility complex antigen, cytokine antigen, amyloid β-peptide antigen, peanut allergen antigen, latex allergen hevein antigen, brown shrimp allergen antigen and major grass pollen allergen antigen.

The present invention also provides compositions comprising a heterologous antigen linked to the amino acid sequence set forth in SEQ ID NO:40, the amino acid sequence comprising a loop region and further comprising from 1 to 100 amino acids at the carboxy end of residue $I^{148}$. In some preferred embodiments, the 1 to 100 amino acids is chosen from $R^{149}$, $C^{149}$, $K^{149}$, $A^{149}$, $R^{149}R^{150}C^{151}$, and SEQ ID NOS:3-6, 22-36, 153, and 183-196. In other preferred embodiments, the 1 to 100 amino acids is chosen from SEQ ID NOS:2, 7-20. In still further preferred embodiments, the 1 to 100 amino acids is chosen from SEQ ID NOS:42-56. Additionally, in particularly preferred embodiments, the heterologous antigen linked to the amino acid sequence set forth in SEQ ID NO:40, comprises a particle having a diameter of 25 to 35 nm. In some embodiments, the amino acid sequence further comprises at least one immune enhancer sequence. The immune enhancer sequence is operably linked to the C-terminus of the amino acid sequence in some embodiments. In exemplary embodiments, the immune enhancer sequence is chosen from but not limited to unmethylated CpG dinucleotides, CD40 ligand, complement C3d fragment, B cell activating factor, and soluble gene product of lymphocyte activation gene-3 and universal human CD4+ T cell epitopes to which the human population has been frequently exposed (e.g., tetanus toxoid epitopes). Also provided are embodiments further comprising ground squirrel hepatitis virus core antigen chosen from wild type ground squirrel hepatitis virus core antigen and modified ground squirrel hepatitis virus core antigen lacking a heterologous antigen. In some embodiments, the composition further comprises one or more compounds chosen from adjuvant, diluent and carrier. In related embodiments, the adjuvant is chosen from but not limited to aluminum hydroxide, aluminum phosphate, squalene and mineral oil. Moreover, the present invention provides a nucleic acid sequence encoding a heterologous antigen linked to the amino acid sequence set forth in SEQ ID NO:40. Related embodiments provide an expression vector comprising a nucleic acid sequence encoding a heterologous antigen linked to the amino acid sequence set forth in SEQ ID NO:40.

Additionally, the present invention provides compositions comprising a heterologous antigen linked to an amino acid sequence which is at least 95% identical to the sequence set forth in SEQ ID NO:40, the amino acid sequence comprising a loop region and forming a particle having a diameter of 25 to 35 nm. In some embodiments, the heterologous antigen comprises at least one modification chosen from insertion of at least one acidic amino acid residue, and substitution of at least one acidic amino acid residue. In some preferred embodiments, the at least one acidic amino acid residue comprises from 1 to 10 residues of one or both of aspartic acid and glutamic acid. In other preferred embodiments, the amino acid sequence comprises at least one modification chosen from insertion of at least one acidic amino acid residue, and substitution of at least one acidic amino acid residue. In some preferred embodiments, the at least one acidic amino acid residue comprises from 1 to 10 residues of one or both of aspartic acid and glutamic acid.

Also provided by the present invention are compositions comprising the amino acid sequence set forth in SEQ ID NO:40, the amino acid sequence comprising a loop region. In some embodiments, the amino acid sequence further comprises from 1 to 100 amino acids (excluding the wild type C-terminus set forth in SEQ ID NO:22) at the carboxy end of residue $I^{148}$. In some preferred embodiments, the 1 to 100 amino acids is chosen from $R^{149}$, $C^{149}$, $K^{149}$, $A^{149}$, $R^{149}R^{150}C^{151}$, and SEQ ID NOS:3-6, 23-36. In other preferred embodiments, the 1 to 100 amino acids is chosen from SEQ ID NOS:2-20. In still further preferred embodiments, the 1 to 100 amino acids is chosen from SEQ ID NOS:42-56. Additionally, in some embodiments, the amino acid sequence further comprises at least one immune enhancer sequence. In preferred embodiments, the immune enhancer sequence is operably linked to the C-terminus of the amino acid sequence. In exemplary embodiments, the immune enhancer sequence is chosen from unmethylated CpG dinucleotides, CD40 ligand, complement C3d fragment, B cell activating factor, and soluble gene product of lymphocyte activation gene-3 and universal human CD4+ T cell epitopes to which the human population has been frequently exposed (e.g., tetanus toxoid epitopes). Also provided is a nucleic acid sequence encoding the amino acid sequence set forth in SEQ ID NO:40, the amino acid sequence comprising a loop region. Related embodiments provide an expression vector comprising the nucleic acid sequence encoding the amino acid sequence set forth in SEQ ID NO:40. Additionally, compositions further comprising a modified ground squirrel hepatitis virus core antigen comprising a heterologous antigen are provided. In some particularly preferred embodiments, compositions are provided comprising an amino acid sequence which is at least 95% identical to SEQ ID NO:40, the amino acid sequence comprising a loop region and forming a particle having a diameter of 25 to 35 nm.

Importantly, the present invention provides methods, comprising: providing: an animal (e.g., mammalian subject); and a composition comprising one or more of a polypeptide comprising a heterologous antigen linked to the amino acid sequence set forth in SEQ ID NO:40, the amino acid sequence comprising a loop region, and an expression vector encoding the polypeptide; and administering the composition to the animal under conditions such that an immune response is generated. In some embodiments, the immune response comprises one or more of lymphocyte proliferative response, cytokine response and antibody response. In some preferred embodiments, the cytokine response comprises IL-2 production. In further embodiments, the antibody response comprises at least three fold higher levels of antibody than that observed before administration of the at least one composition. In particularly preferred embodiments, the antibody response comprises production of IgG antibodies. In related embodiments, the IgG antibodies comprise an autoantibody. In some preferred embodiments, the composition further comprises one or more compounds chosen from adjuvant, diluent and carrier. In related embodiments, the adjuvant is chosen from but not limited to aluminum hydroxide, aluminum phosphate, squalene and mineral oil.

Also provided by the present invention are methods for producing an immunogenic composition, comprising: providing: a heterologous antigen; and a hepatitis virus core antigen; altering at least one of the heterologous antigen and the hepatitis virus core antigen, with a modification chosen from insertion of at least one acidic amino acid residue and substitution of at least one acidic amino acid residue; and inserting the heterologous antigen of step b within the hepatitis virus core antigen of step b to produce a modified hepatitis virus core antigen; expressing the modified hepatitis virus core antigen under conditions suitable for producing particles having a diameter of 25 to 35 nm. In some embodiments, in the absence of the altering, expression of the modified hepatitis virus core antigen yields aggregates rather than particles. In other embodiments, in the absence of the altering, expression of the modified hepatitis virus core antigen yields 25 fold less particles than does expression of a wild type hepatitis virus core antigen. In some preferred embodiments, the at least one acidic amino acid residue comprises from 1 to 10 aspartic acid residues. In other preferred embodiments, the at least one acidic amino acid residue comprises from 1 to 10 glutamic acid residues. In related embodiments, the at least one acidic amino acid residue comprises at least one aspartic acid residue and at least one glutamic acid residue. In some embodiments, the insertion is in at least one position chosen from the N-terminus and the C-terminus of the heterologous antigen. In other embodiments, the substitution comprises a replacement of at least one non-acidic amino acid residue within the heterologous antigen, with the at least one acidic amino acid residue. In preferred embodiments, the altering produces a modified heterologous antigen with an isoelectric point in the range of 2.0 to 7.0. In a subset of these embodiments, the altering produces a modified heterologous antigen with an isoelectric point more preferably in the range of 3.0 to 6.0, and most preferably in the range of 4.0 to 5.0. In a preferred embodiment, the hepatitis virus core antigen is a ground squirrel hepatitis virus core antigen.

Additionally, the present invention provides compositions comprising a heterologous antigen linked to the amino acid sequence set forth in SEQ ID NO:58, the amino acid sequence comprising a loop region and further comprising from 1 to 100 amino acids at the carboxy end of residue $V^{149}$, and wherein the 1 to 100 amino acids does not comprise $C^{150}$ or the sequence set forth in SEQ ID NO:42 (i.e., excluding $C^{150}$, and the wild type C-terminus). In some preferred embodiments, the 1 to 100 amino acids is chosen from $R_{150}$, $K_{150}$, $A_{150}$, $R_{150}R_{151}C^{152}$, and SEQ ID NOS:3-6, 43-56. In other preferred embodiments, the 1 to 100 amino acids is chosen from SEQ ID NOS:2, 7-20. In still further preferred embodiments, the 1 to 100 amino acids is chosen from SEQ ID NOS:22-36. Additionally, in particularly preferred embodiments, the heterologous antigen linked to the amino acid sequence set forth in SEQ ID NO:58, comprises a particle having a diameter of 25 to 35 nm.

In some embodiments, the heterologous antigen is inserted at a position within the loop region. In preferred embodiments, the position within the loop region is chosen from amino acid residues 77, 78, 81, and 82. In another embodiment, the position within the loop region is at amino acid residue 76. In further embodiments, the heterologous antigen is inserted at a position outside of the loop region. In preferred embodiments, the position outside the loop region is chosen from amino acid residues 71, 72, 73, 74, 75, 83, 84, 85, 92, N-terminal and C-terminal. In another embodiment, the position outside the loop region is at amino acid residue 44. In still further embodiments, the heterologous antigen is inserted at a position within the loop region, and in a position outside the loop region. The present invention also provides composition in which the heterologous antigen is conjugated to the amino acid sequence. In preferred embodiments, the heterologous antigen comprises at least one B cell epitope. In further preferred embodiments, the heterologous antigen comprises at least one T helper cell epitope. In exemplary embodiments, the heterologous antigen is chosen from but not limited to human immunodeficiency virus antigen, feline immunodeficiency virus antigen, *Plasmodium* parasite antigen, influenza virus antigen, *Staphylococcus* bacterium antigen, cholesteryl ester transfer protein antigen, major histocompatibility complex antigen, cytokine antigen, amyloid β-peptide antigen, peanut allergen antigen, latex allergen hevein antigen, brown shrimp allergen antigen and major grass pollen allergen antigen.

In some embodiments, the amino acid sequence further comprises at least one immune enhancer sequence. The immune enhancer sequence is operably linked to the C-terminus of the amino acid sequence in some embodiments. In exemplary embodiments, the immune enhancer sequence is chosen from but not limited to unmethylated CpG dinucleotides, CD40 ligand, complement C3d fragment, B cell activating factor, and soluble gene product of lymphocyte activation gene-3 and universal human CD4+ T cell epitopes to which the human population has been frequently exposed (i.e., tetanus toxoid epitopes). Also provided are embodiments further comprising human hepatitis B virus core antigen chosen from wild type human hepatitis B virus core antigen and modified human hepatitis B virus core antigen lacking a heterologous antigen. In some embodiments, the composition further comprises one or more compounds chosen from adjuvant, diluent and carrier. In related embodiments, the adjuvant is chosen from but not limited to aluminum hydroxide, aluminum phosphate, squalene and mineral oil. Moreover, the present invention provides a nucleic acid sequence encoding a heterologous antigen linked to the amino acid sequence set forth in SEQ ID NO:58. Related embodiments provide an expression vector comprising a nucleic acid sequence encoding a heterologous antigen linked to the amino acid sequence set forth in SEQ ID NO:58.

Additionally, the present invention provides compositions comprising a heterologous antigen linked to an amino acid sequence which is at least 95% identical to the sequence set forth in SEQ ID NO:58, the amino acid sequence comprising a loop region and forming a particle having a diameter of 25 to 35 nm. In some embodiments, the heterologous antigen comprises at least one modification chosen from insertion of at least one acidic amino acid residue, and substitution of at least one acidic amino acid residue. In some preferred embodiments, the at least one acidic amino acid residue comprises from 1 to 10 residues of one or both of aspartic acid and glutamic acid. In other preferred embodiments, the amino acid sequence comprises at least one modification chosen from insertion of at least one acidic amino acid residue, and substitution of at least one acidic amino acid residue. In some preferred embodiments, the at least one acidic amino acid residue comprises from 1 to 10 residues of one or both of aspartic acid and glutamic acid.

Also provided by the present invention are compositions comprising the amino acid sequence set forth in SEQ ID NO:58, the amino acid sequence comprising a loop region and further comprising from 1 to 100 amino acids at the carboxy end of residue $V^{149}$. In some preferred embodiments, the 1 to 100 amino acids is chosen from $R^{150}$, $K^{150}$, $A^{150}$, $R^{150}R^{151}C^{152}$, and SEQ ID NOS:3-6, 43-56 (excluding $C^{150}$, and the wild type C-terminus set forth in SEQ ID NO:42). In other preferred embodiments, the 1 to 100 amino acids is chosen from SEQ ID NOS:2, 7-20. In still further preferred embodiments, the 1 to 100 amino acids is chosen from SEQ ID NOS:22-36. Additionally, in particularly preferred embodiments, the heterologous antigen linked to the amino acid sequence set forth in SEQ ID NO:58, comprises a particle having a diameter of 25 to 35 nm.

Additionally, in some embodiments, the amino acid sequence further comprises at least one immune enhancer sequence. In preferred embodiments, the immune enhancer sequence is operably linked to the C-terminus of the amino acid sequence. In exemplary embodiments, the immune enhancer sequence is chosen from but not limited to unmethylated CpG dinucleotides, CD40 ligand, complement C3d fragment, B cell activating factor, and soluble gene product of lymphocyte activation gene-3 and universal human CD4+ T cell epitopes to which the human population has been frequently exposed (i.e., tetanus toxoid epitopes). Also provided is a nucleic acid sequence encoding the amino acid sequence set forth in SEQ ID NO: 58, the amino acid sequence comprising a loop region. Related embodiments provide an expression vector comprising the nucleic acid sequence encoding the amino acid sequence set forth in SEQ ID NO:58. Additionally, compositions further comprising a modified human hepatitis B virus core antigen comprising a heterologous antigen are provided. In some particularly preferred embodiments, compositions are provided comprising an amino acid sequence which is at least 95% identical to SEQ ID NO:58, the amino acid sequence comprising a loop region and forming a particle having a diameter of 25 to 35 nm.

Importantly, the present invention provides methods, comprising: providing: an animal (e.g., mammalian subject); and a composition comprising one or more of a polypeptide comprising a heterologous antigen linked to the amino acid sequence set forth in SEQ ID NO:58, the amino acid sequence comprising a loop region, and an expression vector encoding the polypeptide; and administering the composition to the animal under conditions such that an immune response is generated. In some embodiments, the immune response comprises one or more of lymphocyte proliferative response, cytokine response and antibody response. In some preferred embodiments, the cytokine response comprises IL-2 production. In further embodiments, the antibody response comprises at least three fold higher levels of antibody than that observed before administration of the at least one composition. In particularly preferred embodiments, the antibody response comprises production of IgG antibodies. In related embodiments, the IgG antibodies comprise an autoantibody. In some preferred embodiments, the composition further comprises one or more compounds chosen from adjuvant, diluent and carrier. In related embodiments, the adjuvant is chosen from but not limited to aluminum hydroxide, aluminum phosphate, squalene and mineral oil.

Also provided by the present invention are methods for producing an immunogenic composition, comprising: providing: a heterologous antigen; and a hepatitis virus core antigen; altering at least one of the heterologous antigen and the hepatitis virus core antigen, with a modification chosen from insertion of at least one acidic amino acid residue and substitution of at least one acidic amino acid residue; and inserting the heterologous antigen of step b within the hepatitis virus core antigen of step b to produce a modified hepatitis virus core antigen; expressing the modified hepatitis virus core antigen under conditions suitable for producing particles having a diameter of 25 to 35 nm. In some embodiments, in the absence of the altering, expression of the modified hepatitis virus core antigen yields aggregates rather than particles. In other embodiments, in the absence of the altering, expression of the modified hepatitis virus core antigen yields 25 fold less particles than does expression of a wild type hepatitis virus core antigen. In some preferred embodiments, the at least one acidic amino acid residue comprises from 1 to 10 aspartic acid residues. In other preferred embodiments, the at least one acidic amino acid residue comprises from 1 to 10 glutamic acid residues. In related embodiments, the at least one acidic amino acid residue comprises at least one aspartic acid residue and at least one glutamic acid residue. In some embodiments, the insertion is in at least one position chosen from the N-terminus and the C-terminus of the heterologous antigen. In other embodiments, the substitution comprises a replacement of at least one non-acidic amino acid residue within the heterologous antigen, with the at least one acidic amino acid residue. In preferred embodiments, the altering produces a modified heterologous antigen with an isoelectric point in the range of 2.0 to 7.0. In a subset of these embodiments, the altering produces a modified heterologous antigen with an isoelectric point more preferably in the range of 3.0 to 6.0, and most preferably in the range of 4.0 to 5.0. In a particularly preferred embodiment, the hepatitis virus core antigen is a human hepatitis B virus core antigen.

DESCRIPTION OF THE FIGURES

FIG. 1 depicts the structure of the HBc particle determined at 7.4 angstrom resolution from cryoelectron micrographs. The immunodominant loop from amino acid residues 76 to 82 is shown.

FIG. 2 provides a graph showing the comparative immunogenicity of HBcAg-based (HBc-M) and WHcAg-based (WHc-M) $(NANP)_n$ vaccines. Groups of three mice were immunized with a single dose of 20 μg of the indicated particles in IFA and sera were collected at the indicated time points for determination of anti-NANP titer by ELISA.

FIG. 3 illustrates that the WHcAg accommodates insertion of foreign epitopes at many positions, with insertion sites indicated as numbered symbols. Tolerant (+) insertions sites are shown with an oval, intermediate (+/−) insertion sites are shown with a triangle, and non-tolerant (−) insertion sites are shown with a square.

FIG. 4 provides an image of a 1% agarose gel indicating that wild type HBcAg and WHcAg particles migrate differently under non-denaturing conditions.

FIG. 5 graphically depicts the magnitude of the antibody response elicited by immunizing mice of the indicated H-2 congenic strains with 7.0 μg of either WHcAg or HBcAg or GSHcAg in IFA. Six weeks post immunization (1°, 6 wk), sera were collected and analyzed for anti-WHc (solid) or anti-HBc (hatched) or anti-GSHc (dots) antibody by ELISA. End-point serum titers are shown.

FIG. 6 illustrates that there is a low level of cross-reactivity between the WHcAg/GSHcAg and the HBcAg and a high level of cross-reactivity between the WHcAg and the GSHcAg at the antibody level. The indicated panel of H-2 congenic strains was immunized with 7.0 μg of either WHcAg (solid) or HBcAg (hatched) or GSHcAg (dots) in IFA. Six weeks later sera were collected and tested for binding to WHcAg, GSHcAg and HBcAg. End-point serum titers are shown.

FIG. 7 illustrates that there is a low level of cross-reactivity between the WHcAg and the HBcAg at the T cell level. Balb/c mice were immunized with WHcAg (5.0 μg) in complete Freund's adjuvant. Ten days later draining lymph node (LN) cells were harvested and cultured with varying concentrations of WHcAg and HBcAg in vitro. T cell proliferation was measured by [3H]TdR uptake and corrected for background.

FIG. 8 shows the proliferative response of cells from mice of the indicated strains and H-2 haplotypes after immunization with WHcAg (5.0 μg) in CFA. Ten days later draining LN cells were cultured with WHcAg, HBcAg and the indicated peptides in vitro, and T cell proliferation was measured by $[^3H]$TdR uptake. Panel A shows the proliferative response of B10.S mice to WHc, HBc and the Wp120-131 (VSFGVWIRTPAP, set forth as SEQ ID NO:59; while the corresponding HBV sequence is VSFGVWIRTPPA, set forth as SEQ ID NO:60). Panel B shows the proliferative response of cells of B10.D2 mice to WHc, HBc, and the Wp60-80 peptide (VCWDELTKLIAWMSSNITSEQ, set forth as SEQ ID NO:61; while the corresponding HBV sequence is LCWGELMTLATWVGGNLEDPI, set forth as SEQ ID NO:62). Panel C shows the proliferative response of cells from B10.M mice to WHc, HBc, and the Wp60-80 peptide. The peptide T cell site recognized after HBcAg immunization of B10.S mice is Hp120-131, of B10.D2 mice is Hp85-100, and of B10.M mice is Hp100-120.

FIG. 9 provides the results of a CD4+ T cell epitope mapping analysis in the indicated strains of mice. Briefly, mice were immunized (7.0 μg) and boosted (3.5 μg) with either WHcAg or HBcAg in IFA, and ten days later spleen cells were cultured with WHcAg, HBcAg and a panel of WHcAg-derived or HBcAg-derived peptides in vitro. After 4 days, tissue culture supernatants (SN) were collected and IFNγ (1 μg/ml) was measured by ELISA. The relative strengths of the peptide T cell sites are indicated by the minimum peptide concentrations required to recall IFNγ production in vitro.

FIG. 10 provides the results of a CD4+ T cell epitope mapping analysis in the indicated strains of mice. Briefly, mice were immunized (7.0 μg) and boosted (3.5 μg) with either WHcAg or HBcAg in IFA, and ten days later spleen cells were cultured with WHcAg, HBcAg and a panel of WHcAg-derived or HBcAg-derived peptides in vitro. After 4 days, tissue culture supernatants (SN) were collected and IFNγ (μg/ml) was measured by ELISA. The relative strengths of the peptide T cell sites are indicated by the minimum peptide concentrations required to recall IFNγ production in vitro.

FIG. 11 illustrates that anti-WHc antibodies do not interfere with the commercial anti-HBc diagnostic assay. The commercial anti-HBc assay was performed as recommended by the supplier with the exception that 1:10 dilutions of murine sera were used.

FIG. 12, panels A-E, illustrate that WHc is an effective immunogen in both wild type and transgenic mice. Wild type (+/+) and HBeAg-expressing transgenic (HBe-Tg) mice were immunized with 20 μg of either HBcAg, an HBc-based malaria vaccine candidate (HBc-M, V12.PF3.1) or WHc-based malaria vaccine candidate (WHc-M, HyW-M78) in IFA. Sera were collected at 2, 4 and 8 weeks after immunization and analyzed for anti-core antibody (left panels A, B, and C) and anti-NANP antibody (right panels D and E) by ELISA.

FIG. 13, panels A-F, depict the recall IFNγ-response of wild type and HBe-Tg mice after immunizing with 10 μg of HBcAg (panels A and D), HBc-M (panels B and E) or WHc-M (panels C and F) as determined by ELISA of four day culture SNs. Two weeks later spleen cells were collected and cultured with HBc, WHc and p120-140 peptide, conserved between WHc and HBc (W/H), or the WHc-derived peptides p60-80 (W) and p80-95 (W), which are not conserved.

FIGS. 14 and 15 show the immunogenicity of hybrid core particles. The indicated hybrid particles were injected (20 μg, 1°) and boosted (10 μg, 2°) in IFA. Eight weeks after the primary and 6 weeks after the secondary immunization, sera were collected, pooled, and anti-insert and anti-core antibody titers were determined by ELISA. The hybrid particles are designated by the C-terminus, the inserted epitope (e.g., M=malaria *P. falciparum*) and the position of the insert (e.g., 74). Full descriptions of the C-termini and the inserted epitopes are listed in the accompanying tables.

FIG. 16 shows the effect of the position of the inserted epitope $(NANP)_n$ on the immunogenicity of the WHcAg hybrid particle. Groups of 4 mice were primed with 20 μg of the indicated particles in IFA. Sera were collected, pooled, and analyzed for anti-NANP by ELISA. The hybrid particles are identical except for the position of the insert: $NH_2$-terminus, COOH-terminus, or internal (e.g., amino acid 78 or 74).

FIG. 17 illustrates the effect on immunogenicity of varying the C-termini of hybrid WHcAg particles with the same (M)

heterologous sequence inserted at amino acid 74. In this study, mice were immunized with a single dose of 20 µg of the hybrid particles in IFA.

FIG. 18 graphically depicts the lack of genetic nonresponders and the magnitude of the antibody response elicited by immunizing mice of the indicated H-2 congenic strains with 10 µg of the WHc-based malaria vaccine candidate (HyW-M78) in IFA and boosting with 5.0 µg of HyW-M78 in IFA. Six weeks after the primary (1°) and the secondary (2°) immunizations, sera were collected and anti-WHc and anti-NANP antibodies were determined by ELISA.

FIG. 19 provides the results of a CD4+ T cell epitope mapping analysis in the indicated strains of mice. Briefly, mice of the indicated strains and H-2 haplotypes were immunized and boosted either with WHcAg (7.0 µg) or a WHc-based malaria vaccine candidate (HyW-M78) (10 µg) both in IFA. Two weeks after the boost spleen cells were harvested and cultured with a panel of WHcAg-derived peptides in vitro. Four day culture SNs were collected and IFNγ was measured by ELISA. The minimum concentration of peptide required to recall IFNγ production is indicated by the shaded boxes representing weak (light) to very strong (dark) T cell sites.

FIG. 20 provides a schematic representation of the steps involved in construction of the modified WHcAg vaccine platform.

FIG. 21 depicts the results of capture ELISAs designed to detect either WHcAg polypeptide as a marker for expression or WHcAg particles as a marker for assembly in *E. Coli* lysates. In panel A, a polyclonal antibody that recognizes assembled particles (anti-nWHc) is used to determine relative assembly competence, while in panel B, a mAb specific for a peptidic epitope on WHcAg (anti-pWHc) is used as the detecting antibody to determine relative expression levels. In addition, a malaria (M) epitope-specific mAb was used to detect the malaria repeat epitope (dashed line). The capture antibody does not compete with either detecting antibody.

FIG. 22 provides a list of WHcAg-EM2 or WHcAg-IM2 mutant(−) hybrid constructs expressed in *E. Coli* and analyzed for relative expression level and assembly competence by capture ELISA. Lysates were sequentially screened with mAbs that preferentially recognize denatured WHcAg or assembled WHcAg particles and given relative scores accordingly.

FIG. 23 shows an analysis of a M2e peptide analog panel for binding to mAb 14C2 and to a polyclonal murine anti-HyW-IM2(−)78 antisera. The wild type M2e sequence is set forth herein as SEQ ID NO:64.

FIG. 24 illustrates that particulate HBcAg is preferentially presented by naive B cells to naive T cells. Either splenic adherent cells including macrophage and dendritic cells (MØ/DC) or B cells from naive mice were fractionated and used as APC for fractionated CD4+ T cells derived from naive TCR-Tg (core-specific) mice. Purified APC plus CD4+ T cells were cultured in the presence of HBcAg or peptide for 48 hrs before the level of IL-2 in the SN was determined by ELISA.

FIG. 25 illustrates that particulate WHcAg and hybrid WHcAg particles are preferentially presented by naive B cells to naive T cells. Either naive spleen cells from wild type mice or from B cell knockout (KO) mice were used as APCs for CD4+ T cells derived from core-specific TCR-Tg mice. Purified APC plus CD4+ T cells were cultured in the presence of the indicated antigen for 48 hrs before the level of IL-2 in the SN was determined by ELISA.

Figure 28:
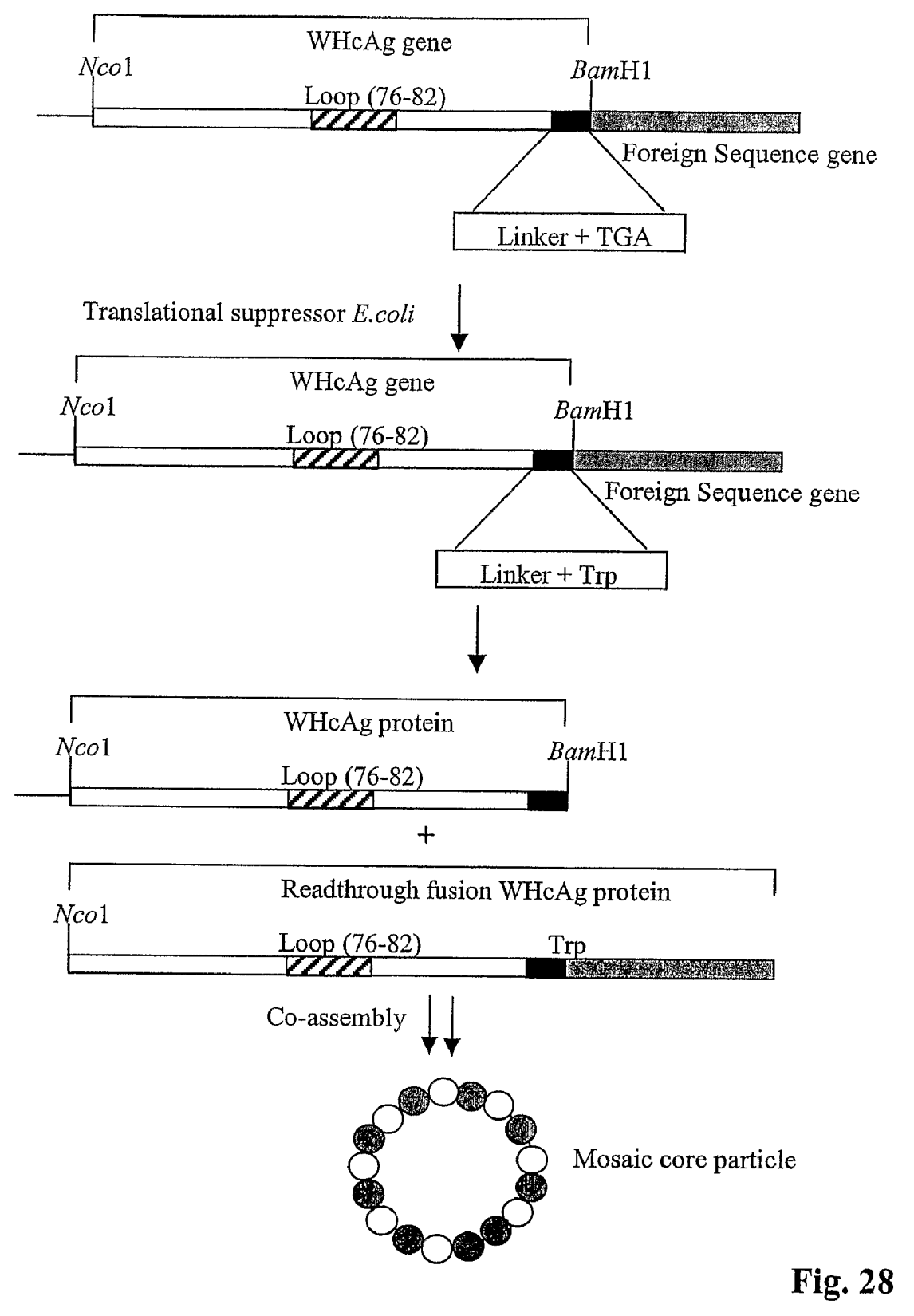

FIG. 28 provides a schematic representation of one of the methods of the present invention used to obtain mosaic WHcAg particles by the read-through mechanism.

Figure 29:
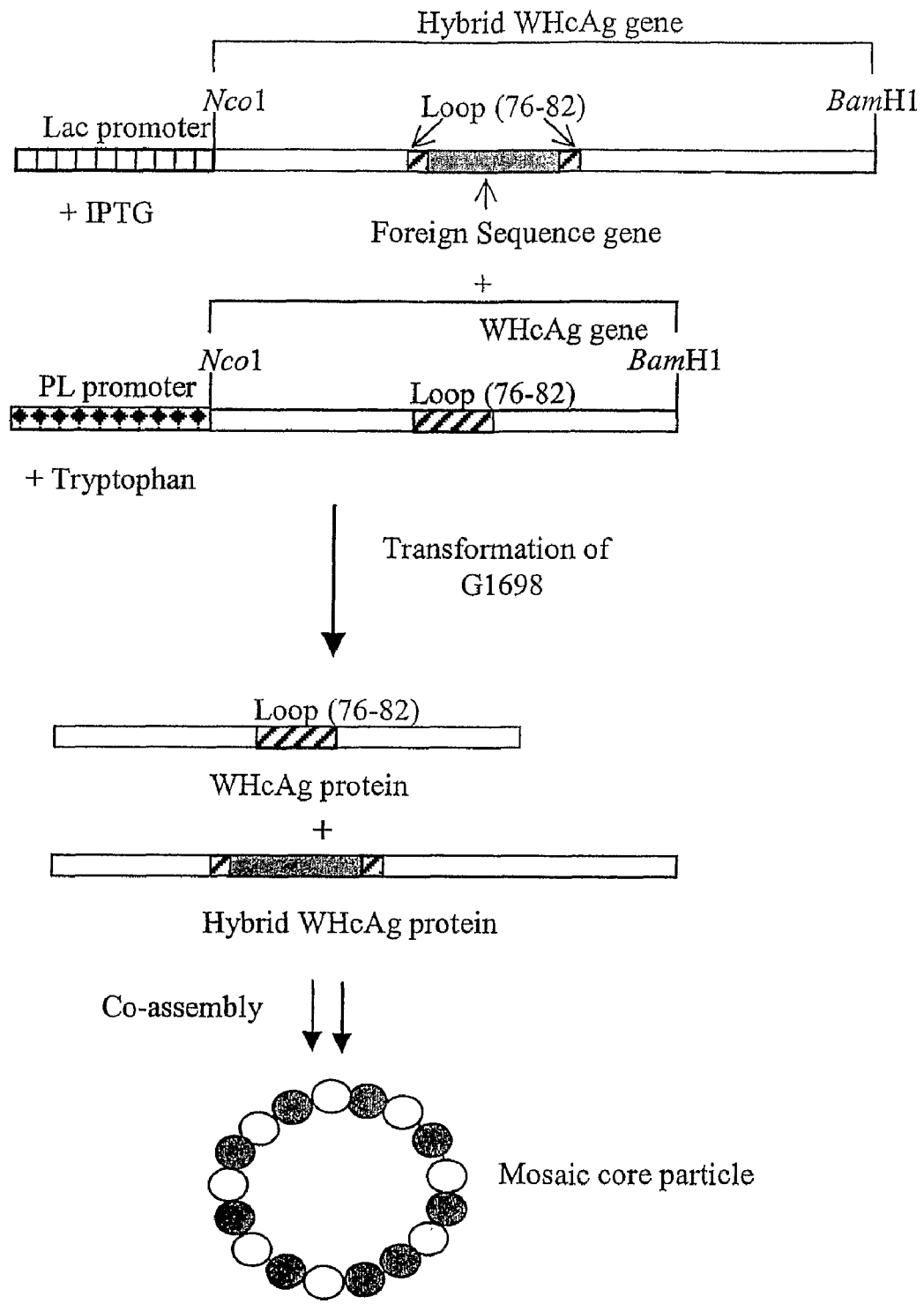

FIG. 29 provides a schematic representation of one of the methods of the present invention used to obtain mosaic WHcAg particles by utilization of differentially induced plasmids.

FIG. 30 shows the effect adjuvant usage on the level of insert-specific antibody production. Groups of mice were immunized with C-longM78 hybrid WHcAg particles in saline (10; primary and 2°, secondary) or formulated in the indicated adjuvants. Sera were collected at 6 weeks post immunization; pooled and analyzed for anti-NANP antibody by ELISA, as shown in Panel A. Panel B depicts the IgG isotype distribution pattern of anti-NANP antibodies elicited by C-longM78 particles administered in saline or the indicated adjuvants.

Figure 31:
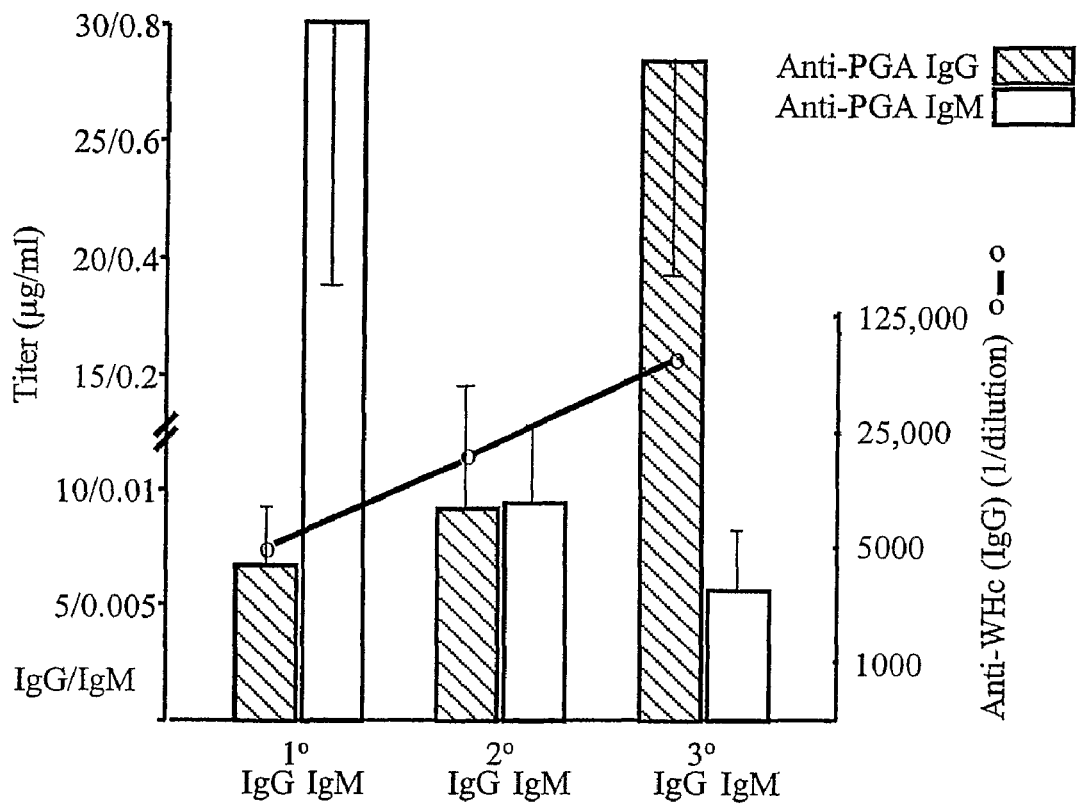

FIG. 31 shows that antibodies are raised to a protein which is chemically-coupled to WHcAg. Balb/c mice were immunized three times with a WHcAg-PGA chemical conjugate (10 µg) adsorbed on alum. Two weeks after each immunization sera were collected and IgM and IgG anti-PGA antibodies and anti-WHc antibody was determined by ELISA.

Figure 32:
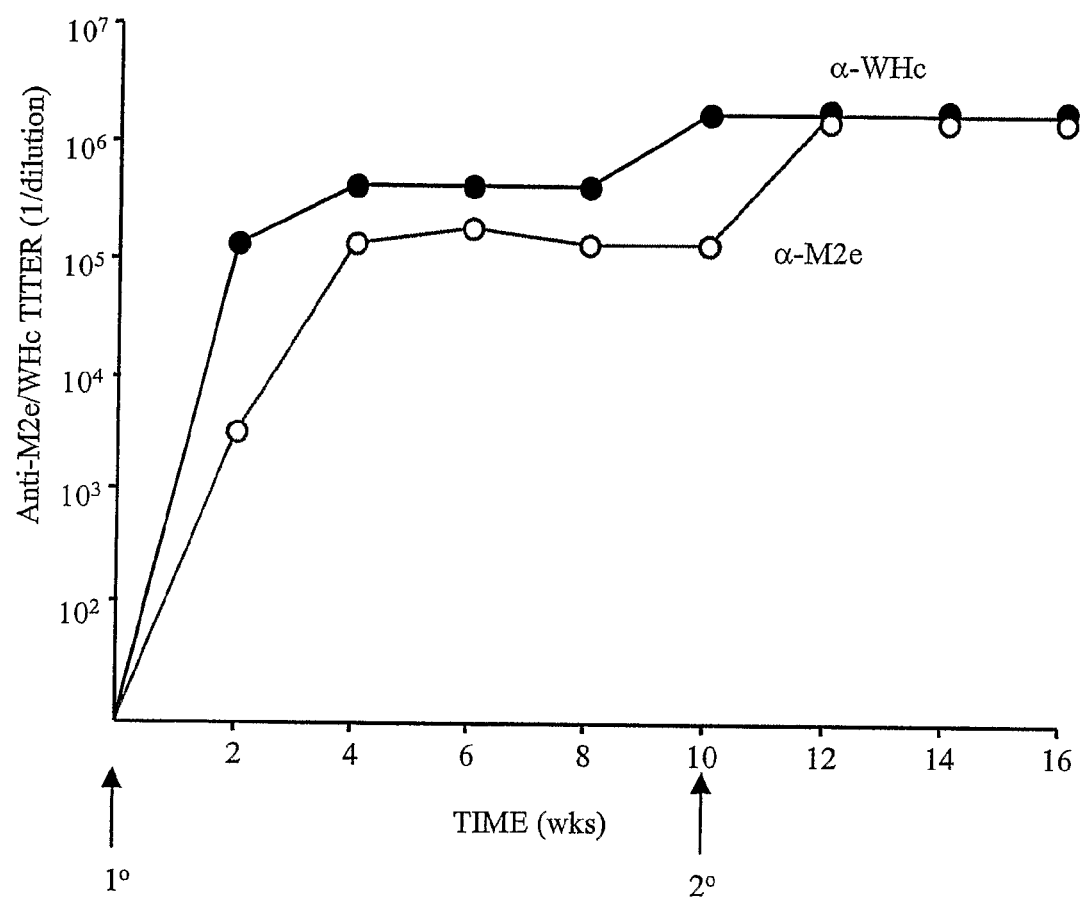

FIG. 32 depicts the antibody response over the course of four months after immunization of mice with an Influenza A M2e-WHcAg hybrid particle (HyW-IM2(−)78). Five mice were immunized with 20 µg (1°) and boosted with 10 µg (2°) of M2e-WHcAg hybrid particles in IFA, and sera was collected, pooled and analyzed for anti-WHc and anti-M2e antibodies by ELISA.

Figure 33:
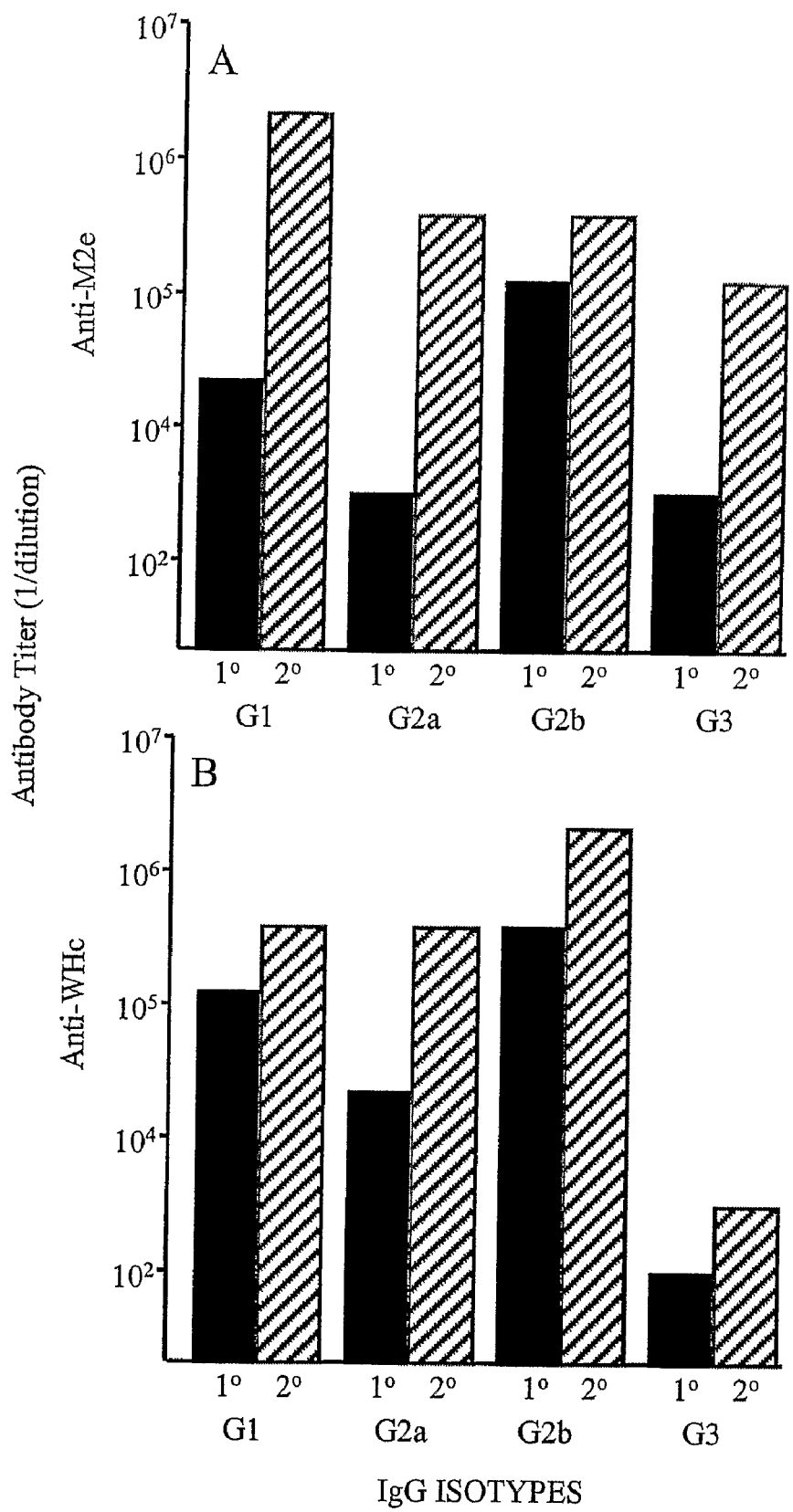

FIG. 33 shows the IgG isotype distribution of primary (10) and secondary (20) sera reactive with M2e (panel A) and WHc (panel B) of mice immunized with M2e-WHcAg hybrid particles as described in FIG. 33.

Figure 34:
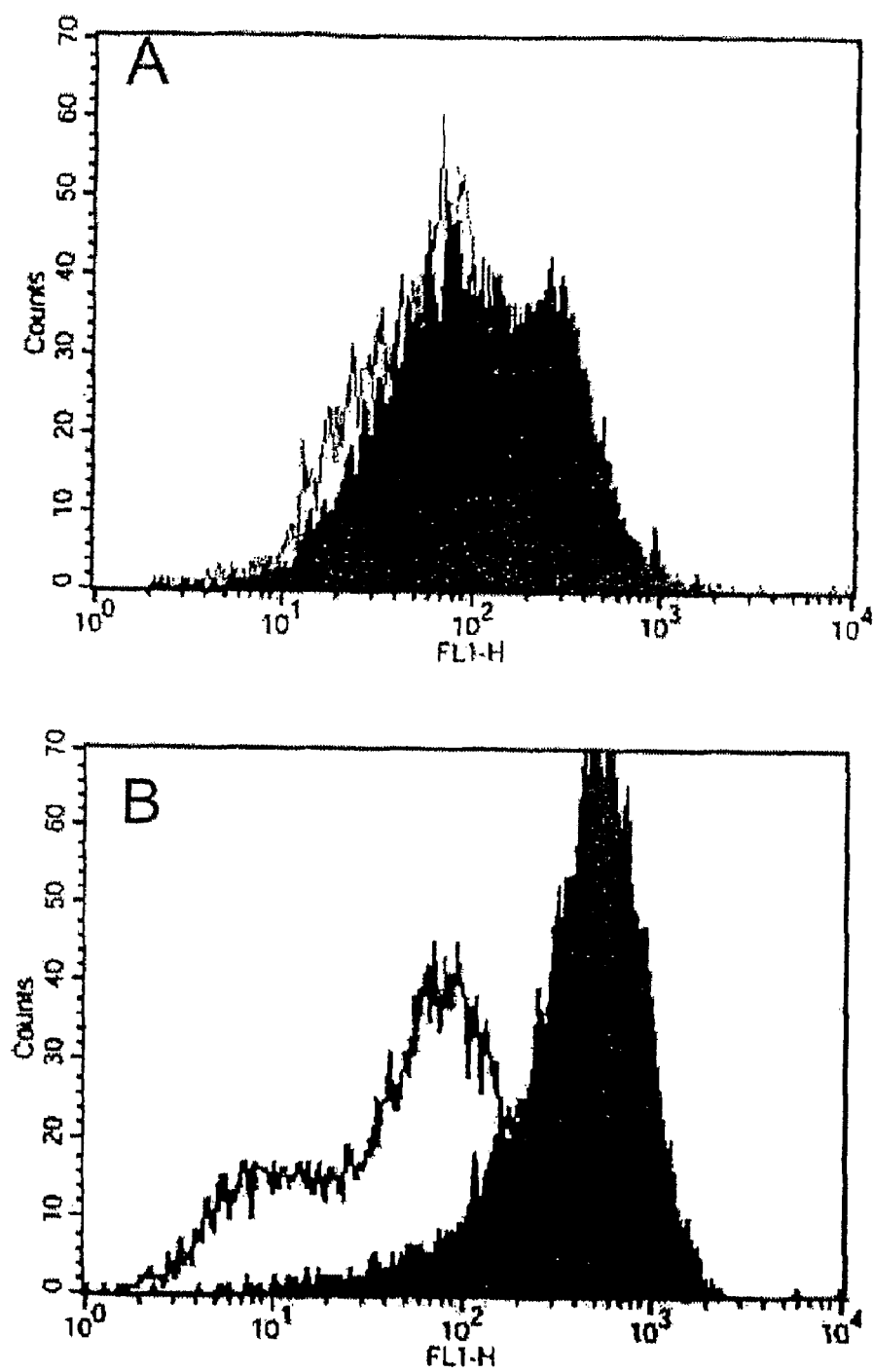

FIG. 34 illustrates that sera from mice immunized with WHcAg-M2e reacts with influenza A virus infected cells. Sera from WHcAg immunized (panel A) or WHcAg-M2e (panel B) immunized mice were incubated with mock (open histograms) or influenza A-infected (filled histograms) 293T cells. After incubation with a goat anti-mouse IgG conjugated to FITC, the cells were analyzed by flow cytometry.

Figure 35:
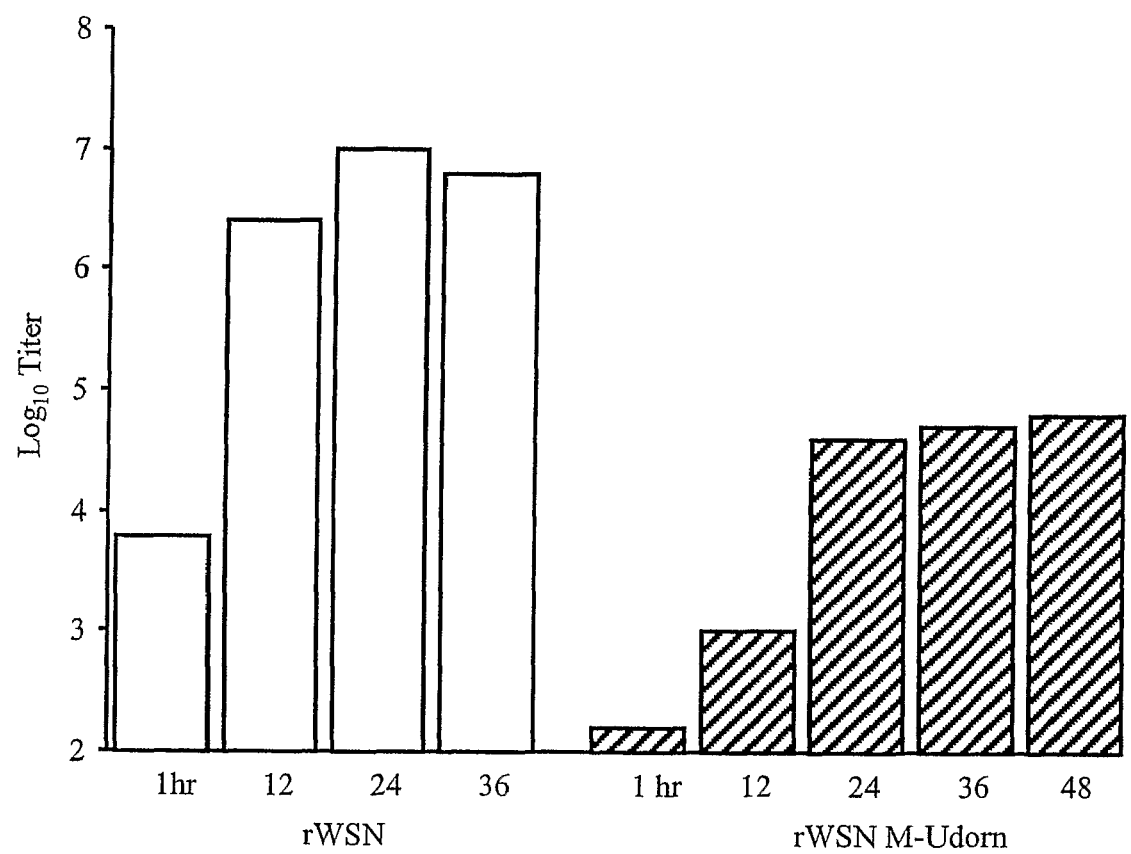

FIG. 35 depicts the inhibition of rWSN M-Udorn replication by sera from WHcAg-M2e immunized mice. MDCK cells were infected at an MOI of 0.1 for 1 hour, with either rWSN (anti-M2e insensitive) (open bars) or the anti-M2e sensitive, rWSN M-Udorn (hatched bars) strain. Cells were washed extensively then incubated in DMEM containing trypsin and 1% sera from WHcAg-M2e immunized mice. At the indicated times post infection supernatants were collected and infectious virus particle concentration determined by plaque assay.

Figure 36:
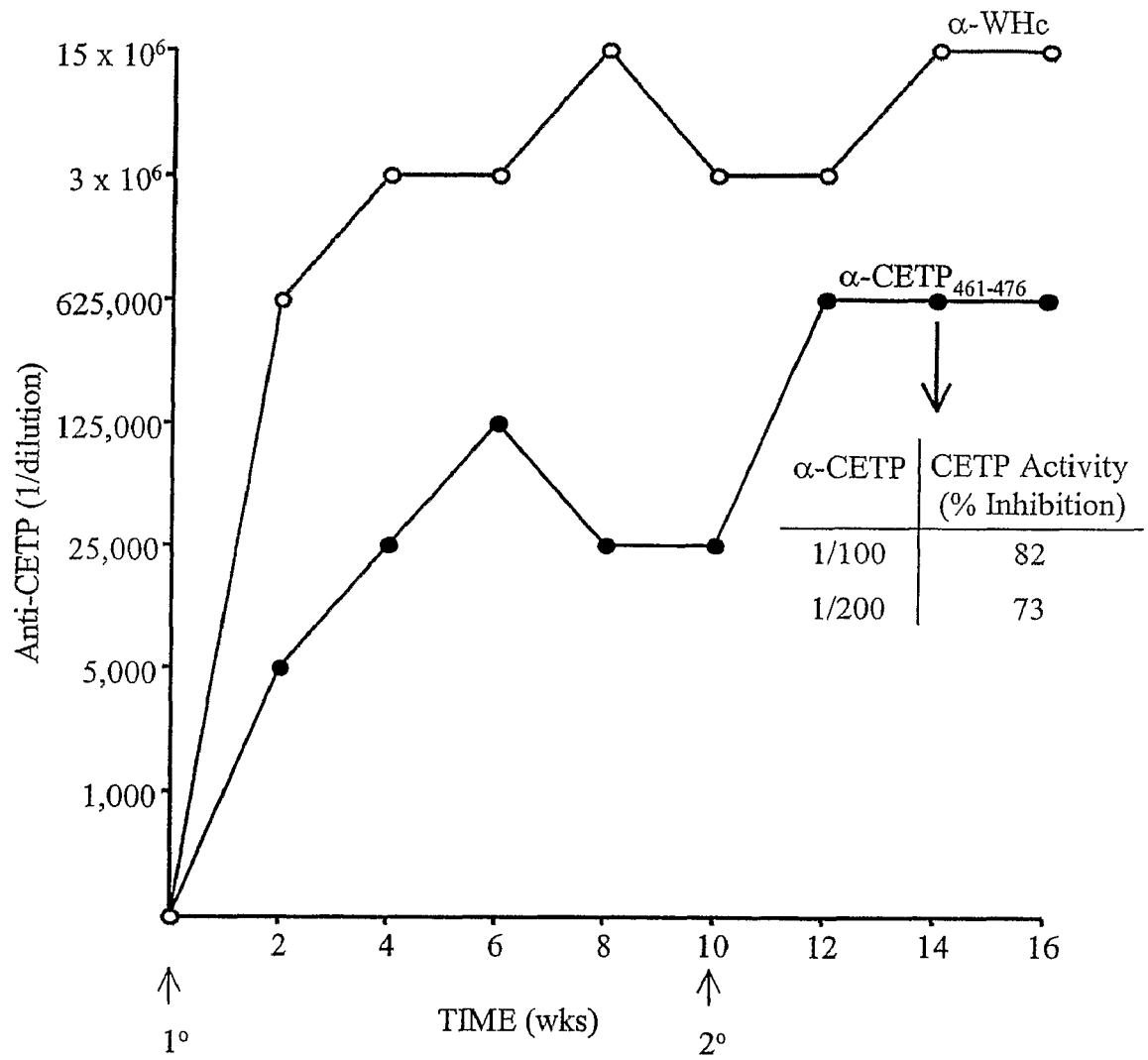

FIG. 36 depicts the antibody response obtained upon immunization (20 µg) and boosting (10 µg) (B10×B10.S)$_{F1}$ mice with hybrid WHcAg particles containing a CETP$_{461-476}$ insert (HyW-CE$_{74}$) in IFA. Sera was collected at the indicated times and anti-WHc and anti-CETP$_{461-476}$ was determined by ELISA. The 14 week sera was tested for the ability to inhibit human CETP enzymatic activity in vitro (inset). The human CETP was obtained from hCETP-Tg mouse sera.

Figure 37:
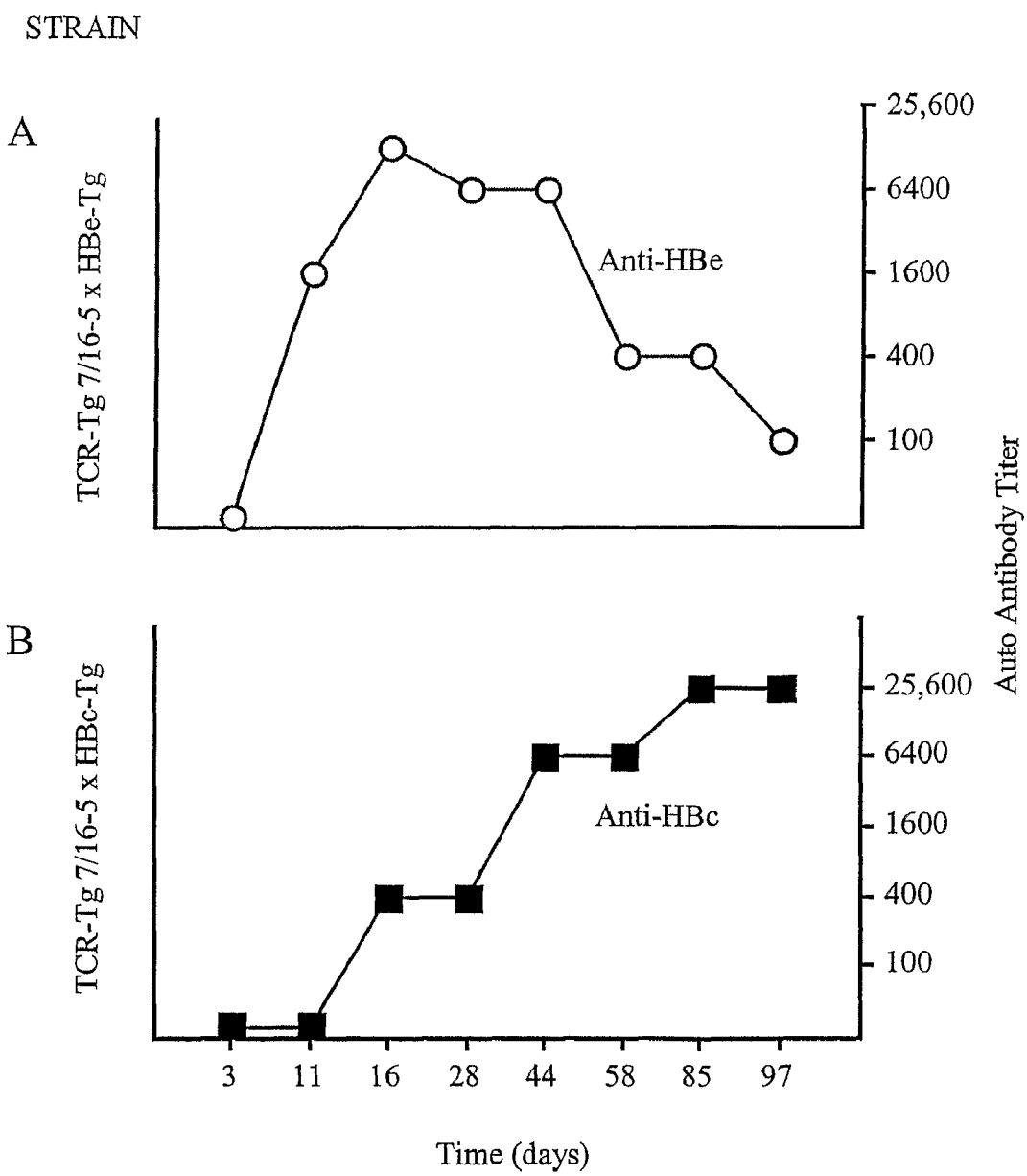

FIG. 37 illustrates the in vivo persistence of induced autoantibody. Double-Tg mice expressing an HBc/HBe-specific TCR (7/16-5) and either HBeAg or HBcAg were injected with the TCR target peptide (aa 129-140) at day O, Sera were collected at the indicated times and anti-HBe (panel A) and anti-HBc autoantibody (panel B) was determined by ELISA.

Figure 38:
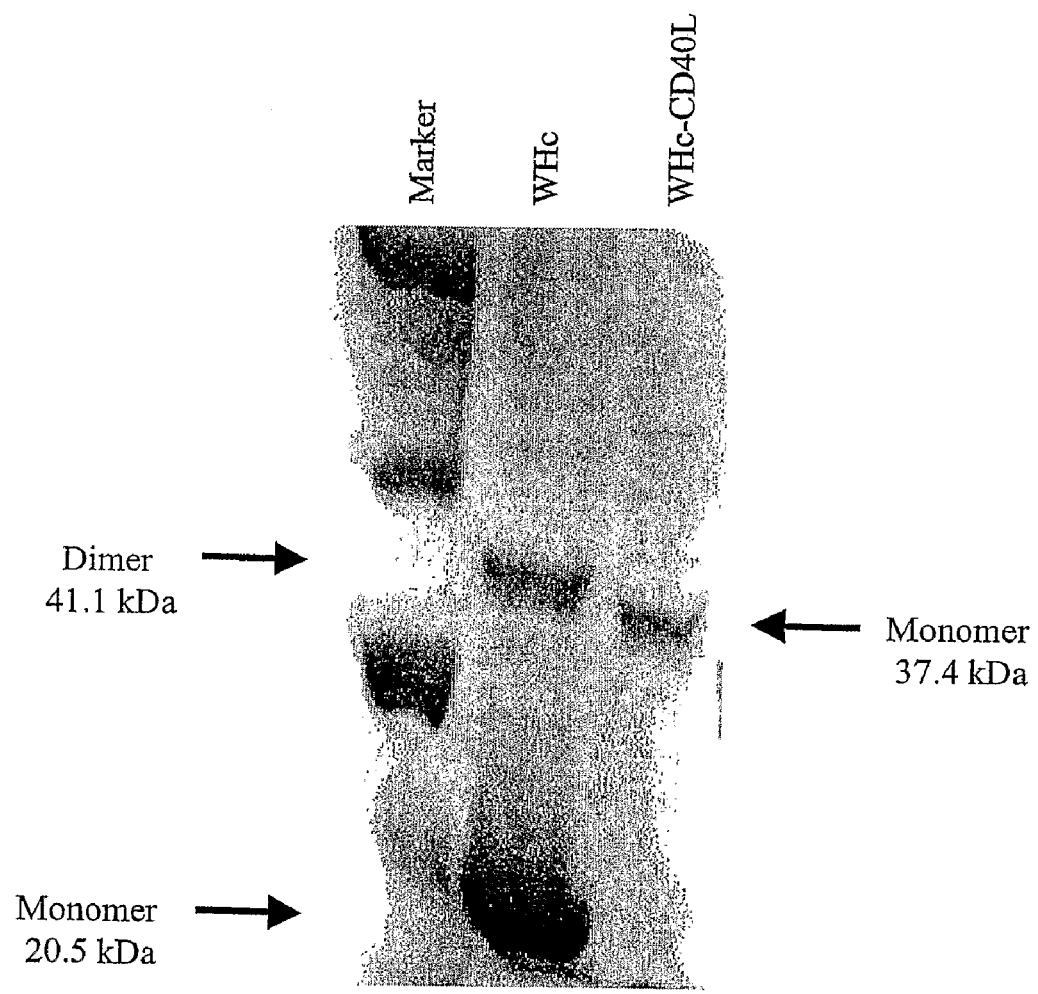

FIG. 38 depicts the migration patterns of WHcAg and WHcAg-CD40L particles in a polyacrylamide gel following denaturing and reducing conditions (SDS plus beta-mercaptoethanol). The amino acid sequence of the WHcAg-CD40L is set forth herein as SEQ ID NO:69. The predicted molecular weights of the two core proteins are shown: WHc travels as a 20.5 kDa monomer and a 41.1 kDa dimer; and WHc-CD40L travels as a 37.4 kDa monomer.

Figure 39:
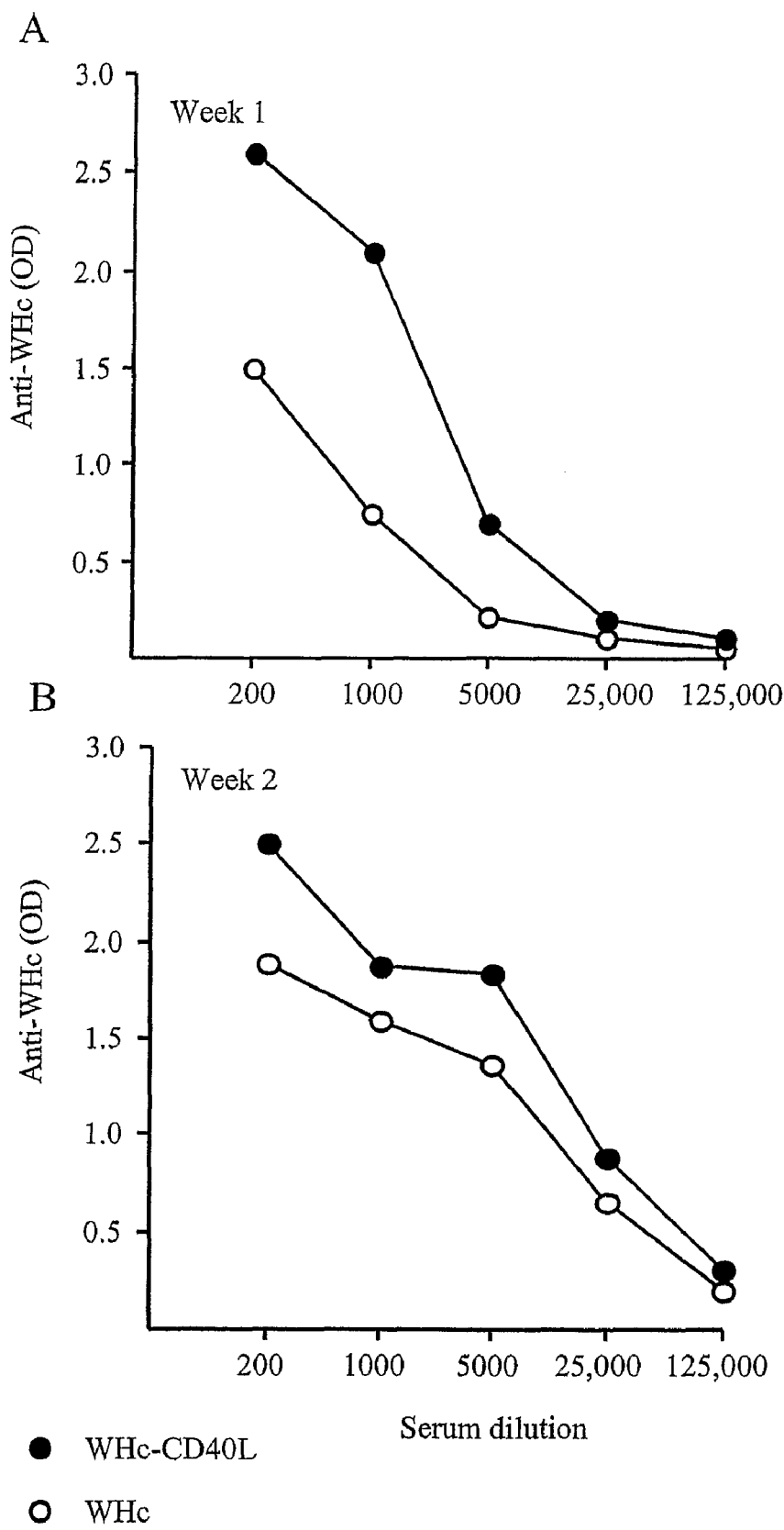

FIG. 39 illustrates that the addition of the molecular adjuvant CD40L enhances the immunogenicity of WHcAg. Mice were immunized with 20 μg of WHcAg particles or WHcAg-CD40L hybrid particles in IFA. At one week (Panel A) and two weeks (Panel B) post-immunization, sera were collected and analyzed for anti-WHc antibody by ELISA.

FIG. 40 provides the wild type WHcAg nucleic acid sequence (Panel A), and the amino acid sequences of both wild type WHcAg (Panel B) and truncated WHcAg (Panel C), as set forth in SEQ ID NO:37, SEQ ID NO:1, and SEQ ID NO:38 respectively.

FIG. 41 provides the wild type GSHcAg nucleic acid sequence (Panel A), and the amino acid sequences of both wild type GSHcAg (Panel B) and truncated GSHcAg (Panel C), as set forth in SEQ ID NO:39, SEQ ID NO:21, and SEQ ID NO:40 respectively.

FIG. 42 provides the wild type HBcAg nucleic acid sequence (Panel A), and the amino acid sequences of both wild type HBcAg (Panel B) and truncated HBcAg (Panel C), as set forth in SEQ ID NO:57, SEQ ID NO:41, and SEQ ID NO:58 respectively.

Figure 43:
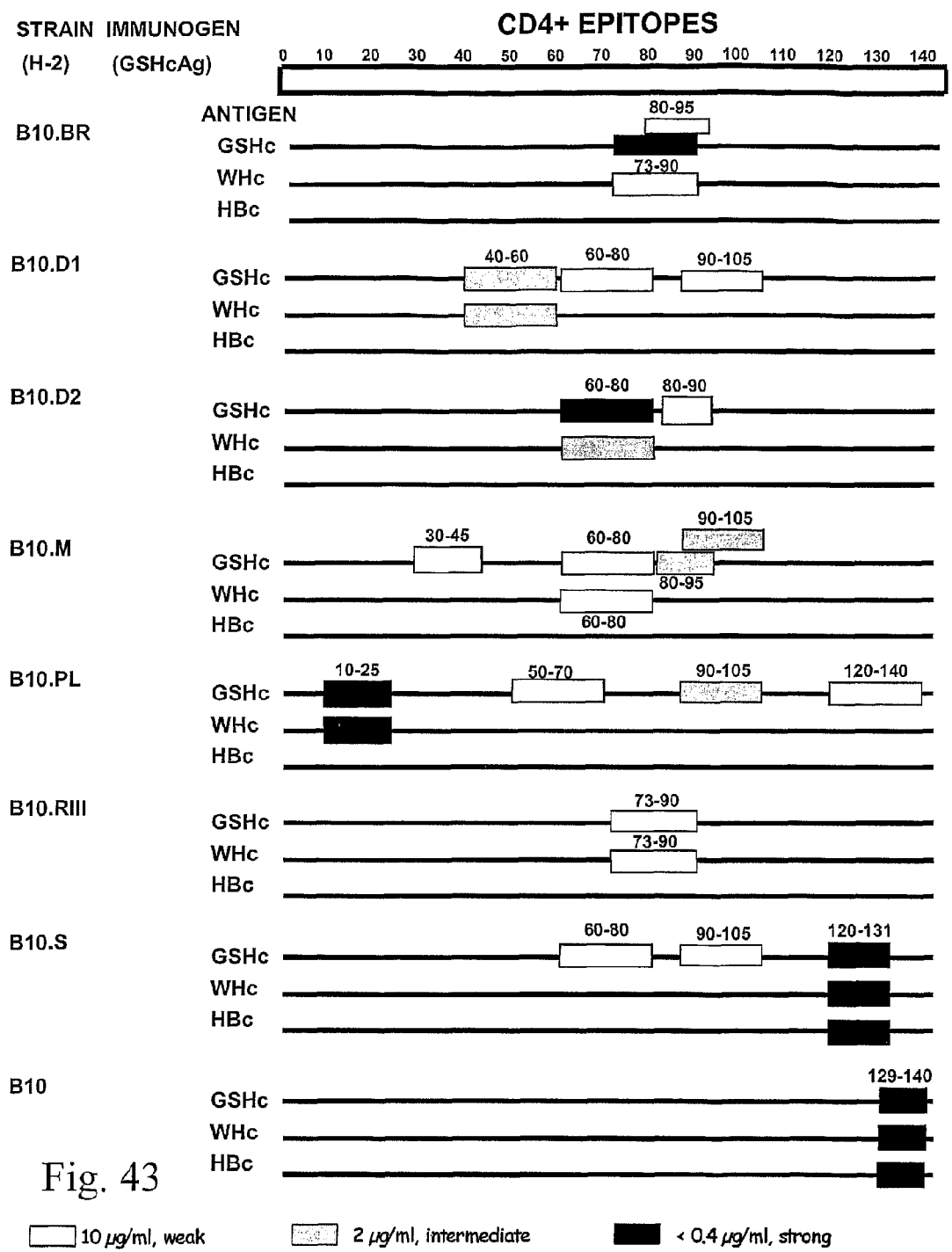

FIG. 43 depicts the results of a CD4$^+$ T cell epitope mapping analysis of GSHcAg-primed mice of the eight indicated strains of H-2 congenic mice. Briefly, mice were immunized with GSHcAg (10 μg in IFA) and 4 weeks later spleen cells were cultured with panels of GSHcAg-derived, WHcAg-derived or HBcAg-derived peptides in vitro. After 2 or 4 days, culture supernatants (SN) were collected and IL-2 or IFNγ, respectively, were measured by ELISA. The relative strengths of the peptide T cell sites depicted are indicated by the minimum peptide concentrations required to recall either IL-2 or IFNγ production in vitro.

Figure 44:
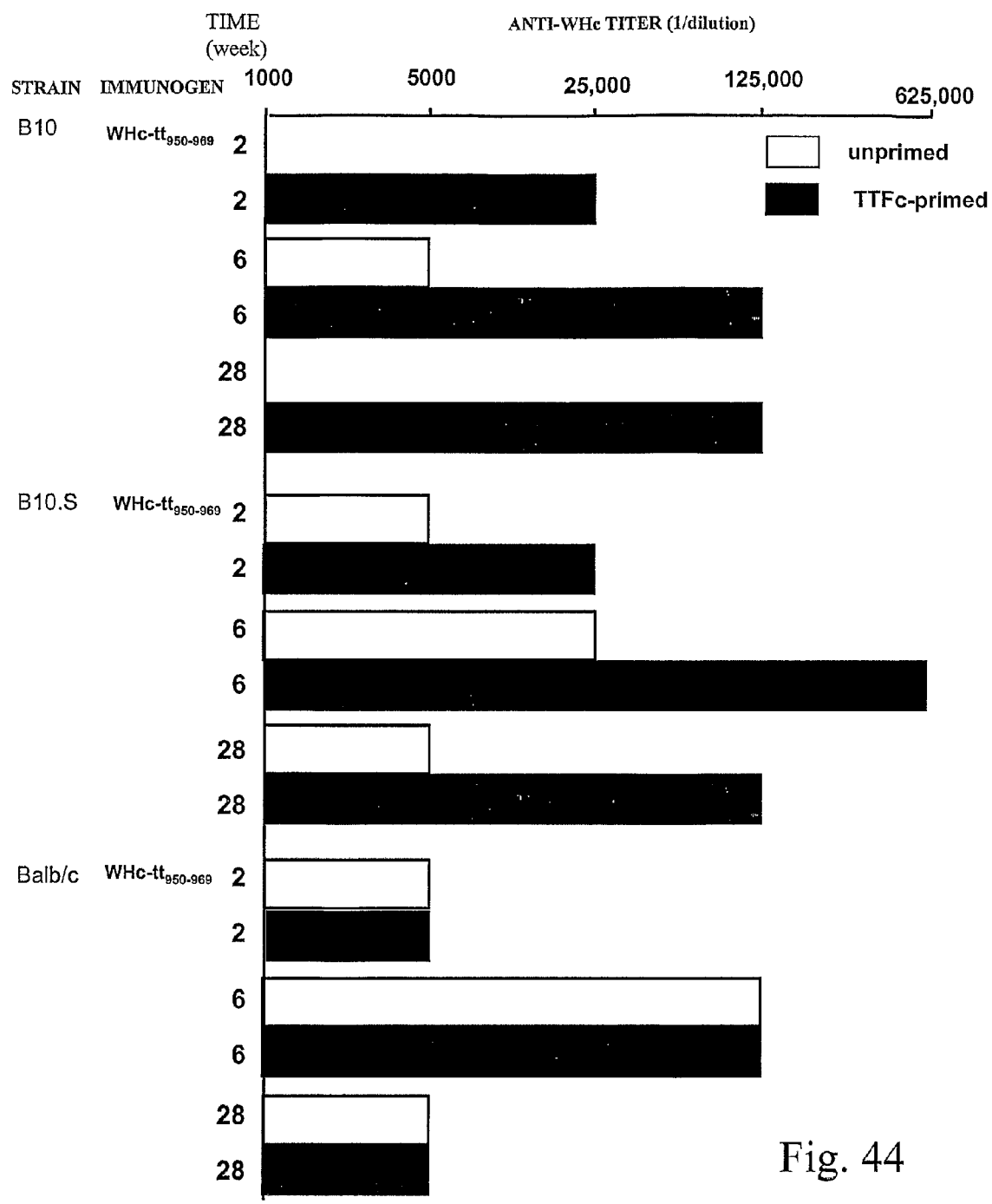

FIG. 44 depicts the ability of hybrid-WHcAg particles carrying an immune enhancer, the tetanus toxin (TT) universal CD4$^+$ T cell epitope TT950-969, to "redirect" the TT-specific T cell help to the WHcAg for anti-WHc antibody production. Mice of the indicated strains were first primed with the tetanus toxin fragment C(TTFc) (20 μg, IFA) to mimic TT immunization in humans. Two months later either TTFc-primed or unprimed mice were injected with hybrid WHc-TT950-969 particles (10 μg, in saline). At 2, 6 and 28 weeks later serum anti-WHc antibody levels were determined by ELISA. B10 and B10.S strain T cells recognize the TT950-969 peptide and Balb/c T cells do not.

FIG. 45 depicts splenic T cell recognition of the TT950-969 peptide in B10, B10.S and Balb/c mice either unprimed or primed with TTFc (20 μg, IFA) and then all groups were injected with hybrid WHc-TT950-969 particles (10 μg, in saline). Six months later spleen cells were harvested and cultured with the TT950-969 peptide and IL-2 produced in the culture media was determined by ELISA and quantitated (U/ml) by comparison to an IL-2 standard in the same ELISA.

FIG. 46 A-C shows a ClustalW alignment of viral core sequences for primates (human, chimpanzee, gibbon, orangutan, etc.); rodents (woodchuck, grounds quirrel, artic grounds quirrel, etc.); and birds/avians (duck, goose, heron, etc.).

GENERAL DESCRIPTION OF THE INVENTION

The present invention is directed to exploitation of hepadna virus nucleocapsids/core antigens as multivalent carrier platforms for enhancing the immune response to weak haptenic-like antigens. During development of the present invention, theoretical and practical limitations inherent to the original human hepatitis B virus (HBV) nucleocapsid/core antigen (HBcAg) platform technology were addressed. In one embodiment, a new combinatorial platform technology, which may be applied to any hepadnavirus, was developed by modification of the exemplary woodchuck hepadna virus (WHV) core antigen (WHcAg). To begin, three variables were identified as considerations in designing WHcAg-hybrid particles: insert position, C-terminal sequence and epitope sequence. A rapid screening method to examine WHcAg-hybrid particle assembly within bacterial lysates was developed as part of a combinatorial approach involving shuffling of the insert position, and C-terminal modifications for each epitope of interest. In another embodiment, a second new combinatorial platform technology was developed by modification of the exemplary ground squirrel hepadna virus (GHV) nucleocapsid/core antigen (GSHcAg). While in a further embodiment, the exemplary human hepatitis B virus core antigen platform was improved through introduction of various modifications As disclosed herein, one advantage of the invention's combinatorial modification that includes epitope insertion at preferred locations in a hepadnavirus core antigen as well as preferred C-terminal modifications of the core antigen is that inclusion of the C-terminal modification rescues assembly of the resulting virus particles that contain the inserted epitope (e.g., Tables 12-14). Conversely, non-permissive C-terminal modifications to hepadnavirus core antigens may be rescued by altering the insertion position of the epitope into the hepadnavirus core antigen (e.g., Tables 13, 14). Moreover, substitution of amino acids with acidic amino acids and/or the use of acidic amino acid linkers in the hepadnavirus core antigen rescue assembly of the inserted epitope (e.g., Table 18).

DEFINITIONS

The term "gene" refers to a nucleic acid (e.g., DNA) sequence that comprises coding sequences necessary for the production of a polypeptide or precursor or RNA (e.g., tRNA, siRNA, rRNA, etc.). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends, such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

In particular, the term "WHcAg gene" refers to the full-length WHcAg nucleotide sequence (e.g., contained in SEQ ID NO:37). However, it is also intended that the term encompass fragments of the WHcAg sequence, and/or other domains within the full-length WHcAg nucleotide sequence. Furthermore, the terms "WHcAg nucleotide sequence" or "WHcAg polynucleotide sequence" encompasses DNA, cDNA, and RNA (e.g., mRNA) sequences.

The term "plasmid" as used herein, refers to a small, independently replicating, piece of DNA. Similarly, the term "naked plasmid" refers to plasmid DNA devoid of extraneous material typically used to affect transfection. As used herein, a "naked plasmid" refers to a plasmid substantially free of calcium-phosphate, DEAE-dextran, liposomes, and/or polyamines. As used herein, the term "purified" refers to molecules (polynucleotides or polypeptides) that are removed from their natural environment, isolated or separated. "Purified" molecules are at least 50% free, preferably at least 75% free, and more preferably at least 90% free from other components with which they are naturally associated.

The term "recombinant DNA" refers to a DNA molecule that is comprised of segments of DNA joined together by means of molecular biology techniques. Similarly, the term "recombinant protein" refers to a protein molecule that is expressed from recombinant DNA. The term "fusion protein" as used herein refers to a protein formed by expression of a hybrid gene made by combining two gene sequences. Typically this is accomplished by cloning a cDNA into an expression vector in frame with an existing gene. The fusion partner may act as a reporter (e.g., βgal) or may provide a tool for isolation purposes (e.g., GST).

Suitable systems for production of recombinant proteins include but are not limited to prokaryotic (e.g., *Escherichia coli*), yeast (e.g., *Saccaromyces cerevisiae*), insect (e.g., baculovirus), mammalian (e.g., Chinese hamster ovary), plant (e.g., safflower), and cell-free systems (e.g., rabbit reticulocyte).

As used herein, the term "coding region" refers to the nucleotide sequences that encode the amino acid sequences found in the nascent polypeptide as a result of translation of an mRNA molecule. The coding region is bounded in eukaryotes, on the 5' side by the nucleotide triplet "ATG" that encodes the initiator methionine and on the 3' side by one of the three triplets which specify stop codons (i.e., TAA, TAG, and TGA).

Where amino acid sequence is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Rather the terms "amino acid sequence" and "protein" encompass partial sequences, and modified sequences.

The term "wild type" when in reference to a gene or gene product refers to a gene or gene product that has the characteristics of that gene or gene product when isolated from a naturally occurring source. A wild type gene or gene product is that which is most frequently observed in a population and is thus arbitrarily designed the "normal" or "wild-type" form of the gene or gene product.

In contrast, the terms "modified," "mutant," and "variant" refer to a gene or gene product that displays changes in sequence and or functional properties (i.e., altered characteristics) when compared to the wild-type gene or gene product. In some embodiments, the modification comprises at least one insertion, deletion, or substitution. In preferred embodiments, the insertion comprises introduction of a heterologous antigen sequence into a hepatitis B virus antigen sequence (e.g., fusion protein).

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to reduction in binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" when used in reference to a first and a second polypeptide means that the first polypeptide with an activity binds to the same substrate as does the second polypeptide with an activity. In one embodiment, the second polypeptide is a variant of the first polypeptide (e.g., encoded by a different allele) or a related (e.g., encoded by a homolog) or dissimilar (e.g., encoded by a second gene having no apparent relationship to the first gene) polypeptide. The efficiency (e.g., kinetics or thermodynamics) of binding by the first polypeptide may be the same as or greater than or less than the efficiency of substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur between nucleic acid fragments that have a high frequency of complementary base sequences (e.g., hybridization under "high stringency" conditions may occur between homologs with 85-100% identity, preferably 70-100% identity). With medium stringency conditions, nucleic acid base pairing will occur between nucleic acids with an intermediate frequency of complementary base sequences (e.g., hybridization under "medium stringency" conditions may occur between homologs with 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 100 to about 1000 nucleotides in length is employed.

"Medium stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 100 to about 1000 nucleotides in length is employed.

"Low stringency conditions" comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, *Adv. Appl. Math.*, 2: 482, 1981) by the homology alignment algorithm of Needleman and Wunsch (Needleman and Wunsch, *J. Mol. Biol.*, 48:443, 1970), by the search for similarity method of Pearson and Lipman (Pearson and Lipman, *Proc. Natl. Acad. Sci., U.S.A.*, 85:2444, 1988), by computerized implementations of these algorithms (GAP, BESTFIT, FASTA, and TFASTA in the Wisconsin Genetics Software Package Release 7.0, Genetics Computer Group, Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., WHcAg)

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having acidic side chains is glutamic acid and aspartic acid; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process specific sequences of nucleic acid in a heterogeneous mixture of nucleic acid. In particular, Tth, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular WHcAg sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of Mullis (U.S. Pat. Nos. 4,683, 195, 4,683,202, and 4,965,188, hereby incorporated by reference), that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the terms "restriction endonucleases" and "restriction enzymes" refer to bacterial enzymes, each of which cut double-stranded DNA at or near a specific nucleotide sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding gene includes, by way of example, such nucleic acid in cells ordinarily expressing gene where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

The terms "fragment" and "portion" when used in reference to a nucleotide sequence (as in "a portion of a given nucleotide sequence") refers to partial segments of that sequence. The fragments may range in size from four nucleotides to the entire nucleotide sequence minus one nucleotide (10 nucleotides, 20, 30, 40, 50, 100, 200, etc.).

Similarly, the terms "fragment" and "portion" when used in reference to a polypeptide sequence refers to partial segments of that sequence. In some embodiments, the portion has an amino-terminal and/or carboxy-terminal deletion as compared to the native protein, but where the remaining amino acid sequence is identical to the corresponding positions in the amino acid sequence deduced from a full-length cDNA sequence. The fragments may range in size from four consecutive amino acid residues to the entire amino acid sequence minus one amino acid. In one embodiment, fragments are preferably at least 4 amino acids long, more preferably at least 50 amino acids long, and most preferably at least 50 amino acids long or longer (the entire amino acid sequence minus on amino acid). In particularly preferred embodiments, the portion comprises the amino acid residues required for intermolecular binding of the compositions of the present invention with its various ligands and/or substrates.

Thus, "at least a portion of" a nucleotide sequence and of an amino acid sequence refers to a sequence that comprises from four (4) contiguous nucleotides and from four (4) contiguous amino acid residues, respectively, of the nucleotide sequence and of the amino acid sequence to the entire nucleotide sequence and amino acid sequence.

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA).

As used herein, the term "purified" refers to molecules (polynucleotides or polypeptides) that are separated from other components with which they are naturally associated. "To purify" refers to a reduction (preferably by at least 10%, more preferably by at least 50%, and most preferably by at least 90%) of one or more contaminants from a sample. For example, WHcAg antibodies are purified by removal of contaminating non-immunoglobulin proteins; they are also purified by the removal of immunoglobulin that does not bind WHcAg. The removal of non-immunoglobulin proteins and/or the removal of immunoglobulins that do not bind WHcAg results in an increase in the percent of WHcAg-reactive immunoglobulins in the sample. In another example, recombinant WHcAg polypeptides are expressed in bacterial host cells and the polypeptides are purified by the removal of host cell proteins; the percent of recombinant WHcAg polypeptides is thereby increased in the sample.

The term "recombinant DNA molecule" as used herein refers to a DNA molecule that is comprised of segments of DNA joined together by means of molecular biological techniques. Similarly, the term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences, that is the native protein contains those amino acids found in the protein as it occurs in nature. A native protein may be produced by recombinant means or may be isolated from a naturally occurring source.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., *Molecular Cloning: A Laboratory Manual*, Cold Spring Harbor Press, NY, pp 9.31-9.58, 1989).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al, supra, pp 7.39-7.52, 1989).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The terms "antigenic determinant" and "epitope" as used herein refer to that portion of an antigen that makes contact with a particular antibody and/or T cell receptor. When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "vaccine" as used herein refers to an antigen which induces immunity against the antigen in an animal to which the antigen is administered. Vaccines include, but are not limited to, antigenic recombinant polypeptides, glycoproteins, and/or nucleic sequences (e.g., plasmids) encoding them. Such plasmids may be inoculated directly into the host, the antigen is expressed in the host and antibody and/or cell-mediated immunity can then be induced to the recombinant antigen. Vaccines may be used for immunizing an animal against the antigen of interest, by administering the vaccine to generate an immune response in animal against the antigen. Vaccines and/or antibodies against the antigen may be used therapeutically and/or prophylactically.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term host cell refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of is modified to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding WHcAg or fragments thereof may be employed as hybridization probes. In this case, the WHcAg encoding polynucleotide sequences are typically employed in an aqueous solution containing salts (e.g., NaCl), detergents (e.g., SDS), and other components (e.g., Denhardt's solution, dry milk, salmon sperm DNA, etc.).

As used herein, the terms "hepadnavirus" and "hepatitis virus" refer to any one of a family of DNA-containing viruses that cause hepatitis (inflammation of the liver) in a wide range of vertebrate species. "Hepadnavirus" includes orthohepadnavirus such as from rodents (e.g. from woodchuck, ground squirrel, arctic ground squirrel, etc.) and from primates (e.g., chimpanzee, gibbon, orangutan, woolly monkey, human, etc.) and avihepadnavirus (e.g., from duck, Ross' goose, heron, stork, etc.). The terms "human hepatitis B virus" and "HBV" refer to a species of the genus orthohepadnavirus which causes human hepatitis B and which is also a causal agent in human hepatocellular carcinoma. Viruses similar to HBV also infect animals (e.g., woodchuck, ground squirrel, duck), and are encompassed by some embodiments of the present invention.

The terms "WHcAg," "woodchuck hepadnavirus core antigen," and "woodchuck hepatitis virus core antigen" as used herein refer to the core antigen of the woodchuck hepadna virus exemplified by SEQ ID NO:1, 103-107, while the WHcAg coding region is exemplified by SEQ ID NO:37, 129-133. The term WHcAg also encompasses the core antigens of other woodchuck hepatitis viruses, such as the woodchuck hepatitis virus clone 2 corresponding to GenBank Accession No. NKVLC2, M90520, M18752, M11082, J04514, and J02442.

As used herein, the terms "GSHcAg," "ground squirrel hepadnavirus core antigen," and ground squirrel hepatitis virus core antigen" refer to the core antigen of the ground squirrel hepadna virus exemplified by SEQ ID NOs:21 and 108, while the GSHcAg coding region is exemplified by SEQ ID NOs:39 and 128. The term GSHcAg also encompasses the core antigens of other ground squirrel hepadna viruses, such as the arctic ground squirrel hepatitis B virus corresponding to GenBank Accession No. NP_040993 and K02715.

The terms "HBcAg" and "human hepatitis B core antigen" refer to the core antigen of the human hepatitis B virus exemplified by SEQ ID NO:41, 109-114, while the HBcAg coding region is exemplified by SEQ ID NO:57, 138-142 (Genbank No. X65257, X02763, X01587, J02202, AY123041). The term HBcAg also encompasses the core antigens of other HBV isolates, including but not limited to the ADW subtypes (e.g., subtype ADW4, strain brazil/isolate w4b; subtype ADW, strain okinawa/podw282; subtype ADW, strain indonesia/pidw420; etc.), and the ADR subtypes. The term "hepadnavirus core antigen" herein refers to a sequence of a hepadnavirus that corresponds (e.g., by sequence alignment, see FIG. 46) to the core antigen sequence of one or more of the hepadnavirus core antigens disclosed herein. In one embodiment, the "hepadnavirus core antigen" contains a region towards the carboxyl terminus which is homologous with that found in protamines (DNA binding proteins) and which interacts with DNA during assembly of core particles (Pasek et al, Nature, 282, 575-579, 1979). In one embodiment, the "hepadnavirus core antigen" has greater than 70%, preferably greater than 80%, and most preferably greater than 90%, homology to the core antigen sequence of one or more of the hepadnavirus core antigens disclosed herein, such the woodchuck hepatitis virus core antigen (e.g., SEQ ID NO:1, 103-107), arctic ground squirrel hepatitis virus core antigen (e.g., SEQ ID NO:102), ground squirrel hepatitis virus core antigen (e.g., SEQ ID NO:21 and 108), chimpanzee hepatitis B virus core antigen (e.g., SEQ ID NO:115), gibbon hepatitis B virus core antigen (e.g., SEQ ID NO:116), orangutan hepatitis virus core antigen (e.g., SEQ ID NO:117), woolly monkey hepatitis virus core antigen (e.g., SEQ ID NO:118), human hepatitis B virus core antigen (e.g. SEQ ID NOS:41, and 109-114), duck hepatitis virus core antigen (SEQ ID NO:119-124), Ross' goose hepatitis virus core antigen (SEQ ID NO:125), heron hepatitis virus core antigen (SEQ ID NO:126), sheldgoose hepatitis virus core antigen (SEQ ID NO:151), and stork hepatitis virus core antigen (SEQ ID NO:152).

The terms "C-terminal sequence," "C-terminal portion," "COOH-terminal portion," "carboxy terminal portion," "C-terminal domain," "COOH-terminal domain," and "carboxy terminal domain," when used in reference to an amino acid sequence of interest (such as a hepadnavirus core antigen as exemplified by WHcAg) refer to the amino acid sequence (and portions thereof) that is located from approximately the middle of the amino acid sequence of interest to the C-terminal-most amino acid residue of the sequence of interest. In one embodiment, the "C-terminal sequence" of a hepadnavirus core antigen as used herein also refers to that portion of the hepadnavirus core antigen, the deletion of which from the core antigen does not result in a complete absence of assembly (although it may result in a reduced level of assembly) of a virus particle. Thus, in one embodiment, the "C-terminal sequence" of a hepadnavirus core antigen as used herein refers to a sequence of the hepadnavirus core antigen that corresponds (e.g., by sequence alignment, see FIG. 46) to the C-terminal sequence of one or more of the hepadnavirus core antigens disclosed herein, such as amino acids 150-188 of the woodchuck hepatitis virus core antigen (e.g., SEQ ID NO:1, 103-107), amino acids 150-187 of the arctic ground squirrel hepatitis virus core antigen (e.g., SEQ ID NO:102), amino acids 149-187 of the ground squirrel hepatitis virus core antigen (e.g., SEQ ID NO:21 and 108), amino acids 150-183 of any one of the chimpanzee hepatitis B virus core antigen (e.g., SEQ ID NO:115), gibbon hepatitis B virus core antigen (e.g., SEQ ID NO:116), and orangutan hepatitis virus core antigen (e.g., SEQ ID NO:117), amino acids 150-182 of the woolly monkey hepatitis virus core antigen (e.g., SEQ ID NO:118), amino acids 150-183 of the human hepatitis B virus core antigen (e.g. SEQ ID NOS:41, and 109-114), amino acids 196-282 of any one of the duck hepatitis virus core antigen (SEQ ID NO:19-124), Ross' goose hepatitis virus core antigen (SEQ ID NO:125), heron hepatitis virus core antigen (SEQ ID NO:126), sheldgoose hepatitis virus core antigen (SEQ ID NO:151), and stork hepatitis virus core antigen (SEQ ID NO:152).

Alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information), by using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4, or by inspection. Sequences are typically compared using either BlastN or BlastX with default parameters. In one preferred embodiment, alignment is conducted using MacVector™ software.

Exemplary C-terminal sequences of hepadnavirus core antigens are illustrated by those from woodchuck hepatitis virus (SEQ ID NO:2), ground squirrel hepatitis virus (SEQ ID NO:22), arctic ground squirrel hepatitis virus (SEQ ID NO:153), chimpanzee hepatitis B virus (SEQ ID NO:161), gibbon hepatitis B virus (SEQ ID NO:159), orangutan hepatitis virus (SEQ ID NO:157), woolly monkey hepatitis virus (SEQ ID NO:155), duck hepatitis virus (SEQ ID NO:163, 165, 167, 169, 171, and/or 173), Ross' goose hepatitis virus (SEQ ID NO:175), heron hepatitis virus (SEQ ID NO:179), sheldgoose hepatitis virus (SEQ ID NO:177), stork hepatitis virus (SEQ ID NO:181), and from human hepatitis B virus (SEQ ID NO:42). Thus, in one embodiment, the C-terminal portion of WHcAg includes the amino acid sequence from position 150 to 188 of WHcAg (SEQ ID NO:2); the C-terminal portion of GSHcAg includes the amino acid sequence from position 149 to 187 of GSHcAg (SEQ ID NO:22); the C-terminal portion of HBcAg includes the amino acid sequence from position 150 to 183 of HBcAg (SEQ ID NO:42).

The terms "truncated hepadnavirus core antigen" and "N-terminal sequence of a hepadnavirus core antigen" refer to a hepadnavirus core antigen from which the C-terminal sequence has been deleted.

The term "hybrid" as used in reference to a hepadna virus core antigen, refers to a fusion protein of the hepadna virus core antigen and an unrelated antigen (e.g., *Plasmodium* antigen). For instance, in some preferred embodiments of the present invention, the term "hybrid WHcAg" refers to a fusion protein comprising both a WHcAg component (full length, or partial) and a heterologous antigen (e.g., non-WHcAg and/or modified WHcAg) component. In particularly preferred embodiments, the heterologous antigen comprises at least one B cell epitope and/or at least one T cell epitope which may be conjugated (e.g., covalently linked) to a residue of the WHcAg and/or which is inserted within the WHcAg via expression as a fusion protein. In contrast, the term "nonhybrid" refers to an antigen of a single origin (e.g., WHcAg in the absence of a heterologous antigen insert or conjugate).

The term "modified antigen" refers to an antigen, any part of which (such as the nucleic acid sequence and/or proteins) has been modified by chemical, biochemical, and/or molecular biological techniques compared to the wild-type antigen. In one embodiment, the antigen is modified by means of molecular biological techniques. In one embodiment, the modification may include one or more of a deletion, an insertion, and a substitution. A "deletion" is defined as a change in a nucleic acid sequence in which one or more nucleotides is absent. An "insertion" or "addition" is that change in a nucleic acid sequence which has resulted in the addition of one or more nucleotides. The term "substitution of an amino acid" and "substitution of a nucleic acid" as used herein refer to the replacement of one or more amino acids and one or more nucleic acids, respectively, by one or more amino acids and by one or more nucleic acids. Similarly, in some preferred embodiments, the term "modified WHcAg" refers to a woodchuck hepadna virus core protein with a C-terminal truncation. In particularly preferred embodiments, the modified WHcAg comprises both carboxy-terminal amino acid deletions, and insertions within the loop and/or outside the loop. In addition the term "modified WHcAg" refers to a woodchuck virus core protein comprising a heterologous antigen in the form of a conjugate or a fusion protein. Thus as used herein, the terms "modified hepatitis virus core antigen" and granunatical equivalents encompass hybrid core antigens, as well as mutant core antigens.

The term insertion of a first amino acid (e.g., alanine) or amino acid sequence (e.g., heterologous antigen) "at amino acid position x" or "in amino acid position x" of a second amino acid sequence (e.g., woodchuck hepadna virus core antigen) means introduction of a first amino acid or sequence into a second amino acid sequence, such that the first amino acid or sequence is placed C-terminal to amino acid x.

The term "conjugating" when made in reference to two molecules (such as a heterologous antigen and hepadna virus core antigen) as used herein means covalently linking the two molecules. In one embodiment, where one of the molecules is a viral core or will be assembled into a viral nucleocapsid, it may be desirable to modify the nature and size of the second molecule and the site at which it is covalently linked to the core antigen such that it does not interfere with the capacity of the modified core to assemble in vitro and/or in vivo. In some embodiments, the heterologous antigen is conjugated to a functional group on the hepadna virus core antigen, chosen from but not limited to a carboxyl group, a primary amine, and a sulfhydryl. In some preferred embodiments, a heterobifunctional cross-linker is used to attach the heterologous antigen to the hepadna virus core antigen. Exemplary cross-linkers include but are not limited to MBS, EDC/Sulfo-NHS and ABH obtained from Pierce (Rockford, Ill.).

As used herein in reference to a hepadna virus core antigen, the term "loop" refers to a portion of the hepadna virus core antigen which links the second and third alpha-helices and which contains an immunodominant B cell epitope. Specifically, in reference to HBcAG, the term "within the loop" refers to residues at positions 76 to 82 of the wild type sequence, while the term "outside the loop" refers to residues amino-terminal to residue 76 and carboxy-terminal to residue 82. Likewise, in reference to WHcAg, the term "within the loop" refers to residues at positions 76 to 82 of the wild type sequence, while the term "outside the loop" refers to residues amino-terminal to residue 76 and carboxy-terminal to residue 82. In contrast, in reference to GSHcAg, the term "within the loop" refers to residues at positions 76 to 81, while the term "outside the loop" refers to residues amino-terminal to residue 76 and carboxy-terminal to residue 81.

The terms "N-terminus" "NH$_2$-terminus" and "amino-terminus" refer to the amino acid residue corresponding to the methionine encoded by the start codon (e.g., position or residue 1). In contrast the terms "C-terminus" "COOH-terminus" and "carboxy terminus" refer to the amino acid residue encoded by the final codon (e.g., last or final residue prior to the stop codon).

The term "antibody" refers to polyclonal and monoclonal antibodies. Polyclonal antibodies which are formed in the animal as the result of an immunological reaction against a protein of interest or a fragment thereof, can then be readily isolated from the blood using well-known methods and purified by column chromatography, for example. Monoclonal antibodies can also be prepared using known methods (See, Winter and Milstein, Nature, 349, 293-299, 1991). As used herein, the term "antibody" encompasses recombinantly prepared, and modified antibodies and antigen-binding fragments thereof, such as chimeric antibodies, humanized antibodies, multifunctional antibodies, bispecific or oligospecific antibodies, single-stranded antibodies and F(ab) or F(ab)$_2$ fragments. The term "reactive" when used in reference to an antibody indicates that the antibody is capable of binding an antigen of interest. For example, a WHcAg-reactive antibody is an antibody which binds to WHcAg or to a fragment of WHcAg.

The terms "auto-antibody" or "auto-antibodies" refer to any immunoglobulin that binds specifically to an antigen that is native to the host organism that produced the antibody (i.e., the antigen is not synthetic and/or has not been artificially supplied to the host organism). However, the term encompasses antibodies originally produced in response to the administration or presence of a foreign and/or synthetic substance in the host, but also cross-react with "self" antigens. Exemplary auto-antibodies include, without limitation, anticholesterol ester transfer protein (CETP) antibody, anti-major histocompatibility complex class II antibody, anti-cytokine antibody, and anti amyloid-β-peptide antibody. The presence of auto-antibodies is termed "autoimmunity."

The term "cytokine" refers to a molecule, such a protein or glycoprotein, involved in the regulation of cellular proliferation and function. Cytokines are exemplified by lymphokines (e.g., tumor necrosis factor-α, tumor necrosis factor-β, interferon-γ, etc.), growth-factors (e.g., erythropoietin, insulin, G-CSF, M-CSF, GM-CSF, EGF, PDGF, FGF, etc.), and interleukins (e.g., IL-2, IL-4, IL-5, IL-6, IL-9, IL-10, EL-13, etc.).

The term "B cell epitope" as used herein refers to as antigenic determinant (protein or carbohydrate) to which a single antibody molecule binds. B cell epitopes may comprise linear epitopes (amino acids adjacent to each other in the primary sequence) or conformational epitopes (moities distant from each other in the primary sequence, but which are brought in proximity to one another during folding of the antigen) of at least four amino acid residues.

The term "T cell epitope" as used herein refers to an antigenic determinant presented by a MHC class I or class II molecule for binding to a single T cell receptor. T cell epitopes are linear epitopes comprising at least seven amino acid residues. In some embodiments of the present invention, the term T cell epitope comprises a T helper cell epitope which is an antigen fragment presented by an MHC class II molecule for binding to T cell receptor on the surface of a helper T cell (e.g., generally CD4⁺).

The term "conservative substitution" as used herein refers to a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine).

The terms "non-acidic amino acid" and "not an acidic amino acid" refer to any amino acid other than glutamic acid and aspartic acid, such as lysine, arginine, histidine, alanine, valine, leucine, isoleucine, proline, phenylalanine, methionine, tryptophan, glycine, asparagine, glutamine, cysteine, serine, threonine, and tyrosine.

Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "nonconservative substitution" refers to a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.).

The terms "antigen," "immunogen," "antigenic," "immunogenic," "antigenically active," and "immunologically active" refer to any substance that is capable of inducing a specific humoral and/or cell-mediated immune response. An immunogen generally contains at least one epitope. Immunogens are exemplified by, but not restricted to molecules which contain a peptide, polysaccharide, nucleic acid sequence, and/or lipid. Complexes of peptides with lipids, polysaccharides, or with nucleic acid sequences are also contemplated, including (without limitation) glycopeptide, lipopeptide, glycolipid, etc. These complexes are particularly useful immunogens where smaller molecules with few epitopes do not stimulate a satisfactory immune response by themselves.

A peptide sequence and nucleotide sequence may be "endogenous" or "heterologous" (i.e., "foreign"). The term "endogenous" refers to a sequence which is naturally found in the cell or virus into which it is introduced so long as it does not contain some modification relative to the naturally-occurring sequence. The term "heterologous" refers to a sequence which is not endogenous to the cell or virus into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell or virus into which it is introduced and which contains some modification relative to the naturally-occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences which encode selectable marker proteins (e.g., proteins which confer drug resistance), etc. In preferred embodiments, the terms "heterologous antigen" and "heterologous sequence" refer to a non-hepadna virus antigen or amino acid sequence including but not limited to microbial antigens, mammalian antigens and allergen antigens.

The terms "peptide," "peptide sequence," "amino acid sequence," "polypeptide," and "polypeptide sequence" are used interchangeably herein to refer to at least two amino acids or amino acid analogs which are covalently linked by a peptide bond or an analog of a peptide bond. The term peptide includes oligomers and polymers of amino acids or amino acid analogs. The term peptide also includes molecules which are commonly referred to as peptides, which generally contain from about two (2) to about twenty (20) amino acids. The term peptide also includes molecules which are commonly referred to as polypeptides, which generally contain from about twenty (20) to about fifty amino acids (50). The term peptide also includes molecules which are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide which is produced by artificial means in vitro.

The terms "oligosaccharide" and "OS" antigen refer to a carbohydrate comprising up to ten component sugars, either O or N linked to the next sugar. Likewise, the terms "polysaccharide" and "PS" antigen refer to polymers of more than ten monosaccharide residues linked glycosidically in branched or uibranched chains.

The terms "microbial sequence" and "sequence of a microbe" refers to synthetic, recombinant or purified sequences (preferably sequence fragments comprising at least one B cell epitope) of a virus, a bacterium, a fungus, and a parasite. Exemplary microbial sequences include those of Influenza A, *Staphylococcus* sp., *Candida* sp., and *Plasmodium* sp.

As used herein, the term "mammalian sequence" refers to synthetic, recombinant or purified sequences (preferably sequence fragments comprising at least one B cell epitope) of a mammal. Exemplary mammalian sequences include cytokine sequence, MHC class I heavy chain sequences, MHC class II alpha and beta chain sequences, and amyloid β-peptide sequences.

The term "allergen" as used herein, refers to an antigenic substance capable of producing an immediate type hypersensitivity reaction (allergy) in a animal. Exemplary allergens include food allergens such as peanut allergen, grass pollen allergen and dust mite allergen.

The term "particle" as used herein refers to a virus-like protein structure of approximately 25-35 nm in diameter, into which hepadnavirus core polypeptides spontaneously assemble. Particle formation is measured by the exemplary methods for assessing hepadnavirus core antigen expression and assembly disclosed herein.

The term "aggregate" as used herein refers to a cluster, clump, or mass of individual polypeptides and/or particles.

As used herein, the terms "immune enhancer" and "molecular adjuvant" refer to molecules or antigens which provide a stimulus to T cells or a co-stimulus to B cells or other antigen presenting cells, thereby increasing the level of the immune response by the cells to an antigen. Exemplary immune enhancers include but are not limited to unmethylated CpG dinucleotides, CD40 ligand, complement C3d fragment, BAFF, and LAG-3 and TT950-969.

An "animal" as used herein refers to any multicellular animal, including mammals, birds (e.g., chickens, ducks, geese, herons, storks, etc.), amphibians (e.g. Xenopus), reptiles, and insects (e.g. mosquito, Drosophila, etc.). The terms "mammals" and "mammalian" refer to members of the class mammalia which nourish their young by fluid secreted from mammary glands of the mother, including human beings. The class "mammalian" includes placental animals, marsupial animals, and monotrematal animals. An exemplary "mammal" may be a rodent, primate (including simian and human) ovine, bovine, ruminant, lagomorph, porcine, caprine, equine, canine, feline, ave, etc. Preferred non-human animals are selected from the order RodentiaPreferred embodiments of the present invention are primarily directed to vertebrate (backbone or notochord) members of the animal kingdom.

The terms "patient" and "subject" refer to an animal (such as a mammal) that may be treated using the methods of the present invention.

The term "control" refers to animals or samples which provide a basis for comparison for experimental animals or samples. For instance, the use of control animals or samples permits determinations to be made regarding the efficacy of experimental procedures. In some embodiments, the term "control animal" refers to a animal that which receives a mock treatment (e.g., saline alone or WHcAg without a heterologous antigen insert or conjugate).

As used herein, the term "immune response" refers to the reactivity of an organism's immune system in response to an antigen. In vertebrates, this may involve antibody production, induction of cell-mediated immunity, and/or complement activation (e.g., phenomena associated with the vertebrate immune system's prevention and resolution of infection by microorganisms). In preferred embodiments, the term immune response encompasses but is not limited to one or more of a "lymphocyte proliferative response," a "cytokine response," and an "antibody response."

In particularly preferred embodiments, the immune response is largely reactive with an antigen of interest. For instance, when used in reference to administration of a hybrid WHcAg-NANP vaccine to an animal (e.g., mammalian subject), the term refers to the immune response produced in the animal, which reacts with either the WHcAg core or the NANP insert/conjugate of the vaccine. Immune responses reactive with an antigen of interest are measured in vitro using various methods disclosed herein.

The term "reactive with an antigen of interest" when made in reference to an immune response refers to an increased level of the immune response to the antigen of interest as compared to the level of the immune response to control antigen. (e.g., unrelated antigen).

The term "lymphocyte proliferative response" refers to antigen-induced lymphocyte (e.g., PBL) increase in cell number. Alternatively, or in addition, the term "proliferation" refers to the physiological and morphological progression of changes that cells undergo when dividing, for instance including DNA replication as measured by tritiated thymidine incorporation.

The term "cytokine response" refers to antigen-induced cytokine secretion by lymphocytes as measured for instance by assaying culture supernatants for cytokine content (e.g., IL-2, IFNγ, TNFα, IL-4, etc) by ELISA.

The term "antibody response" refers to the production of antibodies (e.g., IgM, IgA, IgG) which bind to an antigen of interest, this response is measured for instance by assaying sera by antigen ELISA.

The term "adjuvant" as used herein refers to any compound which, when injected together with an antigen, non-specifically enhances the immune response to that antigen. Exemplary adjuvants include but are not limited to incomplete Freunds adjuvant (IFA), aluminum-based adjuvants (e.g., A10H, AlPO4, etc), and Montanide ISA 720.

The terms "diluent" and "diluting agent" as used herein refer to agents used to diminish the strength of an admixture. Exemplary diluents include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

The terms "carrier" and "vehicle" as used herein refer to usually inactive accessory substances into which a pharmaceutical substance (e.g., WHcAg vaccine) is suspended. Exemplary carriers include liquid carriers (such as water, saline, culture medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins.

The term "derived" when in reference to a peptide derived from a source (such as a microbe, cell, etc.) as used herein is intended to refer to a peptide which has been obtained (e.g., isolated, purified, etc.) from the source. Alternatively, or in addition, the peptide may be genetically engineered and/or chemically synthesized.

The terms "operably linked," "in operable combination," and "in operable order" as used herein refer to the linkage of nucleic acid sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. Similarly, operably linking a nucleic acid sequence encoding a protein of interest means linking the nucleic acid sequence to regulatory and other sequences in a manner such that the protein of interest is expressed. The term also refers to the linkage of amino acid sequences in such a manner so that a functional protein is produced.

The terms "specific binding," "binding specificity," and grammatical equivalents thereof when made in reference to the binding of a first molecule (such as a polypeptide, glycoprotein, nucleic acid sequence, etc.) to a second molecule (such as a polypeptide, glycoprotein, nucleic acid sequence, etc.) refer to the preferential interaction between the first molecule with the second molecule as compared to the interaction between the second molecule with a third molecule. Specific binding is a relative term that does not require absolute specificity of binding; in other words, the term "specific binding" does not require that the second molecule interact with the first molecule in the absence of an interaction between the second molecule and the third molecule. Rather, it is sufficient that the level of interaction between the first molecule and the second molecule is higher than the level of interaction between the second molecule with the third molecule. "Specific binding" of a first molecule with a second molecule also means that the interaction between the first molecule and the second molecule is dependent upon the presence of a particular structure on or within the first molecule; in other words the second molecule is recognizing and binding to a specific structure on or within the first molecule rather than to nucleic acids or to molecules in general. For example, if a second molecule is specific for structure "A" that is on or within a first molecule, the presence of a third nucleic acid sequence containing structure A will reduce the amount of the second molecule which is bound to the first molecule.

As used in this specification and the appended claims, the singular forms "a," "an" and "the" includes both singular and plural references unless the content clearly dictates otherwise. For example, the term "inserted at a position" as used herein in reference to a polypeptide sequence refers to insertion at one or more (such as one, two, three, etc.) amino acid positions in the polypeptide sequence. In one preferred embodiment, insertion is at one amino acid position as exemplified herein.

The phrase "chosen from A, B, and C" as used herein, means selecting one or more of A, B, C.

As used herein, the term "or" when used in the expression "A or B," where A and B refer to a composition, disease, product, etc., means one, or the other, or both.

The term "on" when in reference to the location of a first article with respect to a second article means that the first article is on top and/or into the second article, including, for example, where the first article permeates into the second article after initially being placed on it.

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities of ingredients, properties such as molecular weight, reaction conditions, and so forth as used in the specification and claims are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximation, the numerical values in the specific examples are reported as precisely as possible. Any numerical value, however, inherently contains standard deviations that necessarily result from the errors found in the numerical value's testing measurements.

The term "not" when preceding, and made in reference to, any particularly named molecule (mRNA, etc.) or phenomenon (such as biological activity, biochemical activity, etc.) means that the particularly named molecule or phenomenon is excluded.

The term "altering" and grammatical equivalents as used herein in reference to the level of any substance and/or phenomenon refers to an increase and/or decrease in the quantity of the substance and/or phenomenon, regardless of whether the quantity is determined objectively, and/or subjectively.

The term "increase," "elevate," "raise," and grammatical equivalents when in reference to the level of a substance and/or phenomenon in a first sample relative to a second sample, mean that the quantity of the substance and/or phenomenon in the first sample is higher than in the second sample by any amount that is statistically significant using any art-accepted statistical method of analysis. In one embodiment, the increase may be determined subjectively, for example when a patient refers to their subjective perception of disease symptoms, such as pain, clarity of vision, etc. In another embodiment, the quantity of the substance and/or phenomenon in the first sample is at least 10% greater than the quantity of the same substance and/or phenomenon in a second sample. In another embodiment, the quantity of the substance and/or phenomenon in the first sample is at least 25% greater than the quantity of the same substance and/or phenomenon in a second sample. In yet another embodiment, the quantity of the substance and/or phenomenon in the first sample is at least 50% greater than the quantity of the same substance and/or phenomenon in a second sample. In a further embodiment, the quantity of the substance and/or phenomenon in the first sample is at least 75% greater than the quantity of the same substance and/or phenomenon in a second sample. In yet another embodiment, the quantity of the substance and/or phenomenon in the first sample is at least 90% greater than the quantity of the same substance and/or phenomenon in a second sample.

The terms "reduce," "inhibit," "diminish," "suppress," "decrease," and grammatical equivalents when in reference to the level of a substance and/or phenomenon in a first sample relative to a second sample, mean that the quantity of substance and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, clarity of vision, etc. In another embodiment, the quantity of substance and/or phenomenon in the first sample is at least 10% lower than the quantity of the same substance and/or phenomenon in a second sample. In another embodiment, the quantity of the substance and/or phenomenon in the first sample is at least 25% lower than the quantity of the same substance and/or phenomenon in a second sample. In yet another embodiment, the quantity of the substance and/or phenomenon in the first sample is at least 50% lower than the quantity of the same substance and/or phenomenon in a second sample. In a further embodiment, the quantity of the substance and/or phenomenon in the first sample is at least 75% lower than the quantity of the same substance and/or phenomenon in a second sample. In yet another embodiment, the quantity of the substance and/or phenomenon in the first sample is at least 90% lower than the quantity of the same substance and/or phenomenon in a second sample.

Reference herein to any specifically named protein (such as "WHcAg," "GSHcAg," and "HBcAg," etc.) refers to a polypeptide having at least one of the biological activities of the specifically named protein, wherein the biological activity is detectable by any method. In addition, reference herein to any specifically named protein (such as "WHcAg," "GSHcAg," and "HBcAg," etc.) includes within its scope fragments, fusion proteins, and variants of the specifically named protein. The term "variant" of a protein as used herein is defined as an amino acid sequence which differs by insertion, deletion, and/or conservative substitution of one or more amino acids from the protein. In one embodiment, the sequence of the variant has at least 99% identity, preferably at least 95% identity, and more preferably at least 90% identity with the sequence of the protein in issue.

For example, the term "has the biological activity of a specifically named protein" (such as "WHcAg," "GSHcAg," and "HBcAg," etc.) when made in reference to the biological activity of a variant of the specifically named protein refers, for example, to a quantity of binding of an antibody that is specific for the specifically named protein to the variant which is preferably greater than 50% (preferably from 50% to 500%, more preferably from 50% to 200%, most preferably from 50% to 100%), as compared to the quantity of binding of the same antibody to the specifically named protein.

Reference herein to any specifically named nucleotide sequence (such as a sequence encoding WHcAg, a sequence encoding GSHcAg, and a sequence encoding HBcAg, etc.) includes within its scope fragments, homologs, and sequences that hybridize under stringent condition to the specifically named nucleotide sequence. The term "homolog" of a specifically named nucleotide sequence refers to an oligonucleotide sequence which exhibits greater than or equal to 50% identity to the sequence of interest. Alternatively, or in addition, a homolog of any specifically named nucleotide sequence (such as a sequence encoding WHcAg, a sequence encoding GSHcAg, and a sequence encoding HBcAg, etc.) is defined as an oligonucleotide sequence which has at least 95% identity with the sequence of the nucleotide sequence in issue. In another embodiment, the sequence of the homolog has at least 90% identity, and preferably at least 85% identity with the sequence of the nucleotide sequence in issue.

DETAILED DESCRIPTION OF THE INVENTION

The present invention relates to modified hepatitis virus core proteins and nucleic acids. In particular, the present invention provides compositions and methods comprising recombinant modified hepatitis virus core proteins or nucleic acids for use in, for example, vaccine formulations.

I. Hepatitis B Virus Core Antigen (HBeAg)

Figure 1:
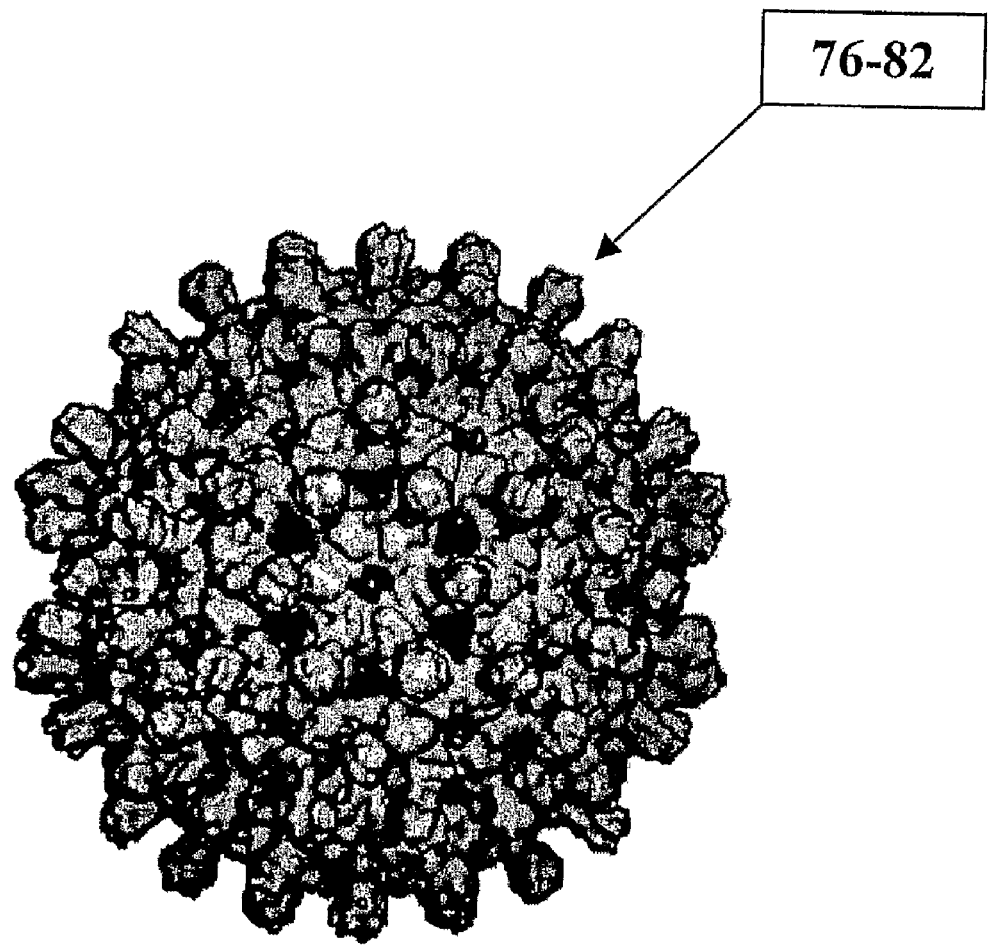

The human hepatitis B virus core antigen is a 21 kDa polypeptide. Two kinds of HBcAg core particles are spontaneously assembled during the course of virion assembly and during heterologous expression in both prokaryotic and eukaryotic systems: particles with T=4 symmetry containing 240 polypeptides, and particles with T=3 symmetry containing 180 polypeptides. Recent cryoelectron microscopy studies have revealed the structure of HBcAg particles to a resolution of 7.4 angstroms (Botcher et al, Nature, 386:88-91, 1997; and Conway et al., Nature, 386:91-94, 1997). Dimer clustering of HBcAg subunits produces spikes on the surface of the core shell, which consist of radial bundles of four long α-helices. The immunodominant B cell epitope on HBcAg is localized around amino acids 76-82 (Salfeld et al., J Virol, 63:798-808, 1989; and Schodel et al., J Virol, 66:106-114, 1992), apparently forming a loop connecting adjacent helices (See, FIG. 1). The spacing of the spikes on the core shell is optimal for B cell mIg receptor cross-linking. In addition, the inherent immunogenicity of the native HBcAg B cell epitopes suggested the desirability of substituting heterologous epitopes in the same position (i.e., at the tip of the spike). In fact, a number of pathogen-specific B cell epitopes have been chemically linked or fused by recombinant methods to HBcAg in order to increase their immunogenicity (See, Milich et al., Ann NY Acad Sci, 754:187-201, 1995; and Pumpens et al., Intervirology, 38:63-74, 1995, for reviews). These studies, conducted by a number of independent laboratories, have met with significant success including complete protection against foot and mouth disease virus (Clarke et al., Nature, 330; 381-384, 1987), *Plasmodium berghei* (Schodel et al., J Exp Med, 180:1037-1046, 1994), and *Plasmodium yoelii* (Schodel et al., Behring Inst Mitt, 114-119, 1997).

Adjuvants are broadly separated into two classes based upon their primary mechanism of action: vaccine delivery systems (e.g, emulsions, microparticles, iscoms, liposomes, etc.) that target associated antigens to antigen presenting cells (APC); and immunostimulatory adjuvants (e.g., LPS, MLP, CpG, etc.) that directly activate innate immune responses. The HBcAg platform provides a delivery system that targets antigen-specific B cells and other primary APC, as well as efficient T cell help for antigen-specific B cells. Additionally, the core platform functions as an immunostimulatory adjuvant by directly activating antigen-specific B cells by virtue of cross-linking membrane immunoglobulin (mIg) receptors for induction of B7.1 and B7.2 costimulatory molecule expression on naive resting B cells (Milich et al., Proc Natl Acad Sci USA, 94:14648-14653, 1997).

II. Non-Primate (e.g., Rodent and Avian) Hepatitis Virus Core Platform

A. Woodchuck Hepatitis Virus (WHV)

Figure 2:
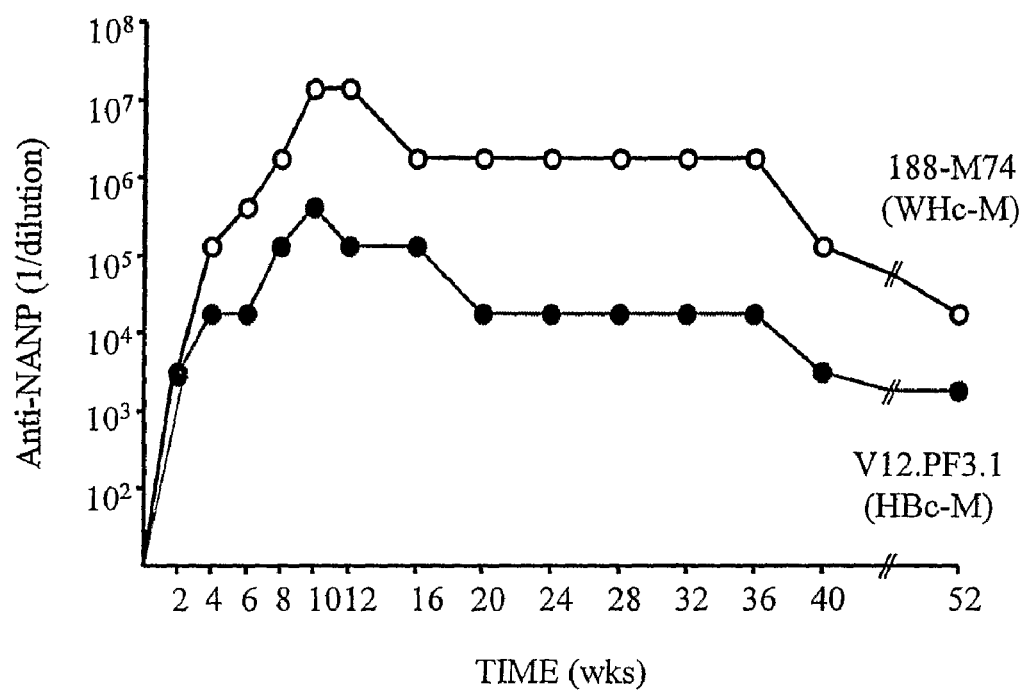
Figure 3:
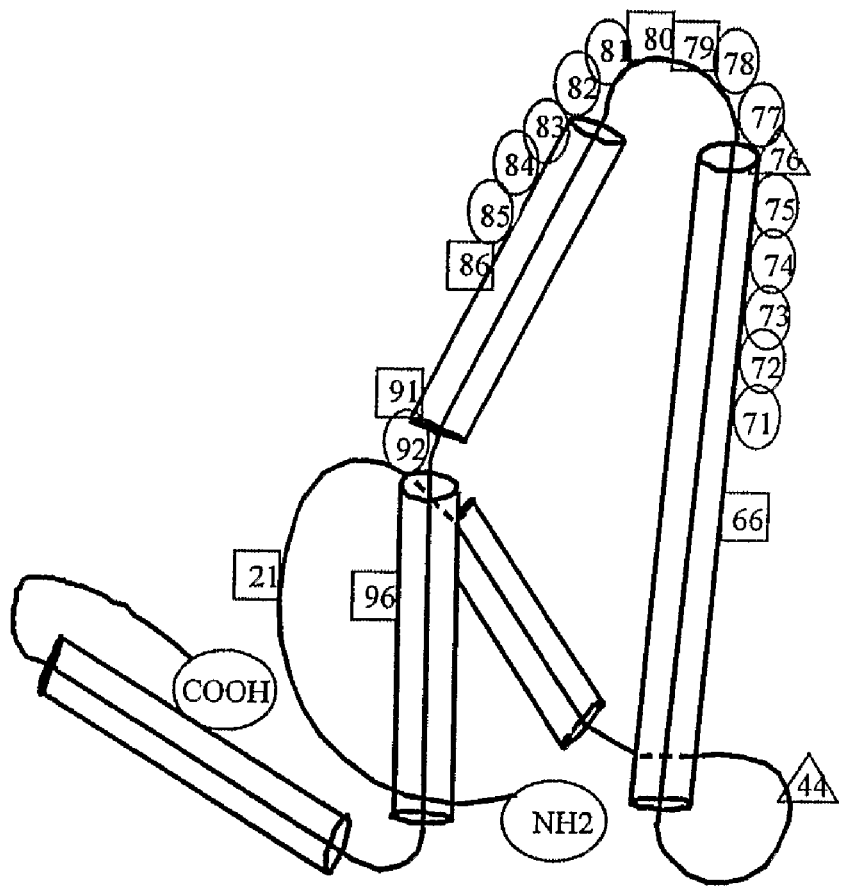

During development of the present invention, comparative studies between the HBcAg and the WHcAg were undertaken. The WHcAg is 67% identical at the amino acid level to the HBcAg, and the comparative studies herein revealed that, the HBcAg and WHcAg proteins do not significantly cross-react at the antibody level and only partially at the CD4$^+$ T cell level. However, these two particulate antigens share a number of characteristics including: enhanced immunogenicity of T cell-independent, as well as T cell-dependent antibody production; the absence of nonresponder MHC-haplotypes; efficient antigen-specific B cell activation; the ability of naive WHcAg or HBcAg-specific B cells to act as primary APC for naive core-specific Th cells; and the ability to act as a carrier moiety for foreign epitopes. In fact, in a direct comparison of an HBcAg-CS vaccine candidate (V12.PF3.1) and a WHcAg-based hybrid particle containing the same CS repeat sequence (188-M74), a single 20 µg dose of the WHcAg hybrid particle in IFA elicited significantly higher levels of anti-NANP antibodies with a better persistence profile than the same dose of the HBcAg hybrid vaccine (See, FIG. 2). Furthermore, the WHcAg appears to tolerate insertions of foreign epitopes at a greater number of positions than the HBcAg, as illustrated in FIG. 3. A number of internal insertions inside the loop region (positions 76-82), as well as internal insertions outside the loop region were tolerated by WHcAg. This is in sharp contrast to the rather limited number of efficient insertion sites described for the HBcAg, including those in loop positions 77, 78, 81, 82 (Pumpens and Grens, Intervirology, 44:98-114, 2001). Importantly, the identification of an expanded number of insertion sites was dependent on additional modifications to the C-terminus that stabilize the internal insertions. Indeed, 21 separate C-terminal modifications (See, Table 1) have been generated for use in combination with 17 insertion sites, to ensure efficient hybrid WHcAg particle assembly. Additionally, the insert sequence was found to effect hybrid WHcAg assembly competence. For example, highly positively-charged epitope inserts tended to destabilize hybrid particle assembly. Thus, three variables relevant to the design of hybrid hepadnavirus core particles have been identified including insert position, C-terminus and epitope sequence.

TABLE 1

Sequences of the C-Termini of the Woodchuck Vaccine Platform[1]

| Designation | WHcAg C-Terminal Sequence | Identifier |
|---|---|---|
| wild type | RRRGGARASRSPRRRTPSPRRRRSQSPRRRRSQSPSANC | SEQ ID NO: 2 |
| 150R | R | N/A |
| 150C | C | N/A |
| 150-2RC | RRC | N/A |
| 150-3RC | RRRC | SEQ ID NO: 3 |
| 150-4RC | RRRRC | SEQ ID NO: 4 |
| 150-3KC | KKKC | SEQ ID NO: 5 |
| 150-3AC | AAAC | SEQ ID NO: 6 |
| WT-R | AAGGARASRSPSQSPSQSPSANC | SEQ ID NO: 7 |
| WT-R1 | AAGGARASRSQSPSQSPSANC | SEQ ID NO: 8 |
| WT-R2 | AAGGARASRSQSSQSPSANC | SEQ ID NO: 9 |
| WT-R3 | AAGGARASRSQSSQSSANC | SEQ ID NO: 10 |
| C-Long | RRGGARASQSANC | SEQ ID NO: 11 |
| C-Long(M1) | ARGGARASQSANC | SEQ ID NO: 12 |
| C-Long(M2) | RAGGARASQSANC | SEQ ID NO: 13 |
| C-Long(M3) | AAGGARASQSANC | SEQ ID NO: 14 |
| HyW | AAGRSPSQSPSQSRESQC | SEQ ID NO: 15 |
| HyW-1 | AAGRSPSQSPSQSPSANC | SEQ ID NO: 16 |
| HyW-2 | AAGRSPSQSPSQSSANC | SEQ ID NO: 17 |
| HyW-3 | AAGRSQSPSQSSANC | SEQ ID NO: 18 |
| HyW-4 | AAGRSPSQSSQSSANC | SEQ ID NO: 19 |
| HyW-5 | AAGRSQSSQSSANC | SEQ ID NO: 20 |

[1]The wild type C-terminal protein sequence corresponds to positions 150-188. The full length protein sequence of WHcAg is set forth herein as SEQ ID NO: 1, while the full length DNA sequence is set forth as SEQ ID NO: 37. Additionally, the wild type N-terminal protein sequence (corresponding to positions 1-149) is set forth as SEQ ID NO: 38.

A combinatorial approach was made feasible by development of an ELISA-based screening system to detect core protein expression level, insert antigenicity and particle assembly in the lysates of transformed bacteria, prior to purification. Although a *Plasmodium* circumsporozoite (CS) repeat was used as a model epitope, this technology is not confined to a limited set of epitopes. In fact, insertion of 22 out of 24 different epitopes into the WHcAg platform has been successfully accomplished during development of the present invention. Another bottleneck that had existed in the characterization of hybrid core particles was the necessity for in vivo immunogenicity testing requiring 4-6 weeks for the analysis of a primary response. This bottleneck has been widened during development of the present invention by utilizing in vitro antibody production as a correlate of in vivo immunogenicity. The in vitro antibody production assay requires just 5 days of tissue culture. Establishment of in vitro antibody production as a predictor of in vivo immunogenicity is a powerful screening tool dramatically shortening the time necessary for the development of hybrid WHcAg particle vaccine candidates. Subsequently, once a vaccine candidate is shown to induce antibody production in vitro, then in vivo studies of dose, route and formulation are completed.

Three exemplary categories of model antigens are contemplated to be successfully accommodated by the WHcAg platform system including: i) peptidic epitopes inserted into WHcAg by recombinant methods; ii) polysaccharide (PS) antigens chemically conjugated to directly to or lysine-modified WHcAg particles; and iii) larger, non-linear protein/polypeptide antigens incorporated into WHcAg by recombinant or chemical methods. In some embodiments, the incorporation of larger protein sequences is accomplished by production of mosaic WHcAg particles comprised of an optimal mixture of wild-type WHcAg and WHcAg-fusion proteins containing the desired inserted sequence. This mosaic approach is also suitable for utilization of so-called molecular adjuvants through linkage to the C-terminal amino acid residue of WHcAg particles. A number of useful molecular adjuvants, which bridge the gap between innate and adaptive immunity, have in common the ability to provide a co-stimulus targeting immune cells (typically B cells or other APCs). Linkage of a molecular adjuvant to a hybrid WHcAg particle is contemplated to be advantageous in that the antigen-specific B cell or APC taking up the particle become activated, as opposed to the non-specific activation induced by merely mixing adjuvant and antigen.

Additionally in other embodiments, the hepadna virus core platforms are utilized in non-infectious disease situations, such as those requiring high level in vivo antibody production (as an alternative to monoclonal antibody therapy). For example, active immunization to elicit anti-TNFα therapeutic autoantibodies is contemplated to have a number of advantages over monoclonal anti-TNFα therapy for the treatment of arthritis and other inflammatory diseases.

Without limiting the invention, advantages of using modified WHcAg particle vaccine provided by the present invention include: i) WHcAg is equally or more immunogenic than the HBcAg at the T and B cell levels; ii) WHcAg will not substantially compromise the use of the anti-HBc diagnostic assay because the WHcAg and HBcAg are not substantially crossreactive at the antibody level; iii) pre-existing anti-HBc antibodies in HBV chronically infected patients or in previously infected and recovered persons may limit the efficacy of the HBcAg platform, whereas, the WHcAg and GSHcAg platforms do not bind pre-existing anti-HBc antibodies; (iv) immune tolerance in HBV chronic carriers can be circumvented by the use of the WHcAg, GSHcAg, and/or ArGSHcAg platform because the HBcAg is only partially crossreactive at the T cell level with WhcAg, GSHcAg, and/or ArGSHcAg; and v) the WhcAg, GSHcAg, and/or ArGSHcAg combinatorial technologies are more versatile than the HBcAg in terms of accommodating the insertion of a greater variety of foreign epitopes (Also see Table 2).

TABLE 2

Summary of Some Advantages Of Using WHcAg, GSHcAg, and/or ArGSHcAg as Vaccine Platforms

| No. | Advantage |
|---|---|
| 1 | Efficient self-assembly into 25-35 nm particles allowing for multivalency of inserted epitopes and combination vaccines. |
| 2 | Highly immunogenic during natural infection and vaccination. |
| 3 | 1-2 doses required in animal models. |
| 4 | A library comprising 17 insertion positions and 21 C-terminal modifications is provided by the current invention. |
| 5 | A combinatorial technology involving insert position, C-terminus and foreign sequence is provided by the current invention. |
| 6 | Linker residues permitting assembly of core particles containing destabilizing foreign sequences is provided by the current invention. |
| 7 | Th cell as well as B cell epitopes are accommodated on hybrid particles. |
| 8 | Hybrid particles elicit a broad spectrum of IgG isotypes. |
| 9 | Hybrid particles do not require an adjuvant, although immunogenicity can be enhanced by a metabolizable oil/alum depot effect. |
| 10 | Core particles can accommodate incorporation of a molecular adjuvant and/or immune enhancer. |
| 11 | Core particles can accommodate linkage of carbohydrate antigens and large non-linear protein antigens. |
| 12 | Hybrid particles are very stable (e.g., a cold chain is not necessarily required). |
| 13 | Use of core particles does not compromise the anti-HBc diagnostic assay. |
| 14 | Use of core particles avoids the problem of immune tolerance in HBV-infected individuals. |
| 15 | Recombinant core particles can be produced in E. coli, which is cost effective and scaleable. |
| 16 | Use of core particles avoids the problem of pre-existing anti-HBc antibodies. |

B. Ground Squirrel Hepatitis Virus (GSHV) and Arctic Ground Squirrel Hepatitis Virus (ArGHV)

In another embodiment, a second new combinatorial platform technology is developed by modification of the ground squirrel hepadna virus (GHV) core protein (GSHcAg) and the arctic ground squirrel hepadna virus (ArGHV) core protein (ArGHcAg). The GSHcAg is 91% identical at the amino acid level to the WHcAg. Modifications to the C-terminus of the of the GSHcAg and ArGHcAg proteins, similar to those described above for WHcAg, are made as shown in Tables 3-1 and 3-2.

Figure 5:
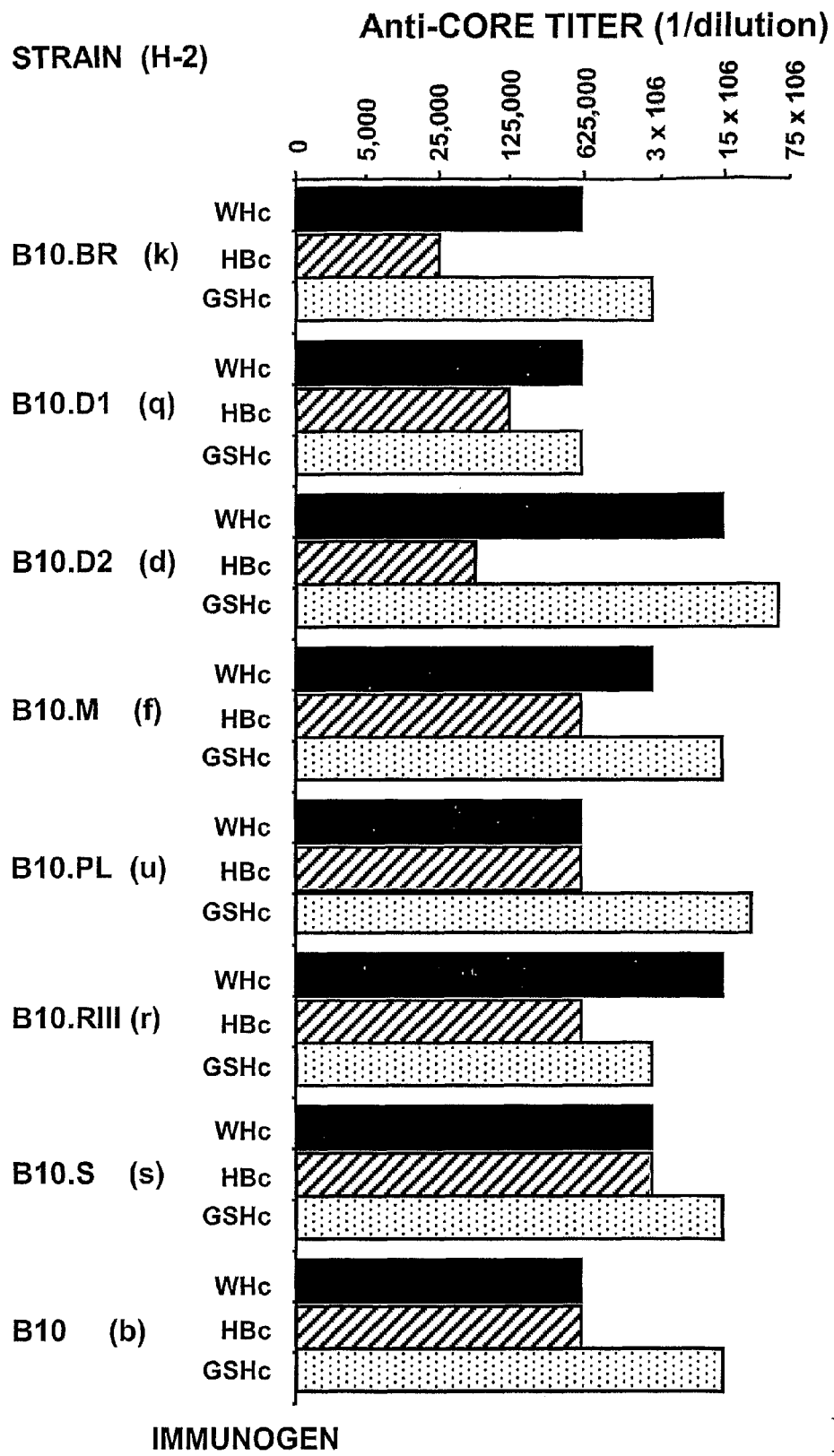

The GSHcAg is 67% identical at the amino acid level to the HBcAg and the comparative studies revealed that, the HBcAg and GSHcAg proteins do not significantly crossreact at the antibody level (FIG. 6 and Table 19) and only partially at the CD4$^+$ T cell level (Table 20 and FIG. 43). However, the GSHcAg and the WHcAg do show significant crossreactivity at both the antibody level (FIG. 6 and Table 19) and at the CD4$^+$ T cell level (Table 20 and FIG. 43). It is notable that the B cell crossreactivity between the GSHcAg and the WVcAg occurs outside the loop regions, which are variable between the GSHcAg and the WHcAg. For example, polyclonal anti-WHc antibodies recognize WHcAg 25-times better than GSHcAg, whereas, these same antibodies recognize WVcAg with a disrupted loop region (WHc Δloop) equivalently to GSHcAg and GSHcAg (Δloop). The reciprocal is also true, polyclonal anti-GSHc antibodies recognize GSHcAg 125-times better than WHcAg yet recognize WHcAg, WHc (Δloop) or GSHc (Δloop) equivalently (Table 19). Both anti-WHc and anti-GSHc antibodies demonstrate a significant degree of crossreactivity for Arctic Ground Squirrel Core particles (ArGSHc). Additionally, as shown in FIG. 5, the GSHcAg is an efficient immunogen. Whereas the WHcAg is more immunogenic than the HBcAg in 5 of 8H-2 congenic strains and equivalent in 3 other strains, the GSHcAg is equally or more immunogenic than the WHcAg in the 8H-2 congenic strains and more immunogenic than the HBcAg in all 8 strains.

In terms of T cell crossreactivity, the GSHcAg and the WHcAg demonstrate crossreactivity in all 8H-2 congenic strains, whereas the GSHcAg and the HBcAg demonstrate CD4+ T cell crossreactivity in 2 of 8 strains (Table 20). The basis for T cell crossreactivity between GSHcAg, WHcAg and HBcAg is demonstrated by T cell epitope mapping studies (FIG. 43). The GSHcAg and the WHcAg share at least 1 overlapping T cell epitope in all 8 strains examined, whereas the GSHcAg and HBcAg share overlapping T cell sites in 2 of 8 strains.

TABLE 3-1

Sequences of the C-Termini of the Ground Squirrel Vaccine Platform[1]

| Designation | GSHcAg C-Terminal Sequence | Identifier |
|---|---|---|
| wild type | RRRGGSRAARSPRRRTPSPRRRRSQS PRRRRSQSPASNC | SEQ ID NO: 22 |
| 150R | R | N/A |
| 150C | C | N/A |
| 150-2RC | RRC | N/A |
| 150-3RC | RRRC | SEQ ID NO: 3 |
| 150-4RC | RRRRC | SEQ ID NO: 4 |
| 150-3KC | KKKC | SEQ ID NO: 5 |
| 150-3AC | AAAC | SEQ ID NO: 6 |
| WT-R | AAGGSRAARSPSQSPSQSPASNC | SEQ ID NO: 23 |
| WT-R1 | AAGGSRAARSQSPSQSPASNC | SEQ ID NO: 24 |

TABLE 3-1-continued

Sequences of the C-Termini of the Ground Squirrel Vaccine Platform[1]

| Designation | GSHcAg C-Terminal Sequence | Identifier |
|---|---|---|
| WT-R2 | AAGGSRAARSQSSQSPASNC | SEQ ID NO: 25 |
| WT-R3 | AAGGSRAARSQSSQSASNC | SEQ ID NO: 26 |
| C-Long | RRGGSRAASQASNC | SEQ ID NO: 27 |
| C-Long(M1) | ARGGSRAASQASNC | SEQ ID NO: 28 |
| C-Long(M2) | RAGGSRAASQASNC | SEQ ID NO: 29 |
| C-Long(M3) | AAGGSRAASQASNC | SEQ ID NO: 30 |
| HyW | AAGRSPSQSPSQSRESQC | SEQ ID NO: 31 |
| HyW-1 | AAGRSPSQSPSQSPASNC | SEQ ID NO: 32 |
| HyW-2 | AAGRSPSQSPSQSASNC | SEQ ID NO: 33 |
| HyW-3 | AAGRSPSQSPQSASNC | SEQ ID NO: 34 |
| HyW-4 | AAGRSPSQSSQSASNC | SEQ ID NO: 35 |
| HyW-5 | AAGRSQSSQSASNC | SEQ ID NO: 36 |

[1]The wild type C-terminal sequence corresponds to positions 149-187. The full length protein sequence of GSHcAg is set forth herein as SEQ ID NO: 21, while the full length DNA sequence is set forth as SEQ ID NO: 39. Additionally, the wild type N-terminal protein sequence (corresponding to positions 1-148) is set forth as SEQ ID NO: 40.

TABLE 3-2

Sequences of the C-Termini of the Arctic Ground Squirrel Vaccine Platform[1]

| Designation | ArGSHcAg C-Terminal Sequence | Identifier |
|---|---|---|
| wild type | RRRGSARVVR-SPRRRTPSPRRR RSQSPRRRPQSPASNC | SEQ ID NO: 153 |
| 150R | R | N/A |
| 150C | C | N/A |
| 150-2RC | RRC | N/A |
| 150-3RC | RRRC | SEQ ID NO: 3 |
| 150-4RC | RRRRC | SEQ ID NO: 4 |
| 150-3KC | KKKC | SEQ ID NO: 5 |
| 150-3AC | AAAC | SEQ ID NO: 6 |
| WT-R | AAGSARVVRSPSQSPQS-PASNC | SEQ ID NO: 183 |
| WT-R1 | AAGSARVVRSSQSPQSPASNC | SEQ ID NO: 184 |
| WT-R2 | AAGSARVVRSSQSQSPASNC | SEQ ID NO: 185 |
| WT-R3 | AAGSARVVRSSQSQSASNC | SEQ ID NO: 186 |
| C-Long | RRGSARVVSQASNC | SEQ ID NO: 187 |
| C-Long(M1) | ARGSARVVSQASNC | SEQ ID NO: 188 |
| C-Long(M2) | RAGSARVVSQASNC | SEQ ID NO: 159 |
| C-Long(M3) | AAGSARVVSQASNC | SEQ ID NO: 190 |

TABLE 3-2-continued

Sequences of the C-Termini of the Arctic Ground Squirrel Vaccine Platform[1]

| Designation | ArGSHcAg C-Terminal Sequence | Identifier |
|---|---|---|
| HyW | AAGRSPSQSPQSRESQC | SEQ ID NO: 191 |
| HyW-1 | AAGRSPSQSPQSPASNC | SEQ ID NO: 192 |
| HyW-2 | AAGRSPSQSPQSASNC | SEQ ID NO: 193 |
| HyW-3 | AAGRSQSPQSASNC | SEQ ID NO: 194 |
| HyW-4 | AAGRSQSQSASNC | SEQ ID NO: 195 |
| HyW-5 | AAGRSQSQSASNC | SEQ ID NO: 196 |

[1]The wild type C-terminal protein sequence corresponds to positions 150-187. The full length protein sequence of ArGSHcAg is set forth herein as SEQ ID NO: 102, while the full length DNA sequence is set forth as SEQ D NO: 127. Additionally, the wild type N-terminal protein sequence (corresponding to positions 1-149) is set forth as SEQ ID NO: 154.

C. Avian Hepatitis Virus

In another embodiment, avian hepatitis virus core antigens (such as from duck, Ross' goose, Sheldgoose, heron, stork, etc.) may be modified as shown in Table 3-3.

TABLE 3-3

Sequences of the C-Termini of the Avian Vaccine Platform[1]

| Designation | Avian HcAg C-Terminal Sequence | Identifier |
|---|---|---|
| wild type duck | AQGGRKTSSGTRKPRGLEPRR RRKVKTTFVYGRRRSKSRERR APSPQRAGSPLPRSSSSHHRS PSPRK | SEQ ID NO: 163 |
| wild type duck | AQGGRKTTTGTRKPRGLEPRR RKVKTTVVYGRRRSKSRERRA PTPQRAGSPLPRSSSSHHRSP SPRK | SEQ ID NO: 165 |
| wild type duck | AQGGRKTSSGTRKPRGLEPRR RKVKTTVVYGRRRSKSRDRRA PSPQRAGSPLPRSSSSHHRSP SPRK | SEQ ID NO: 167 |
| wild type duck | AQGGRKTSSGTRKPRGLEPRR RKVKTTVVYGRRRSKSRERRA PSPQRAGSPLPRSSSSHHRSP SPRK | SEQ ID NOs: 169, 171, 173 |
| wild type Ross' goose | AQGGRNKTQGVRKSRGLEPRR RRVKTTIVYGRRRSKSRERRA PTPQRAGSPLPRTSRDHHRSP SPRE | SEQ ID NO: 175 |
| wild type Sheldgoose | AQGGRNKTQGSRKPRGLQPRR RKVKTTVVYGRRRSKSRDRRA PSPQRAGSPLPRPSTSHHRSP SPRK | SEQ ID NO: 177 |
| wild type heron | AQGGRNQTKGTRKPRGLEPRR RKVKTTVVYGRRRSKSRGRRS SPSQRAGSPLPRNRGNQTRSP SPRE | SEQ ID NO: 179 |
| wild type stork | AQGGSRNQTKGVRKPRGLEPRR RKVKTTVVYGRRRSKSRGRRS SPSQRAGSPIPRNRENQSRSS SPRE | SEQ ID NO: 181 |

TABLE 3-3-continued

Sequences of the C-Termini of the Avian Vaccine Platform[1]

| Designation | Avian HcAg C-Terminal Sequence | Identifier |
|---|---|---|
| 150R | R | N/A |
| 150C | C | N/A |
| 150-2RC | RRC | N/A |
| 150-3RC | RRRC | SEQ ID NO: 3 |
| 150-4RC | RRRRC | SEQ ID NO: 4 |
| 150-3KC | KKKC | SEQ ID NO: 5 |
| 150-3AC | AAAC | SEQ ID NO: 6 |
| WT-R | AAGGERGVRS TABLE 4-2-continued Sequences of the C-Termini of the Woolly Monkey Vaccine Platform[1]

| Designation | WMHcAg C-Terminal Sequence | Identifier |
|---|---|---|
| 150-3AC | AAAC | SEQ ID NO: 6 |
| WT-R | AARPSPSQSPSQSPASSC | SEQ ID NO: 197 |
| WT-R1 | AARPSQSPSQSPASSC | SEQ ID NO: 198 |
| WT-R2 | AARPSQSSQSPASSC | SEQ ID NO: 199 |
| WT-R3 | AARPSQSSQSASSC | SEQ ID NO: 200 |
| C-Long | RRGSQSRRSQSSC | SEQ ID NO: 201 |
| C-Long(M1) | ARGSQSRRSQSSC | SEQ ID NO: 202 |
| C-Long(M2) | RAGSQSRRSQSSC | SEQ ID NO: 203 |
| C-Long(M3) | AAGSQSRRSQSSC | SEQ ID NO: 204 |
| HyW | AARRRPSQSPSQSPASSC | SEQ ID NO: 205 |
| HyW-1 | AARRRPSQSPSQSASSC | SEQ ID NO: 206 |
| HyW-2 | AARRRPSQSPSQSSSC | SEQ ID NO: 207 |
| HyW-3 | AARRSQSPSQSSSC | SEQ ID NO: 208 |
| HyW-4 | AARRSPSQSSQSSSC | SEQ ID NO: 209 |
| HyW-5 | AARRSQSSQSSSC | SEQ ID NO: 210 |

[1]The wild type C-terminal protein sequence corresponds to positions 150-182. The full length protein sequence of WMHcAg is set forth herein as SEQ ID NO: 118, while the full length DNA sequence is set forth as SEQ ID NO: 135. Additionally, the wild type N-terminal protein sequence (corresponding to positions 1-149) is set forth as SEQ ID NO: 156.

TABLE 4-3

Sequences of the C-Termini of the Orangutan, Gibbon, and Chimpanzee Vaccine Platform[1]

| Designation | Orangutan, Gibbon, and Chimpanzee Ag C-Terminal Sequence | Identifier |
|---|---|---|
| wild type | RRRGRSPRRRTPSPRRRRSQS PRRRSQSPASQC | SEQ ID NO: 157, 159 and 161 |
| 150R | R | N/A |
| 150C | C | N/A |
| 150-2RC | RRC | N/A |
| 150-3RC | RRRC | SEQ ID NO: 3 |
| 150-4RC | RRRRC | SEQ ID NO: 4 |
| 150-3KC | KKKC | SEQ ID NO: 5 |
| 150-3AC | AAAC | SEQ ID NO: 6 |
| WT-R | AAGRSPSQSPSQSPASQC | SEQ 1iD NO: 211 |
| WT-R1 | AAGRSPSQSPSQSPASQC | SEQ IIJ NO: 212 |
| WT-R2 | AAGRSQSSQSPASQC | SEQ ID NO: 213 |
| WT-R3 | AAGRSQSSQSASQC | SEQ ID NO: 214 |
| C-Long | RRGSQSPASQC | SEQ ID NO: 215 |

TABLE 4-3-continued

Sequences of the C-Termini of the Orangutan, Gibbon, and Chimpanzee Vaccine Platform[1]

| Designation | Orangutan, Gibbon, and Chimpanzee Ag C-Terminal Sequence | Identifier |
|---|---|---|
| C-Long(M1) | ARGSQSPASQC | SEQ ID NO: 216 |
| C-Long(M2) | RAGSQSPASQC | SEQ ID NO: 217 |
| C-Long(M3) | AAGSQSPASQC | SEQ ID NO: 218 |
| HyW | AAGRSPSQSPSQSPASQC | SEQ ID NO: 219 |
| HyW-1 | AAGRSPSQSPSQSASQC | SEQ ID NO: 220 |
| HyW-2 | AAGRSPSQSPSQSASQC | SEQ ID NO: 221 |
| HyW-3 | AAGRSQSPSQSASQC | SEQ ID NO: 222 |
| HyW-4 | AAGRSPSQSSQSASQC | SEQ ID NO: 223 |
| HyW-5 | AAGRSQSSQSASQC | SEQ ID NO: 224 |

[1]The wild type C-terminal protein sequence corresponds to positions 150-183. The full length protein sequence of Orangutan HcAg, Gibbon HcAg, and Chimpanzee HcAg, are set forth herein as SEQ ID NO: 117, 116, 115, respectively, while the full length DNA sequences are set forth as SEQ ID NOs:134, 136, 137, respectively. Additionally, the wild type N-terminal protein sequences (corresponding to positions 1-149) are set forth as SEQ ID NOs:158, 160, and 162, respectively.

IV. Additional Modifications to the WHcAg Vaccine Platform

In some embodiments, the 188 amino acid wild-type (WT) WHcAg is further modified by recombinant technology to increase the number of potential insertion sites. The WT WHcAg core gene is modified by creating and inserting unique cloning restriction nucleic acid sequences flanked by the conserved ends. The number of sites per core gene is varied to obtain bi or multivalent particles. In particular additional insertion sites are created in the following locations: i) in the alpha-helical core regions forming the stem of the spike, and ii) in the N-terminal and non-helical regions of the protein. Different cloning restriction sites are used at different positions, and different linkers are used with different heterologous inserted sequences.

The pUCWHc vector expressing the WHcAg sequence under the control of the Lac Operon promoter is inserted between Nco1-BamH1 sites for subcloning convenience. The foreign inserted sequences are designed as follows: i) for small linear peptidic epitopes, direct synthesis of the corresponding nucleotide sequences is done in order to flank the foreign sequence with the desired unique restriction site(s) created on the plasmid; ii) for larger protein fragments, the foreign sequence is first obtained by PCR from plasmids encoding the complete corresponding gene, and modified accordingly with unique flanking restriction sites.

A. Creation of New Insertion Sites

Figure 20:
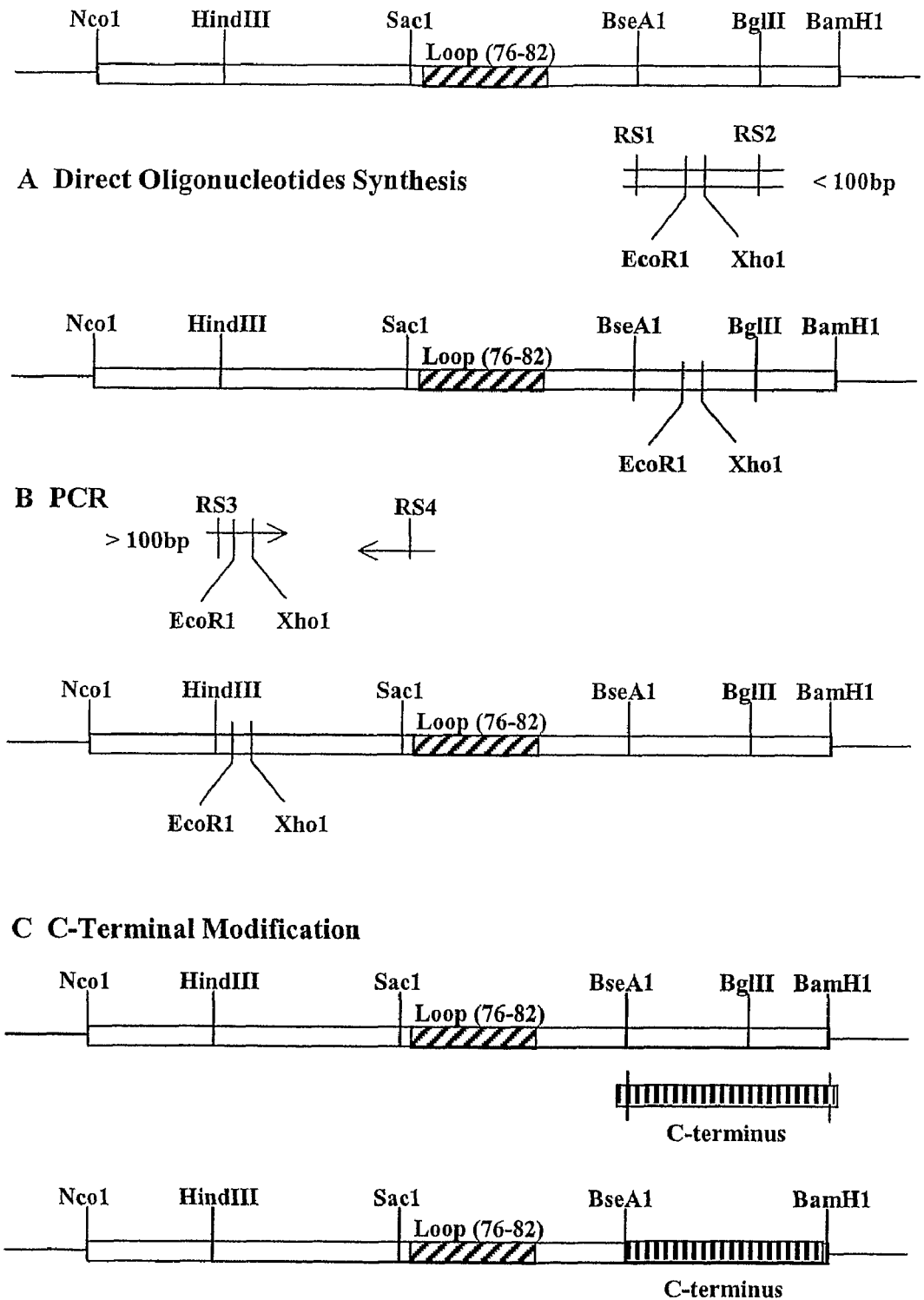

All insertions are accomplished by either using the EcoR1-Xho1 sites or SacI sites, with the position of the insertion differing between contructs (See, FIG. 20). Accordingly, new primers/oligonucleotides are designed in order to encompass either one or two restriction sites present on the wild-type WHcAg gene and to code for 5'EcoR1-3'Xho1 sites or SacI sites.

1. Direct Synthesis of Sense and Antisense Oligonucleotides

The oligonucleotides span two other WHcAg gene restriction sites (e.g., RS1, RS2) and do not exceed 100 nucleotides in length (limit for direct synthesis). Both the plasmid pUC-WT and the oligonucleotides are then digested by the RS1 and RS2 enzymes and purified from a low-melting point agarose gel. The RS1-EcoR1-Xho1-RS2 fragment replaces the corresponding RS1-RS2 sequence of the pUC-WT plasmid via ligation to produce pUC-WTA insertion site (e.g., pUC WTA 98-99 corresponds to WT WHcAg gene with insertion between amino acids 98 and 99).

2. Design of PCR Primers

In some instances, the direct synthesis of oligonucleotides cannot be realized because the desired insertion site is distanced from one of two usable restriction sites of the WHcAg gene by more than 100 nucleotides. In these cases, one of the primers (forward or reverse depending on the desired orientation) is designed to match the exact sequence of the WT WHcAg gene and to include a unique restriction site (RS3). The other primer is designed to create a mismatch (PCR mutagenesis) from the WT sequence and to introduce EcoR1-Xho1 sites, plus an RS4 site belonging to the WT gene. PCR with the forward-RS3, and the reverse-EcoR1-Xho1-RS4 primers is performed using the pUC-WT plasmid as a template. The resulting PCR product and the pUC-WT plasmid are then digested by RS3-RS4 and ligated to create the new pUC-WTA insertion site. Linkers are used when necessary to accommodate foreign sequences such as for insertion of large fragments (Kratz et al., Proc Natl Acad Sci USA, 96:1915-1920, 1999). By creating 5' EcoR1-Aho1 3' as insertion sites, and keeping the same reading frame as that of the WT WHcAg gene, each foreign sequence is flanked by the same linker, Gly-Ile-Leu on their N-terminus, and Leu-Glu on their C-terminus. Similarly by creating 5' SacI-SacI 3' as insertion sites, and keeping the same reading frame as that of the WT WHcAg gene, each foreign sequence is flanked by the same linker, Ser-Ser, on both their N- and C-termini. The following primer sequence containing both EcoR1 and Aho1 restriction sites, GGAAATTCTTCTCCTCGAG (SEQ ID NO:63) is used for this purpose. Similarly, others sequences are introduced to code for new linkers (e.g., Gly4-S-Gly4) on each side of the foreign sequence.

B. Modifications of the C-Terminus

The library of C-termini is expanded to eliminate certain motifs (e.g., RNA/DNA binding motifs) and to accommodate the addition of other linker/spacer sequences. As described below in the examples, modifications of the C-terminus that enhance expression/assembly and/or antigenicity/immunogenicity of various hybrid core constructs have been characterized. The new C-termini are modified by designing oligonucleotides encoding the sequence of interest and flanked by 5' BseA1 and 3' BamH1 sites as a general pattern, and then using the oligonucleotides to replace the corresponding native fragment on the pUC-WT plasmid. All the WHcAg constructs (insert sites, C-termini, +/–foreign sequences) are sequenced in both directions at an automated sequencing facility. The hybrid WHcAg constructs (pUC vectors) are then used to transform chemically-competent Top10 E. coli by heat shock. The transformed Top 10 grow overnight at low temperature 28° C. to avoid inclusion body formation, before the expression of the protein is induced by addition of IPTG (1 mM for 4 h). The bacteria are lysed in a lysozyme-salt solution containing proteolysis inhibitors. The resulting supernatant is precipitated overnight in the cold with 50% ammonium sulfate. The proteins are then purified by chromatography on hydroxylapatite and Sepharose 4B columns. In some embodiments, for better and tighter control of the expression, each hybrid WHcAg construct is subcloned into another expression vector, pET11d, at the Nco1-BamH1 sites. The pET11d vector allows expression of the corresponding protein under an inducible T7/Lac Operon promoter. These hybrid constructs are then transformed in the BL21 (DE3) E. coli strain.

C. Rapid Screening Technology

Figure 21:
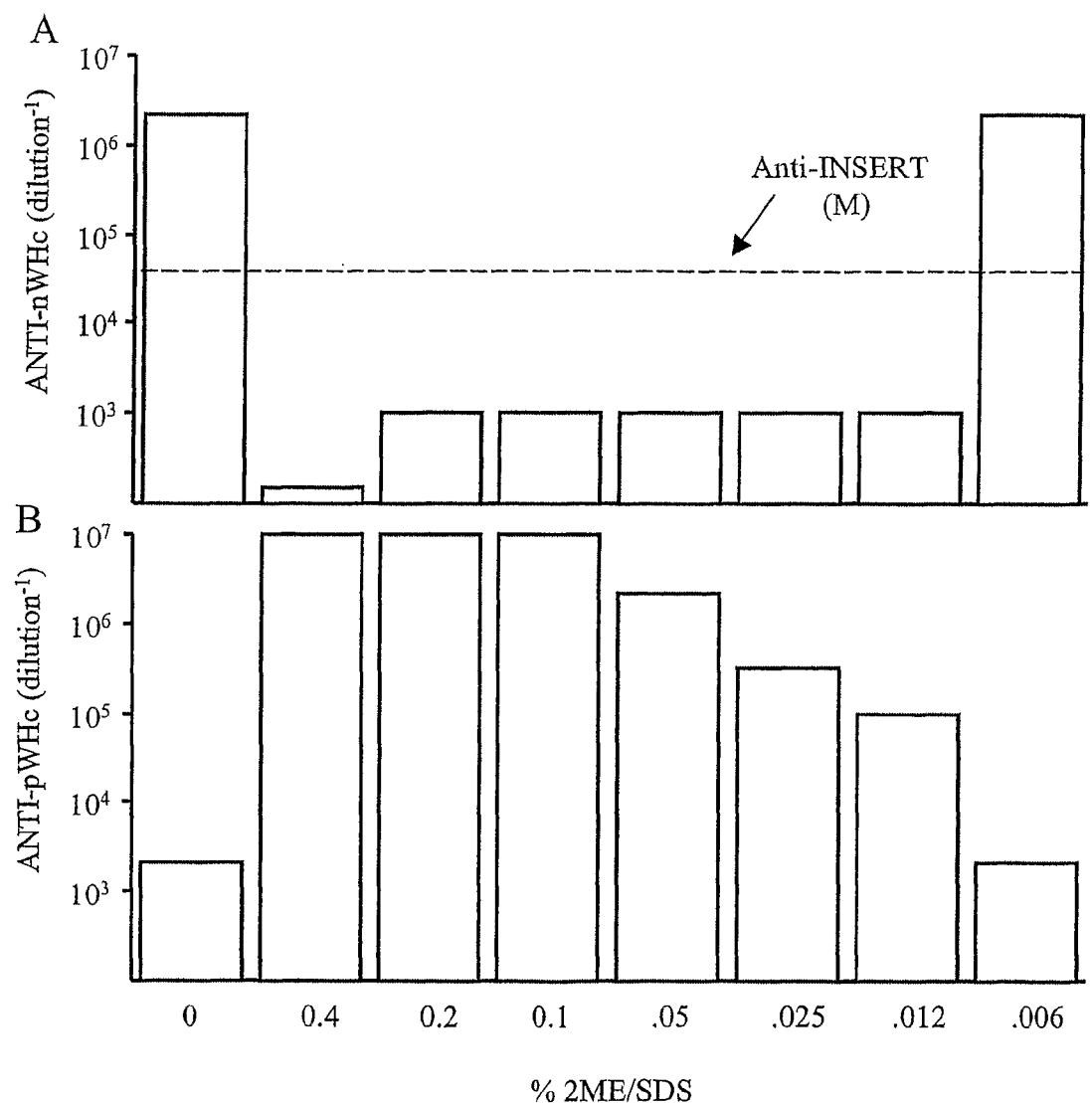

The approach of combining the optimal C-terminus from a selection of 21 termini and the optimal insert position from a choice of 17 positions, in the context of a given epitope requires a rapid screening technology that can be applied early in the manufacturing process. Therefore, an antibody-based method for detecting expression of core polypeptide, assembly of polypeptide into core hybrid particles and for assessing antigenicity of the inserted heterologous epitope has been developed. This rapid screening technique is applied to lysates of the transformed E. coli to assess the desirability of any given hybrid core before a significant investment in vaccine production is made. As described in the examples, capture ELISAs were designed either to detect the WHcAg polypeptide as a marker of expression or to detect the WHcAg particle as a marker for assembly, while insert-specific mAbs were used to assess the expression level and antigenicity of the insert (See, FIG. 21). Lysates were sequentially screened with mAbs that preferentially recognize denatured WHcAg (anti-pWHc), assembled WHcAg particles (anti-nWHc), and proper display of insert sequence (insert-specific mAbs). Based on relative assembly scores of the lysates, optimal hybrid particle gene constructs were selected for further purification. The assembly score was based on the dilution of detecting antibody that binds the hybrid particle relative to its binding to wild-type WHcAg. A strong correlation between the relative lysate assembly scores and the ability to purify hybrid core particles in high yield has been observed during development of the present invention. Every hybrid particle construct with an assembly score of three or greater in the transformed bacterial lysate has yielded easily-purifiable particles. In contrast, constructs with assembly scores of two or less have been problematic to purify (Table 11).

V. Antigenic and Immunogenic Characterization of WHcAg-Hybrid Particles

A. Epitope Selection

A group of model epitopes/antigens has been selected for use to further develop the WHcAg platform technology. Three categories of antigens are examined: (1) peptidic epitopes are inserted using recombinant methods; (2) polysaccharide (PS) antigens are chemically conjugated to lysine-modified core particles; and (3) larger or non-linear protein antigens are incorporated onto core particles by recombinant or chemical methods. Selected peptidic epitopes include those shown in Table 9. Selected protein/polypeptide antigens include but are not limited to the Bacillus anthracis capsular polypeptide poly-gamma-D-glutamic acid, which has been chemically conjugated to WHcAg (See, FIG. 31).

B. Epitope Optimization on Hybrid Core Particles

Figure 22:
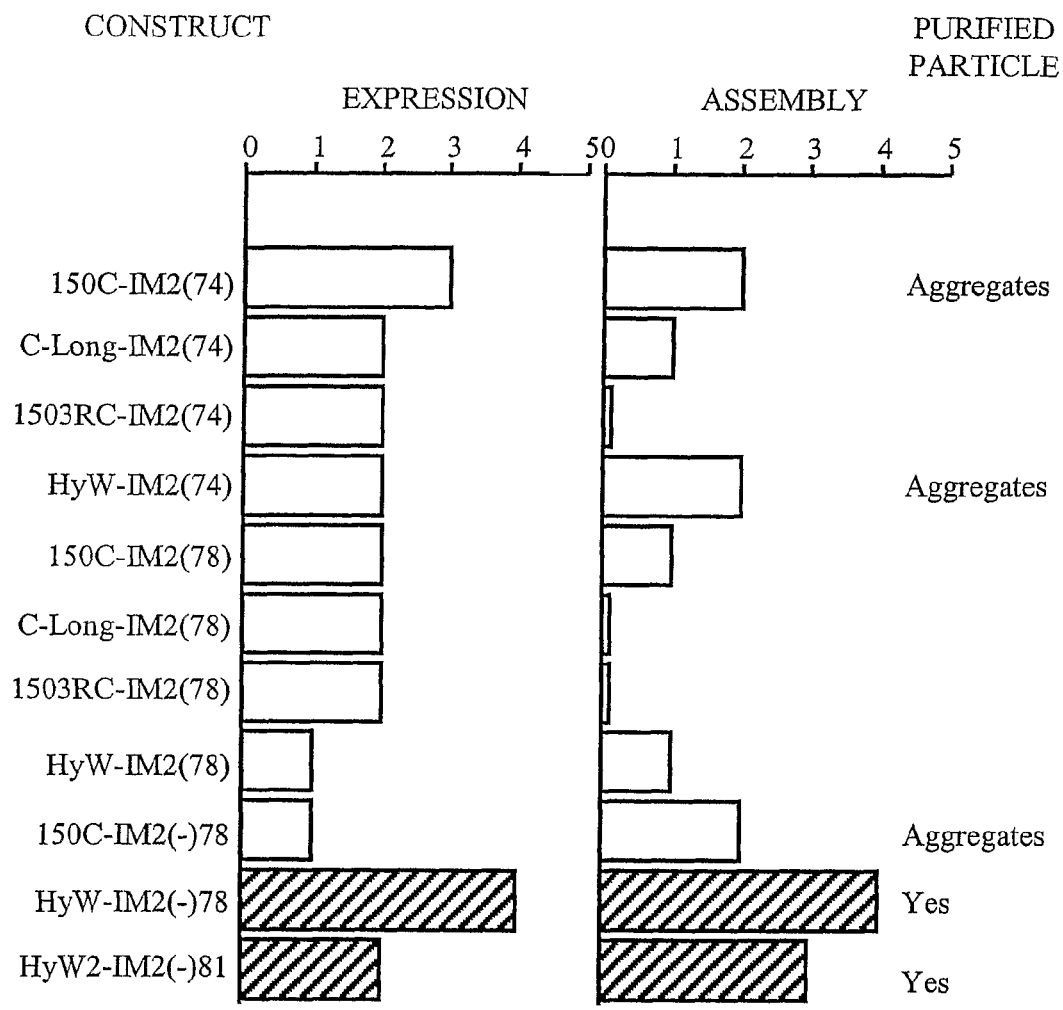

Because the inserted epitope sequence can effect hybrid core assembly or stability, it is useful to perform mutational analysis of the epitope in order to map the necessary antibody contact residues. Non-essential residues are subsequently substituted with other less disruptive residues as needed. This strategy is also useful for identifying analogs with improved antibody binding. The M2e epitope serves as an example of this strategy. A list of M2-WHcAg hybrid constructs (—IM2 series) with different C-termini and two different insert sites were produced and the relative expression levels and assembly competence scores are shown in FIG. 22. Note that all constructs harboring the wild-type M2e sequence either assembled poorly or were purified as aggregates instead of core particles. It is contemplated that the two cysteines in the wild-type M2e sequence result in inappropriate inter- or intra-particle disulfide bridges. Therefore, an M2e-specific mAb (14C2, which inhibits Influenza A growth of most strains) was tested for binding to a peptide analog panel, including cysteine-substituted peptides as shown in FIG. 23. Because substitution of either or both cysteine residues did not effect the binding of the 14C2 mAb, hybrid core constructs carrying the mutated M2e sequence, IM2(−), inserted at position 78 were produced. The IM2(−) sequence expressed in the context of the 150C C-terminus still resulted in aggregates during purification. However, the IM2(−) sequence inserted at position 78 in the context of the HyW-C-terminus allowed assembly and was easily purified (See, FIG. 22). Subsequently, other combinations of C-termini and insert positions have been found to accommodate the IM2(−) sequence, such as HyW2-IM2(−)81. These other M2e-WHcAg hybrid particles have also been tested for immunogenicity. Additional modifications to the M2e epitope are also done to optimize the hybrid WHcAg expression and particle assembly. In some embodiments, substitution of single cysteine residues (C16 and C18) have been made, and multiple copies of a M2e(−) truncated sequence were inserted. Note that P4 (a 15-mer) also bound mAb 14C2 efficiently, as did the polyclonal anti-HyW-IM2(−)78 antisera (See, FIG. 23).

C. Antigenicity

Prior to in vivo immunogenicity testing all purified hybrid WHcAg particles are characterized for antigen expression at the B cell level by measuring the ability to bind polyclonal or mAbs specific for the WHcAg carrier and the peptidic, protein or PS insert. The same capture ELISA system used to detect hybrid WHcAg particles in bacterial lysates is used for purified particles. T cell antigenicity is determined by assessing the ability of the hybrid WHcAg particles to activate core-specific T cells in vitro. For this purpose naive splenic T cells from T cell receptor (TCR) transgenic (Tg) (7/16-5-TCR) mice which have a high frequency of HBcAg-specific CD4$^+$ T cells (~50%) are used. The 7/16-5 TCR crossreacts with HBcAg and WHcAg as it recognizes HBcAg$_{129-140}$ presented by IA$^b$ and this sequence is very similar between HBcAg and WHcAg. After a 2 day culture of 7/16-5-TCR spleen cells with HBcAg/WHcAg, the IL-2 that is secreted into the supernatant (SN) is measured by ELISA (See, FIGS. 24 and 25). This is a convenient and rapid screen to check if any of the modifications to the WHcAg protein have disrupted core-specific T cell recognition. Additional WHcAg-specific TCR-Tg lineages that recognize different T cell sites are similarly employed (Chen et al., J. Virol. 74: 7587-7599, 2000). In cases when a pathogen-specific heterologous CD4$^+$ T cell epitope is inserted into the hybrid core particle, mice of the appropriate H-2 haplotype (e.g., high responder) are immunized with the hybrid particle (10 μg, subcutaneously in IFA) and draining lymph node cells are harvested 7-10 days later for culture with the heterologous peptide, as well as a WHcAg-derived peptide panel. T cell activation and specificity is determined by cytokine production (IL-2, IL-4, IFNγ) recalled by the peptide antigen panel. Cytokines are measured in 2 day (IL-2) or 4 day (IL-4, IFNγ) SNs by ELISA.

D. Immunogenicity

The immune response to hybrid-WHcAg particles and WHcAg-PS conjugates is examined in detail. In addition to anti-insert or anti-PS and anti-WHcAg antibody end-point titers, antibody specificity, isotype distribution, antibody persistence and antibody avidity are monitored. Examples of these assays are provided below. In vivo immune responses to PS-WHcAg conjugates are compared to free PS and to the same PS linked to other protein carriers (e.g., tetanus toxoid).

In vivo antibody production is studied in inbred murine strains, in athymic mice, in H-2 congenic mice, and in core-specific TCR-Tg mice. The use of these strains permits the evaluation of non-H-2 and H-2 dependent genetic influences on immune responsiveness, as well as T cell independence (athymic mice). In addition, the TCR-Tg mice permit the screening of a number of hybrid particles/conjugates rapidly in vivo (e.g., 2-4 weeks), because the kinetics of antibody production to the WHcAg carrier and inserted epitopes is accelerated in these mice.

Carrier-specific and insert-specific Th cell immunogenicity is monitored by assessing T cell activation, fine-specificity and cytokine production. For B cell peptidic epitopes inserted into WHcAg, or PS antigens linked to WHcAg, the source of T cell help is predictably WHcAg-specific Th cells. However, if peptidic T cell sites are inserted into WHcAg or larger protein fragments are incorporated into WHcAg particles, then the source of functional T cell help is not readily apparent. To determine if exogenous T cell sites are functional, mutant core particles with a single substitution at residue 132 (Y132A) have been produced. The tyrosine at position 132 represents a dominant aggretopic (MHC-binding) residue in H-2$^b$ mice, and this alanine substitution converts H-2$^b$ mice into WHcAg-nonresponders at the Th cell level. Therefore, production of hybrid WHcAg particles containing the Y132A mutation in WHcAg allow the T cell helper function of the exogenous T cell site to be measured as a function of in vivo antibody production to the inserted B cell epitope.

E. In Vitro Correlates of the Immune Response to Hybrid Core Particles

The hepatitis core proteins are extremely immunogenic in vivo during natural infection and as immunogens. It is contemplated that in vitro correlates of immunogenicity can serve as rapid screening methods to circumvent long term in vivo studies.

1. Induction of Costimulatory Molecules and T Cell Activation

Figure 24:
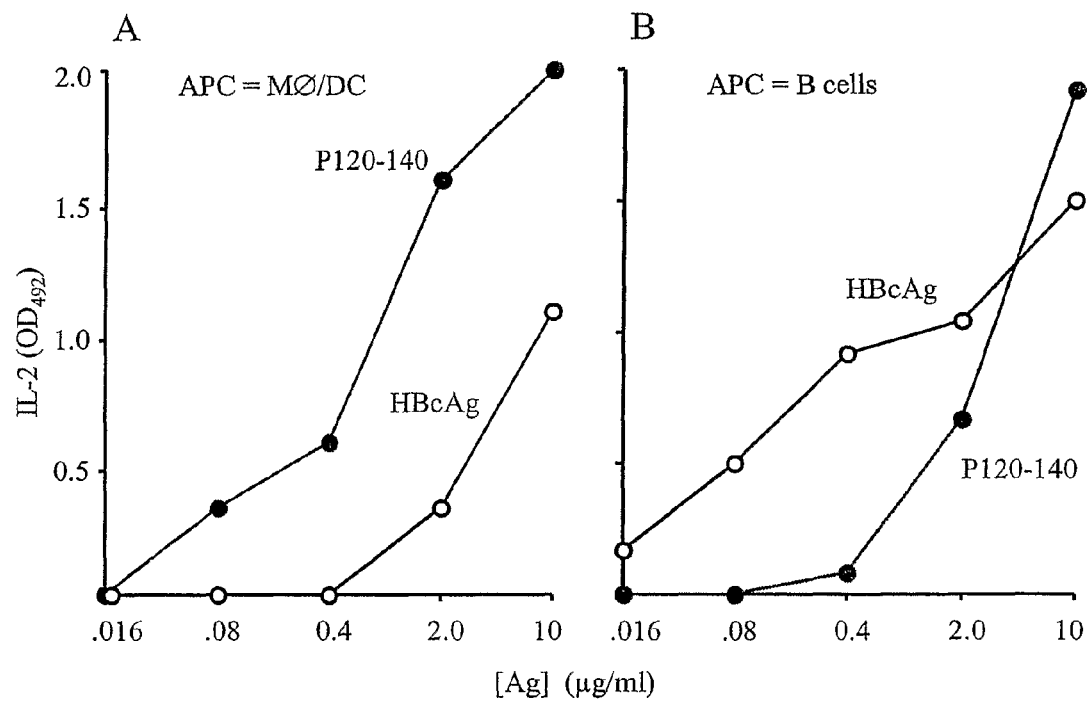
Figure 25:
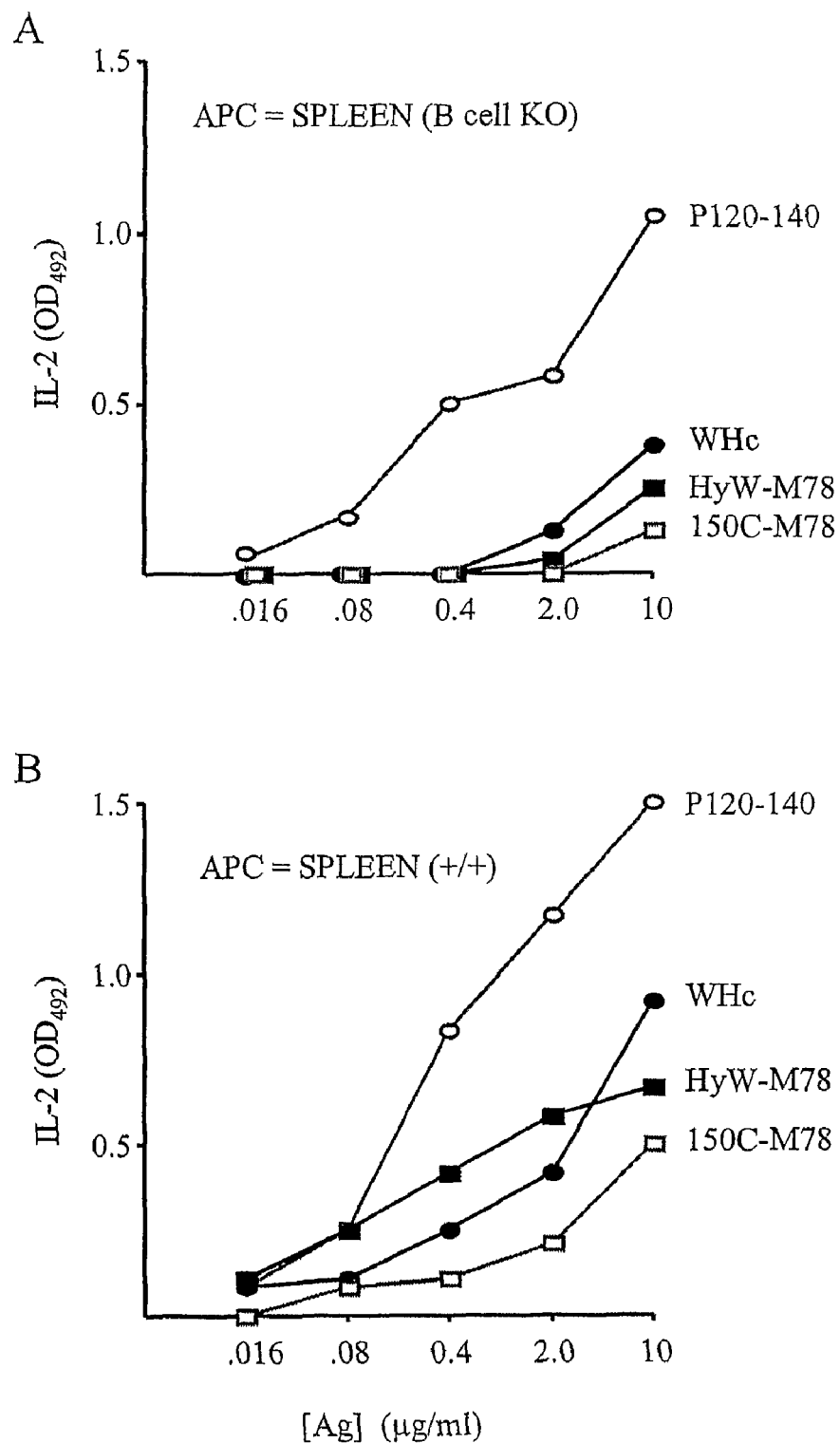
Figure 26:
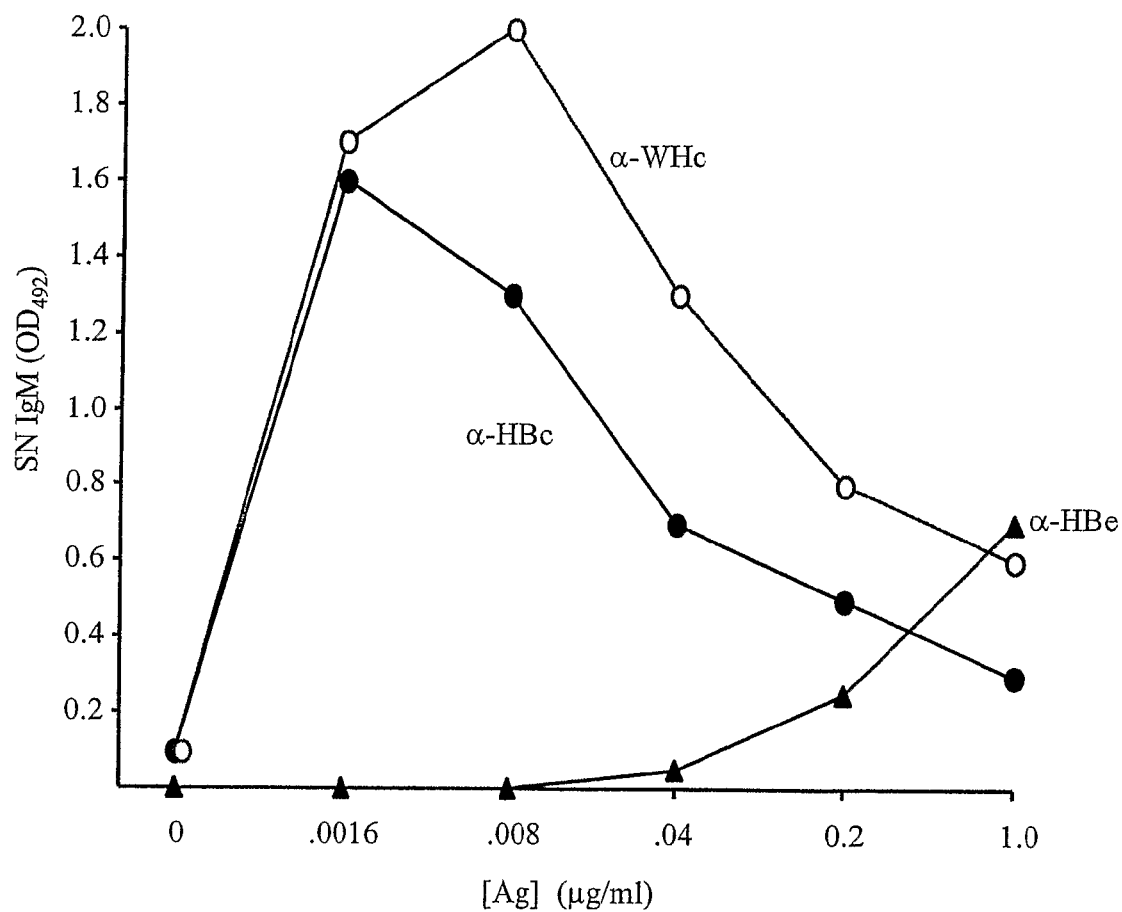
FIG. 26 shows the magnitude of the in vitro primary antibody response elicited by HBc, HBe, and WHc. Briefly, spleen cells derived from core-specific TCR-Tg mice were cultured for 5 days in the presence of the indicated antigen before SNs were collected and analyzed for the respective IgM antibodies by ELISA.
Figure 27:
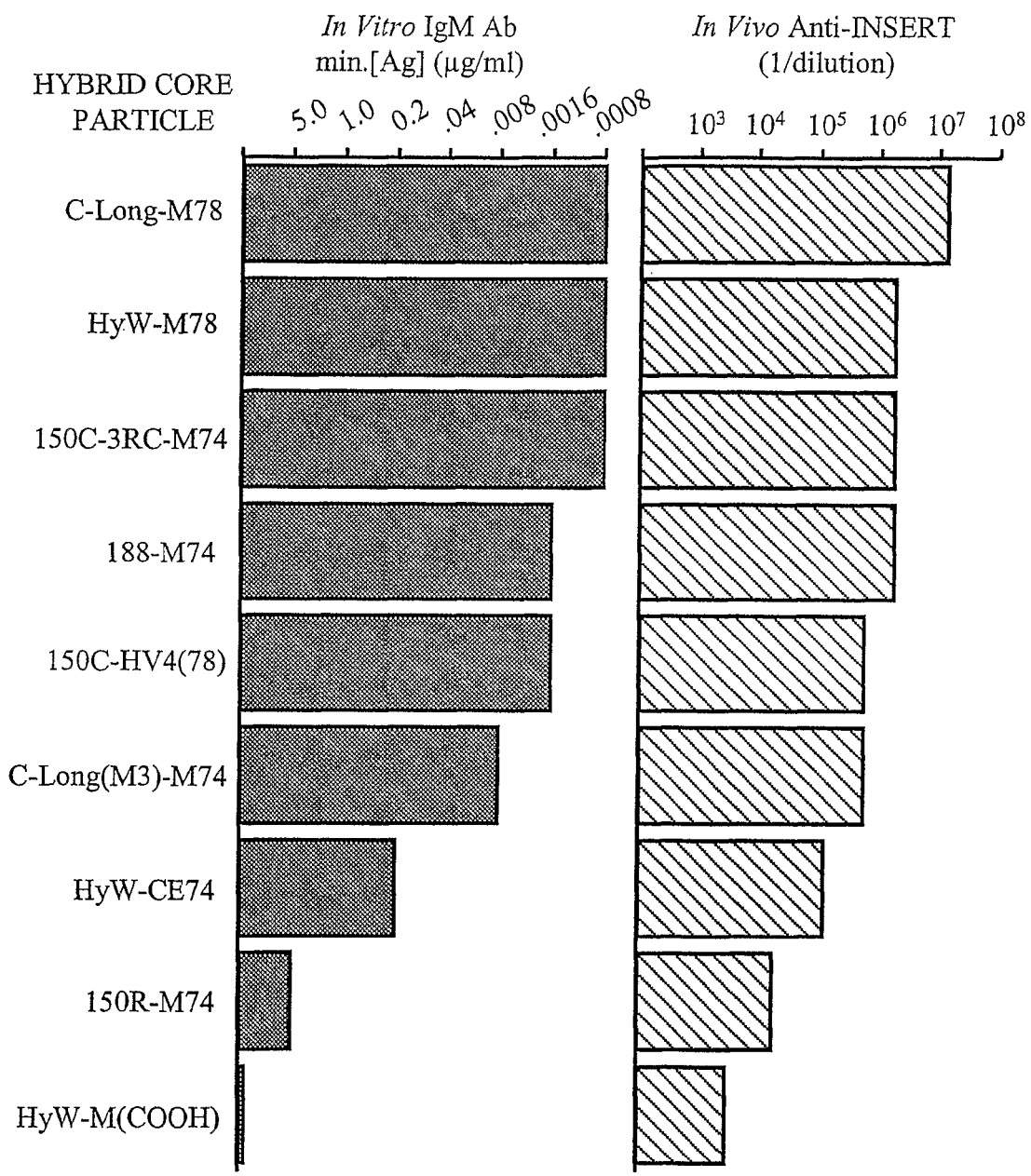
FIG. 27 illustrates the correlation observed between in vivo anti-insert IgG antibody production and primary in vitro IgM antibody production. In vitro IgM was determined by ELISA, using the respective hybrid particles as solid phase ligands, while the in vivo anti-insert IgG level was measured on solid phase peptides.

In vitro culture of naive resting murine B cells with native HBcAg or WHcAg sufficiently crosslinks mIg receptors on core-specific B cells for induction of the costimulatory B7.2 (24 hrs.) and B7.1 (72 hrs.) molecules (Milich et al., Proc Natl Acad Sci, USA, 94:14648-14653, 1997). The HBV envelope particulate antigen (HBsAg) does not demonstrate this property nor do many non-particulate experimental antigens (e.g., hen egg lysozyme, pigeon cytochrome C, etc.). This property is important because it allows naive, resting B cells to become competent APC for primary T cells. FIG. 24 illustrates that naive B cells more efficiently present the HBcAg to naive CD4$^+$ cells derived from 7/16-5-TCR Tg mice than do the more classic APCs, splenic adherent cells (MØ/DC). In contrast, MØ/DC APC present peptide HBcAg 120-140 more efficiently than do B cells. Previously it has been shown that HBcAg-specific B cells are the primary APC in murine spleen cultures (Milich et al., supra, 1997), and that there is a high frequency (8%) of HBcAg-binding B cells among naive murine spleen cells (Lazdina et al., J Virol, 75:6367-6374, 2001), as well as in naive human PBL (Cao et al., J Virol, 75:6359-6366, 2001). Preliminary studies illustrate that the WHcAg and hybrid-WHcAg particles containing malaria inserts in the loop are also preferentially presented to T cells by naive splenic B cells (See, FIG. 25). To confirm that this B cell APC function is dependent upon induction of B7.1 and B7.2 costimulatory molecules a variety of WHcAg-hybrid particles are cultured with naive resting, splenic B cells over a 72 hour period. Induction of B7.1 and B7.2 mRNA is then measured by RT-PCR, and expression of B7.1 and B7.2 protein is measured by FACs analysis. WHcAg hybrid particles differing in number of inserts, position of those inserts, and C-termini are compared to identify correlations between structure and induction of B7.2 and/or B7.1. Inhibition of B7.2/B7.1 induction with anti-mIg and anti-insert monoclonal antibodies is contemplated to confirm that B7.2/B7.1 induction is mediated through crosslinking of the antigen-specific mIg receptor.

2. In Vitro Primary Antibody Production as an In Vitro Model of Immunogenicity

It is contemplated that like T cell activation, that anti-core antibody production is mediated through core antigen-specific B cells acting as the primary APC source. Indeed, after five days in culture with either HBcAg or WHcAg, spleen cells from 7/16-5 TCR-Tg mice were shown to produce high levels of IgM anti-HBc or anti-WHc (See, FIG. 26). Strikingly, the WHcAg induced higher levels of IgM anti-core antibody than did the HBcAg at all antigen concentrations. During development of the present invention, In vitro IgM anti-core production was found to: (1) require core-specific T cells since this response does not occur in non-$TCR^+$ control splenic cultures; (2) require particulate core antigens since non-particulate HBeAg or WHeAg elicit low levels of antibody; and (3) be antigen-specific since the IgM anti-HBc and anti-WHc antibodies produced are non-crossreactive. To determine the generality of this finding, a variety of hybrid WHcAg particles containing different inserted epitopes at different positions with varying C-termini were tested in the in vitro IgM antibody production assay using 7/16-5-TCR spleen cells. Indeed, as shown in FIG. 27, hybrid core particles did elicit in vitro IgM antibody production variably from high levels to no antibody. Importantly, the level of in vitro IgM antibody production positively correlated with anti-insert IgG antibody production in vivo after primary immunization with hybrid WHcAg particles. Thus, substitution of primary in vitro IgM production for in vivo immunization is contemplated to be an efficient method for screening large numbers of hybrid WHcAg particles relatively quickly. Interestingly, the IgM antibodies present in the SNs bind to their respective hybrid WHcAg particles better than to native WHcAg, and better than to their respective peptide inserts. Thus, the IgM antibodies are contemplated to recognize a combined structural component on the surface of the hybrid particles F. Functional Characteristics of Immune Responses to Hybrid Core Particles As many of the heterologous epitopes utilized are engineered or weak peptidic and PS epitopes, it is important to determine the extent to which antibodies induced by hybrid WHcAg particle or core-glycoconjugate immunization recognize the native antigen (preferably in the context of the pathogen). For instance, anti-M2e antibodies elicited by immunization with HyW-IM2(−)78 particles recognize native M2 in Influenza A infected cell cultures (See, FIG. 34). In some embodiments when it is not practical to test antibody binding on the pathogen, at least a purified native protein is also tested. For example anti-$SEB_{140-151}$ and anti-$SEB_{152-161}$ antisera are tested by ELISA on a panel of SEs. Similarly IgG antibody avidity for the native protein is determined. For this purpose, Na SCN is used as a chaotropic agent as previously described (Anttila et al., J Infect Dis, 177:1614-1621, 1998). The basic ELISA is performed with one exception, before the detecting antibody is introduced, 100 μl of 0.5M Na SCN in PBS or PBS alone is added to each microtiter well for 15 minutes at RT. The wells are then washed four times and the ELISA is completed as usual. The results are expressed as avidity indices (e.g., titer with Na SCN/titer without Na SCN)×100.

1. Antibody Function

For example, anti-M2e antisera is assayed for in vitro plaque size reduction (See, FIG. 35), as a measure of antibody function. Another example involves an analysis of antibodies reactive with SEB (a super antigen for $V\beta8^{+}\pi T$ cells). Both the $SEB_{140-151}$ and $SEB_{152-161}$ peptides and antibodies have been shown to inhibit human Vβ8+T cell activation in vitro (Arad et al., Nat Med, 6:414-421, 2000; and Visvanathan et al., Infect Immunol, 69:875-884, 2001). Similarly, passive transfer of anti-$SEB_{152-161}$ and anti-$SEB_{140-151}$ antisera have been shown to protect mice against a lethal intra-peritoneal challenge with SEB and LPS. Although mice are not very sensitive to SE-induced toxic shock, Balb/c mice primed with D-galactosamine (20 mg) followed by low dose LPS (1-10 ng) become extremely sensitive to SEB (20 ng) and exhibit 100% lethality (Visvanathan et al., supra, 2001). Antisera generated by immunization with HyW2-SE75 is tested in these two functional assays. The host defense against many bacterial pathogens depends on the opsonic activity of anti-PS antibodies, the complement pathway, and phagocytosis by macrophages. Opsonic activity of mouse antisera to WHcAg-PS conjugates is determined in an opsonophagocytosis assay as described (DeVelasco et al, Vaccine, 12:1419-1422, 1994). Fluorescein-labelled bacteria are opsonized with dilutions (0-20%) of heat-inactivated mouse antisera in the presence or absence of complement (2%). Anti-PS antibodies are neutralized prior to performing the assay. The mouse macrophage cell line RAW-264 ($10^7$ cells/ml) is used for phagocytosis of bacteria at a bacteria/macrophage ratio of 10:1. Macrophages are washed and analyzed by flow cytometry. The mean of the FITC-intensity of the cells in each sample is used to estimate the opsonic capacity of the antisera.

2. Immunization and Challenge Studies

Once hybrid WHcAg particles or WHcAg-PS conjugates have been optimized for immunogenicity and antibody function in vitro or via passive transfer of immune sera, immunization/challenge experiments are performed, dependent upon a number of factors. For example, the availability of an infectious model system, the biosafety level of the pathogen, and the appropriate collaborations with disease model experts. In one embodiment, challenge experiments are done using the Influenza A system.

VI. Expansion of the WHcAg Platform to Accommodate Non-Linear, Large Protein and Carbohydrate Epitopes A. Construct Design for Expression of Mosaic Core Particles The WHcAg platform technology is also applicable to non-linear larger domains or protein fragments. Insertion of larger amino acid sequences is advantageous not for presentation of a larger number of epitopes, but also to allow appropriate folding of conformational epitopes. Attempts to obtain stable large protein hybrid HBcAg particles have failed (Koletzki et al., J Gen Virol, 78:2049-2053, 1997), with the single exception of the entire green fluorescence protein inserted into the loop of the HBcAg (Kratz et al., Proc Natl Acad Sci USA, 96:1915-1920). In addition to the molecular adjuvants described below, the non-toxic C fragment of tetanus toxoid (TTFC) is used as a model protein antigen. Since challenge with tetanus toxoid (TT) is well established in the mouse model, expression of TTFC is used to evaluate the ability of a vaccine vector to elicit a protective antibody response. Recombinant particles with TTFC inserted at the N- or C-terminus or into the loop region of WHcAg are produced. In some embodiments, the incorporation of TTFC into core particles is accomplished by production of mosaic TTFC-WHcAg particles. Specifically, decreasing the number of large foreign sequences per hybrid WHcAg particle to be co-incorporated with unmodified WHcAg protein subunits is contemplated to overcome any steric hindrance. The following approach has been shown to be effective (Smiley and Minion, Gene, 134:33-40, 1993) and is compatible with the cloning and expression vectors (pUC, and pET11d) described herein, although other approaches are also suitable.

1. Co-Expression of Wild-Type and WHcAg Fusion Proteins Mediated by a Suppressor tRNA-Readthrough of a Stop Codon As shown in FIG. 28, oligonucleotides are generated to possess a TGA stop codon, as well as the coding information for an additional five amino acids predicted to form a coil secondary structure (Gly5). The oligonucleotides are annealed and the resulting duplex is inserted between the wild-type WHcAg and the fused protein (e.g., WHcAg-TTFC). The derivative plasmid (coding for the fusion WHcAg protein) is used to transform the E. coli K12 K802 strain or others bacterial strains that possesses an opal TGA-Trp suppressor tRNA under lac repressor control as one example (Smiley and Minion, supra 1993). This approach results in the co-expression of both the wild-type WHcAg protein (HyW) and the fusion-WHcAg protein (HyW-TTFC) in the same bacterial cell. To design the fusion-WHcAg core protein, several of the C-terminal modifications are tested to identify those that favor the expression/assembly of a mosaic core particle.

2. Co-Expression of Wild-Type and WHcAg Fusion Proteins by Using Differentially Inducible Plasmids As shown in FIG. 29, a second approach is taken which utilizes two plasmids differentially-induced to express the wild-type and the fusion-WHcAg proteins. In some embodiments, the constructs have been made in pUC18 as the cloning and expression vector, permitting IPTG-inducible expression due to the presence of the Lac promoter. For convenience, the gene coding for the wild-type WHcAg is subcloned into the pLEX expression vector. The pLex expression vector contains the strong $P_L$ promoter to drive the expression of the gene of interest (e.g., wild-type WHc gene). The $P_L$ promoter is controlled by the lambda cI repressor protein, which is expressed in the E. coli host (G1698 strain). The cI repressor was engineered into the bacterial chromosome under control of the tightly regulated trp promoter. The expression of the gene is induced by addition of tryptophan thereby suppressing the synthesis of the cI repressor. Therefore, the same E. coli (G1698) is co-transformed with pUC encoding the fusion-WHcAg protein and with pLEX encoding the wild-type WHcAg protein. The induction of expression of the proteins is then induced differentially by using IPTG and Tryptophan.

B. Traditional and Molecular Adjuvants

Although adjuvants are not required when using the WHcAg delivery system, some embodiments of the present invention employ traditional and/or molecular adjuvants. Specifically, immunization in saline effectively elicits anti-insert antibody production. However, formulation in non-inflammatory agents such as IFA (mineral oil), Montanide ISA 720 (squalene), and aluminum phosphate (AlPO$_4$), enhance immunogenicity (See, FIG. 30, Panel A). Additionally, administration of WHcAg results in the production of all four IgG isotypes, regardless of which if any adjuvant is employed (See, FIG. 30, Panel B). Inclusion of a CpG motif also enhances the primary response. Moreover, use of an inflammatory adjuvant such as the Ribi formulation is not more beneficial than is the use of non-inflammatory adjuvants, indicating that the benefits of the adjuvants result from a depot effect rather than from non-specific inflammation.

Thus, the core platform is used with no adjuvant or with non-inflammatory adjuvants depending upon the application and the quantity of antibody desired. In some embodiments of the present invention, IFA is used in murine studies, whereas alum or squalene is used in human studies.

In instances where it is desirable to deliver hybrid WHcAg particles in a single dose in saline (e.g., a nasal influenza A M2e-core post-exposure vaccine), a molecular adjuvant is employed. A number of molecular adjuvants are employed to bridge the gap between innate and adaptive immunity by providing a co-stimulus to target B cells or other APCs. For this purpose in some embodiments, the complement C3d fragment (GenBank Accession No. NM 009778) is employed, as two or three copies of C3d linked to the experimental antigen hen egg lysozyme (HEL) was shown to be three to four orders of magnitude more immunogenic than HEL alone (Dempsey et al., Science, 271:348-350, 1996), even in the absence of a traditional adjuvant. C3d targets antigen to B cell and follicular dendritic cells via binding to CD21, thereby costimulating B cells through its association with CD19, a B cell membrane protein that amplifies B cell activation (Tedder et al., Immunol Today, 15:437-442, 1994).

Similarly, soluble dimeric or trimeric forms of CD40L (GenBank Accession No. X65453) have been shown to bind and cross-link membrane CD40 sufficiently to induce B cell proliferation, costimulate Ig class switching, suppress B cell apoptosis and activate APC (Morris et al., J Biol Chem, 274: 418-423, 1999). Additional potential molecular adjuvants include but are not limited to: i) soluble BAFF (B cell activating factor belonging to the TNF family; GenBank Accession No. AF119383), which exclusively binds to B cells and functions as a potent B cell growth factor (Mackay and Browning, Nature Reviews Immunology, 2:465-475, 2002), ii) soluble LAG-3 (lymphocyte activation gene-3; GenBank Accession No. NM 008479), which binds MHC class II molecules with high avidity and elicits activation/maturation of dendritic cells (ElMir and Triebel, J Immunol, 164:5583-5589, 2000), and iii) immunostimulatory CpG oligodeoxynucleotides, which costimulate a variety of immune cells (Krieg et al., Nature, 374:546-549, 1995). In some embodiments, these molecules are linked to the C-terminus of hybrid core particles to activate the antigen-specific B cell or APC that takes up the particle, as opposed to the non-specific activation induced by merely mixing the adjuvants with antigen. Less than 100% substitution is desirable because of potential negative effects on particle assembly and/or overstimulation of the targeted cell. Therefore, in some embodiments, mosaic hybrid core particles carrying fewer adjuvant molecules are produced.

1. Inclusion of CpG Dinucleotides in Hybrid Core Particles

Unmethylated CpG dinucleotides have been shown to be potent immune activators of B cells and macrophages (Krieg et al., supra, 1995; and Davis et al, J Immunol, 160:870-876, 1998). Additionally, co-immunization of antigen and CpG dinucleotides (DN) enhances the immune response similar to traditional adjuvants. Two characteristics of the CpG effect include: i) B cell uptake is required for activation; and ii) the CpG motif preferentially activates B cells that simultaneously encounter their specific antigen. Given the non-specificity of the effects (e.g., all B cells will internalize CpG DN), large quantities of CpG DN are necessary in vivo.

Hybrid core-CS(NANP) particles are a very efficient method for delivery of CpG DN to the interior of antigen-specific B cells. A core-CpG DN complex directly binds to core-specific B cells, and B cell activation occurs due to crosslinking of the mIg receptor and simultaneous delivery of the CpG DN to the B cell interior. This permits efficient, selective delivery of CpG DN to activated, antigen-specific B cells (e.g., NANP-specific B cells in the case of core-CS hybrid particles). Indeed, preliminary data indicate that HBcAg or HBcAg-CS hybrid particles carrying bacterial RNA/DNA are more immunogenic than particles devoid of *E. coli*-derived RNA/DNA. Full-length HBcAg possesses a RNA/DNA binding sequence at the C-terminus, which is lost upon truncation at residue 149. Unmethylated CpG DNs are much more frequently found in bacterial DNA than in vertebrate DNA. As shown in Table 5, full-length $HBcAg_{183}$ is significantly more immunogenic than truncated $HBcAg_{149}$ when limiting doses (0.2 µg) are injected in saline in the absence of a traditional adjuvant. Unexpectedly, this difference in immunogenicity is abolished when an adjuvant is used (e.g., CFA).

TABLE 5

Bacterial Nucleic Acid Augments the Immunogenicity of HBcAg Particles[1]

| Immunogen | Dose (µg) | RNA DNA | Anti-HBc Titer | | | | Anti-NANP Titer | | | |
|---|---|---|---|---|---|---|---|---|---|---|
| | | | $G_1$ | $G_{2a}$ | $G_{2b}$ | $G_3$ | $G_1$ | $G_{2a}$ | $G_{2b}$ | $G_3$ |
| HBcAg183 | 0.2 | + | 0 | 40,960 | 40,960 | 650 | | | | |
| HBcAg149 | 0.2 | − | 0 | 0 | 640 | 0 | | | | |
| HBcAg183-NANP | 1.0 | + | 10,240 | 2,560 | 10,240 | 640 | 160 | 160 | 10,240 | 640 |
| HBcAg149-NANP | 1.0 | − | 0 | 160 | 640 | 0 | 40 | 40 | 160 | 160 |

[1]Balb/c mice were immunized with the indicated dose of full-length HBcAg (183 amino acids), truncated HBcAg (149 amino acids), or full-length or trucated HBcAg containing (NANP)4 inserts in the loop region suspended in saline. Serum was collected four weeks after primary immunization and analyzed by IgG isotype-specific ELISA.

The positive effect of bacterial RNA/DNA was also observed when full-length versus truncated HBcAg-CS hybrid particles were used, resulting in significantly higher anti-NANP antibody production. Synthetic CpG DNs are first chemically coupled to WHcAg or WHcAg-CS hybrid particles. For this purpose, CpG DNA is modified to contain 5' amino groups, which are subsequently used to conjugate the oligonucleotides to WHcAg particles. In other embodiments, recombinant methods are used to incorporate CpG motifs into the interior of WHcAg using nucleic acid-binding motifs. Internalization of the CpG sequence is expected to reduce its sensitivity to nucleases. The effects of inclusion of CpG DN into hybrid W-HcAg particles is determined by immunization of hybrid particles with and without CpG DN, by comparing the anti-insert and anti-WHcAg humoral responses and the WHcAg-specific Th cell responses in various in vivo assays. CpG DN-coupled hybrid particles are also used in various TCR-Tg splenic in vitro assays of cytokine production and IgM antibody production.

2. Other Molecular Adjuvants

Genes encoding the murine CD40L (both 655 and 470 nucleic acid versions) have been used successfully to express these ligands at the C-terminus of WHcAg (See, FIG. 38). Moreover, immunization of mice with hybrid WHcAg-CD40L particles results in the production of higher anti-core antibody titers than does the immunization of mice with WHcAg particles (See, FIG. 39). However, lower than desirable yields of purified particles have been obtained. Therefore, mosaic particles containing less than 100% CD40L-fused polypeptides are produced to overcome this problem.

The other molecular adjuvants inserted within the WHcAg, including the C3d fragment, BAFF and LAG-3, have a tendency to become internalized when inserted at the C-terminus. Therefore tandem repeats of molecular adjuvants are used to resist internalization. Alternatively, various mutations within the so-called hinge region of WHcAg, between the assembly domain and the DNA/RNA-binding region of the core particle are made to prevent internalization of C-terminal sequences. However, internalization represents a problem for those molecular adjuvants such as CD40L, C3d, BAFF and LAG-3, which function at the APC/B cell membrane. In contrast, internalization of molecular adjuvants such as CpG DN is not an issue as these types of adjuvants function at the level of cytosolic receptors.

Another type of molecular adjuvant or immune enhancer is the inclusion within hybrid core particles of a $CD4^+$ T cell epitope, preferably a "universal" $CD4^+$ T cell epitope that is recognized by a large proportion of $CD4^+$ T cells (such as by more than 50%, preferably more than 60%, more preferably more than 70%, most preferably greater than 80%), of $CD4^+$ T cells. In one embodiment, universal $CD4^+$ T cell epitopes bind to a variety of human MHC class II molecules and are able to stimulate T helper cells. In another embodiment, universal $CD4^+$ T cell epitopes are preferably derived from antigens to which the human population is frequently exposed either by natural infection or vaccination (Falugi, et al., Eur. J. Immunol., 31:3816-3824, 2001). A number of such universal $CD4^+$ T cell epitopes have been described including, but not limited to: Tetanus Toxin (TT) residues 632-651 (SEQ ID NO:239); TT residues 950-969 (SEQ ID NO:240); TT residues 947-967 (SEQ ID NO:241), TT residues 830-843 (SEQ ID NO:242), TT residues 1084-1099 (SEQ ID NO:243), TT residues 1174-1189 (SEQ ID NO:244) (Demotz, et al., Eur. J. Immunol., 23:425-432, 1993); Diphtheria Toxin (DT) residues 271-290 (SEQ ID NO:245); DT residues 321-340 (SEQ ID NO:246); DT residues 331-350 (SEQ ID NO:247); DT residues 411-430 (SEQ ID NO:248); DT residues 351-370 (SEQ ID NO:249); DT residues 431-450 (SEQ ID NO:250) (Diethelm-Okita, et al., J. Infect. Dis., 1818:1001-1009, 2000); *Plasmodium falciparum* circumsporozoite (CSP) residues 321-345 (SEQ ID NO:251) and CSP residues 378-395 (SEQ ID NO:252) (Hammer, et al., Cell, 74:197-203, 1993); Hepatitis B antigen (HbsAg) residues19-33 (SEQ ID NO:253) (Greenstein, et al., J. Immunol., 148:3970-3977, 1992); Influenza hemagglutinin residues 307-319 (SEQ ID NO:254); Influenza matrix residues 17-31 (SEQ ID NO:255) (Alexander, et al., J. Immunol., 164:1625-1633, 2000); and measles virus fusion protein (MVF) residues 288-302 (SEQ ID NO:256) (Dakappagari, et al., J. Immunol., 170:4242-4253, 2003). One purpose of including a universal $CD4^+$ T cell epitope into hybrid core particles is to take advantage of pre-existing memory $CD4^+$ T cells primed by previous infection or vaccination and redirecting the T cell helper function to the B cell epitope present on the core particle carrier. For example, we chose to insert the TT950-969 sequence on the C-terminus of hybrid WHcAg particles. The TT950-969 sequence is recognized by 86% of humans at the T cell level due to TT vaccination according to a report by Diethelm-Okita, et al., (J. Inf. Dis., 181:1001-1007, 2000). Furthermore, this CD4+ T cell epitope is recognized by B11 and B10.S murine strains but not by Balb/c mice. A single injection in B10 and B10.S TT-immune mice with 10 μg of WHc-TT950-969 hybrid particles in saline, without the use of an adjuvant elicited extremely high levels of anti-WHc antibodies, which persisted beyond 7 months. Non-TT-immune B10 and B10.S mice produced significantly less anti-WHc antibodies, which persisted poorly (FIG. 44). While not intending to limit the invention to any mechanism, in one embodiment, the mechanism responsible for enhanced anti-WHc antibody production was demonstrated to be due to TT950-969-specific T helper cell function (FIG. 45). Therefore, pre-existing TT950-969-specific memory T helper cell function can be "redirected" to provide T cell help for antibody production to B cell epitopes presented on the WHcAg platform and this procedure can obviate the need for an adjuvant and reduce the number of vaccine doses required.

C. Chemical Coupling of Protein and Carbohydrate Antigens

In those instances when it is not possible to incorporate large protein epitopes or molecular adjuvants into the WHcAg by recombinant methods, chemical conjugation is used. Similarly, the WHcAg also serves as a new type of carrier platform for polysaccharide or oligosaccharides (PS/OS) antigens upon chemically coupling PS/OS epitopes to the WHcAg core.

1. Modification of Core Genes for Subsequent Chemical Conjugation

The wild type WHcAg is not efficiently chemically derivatized. Therefore, reactive amine groups are added by the insertion of one to several lysines via recombinant technologies. The position and number of the added lysines is varied (e.g, N- and C-termini, and within or outside the exposed loop region).

2. Model Protein Antigen

One protein and two carbohydrate model antigens are used for testing the feasibility of chemical conjugation to lysine-modified WHcAg. The model protein antigen, Poly-gamma-D-glutamic acid (PGA), is the capsular polypeptide of *Bacillus* sp. including *B. anthracis* (Fouet et al., J Appl Microbiol, 87:251-255, 1999). The capsular PGA of anthrax pathogens is very similar to bacterial cell surface PS antigens in that they are both poorly immunogenic, repetitive polymers require coupling to a carrier moiety. To produce WHcAg-PGA conjugates, a carbodiime-mediated coupling reaction is used because PGA molecules contain abundant carboxylate groups. The cores initially employed for this purpose include WHcAg-HyW2 and WHcAg-HyW2 modified with a lysine insert within the loop ($K^{75}$) or at the C-terminus. In preliminary studies using WHcAg-HyW2 and a saturation coupling approach, equal amounts of PGA and WHcAg-HyW2 (1.3 mg) and 5.0 mg of carbodiimide were mixed and after a four hour reaction time, SDS-PAGE analysis revealed that most of the PGA was coupled to WHcAg. As shown in FIG. 31, immunization of Balb/c mice with 101 g of the PGA-WHcAg-HyW2 conjugate formulated in alum resulted in production of significant IgM and IgG anti-PGA antibodies, whereas the uncoupled PGA in alum was non-immunogenic. Note that IgM anti-PGA decreased from the first immunization to the third and IgG anti-PGA antibodies increased from the first immunization to the third. In other embodiments, the lysine-modified WHcAg particles are used with various PGA polymer sizes and WHcAg/PGA ratios, to optimize conjugate production and immunogenicity. The WHcAg carrier is expected by the inventors to compare favorably with common toxoid carriers (e.g., tetanus toxoid and diptheria toxoid). In vitro opsonophagocytic assays (DeVelasco et al., Vaccine, 12:1419-1422, 1994) are used to test the function of anti-PGA antibodies. As a surrogate for *B. anthracis, B. licheniformis* 9945A (not a human pathogen) which has the same PGA capsule is used. In some embodiments, the ability of the PGA-WHcAg conjugate to protect immunized mice against lethal *B. anthracis* challenge is assessed.

3. Model Carbohydrate Antigens

The O-antigenic PSs are both essential virulence factors and protective *Shigella* antigens. Moreover, serum IgG specific for O—PS has been demonstrated to confer immunity against shigellosis. Despite these findings, to date no licensed *Shigella* vaccines exist. To meet this need in the art, a lysine-modified WHcAg is used as a carrier platform for the O—PSs of *Shigella*, with a particular focus on *S. dysenteriae* 1 and *S. flexneri* 2a. A recent study using recombinant core protein derived from the duck hepadna virus coupled to purified type III capsular PS from group B *streptococcus* (GBS) demonstrated 97% survival after GBS type III challenge in newborn pups born to vaccinated mouse dams (Paoletti et al., Vaccine, 20:370-376, 2002). A method is used that permits the chemical synthesis of an array of glycoconjugates containing saccharide antigens of desired molecular sizes and that employs chemically controlled site-specific coupling (Wang et al, Vaccine, 21:1112-1117, 2003). Utilizing these chemical methods, particulate PS-WHcAg conjugates are prepared incorporating PS epitopes of known molecular size and orientation which are linked at specified sites to core particles. The size of OS antigens deserves particular attention in the context of using WHcAg as the carrier. The spacing of natural WHcAg B-cell epitopes and of peptidic antigens inserted in the tips of the spikes is contemplated to be an important determining factor for immunogenicity. Therefore, it is important to test a range of sizes of OS antigens beginning with sizes comparable to peptidic antigens (e.g., 2,000-3,000 kDa), which exhibit high levels of immunogenicity. In addition to coupling large numbers of a single PS epitope to a single particle, the multivalency of the particles provides the opportunity to couple PS epitopes from many different serotypes to the same particle yielding a multivalent vaccine. Alternatively, particles conjugated with one PS serotype are mixed with other conjugated particles carrying a different serotype PS. The WHcAg is contemplated to be superior to commonly used carrier proteins for delivery of OS/PS antigens.

VII. Applications of the Hepadnavirus Core Antigen Combinatorial Technology

A. Infectious Diseases

Historically the use of the HBcAg as a platform has been confined to use as a T cell carrier for neutralizing epitopes of infectious disease pathogens. Subunit vaccine development for infectious diseases remains an important application for the WHcAg platform technology. In one embodiment, the *P. falciparum* CS repeat epitope NANPNVDP(NANP)$_3$ (SEQ ID NO:75) was inserted in many positions within the WHcAg, and complemented with diverse C-termini as a model system to further develop the WHcAg as a vaccine platform (See, FIGS. 2, 14 and 15).

1. *Plasmodium Vivax*

This *P. vivax* malaria species is predominant in South and Central America and is also found in Southeast Asia. A bivalent WHcAg hybrid particle was produced containing the *P. falciparum* CS repeat at the N-terminus, and the Type I variants of the *P. vivax*-CS repeat as an insertion at position 78. Preliminary data indicate that the vaccine candidate is effective and that antibodies to both inserts were produced. Thus, the present invention also provides bivalent vaccines based upon the WHcAg technology (See, FIG. 15). Since the *P. vivax* system is more complex (because several genotypes exist), more than one vaccine particle is produced and tested. Alternatively, several genotype-specific B cell epitopes are inserted into the same particle at different sites to produce a bivalent or trivalent vaccine particle. For instance, the Type II and Type III variants of the *P. vivax* CS repeat epitopes (See, Table 6) are inserted into the WHcAg platform in addition to the Type I variant:

TABLE 6

*Plasmodium vivax* Circumsporozoite (CS) Sequences

| Type | Sequence[1] | Identifier |
|---|---|---|
| I | DRAAGQPAGDRADGQPAG | SEQ ID NO: 74 |
| II | ANGAGNQPGANGAGDQPG | SEQ ID NO: 65 |
| II | ANGADNQPGANGADDQPG | SEQ ID NO: 66 |
| III | APGANQEGGAAAPGANQEGGAA | SEQ ID NO: 67 |

[1]Bold type denotes variant residues.

2. Foot and Mouth Disease (FMDV)

One of the first examples of the use of the HBcAg as a vaccine carrier was for the major immunogenic B cell epitope of the $FMDV_{141-160}$. Previously, a hybrid HBcAg-FMDV particle was shown to elicit protective antibodies (Bittle et al., Nature, 298:30-35, 1982), although there were problems eliciting sufficiently high levels of anti-FMDV antibodies. The WHcAg combinatorial technology described herein is contemplated to provide a more effective vaccine candidate. Two protective linear epitopes derived from the VP1 protein have been defined: $VP1_{141-160}$ and $VP1_{200-213}$ (Van Lierop et al., Immunol, 75:406-413, 1992). Recently a DNA vaccine encoding $VP1_{141-160}$ and $VP1_{200-213}$ was shown to protect swine from a FMDV challenge (Wong et al., Virol, 278:27-35, 2000). Thus, both neutralizing epitopes are selected for incorporation into hybrid WHcAg particles.

3. Influenza A Virus

The extracellular domain of the matrix 2 (M2e) sequence of influenza A has also been chosen as a model neutralizing B cell epitope for insertion within WHcAg, as this sequence has a number of features in common with the malaria CS repeat. The M2e sequence is a linear protective epitope that is poorly immunogenic during natural infection and in the context of various vaccine formulations. Additionally, the M2e sequence permits the comparison of the WHcAg and HBcAg vaccine platforms (Jegerlehner et al., Vaccine, 3104, 2002; Neirynck et al., Nat Med, 5:1157-1163, 1999; and Heinen et al, J Gen Virol, 83:1851-1859, 2002). The kinetics of the antibody response elicited by a M2e-WHcAg hybrid particle (HyW-IM2(−)78) is shown in FIG. 32. Anti-WHc and anti-M2e antibodies are detected within 2 weeks of primary immunization, with serum titers reaching a plateau four weeks after the primary immunization, and rising approximately 10-fold after boosting. Although, an anti-M2e titer of $3 \times 10^6$ after two doses is two orders of magnitude higher than the levels previously obtained using the HBcAg platform, improvements on the immunogenicity of the HyW-IM2(−)78 particle are contemplated. The sera from mice immunized with HyW-IM2(−)78 were analyzed to determine the isotype distribution of anti-2Me and anti-WHc antibodies. As shown in FIG. 33, the response was well represented by all the IgG isotypes. After the second immunization, anti-M2e serum titers greater than 1:100,000 were obtained for all four IgG isotypes. A similar pattern was observed in the anti-WHc response with the exception of a relatively low $IgG_3$ response to the carrier. The broad spectrum IgG isotype profile specific for the M2e epitope is a positive characteristic, which guarantees a full spectrum of biologic effector functions (complement fixation, ADCC, etc.). Importantly, the HyW-IM2(−)78 antisera also binds to viral M2 and inhibits influenza virus growth.

Quantitating the reactivity of sera from WHcAg-M2e immunized mice against authentic M2 protein is the first step in characterizing WHcAg-M2e as a vaccine candidate. The use of flow cytometry against virus-infected cells is performed on live, unfixed cells thereby ensuring the sera can recognize M2 in its native conformation in the plasma membrane (Pekosz and Lamb, J Virol, 73:8808-8812, 1999). Sera from WHcAg-M2e immunized mice (diluted 1:100) were incubated at 4° C. with cells infected with influenza A virus for 12 hours. The samples were washed, incubated with FITC-conjugated goat IgG recognizing mouse IgG, washed and analyzed by flow cytometry. Sera from mice immunized with core particle alone did not specifically react with influenza A virus infected cells in comparison to mock-infected cells (See, FIG. 34, panel A). In contrast, sera from WHcAg-M2e immunized mice recognized influenza A virus infected cells, as judged by the shift to increased fluorescence intensity displayed in the virus-infected cell population (See, FIG. 34, panel B). Thus, the hybrid particle generates a physiologically relevant antibody response recognizing influenza A virus infected cells.

Certain monoclonal antibodies targeting the M2 extracellular domain restrict virus replication in vitro by inhibiting virus particle budding (Hughey et al., Virol, 212:411-412, 1995). The ability of WHcAg-M2e immunized mouse sera to inhibit influenza A virus budding was assayed as described (Zebedee and Lamb, Proc Natl Acad Sci USA, 86:1061-1065, 1989). Influenza A virus strain rWSN (a M2 monoclonal antibody resistant strain), produced equivalent numbers of infectious particles irrespective of the presence of anti-WHcAg-M2e sera. In contrast, rWSN M-Udorn reassortant virus possessing an RNA segment 7 from a/Udorn/72, but all other segments derived from rWSN (a M2 monoclonal antibody sensitive strain) consistently produced less infectious virus particles at all time points tested when WHcAg-M2e anti sera was present (See, FIG. 35). The reduction in virus titer indicated that sera from WHcAg-M2e immunized mice has the ability to inhibit the production of infectious influenza A virus particles in vitro. Immunization/challenge studies are also done to assess the ability of the WHcAg-M2e particles to provide protection against influenza A infection.

Previously, the HBcAg has been used as a platform for the M2e epitope by positioning the M2e region at the $NH_2$-terminus of HBcAg. The first study reported relatively low serum anti-M2e titers ($4 \times 10^4$) after three doses of hybrid HBcAg particles in a strong adjuvant system (Neirynck et al., Nat Med, 5:1157-1163, 1999). Nonetheless, this level of anti-M2e was sufficient to significantly protect mice against a lethal challenge. Another group using the same hybrid HBcAg vaccine candidate in pigs raised less serum anti-M2e antibody ($3 \times 10^3$), and failed to achieve protection. Similarly, a murine study in mice using hybrid HBcAg particles without adjuvant achieved very low anti-M2e serum:titers (1:80) and challenged mice were not protected. However, mice receiving a chemical conjugate were protected which correlated with higher anti-M2e serum titers (1:5, 120). Thus, it is contemplated that the quantity of protective antibody produced is important and that a threshold serum level is necessary and should be maintained for antibody-mediated protection. As described herein, the M2e sequence was inserted within the loop of WHcAg, and this prototype M2e-WHcAg particle was found to elicit 100-fold more anti-M2e serum antibody ($3\times10^6$), than the HBcAg-M2e particles shown in Table 7-1, even after fewer doses in IFA.

TABLE 7-1

Hybrid Core Particles Containing the Influenza Virus M2e Sequence

| Particle | Dose (adjuvant) | Antibody Titer (1/dilution) | | Comment (reference) |
|---|---|---|---|---|
| | | Anti-M2e | Anti-Core | |
| M2e-HBc | 3 (Ribi) | $4 \times 10^4$ | $2.7 \times 10^6$ | protection (Neirynck, supra, 1999) |
| M2e-HBc | 3 (adjuvant) | $3 \times 10^3$ | — | no protection (Heinen, supra, 2002) |
| M2e-HBc | 2 (no adjuvant) | 80 | — | no protection (Jegerlehner, supra, 2002) |
| HyW-IM2(—)78 | 2 (IFA) | $3 \times 10^6$ | $3 \times 10^6$ | in vitro neutralization (present invention) |

4. Anti-Toxin Vaccine Design

Another suitable application of the WHcAg platform technology is as a toxin subunit vaccine. One advantage of using the WHcAg platform is that a neutralizing epitope of the toxin is inserted into the particles. This is contemplated to be more immunogenic than the whole toxin or toxoid, while circumventing the expense and hazard of dealing with the whole toxin.

As a prototype, two peptidic B cell epitopes from Staphylococcal enterotoxin B (SEB) were selected. Anti-$SEB_{152-161}$, antibodies recognize native SEB, as well as other SE's and inhibit transcytosis of SEB, SEA, SEE and TSST-1 (Arad et al, Nat Med, 6:414-421, 2000). To prevent SE-mediated disease, a hybrid core particle vaccine has been constructed by inserting the $SEB_{152-161}$ sequence in WHcAg at position 75, in combination with the HyW2 C-terminus. Similarly, the $SEB_{140-151}$ peptide and antibody have also been shown to be biologically active and highly conserved (Visvanathan et al., Infect Immunol, 69:875-884, 2001). Therefore, the $SEB_{140-151}$ sequence is used as well, to produce WHcAg-$SEB_{140-151}$ insert particles.

B. Therapeutic Autoantibodies

The ability of the WHcAg platform to raise very high levels of anti-insert antibody is contemplated to be useful for a number of applications beyond the infectious disease setting. One such application is for the production of therapeutic autoantibodies. Several mAb-based therapies have shown encouraging results in small animal studies and in clinical trials. For instance, mAb therapy targeting c-erbB2 (HER 2/neu) has been used to treat breast cancer (Pegram and Slamon, Semin Oncol, 27:13-19, 2000); antibody to β-amyloid has been used to treat an Alzheimer's-like disease in mice (Schenk et al., Nature, 400:173-177, 1999), anti-IgE mAb has been tested to treat allergy (Cheng, Nat Biotechnol, 18:157-162, 2000), and in human clinical trials an anti-TNFα mAb therapy reduced the symptoms of rheumatoid arthritis and Crohn's disease (Maini and Taylor, Annu Rev Med, 51:207-229, 2000). However, active immunization has a number of advantages over passive mAb therapy: i) patient convenience and cost (several immunizations as opposed to numerous infusions, each requiring several hours in the clinic); ii) costs for large scale mAb production are extremely high; iii) active immunization produces more consistent levels of antibody over time; and iv) mAb therapy is likely to induce an inactivating antibody response. In fact, others have begun using Papillomavirus-like-particles chemically conjugated to self antigens to elicit therapeutic autoantibodies (Chackerian et al., J Clin Invest, 108:415-423, 2001; and Chackerian et al., Proc Natl Acad Sci USA, 96:2373-2378, 1999). Thus, several model epitopes in the context of WHcAg are used to induce production of autoantibodies possessing therapeutic functions.

1. Anti-CETP Autoantibody

There is a strong inverse relationship between the plasma concentration of cholesterol in HDLs and the development of coronary heart disease. One therapeutic approach that has been suggested for increasing HDL concentrations is the inhibition of cholesteryl ester transfer protein (CETP) activity (Tall, J Lipid Res, 34:1255-1274, 1993). The CETP functions in the plasma to lower HDL by moving cholesteryl esters from HDLs to VLDLs and LDLs (Barter et al., Biochem J, 208:1-7, 1982). Transient inhibition of CETP activity in rabbits and hamsters by mAb, small molecules, or antisense oligonucleotides (Whitlock et al., J Clin Invest, 84:129-137, 1989; Kothari et al., Atherosclerosis, 128:59-66, 1997; and Sugano and Makino, J Biol Chem, 271:19080-19083, 1996) causes an increase in plasma HDL. In addition, sustained inhibition of CETP expression by antisense oligonucleotides increased plasma HDL and reduced atherosclerotic lesions in rabbits (Sugano et al., J Biol Chem, 273:5033-5036, 1998). In contrast, transgenic mice and rats expressing human CETP have decreased plasma HDL (Agellon et al., J Biol Chem, 266:10796-10801, 1991; and Herrera et al., Nat Med, 5:1383-1389, 1999). Similarly, human populations with reduced or absent CETP activity due to genetic mutations have markedly elevated plasma HDL (Koizumi et al., Atherosclerosis, 58:175-186, 1985). Recently a vaccine approach was used to generate antibodies against CETP in vivo in rabbits using a dominant linear B cell epitope consisting of residues 461-476 of human CETP. The immunized rabbits had reduced CETP activity, a substantial increase in HDL, and a significant reduction in aortic atherosclerotic lesions (Rittershaus et al., Arterioscler Thromb Vasc Biol, 20:2106-2112, 2000). For this reason, the $CETP_{461-476}$ sequence was inserted within the WHcAg platform at position 74 in combination with the HyW C-terminal platform (HyW2-$CETP_{74}$). Interestingly, attempts to insert the CETP sequence at positions 75 or 78 were unsuccessful illustrating the versatility of the WHcAg combinatorial technology. As shown in FIG. 36, significant levels of anti-$CETP_{461-476}$ antibodies were raised in mice immunized with HyW2-CETP74, and secondary anti-$CETP_{461-476}$ antibodies also neutralize CETP activity in vitro. Because mice do not express CETP, this does not represent an autoantibody response. However, immunizing Tg mice expressing human CETP (and having lowered HDL levels) with HyW-$CETP_{74}$ particles is contemplated to induce anti-CETP antibodies capable of both neutralizing CETP activity and raising plasma HDL levels in vivo. The ability of immunization with the $CETP_{461-476}$ peptide linked to a tetanus toxoid peptide to raise HDL levels in vaccine recipients is currently being assessed in human clinical trials (Rittershaus et al., supra, 2000). A particulate WHcAg-$CEPT_{461-476}$ vaccine is contemplated to be a superior immunogen in humans as compared to a totally peptidic vaccine.

2. Anti-Cytokine Autoantibody

In many autoimmune diseases such as multiple sclerosis and diabetes, Th cells play a predominant role. The Th cells function both to help B cells produce antibody (Th$_2$ cells) and to mediate inflammatory responses (Th$_1$ cells). Th$_1$ cells mediate their inflammatory function through the production of cytokines, which have direct anti-pathogen effects, as well as effects on other immune cell types. Tumor necrosis factor-alpha (TNFα) is an inflammatory cytokine that is often produced during autoimmune reactions and is responsible for many of the lesions or symptoms. Therefore, B cell epitopes from TNFα are inserted into the WHcAg platform and the effect of high levels of anti-cytokine (e.g., anti-TNFα) antibodies is assessed in animal models of ongoing autoimmune disease. Analogues of TNFα and soluble receptors for TNFα, as well as anti-TNFα mAbs are currently tested with promising results in clinical trials. However, these drugs are very expensive and require continual dosing, whereas anti-TNFα antibodies produced by the patient following vaccination are inexpensive and work via the same TNFα-blocking mechanism. The murine TNFα$_{3-22}$ epitope is used as a model antigen because this region is homologous to human TNFα, has been reported to interact with the TNFα receptor and in a mouse model vaccination with this TNFα peptide chemically conjugated to Papillomavirus-like-particles produced anti-TNFα autoantibodies and inhibited development of type II collagen-induced arthritis (Chackerian et al., J Clin Invest, 108:415-423, 2001). WHcAg-TNFα$_{3-22}$ hybrid particles are produced and their immunogenicity is examined using methods disclosed herein. Moreover, the effects of anti-TNFα autoantibody production on the induction and/or maintenance of type II collagen-induced arthritis in a mouse model is assessed.

Although the delivery of self B cell epitopes on a particulate structure can circumvent T cell self-tolerance and elicit autoantibodies, this is a more complicated system than simply eliciting antibodies to foreign epitopes. Various properties of this system are examined using HBcAg- and HBeAg-Tg mice and T cell receptor (TCR) double-Tg mice. For instance, autoantibodies were elicited (anti-HBe/anti-HBc) in TCR× HBe/HBc-double Tg mice by the single injection of a peptide that activates the HBe/HBcAg-specific transgenic CD4$^+$ T cells (See, FIG. 37). Note that anti-HBe autoantibody production is transient lasting approximately three months. In HBeAg-Tg mice expressing a higher serum level of HBeAg, autoantibody production is even more transient (e.g., 2-3 weeks). In contrast, anti-HBc autoantibody is persistent for the life of the animal. Several characteristics of HBeAg and HBcAg most likely explain these differences. The HBeAg is a secreted antigen, whereas the HBcAg is a cytosolic protein expressed in hepatocytes and relatively small amounts of HBcAg leak out of the liver. Therefore, the presence of the autoantigen in the serum is contemplated to clear the autoantibody via immune complex formation and secondly via the constant exposure of HBeAg-specific T cells to soluble HBeAg which has been shown to be immunosuppressive through Fas-mediated apoptosis (Milich et al., J Immunol, 160:2013-2021, 1998). However, in the WHcAg platform system immune tolerance is predominantly relevant at the B cell level, because the insert is a self-B cell epitope, whereas the Th cells are specific for the WHcAg carrier. The reversibility of autoantibody production is dependent upon whether the antigen within the inoculum is driving antibody production mediated by WHcAg-specific Th cells or whether at some point the endogenous self protein itself drives autoantibody production. This is contemplated to occur if the expanded autoreactive B cells become efficient APCs to present the entire self protein to self-specific Th cells to an extent capable of breaking Th cell tolerance.

3. Alzheimer's Disease

Cleavage of amyloid precursor protein (APP) yields amyloid-β-peptide (Aβ) a 40-42 amino acid fragment which is present in abundance in the plaques or brain lesions found in Alzheimer's patients. Transgenic mice expressing human Aβ serve as an animal model for Alzheimer's disease. Recently it was reported that antibody production to Aβ in these transgenic mice inhibited plaque formation in the brains of the mice (Morgan et al., Nature, 408:982-985, 2000). However, the Aβ peptide was not very immunogenic and required many immunizations to induce rather low levels of antibody. The murine studies prompted several clinical trials, which were halted due to a number of cases of aseptic meningoencephalitis (Smith et al., Lancet, 359:1864-1865, 2002). Two recent studies have more carefully mapped the specificity of the therapeutic anti-Aβ antibodies and showed that the beneficial effects in mice arise from antibodies selectively directed against residues 4-10 of Aβ$_{42}$, which do not in themselves elicit an inflammatory response (Hock et al., Nat Med, 8:1270-1275, 2002; and McLaurin et al., Nat Med, 8:1263-1269, 2002). The Aβ$_{4-10}$ epitope represents a B cell epitope possessing no predicted T cell sites. In contrast, use of the full-length Aβ$_{42}$ is contemplated to have elicited an inflammatory T cell response. Furthermore, it was observed that the induction of IgG$_{2b}$ antibodies to Aβ$_{4-10}$ had an optimal therapeutic effect. These recent studies have revived interest in an Alzheimer's disease vaccine. The WHcAg platform is well suited for this purpose because it has the potential to raise very high titer antibodies to the small Aβ$_{4-10}$ epitope, without activating Aβ-specific T cells. The WHcAg platform elicits a spectrum of IgG isotypes, (predominantly IgG$_{2b}$ isotype), although the platform and/or formulation are manipulable to focus antibody production to a particular IgG isotype. The Aβ$_{4-10}$ sequence and/or tandem repeats are inserted into the WHcAg platform at various positions inside and outside the loop, in combination with different C-termini. The platform(s) which is most immunogenic or otherwise advantageous (e.g., IgG isotype induction profile), is assessed in vaccination experiments in the appropriate transgenic mouse model of Alzheimer's disease.

C. Allergic Disorders

Simplistically, allergy occurs when exposure to an allergen (e.g., pollen) elicits an antibody of the IgE class, as opposed to an antibody of the IgG class. IgE antibody binds to a particular cell type (Mast cell) and to the allergen, yielding an allergen-IgE complex on the surface of the Mast cell, which activates the Mast cell to release effector molecules such as histamine thereby mediating the symptoms of an allergic response. One allergy treatment termed desensitization involves injecting many doses of the allergen over long periods to bias the antibody response towards IgG rather than IgE production. The WHcAg technology is contemplated to be useful in this application because WHcAg elicits strong IgG responses, but not IgE responses. B cell epitopes derived from known allergens are inserted into the WHcAg platform and used to immunize/desensitize allergic patients. One or two injections are contemplated to be necessary, in contrast to the numerous injections used in typical desensitization therapy. A number of linear peptidic B cell epitopes have been mapped for common allergens including: peanut allergen (Ara h 3; Rabjohn et al., hit Arch Allergy Immunol, 128:15-23, 2002); latex allergen hevein (Her b 5; Beezhold et al., J Allergy Clin Immunol, 107:1069-1076, 2001); brown shrimp allergen (Pen a 1; Reese et al, J Chromatogr B Biomed Sci Appl, 756:157-163, 2001); and the major grass pollen allergen (Ph1 p 1; Suphio et al., FEBS Lett, 502:46-52, 2001). Often allergen-derived peptides lack IgE binding capacity, yet anti-peptide IgG antibodies react with the native allergen and inhibiting IgE from binding to the native allergen (Focke et al., FASEB J, 15:2042-2044, 2001). This is contemplated to occur via anti-peptide antibodies sterically hindering IgE binding, as well as by allergen clearance by anti-peptide IgG antibodies before IgE synthesis can occur. Hybrid WHcAg particles containing selected allergen-specific B cell epitopes are produced and selected for high titer IgG anti-allergen production, which is examined for the capacity to inhibit patient IgE binding to mast or basophil cells.

VII. Enhanced Particle Assembly Via Addition or Insertion of Acidic Amino Acids

A. Hepadna Virus Core Antigens

During development of the present invention, the presence of a number of highly basic amino acids (especially K, R, H) in a candidate insert epitope was found to correlate negatively with the assembly of hybrid WHcAg particles and hybrid HBcAg particles (PCT/US01/25625; and Karpenko, et. al., Amino Acids, 18:329-337, 2000). As shown in Table 17 and 18, the isoelectric point (pI) of epitope sequences inserted into the loop region, effects assembly of hybrid WHcAg, hybrid GSHcAg and hybrid HbcAg. Previously, three parameters of the epitope insert that prevented self-assembly of hybrid HBcAg particles were identified: i) high epitope hydrophobicity; ii) large epitope volume; and iii) a high β-strand index.

The pI of the wild type WHcAg loop (76-82) region is approximately 6.14 and that of the wild type HBcAg loop approximately 4.12. Because the wild type WHcAg and HBcAg 76-82 loop regions are acidic, the inventors predicted that epitope inserts more positively charged than the wild type sequence may have adverse effects on dimer formation (e.g., particle subunit) and secondly, particle assembly (e.g., core). Theoretically, excess positive charge in the loop may result in a repulsive force between the monomers and negatively effect dimerization or the efficient assembly of dimer subunits. However, an understanding of the mechanism(s) is not necessary in order to make and use the present invention.

Thus, several epitopes with pI's of seven or greater, which did not permit assembly of hybrid WHcAg, hybrid GSHcAg or HBcAg particles, were either modified to contain the acidic amino acid glutamic acid or were bracketed by glutamic acid residues (e.g., linker sequences). The effect of addition of glutamic acid substitutions or linker sequences to the insert sequence was then tested for the ability to rescue hybrid particle assembly. As shown in Table 18, in all cases addition of glutamic acid linker sequences on hybrid WHcAg, hybrid GSHcAg and hybrid HbcAg rescued particle assembly on the WHcAg, the HBcAg and the GSHcAg platforms. Substitution of a non-acidic amino acid within the heterologous insert (at a nonessential position) with a glutamic acid residue also rescued hybrid particle assembly. Surprisingly even placement of negatively charged amino acids at a distance from the positively charged residues in the insert sequence resulted in hybrid particle assembly.

Additionally, the effect of addition of other amino acid residues on hybrid particle assembly was examined. A single basic (e.g., pI=8.74) epitope sequence was selected and multiple amino acid linkers were tested. Interestingly, peptidic linkers that significantly lowered the insert pI (i.e., glutamic acid and aspartic acid) permitted WHcAg hybrid particle assembly. Thus, assembly of particles containing inserts with pIs of greater than seven are rescued by the addition of acidic acid substitutions and/or acidic amino acid linker sequences. Therefore, when possible a negatively-charged epitope should be selected. However, when this is not possible a positively-charged epitope is modified to include acidic amino acid substitutions and/or linker sequences, in order to obtain hybrid particles which assemble efficiently.

B. Other Self-Assembling Virus-Like-Particles (VLP)

Additional self-assembling virus-like-particles (VLP) are finding use as vaccine carrier platforms. A major, universal problem of VLP assembly has been the destabilizing effects of adding or inserting foreign peptidic sequences (PCT/US01/25625, Jegerlehner et al., Vaccine, 20:3104, 2002; Chackerian et al., J. Clin. Invest., 108:415-423, 2001; and Casal et al., Methods 19:174-186, 1999). Hybrid VLP stability has represented such a serious problem that users of the HBcAg platform technology (Jegerlehner et al., supra, 2002) and the Papillomavirus platform technology (Chackerian et. al., supra, 2001) have opted to chemically conjugate foreign epitopes to wild type VLPs, instead of attempting to produce hybrid particles via recombinant means. In particular, Chackerian found that the ability of L1-self-peptide chimeras to assemble into VLPs was highly unpredictable. Similarly, Jegerlehner found that the size and nature of epitopes that can be inserted into the immunodominant region of VLPs was restricted and that VLPs containing inserts longer than 20 amino acids often failed to assemble.

Similar to the hepadnavirus core proteins, preferred insertion sites on many VLPs are within the immunodominant exposed loop structures which are accessible for antibody recognition and which may be less likely to compromise the structural integrity of the particle, as opposed to insertions into α-helical or β-sheet regions (Sadeyen et al., Virology 309:32-40, 2003). Thus, the inventors contemplate that the insertion of positively-charged epitopes into the exposed loop region of other types of hybrid cores, is also expected to negatively effect assembly of these cores. Consequently, the inventors propose using acidic amino acids to rescue assembly of other viral core particles containing positively-charged epitopes. In fact, rational insertion or substitution of acidic amino acid residues into either the heterologous antigen of interest or the vaccine platform, is contemplated to be useful for the following exemplary list of viruses from which VLPs are obtained: human papillomavirus type 16 (Varsani et al., J. Virol., 77:8386-8393); human papillomavirus type 11 (Rose et al., J. Virol., 67:1936-1944, 1993); hamster polyomavirus (Gedvilaite et al, Virol., 20:21-35, 2000); hepatitis B virus (Pumpens et al., Intervirol., 45:24-32, 2002); yeast Ty1 and Ty3 (Roth, Yeast, 16:785-795, 2000); human immunodeficiency virus (Wagner et al., intervirol., 39:93-103, 1996); hepatitis C virus (Baumert et al., Gastroenterology, 117:1397-1407, 1999); bovine rotavirus strain C486 (Sabara et al., J. Virol., 65:6994-6997, 1991); norwalk virus (Ball et al., Gastroenterology, 117:40-48, 1999); human parvovirus B19 (Brown et al., J. Virol., 65:2702-2706, 1991); herpes simplex virus (Thomsen et al., J. Virol., 68:2442-2457, 1994); poliovirus (Urakawa et al., J. Gen. Virol., 70:1453-1463, 1989); RNA bacteriophage (Brown et al., Intervirol., 45:371-380, 2002); bluetongue virus (French et al, J. Virol., 64:5695-5700, 1990); duck hepatitis B virus (Paoletti et al., Vaccine, 20:370-376, 2001); simian immunodeficiency virus (Yamshchikov et al., Virol., 214:50-58, 1995); rabbit hemorrhagic disease virus (Plana-Duran et al., Arch. Virol., 141:1423-1436, 1996); hepatitis E virus (Nikura et al, Virol., 293:273-280, 2002); simian-human immunodeficiency virus (Yao, Res. Initiat. Treat Action, 8:20-21, 2003) and bovine leukemia virus (Kakker et al., Virol., 265:308-318, 1999).

VIII. Exemplary Hepadnavirus Core Antigen Modifications May be Applied to Any Hepadnavirus Exemplary modifications to hepadnavirus core antigens are illustrated herein using orthohepadnavirus core antigens (e.g., from woodchuck, ground squirrel, and arctic ground squirrel) (Tables 1, 3-1, 3-2), avihepadnavirus core antigens (e.g., from duck, Ross' goose, Sheldgoose, heron, stork) (Table 3-3), human hepatitis B virus core antigens (Table 4-1), and non-human primate hepatitis virus core antigens (e.g., from orangutan, gibbon, chimpanzee and woolly monkey) (Tables 4-2, 4-3) (see also FIG. 20 and Tables 9, 10, 17, 18). However, the invention is not limited to these exemplary hepadnavirus core antigens, but rather includes any hepadnavirus core antigen. The invention's illustrative modifications are summarized in Table 7-2 below, and may be applied to any hepadnavirus core antigen using routine methods in combination with guidance herein, including alignment of the hepadnavirus core antigens as shown in FIG. 46. For example, unique restriction cloning sites may be designed to allow insertion at desired sites, modification of the C-terminus of the hepadnavirus core antigen, and/or use of acidic amino acid linkers and/or substitution with acidic amino acids.

TABLE 7-2

Exemplary Hepadnavirus Core Protein Combinatorial Modifications

| Species | Exemplary Insertion Points inside loop at Amino Acid No.[a] | Exemplary Insertion Points outside loop at Amino Acid No.[a],[b] | Exemplary C-Terminal Amino Acid | Exemplary C-Terminal Modification | Exemplary Acidic Amino Acid substitution[d] (SEQ ID NO:) |
|---|---|---|---|---|---|
| Human | 76, 77, 78, 81, and 82 | 44, 71, 72, 73, 74, 75, 83, 84, 85, 92, N-terminal and C-terminal | $V^{149}$ | R, K, A, RRC, SEQ ID NO: 2-20, 22-36, 42-56, 153, 155, 157, 159, 161, 163-181, 183-238 | 99-101 |
| Woolly Monkey | 76, 77, 78, 81, and 82 | 44, 71, 72, 73, 74, 75, 83, 84, 85, 92, N-terminal and C-terminal | $V^{149}$ | R, K, A, RRC, SEQ ID NO: 2-20, 22-36, 42-56, 153, 157, 159, 161, 163-181, 183-238 | 99-101 |
| Orangutan, Gibbon, and Chimpanzee | 76, 77, 78, 81, and 82 | 44, 71, 72, 73, 74, 75, 83, 84, 85, 92, N-terminal and C-terminal | $V^{149}$ | R, K, A, RRC, SEQ ID NO: 2-20, 22-36, 42-56, 153, 155, 163-181, 183-238 | 99-101 |
| Woodchuck | 76, 77, 78, 81, and 82 | 44, 71, 72, 73, 74, 75, 83, 84, 85, 92, N-terminal and C-terminal | $I^{149}$ | R, C, K, A, RRC, and SEQ ID NOs: 2-20, 22-36, 42-56, 153, 155, 157, 159, 161, 163-181, 183-238 | 99-101 |
| Ground Squirrel | 76, 77, 78, 81, and 82 | 44, 71, 72, 73, 74, 75, 83, 84, 85, 92, N-terminal and C-terminal | $I^{148}$ | R, C, K, A, RRC, and SEQ ID NOs: 2-20, 22-36, 42-56, 153, 155, 157, 159, 161, 163-181, 183-238 | 99-101 |
| Arctic Ground Squirrel | 76, 77, 78, 81, and 82 | 44, 71, 72, 73, 74, 75, 83, 84, 85, 92, N-terminal and C-terminal | $I^{149}$ | R, C, K, A, RRC, and SEQ ID NOs: 2-20, 22-36, 42-56, 153, 155, 157, 159, 161, 163-181, 183-238 | 99-101 |
| Avian | 91, 92, 93, 96 and 97[c] | 40, 86, 87, 88, 89, 90, 98, 99, 131, 138, N-terminal and C-terminal | $V^{195}$ and $A^{195}$ | R, C, K, A, RRC, and SEQ ID NOs: 2-20, 22-36, 42-56, 153, 155, 157, 159, 161, 163-181, 183-238 | 99-101 |

[a]Bold denotes exemplary preferred embodiments.
[b]Insertion may also be anywhere within the 1-100 amino acids that are inserted at the C-terminal, such as insertion within one or more of SEQ ID NO: 2-20, 22-36, 42-56, 153, 183-238.
[c]Insertion may be accompanied by deletion of at least a portion of the loop.
[d]Substitution may be in one or more of the hepadnavirus core protein and the inserted heterologous amino acid sequence of interest.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); U (units); mU (milliunits); min. (minutes); sec. (seconds); % (percent); kb (kilobase); bp (base pair); PCR (polymerase chain reaction); WHV (woodchuck hepadnavirus); GHV (ground squirrel hepadnavirus); HBV (human hepatitis B virus); HBcAg (hepatitis B core antigen); WT (wild type); OS (oligosaccharide); PS (polysaccharide); Tg (transgenic); TCR (T cell receptor); Th (helper T cell); MHC (major histocompatibility complex); TNF (tumor necrosis factor); IFN (interferon); mAb (monoclonal antibody), mIg (membrane immunoglobulin); APC (antigen presenting cell); MO (macrophage); LN (lymph node); SN (supernatant); RS (restriction site); ELISA (enzyme linked immunosorbent assay); MOI (multiplicity of infection); 1° (primary); and 2° (secondary).

The following reagents find use in the methods and compositions of the present invention: TCR-Tg mice: 7/16-5 mice recognizing $HBcAg_{129-140}/A^b$; 11/4-12 mice recognizing $HBcAg_{129-140}/A^b$ (Chen et al., J. Virol. 74:7587-7599, 2000); and 8/6-10 mice recognizing $HBcAg_{120-131}/A^s$; HBV-Tg mice: HBcAg-Tg mice (Milich et al., J. Immunol. 152:455-466, 1994); and HBeAg-Tg mice (Milich et al., Proc. Natl. Acad. Sci. USA, 87:6599-6603, 1190); particle-reactive antibodies (polyclonal anti-WHcAg particles; mAb 2221, anti-WHcAg monomers; mAb 3120, anti-HBcAg particles; and mAb 3105, anti-HBcAg loop); insert-reactive antibodies (mAb 2A10, anti-*P. falciparum* NANP; mAb 2B608, anti-*P. falciparum* NVDP; mAb 14C2, anti-influenza M2e; mAb TP2, anti-CETP; and mAb 2F2, anti-*P. vivax* repeat); CD40L plasmid pDC406-mCD40L (ATCC No. 68872); tetanus toxin plasmid pMEC4 (Dr. Locht, Pasteur, Lille, France); 50mer or smaller peptides (Invitrogen); plasmids PET11d and BL21 (DE3) (Stratagene); and pLEX and K12 K802 *E. coli* (Invitrogen).

EXAMPLE 1

Immunization of Mice

Groups of 3-5 female mice, approximately 6-8 weeks old of various strains (either bred at the Vaccine Research Institute of San Diego, San Diego, Calif. or obtained from Jackson Laboratories, Bar Harbor, Me.) were immunized intraperitoneally for antibody assays and subcutaneously for T cell assays. Antigens were injected in saline, or absorbed in 0.1% (w/v) AlPO4 suspension, or emulsified in IFA or the squalene water-in-oil adjuvant Montanide ISA 720 (Seppic, Paris) depending on the experiment. Mice were bled pre-immunization and at various times after primary and booster immunizations for anti-insert/PS and anti-WHcAg antibody determinations. A larger number of mice/group (at least 10) were used to perform mouse potency (dose) studies because at limiting antigen doses, less than 100% of mice produce antibody, and the limiting dose was typically defined as the dose at which 50% of the mice produce antibody.

EXAMPLE 2

Antibody Assays

Anti-WHcAg or peptide antibodies were measured in pooled or individual, murine sera by indirect solid phase ELISA using solid phase WT WHcAg (50 ng/well) or insert peptide (0.5 µg/well) and goat anti-mouse Ig (or IgG isotype-specific) antibodies were used as the secondary antibody. The ELISA was developed with a peroxidase-labelled, affinity-purified swine anti-goat Ig. The data were expressed as antibody titer representing the highest dilution yielding three times (3×) the optical density of the pre-immunization sera. Anti-PS antibodies were measured in an identical manner on solid phase purified PSs (10 µg/ml), except that PolySorp plates (Nunc, Rosklide, Denmark) were used to coat PS antigens. Fifty micrograms of pneumococcal cell wall polysaccharide (C—PS) per ml of sera were added to absorb any anti-C—PS antibodies.

EXAMPLE 3

T Cell Assays

To measure T cell proliferation, groups of 3-5 mice were primed with either 10 µg of WT core, hybrid core or PS-core conjugates by hind footpad injection. Approximately, 7-10 days after immunization, draining popliteal lymph node (LN) cells were harvested, and 5×10⁵ cells in 0.1 ml of Click's medium were cultured with 0.1 ml of medium containing WT core, hybrid core or PS-core conjugates, various synthetic peptides, or medium alone. Cells were cultured for 96 hr at 37° C. in a humidified 5% $CO_2$ atmosphere, and during the final 16 hr, 1 µCi of ³H-thymidine (3H-TDR; at 6.7 Ci/mmol, New England Nuclear, Boston, Mass.) was added to each well. The cells were then harvested onto filter strips for determination of ³H-TdR incorporation. The data were expressed as counts per minute corrected for background proliferation in the absence of antigen (Acpm). The T cell nature of the proliferation was confirmed by analyzing nylon-wool column-enriched T cells in selected experiments. To measure cytokine production, identical culture procedures were used with the exception that 24-72 hr supernatants were harvested and analyzed for the presence of cytokines (IL-2, IL-4, IFNγ) in standard ELISPOT assays.

EXAMPLE 4

In Vivo Antibody Production in Response to WHcAg and GSHcAg Immunization

Figure 4:
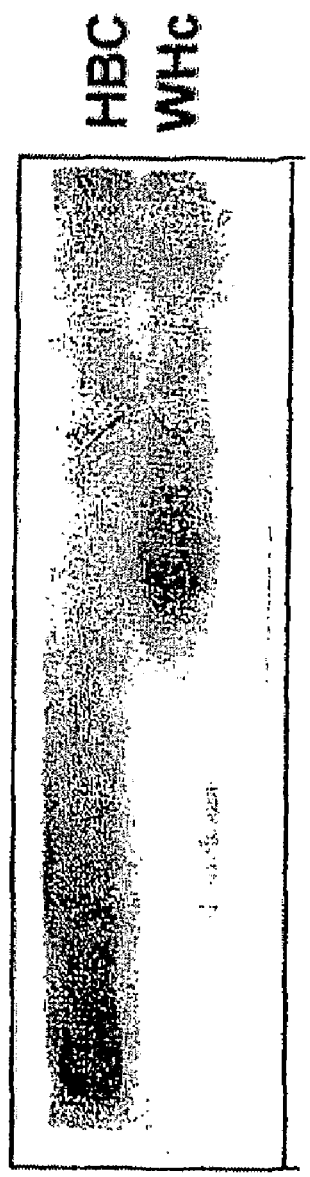

As discussed above, the WHcAg and the GSHcAg are approximately 67% conserved as compared to the HBcAg at the amino acid level. In contrast, the WHcAg and the GSHcAg are 91% conserved. In addition, the HBcAg and the WHcAg migrate differently in a 1% agarose gel (See, FIG. 4). Furthermore, the WHcAg and the HBcAg do not significantly crossreact at the antibody (B cell) level (See, FIG. 6) and are partially crossreactive at the CD4⁺ T helper cell level (See, FIGS. 7-10). Similarly, the GSHcAg and the HBcAg are not crossreactive at the B and T cell levels (FIGS. 6, 43; Table 19, 20). Therefore, the following studies were conducted to determine the immunogenicity of the WHcAg and the GSHcAg for evaluation of their potential as vaccine carrier platforms.

Figure 6:
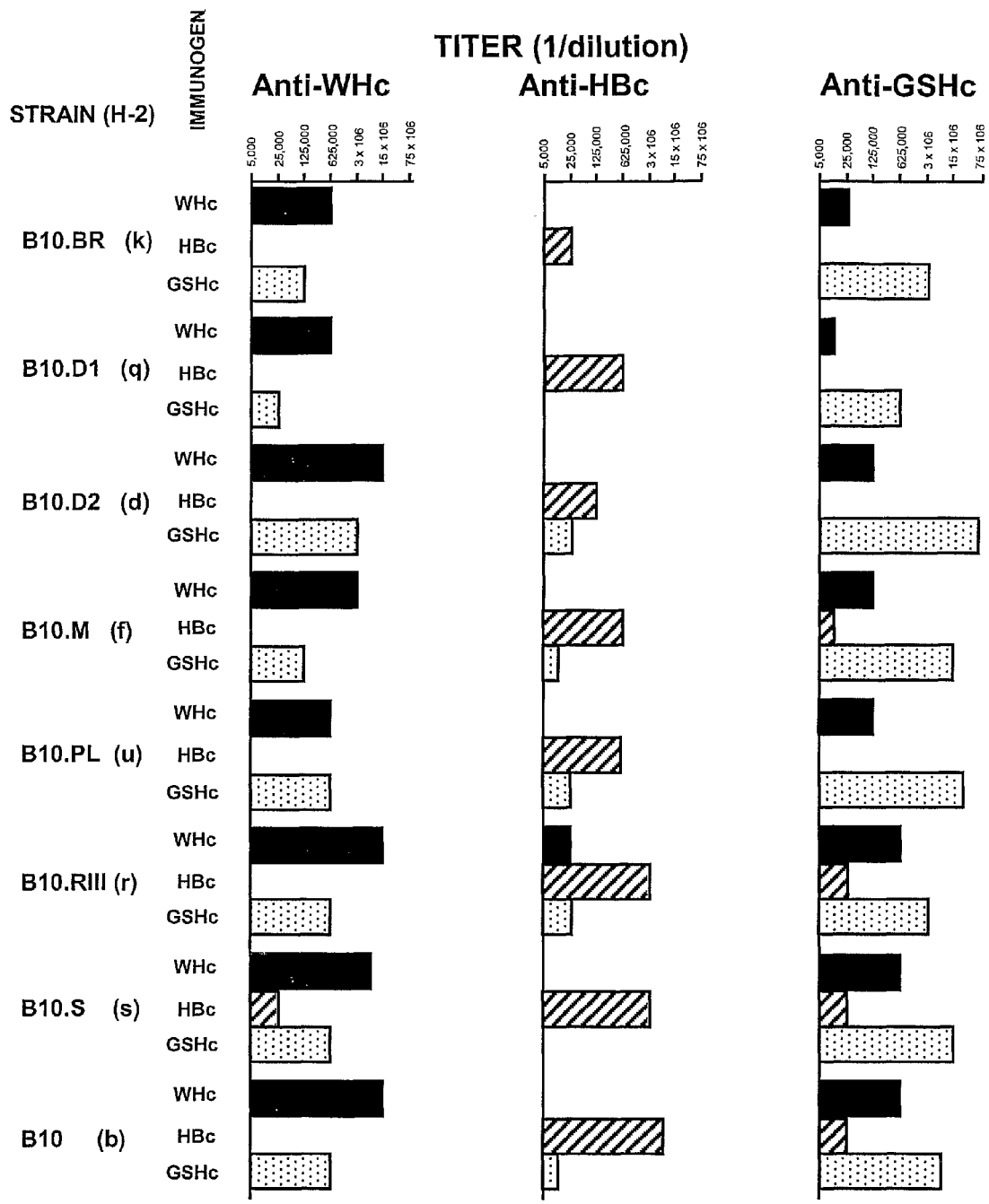

Briefly, eight H-2 congenic murine strains, differing in MHC-haplotype, were immunized with equal doses of WHcAg, GSHcAg or HBcAg (7.0 µg) emulsified in incomplete Freund's adjuvant (IFA). As shown in FIG. 5, the WHcAg elicited higher levels of anti-core antibodies in 5 (B10.BR, B10.D1, B10.D2, B10.M and B10.RIII) of the 8 strains and equivalent anti-core antibodies in 3 strains (B10.PL, B10.S and B10) as compared to the HBcAg (6 weeks after administration of a single dose). The GSHcAg elicited higher levels of anti-core antibodies than the HBcAg in all 8 strains. This analysis lso indicated that there are no genetic nonresponders to the WHcAg or the GSHcAg consistent with what has been previously reported for the HBcAg (Milich and McLachlan, Science, 234:1398-1401, 1986). However, the hierarchy of responder H-2 haplotypes differs somewhat for the WHcAg and the GSHcAg as compared to the HBcAg due to the fact that the proteins are partially crossreactive at the CD4$^+$ T cell level and each protein possesses a unique repertoire of CD4$^+$ T cell epitopes including several shared epitopes. FIG. 6 depicts the extremely low level of antibody crossreactivity between the HBcAg and either the GSHcAg or the WHcAg. In contrast, the WHcAg and the GSHcAg demonstrate significant crossreactivity. Crossreactivity between anti-WHc and anti-HBc antibodies ranged between 0 and 0.8%. Similarly, a panel of monoclonal antibodies (mAb) specific for the HBcAg was found to be totally non-crossreactive with the WHcAg when tested for binding to solid phase HBcAg and WHcAg by ELISA. The anti-HBcAg mAB panel included #3105, #3120 (Takashi, et al., J. Immunol., 130:2903-2911, 1983), $C_{1-5}$ (Chemicon, Temecula, Calif.), C3-1, #440 and #442 (Boehringer Mannheim, Germany), and H40-C47.

TABLE 8

In Vivo Antibody Production to WHcAg and WHeAg in Athymic Mice

| Strain | Immunogen | Bleed (day) | Antibody Titers (1/dilution) | |
|---|---|---|---|---|
| | | | Anti-WHc | Anti-WHe |
| Balb/c (+/+) | WHcAg | 10 | 163,840 | 10,240 |
| | | 24 | 40 × 10$^6$ | 2.6 × 10$^6$ |
| | WHeAg | 10 | 20,480 | 20,480 |
| | | 24 | 2.6 × 10$^6$ | 655,360 |
| Balb/c (nu/nu) | WHcAg | 10 | 10,240 | 640 |
| | | 24 | 10,240 | 0 |
| | WHeAg | 10 | 0 | 0 |
| | | 24 | 0 | 0 |

EXAMPLE 5

CD4$^+$ T cell Responses to the WHcAg

Figure 7:
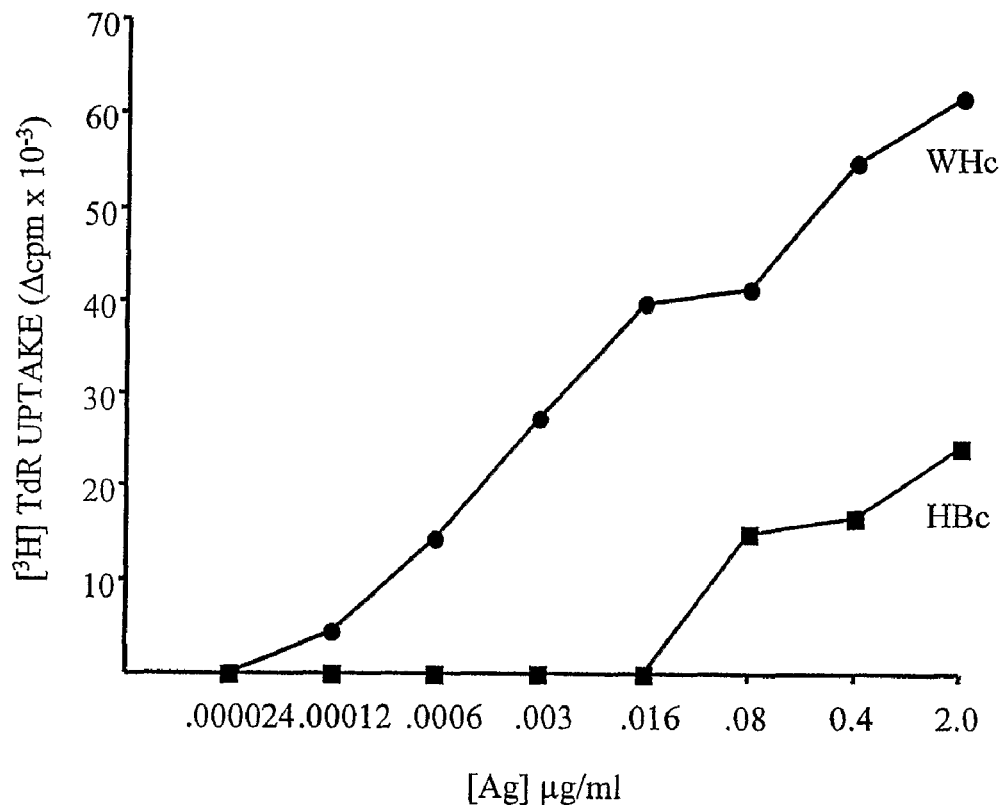
Figure 8:
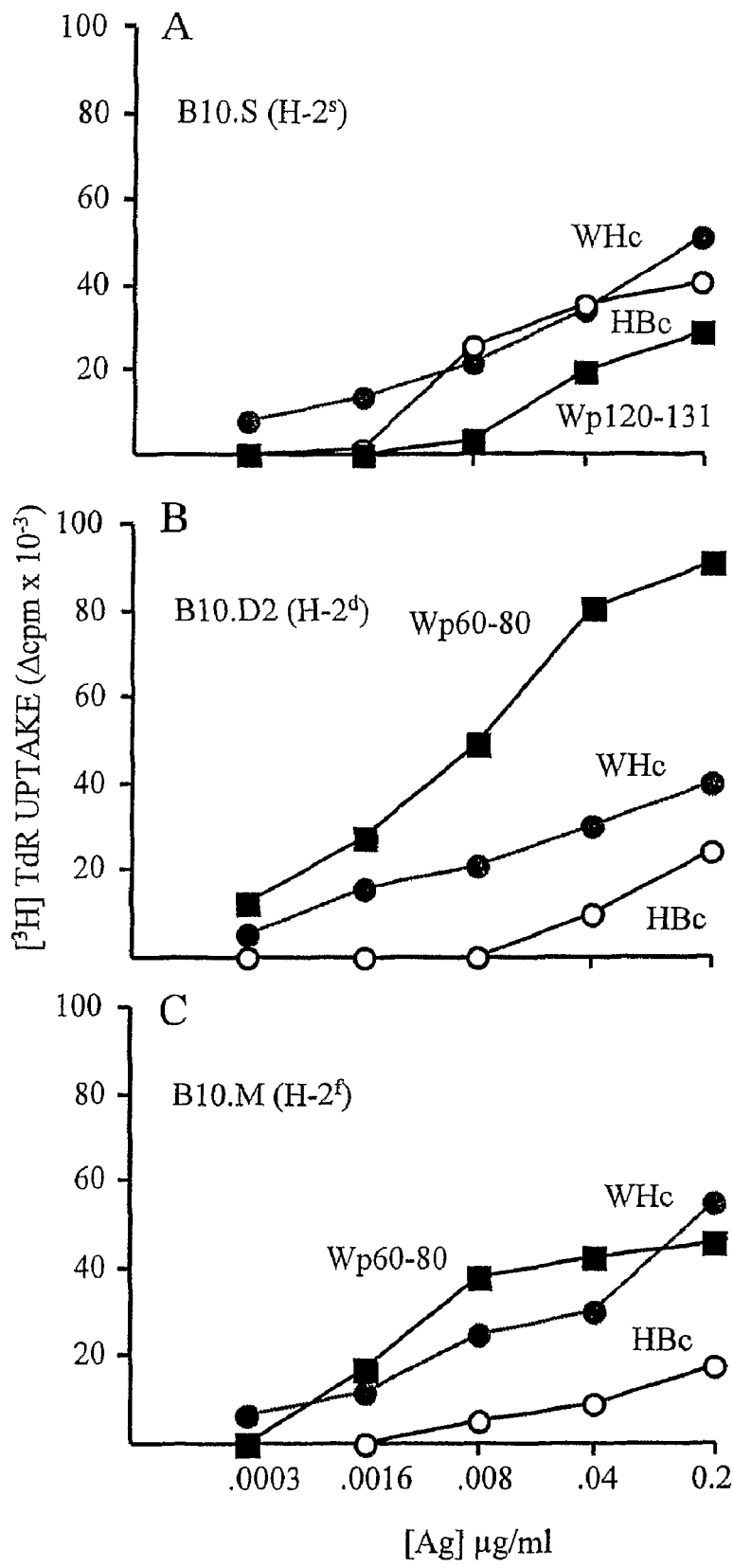

Importantly, a carrier platform must possess sufficient Th cell (CD4$^+$) recognition sites to ensure that every MHC haplotype will be able to associate with at least one T cell site in order to avoid genetic (MHC-linked) nonresponsiveness. FIG. 7 illustrates the CD4$^+$ T cell proliferative response to WHcAg and HBcAg upon immunization of Balb/c mice with WHcAg. The WHcAg was able to recall a proliferative response at a relatively low in vitro concentration of 0.12 ng/ml. Also note the low level of crossreactivity between the WHcAg and the HBcAg. Specifically, the HBcAg required an in vitro concentration of 80 ng/ml to recall a proliferative response from WHcAg-primed T cells which amounts to a 666-fold difference from the recall response observed for WHcAg. This result and additional studies indicate that the WHcAg-primed T cells in Balb/c mice (H-2$^d$) recognize a site(s) on WHcAg which is not conserved on the HBcAg. Specifically, B10.D2 mice (H-2$^d$) recognize the p60-80 sequence of WHcAg, which is not conserved on the HBcAg sequence (See, FIG. 8, panel B). Similarly, the B10.M (H-2$^f$) strain also recognizes a T cell epitope within p60-80 on WHcAg, and WHcAg-primed T cells from this strain are poorly crossreactive with HBcAg (See, FIG. 8, panel C). Alternatively, if an WHcAg-specific T cell recognizes a site on WHcAg which is highly conserved between WHcAg and HBcAg, than the WHcAg and HBcAg epitopes will be crossreactive for that particular T cell. Such a circumstance occurs in the B10.S(H-2$^s$) strain in which the dominant T cell recognition site is within p120-131, a region which is highly conserved on HBcAg. Therefore, in strains bearing the H-2$^s$ haplotype the WHcAg and the HBcAg are crossreactive at the T cell (CD4$^+$) level as shown in FIG. 8, panel A. Thus, the T cell crossreactivity of the WHcAg and the HBcAg has been shown herein to be variable and dependent upon the T cell site recognized (as dictated by MHC genotype).

Figure 9:
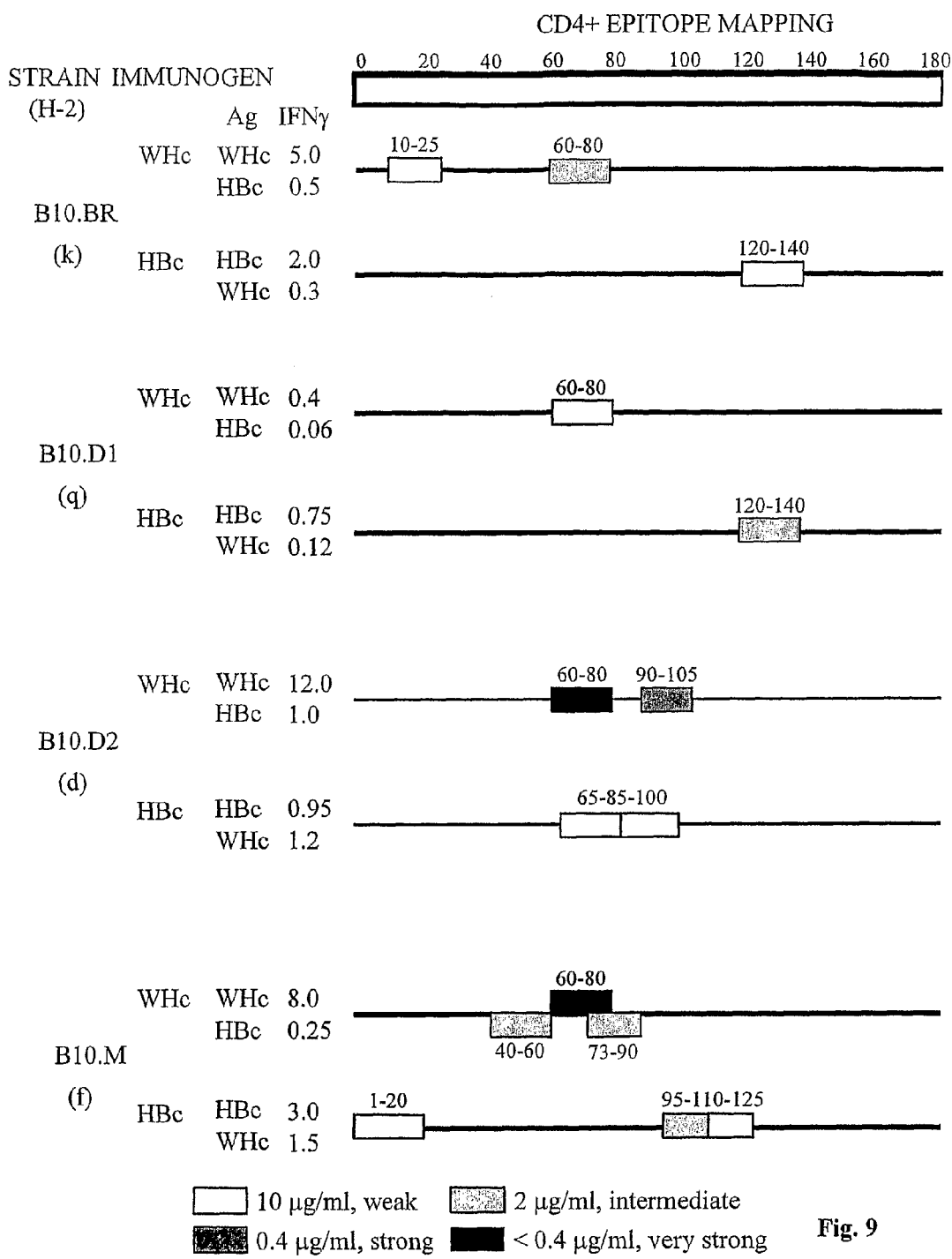
Figure 10:
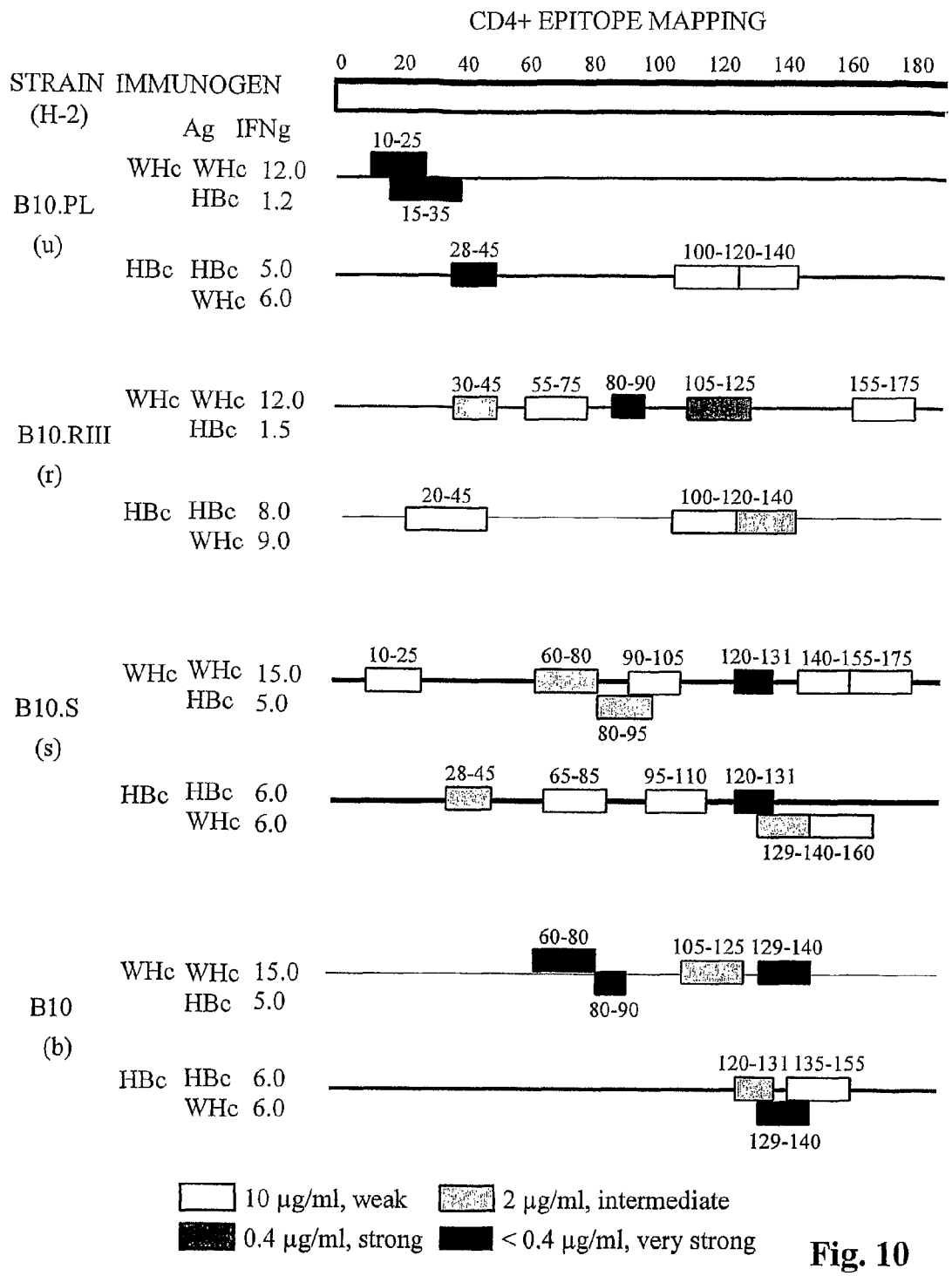

Additionally, the fine specificity of T cell recognition of the WHcAg and the HBcAg in 8 different H-2 congenic strains representing 8 separate MHC genotypes was determined using panels of WHcAg- and HBcAg-derived synthetic peptides as antigens (See, FIGS. 9 and 10). In the first place, all 8 MHC genotypes responded to the WHcAg at the T cell level (no genetic nonresponders). Secondly, in general, most strains recognize totally distinct sets of T cell sites on WHcAg and HBcAg, and even when similar regions are recognized, WHcAg-primed T cells rarely crossreact with HBcAg-derived peptides and vice versa. The two exceptions are the H-2$^s$ and the H-2$^b$ haplotypes, which predominantly recognize the 120-131 (H-2$^s$) and 129-140 (H-2$^b$) sites, both of which are highly conserved between the WHcAg and the HBcAg. However, even in H-2$^s$ and H-2$^b$-bearing strains a number of additional non-crossreactive T cell sites are recognized by WHcAg or HBcAg-primed T cells. For example, the T cells of B10 (H-2$^b$) mice primed with WHcAg recognize non-crossreactive T cell sites at residues 60-80, 80-90 and 105-125 in addition to the 129-140 T cell site.

Strikingly, in comparing T cell (CD4$^+$) recognition of WHcAg versus HBcAg, WHcAg was found to be a more efficient T cell immunogen than HBcAg. First, in most murine strains the WHcAg appears to possess a greater number and more potent CD4$^+$ T cell epitopes. Second, comparing the amount of IFNγ produced by WHcAg-primed T cells recalled with WHcAg, with the amount of IFNγ produced by HBcAg-primed T cells recalled with HBcAg reveals that WHcAg elicits greater IFNγ production in all but one strain (i.e., B10.D1). Third, when the WHcAg is used as the immunogen the ratio of IFNγ produced after in vitro recall with WHcAg as opposed to in vitro recall with HBcAg is always greater than 1 (ranges between 3.0 for the B10 and B10.S strains, and 32 for the B10.M strain). In contrast, when the HBcAg is used as the immunogen the ratio of IFNγ production after in vitro recall with HBcAg as compared to recall with WHcAg is 1 or less in 5 of the 8 strains tested. A T cell response, which is recalled more efficiently by a heterologous antigen than the priming antigen is referred to as a heteroclitic T cell response. The ability of the WHcAg to elicit a heteroclitic T cell response from HBcAg-primed T cells in 3 strains (i.e., B10.D2, B10.PL and B10.RIII) indicates that the WHcAg is processed and/or presented by antigen presenting cells (APCs) more efficiently than the HBcAg.

EXAMPLE 6

Effect of WHcAg Use as a Vaccine Platform on the Anti-HBc Diagnostic Assay

Figure 11:
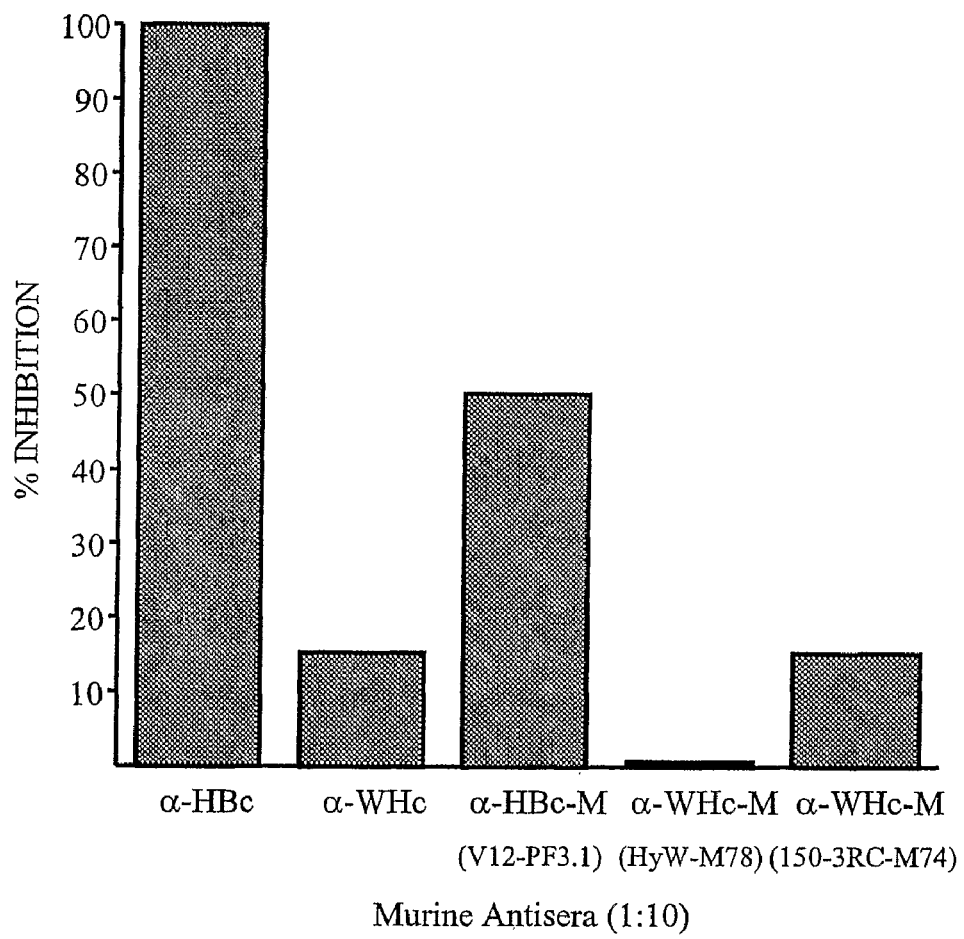

One of the advantages to using WHcAg as a vaccine platform is because unlike HBcAg, WHcAg is not expected to elicit anti-HBc antibodies which could compromise the use of the commercial anti-HBc assay as a diagnostic marker of previous or current HBV infection. To directly examine this issue murine anti-HBc, anti-WHc and antisera to the HBcAg-based malaria vaccine candidate V12.PF3.1 and several WHcAg-based malaria-core particles were tested in a commercial anti-HBc assay (Sorin, Italy). This assay is an inhibition assay and positivity is measured by % inhibition. As shown in FIG. 11, anti-HBc demonstrated 100% inhibition and antisera to the V12-PF3.1 malaria vaccine candidate demonstrated 50% inhibition, respectively. The anti-V12-PF3.1 antisera inhibited 50% because the malaria insert in the loop disrupts one of two dominant endogenous B cell epitopes on HBcAg (Schodel et al., J Virol, 66:106-114, 1992). In contrast, murine antisera to native WHcAg showed low level inhibition (16%), as did antisera to one of the WHcAg-based hybrid-core particles (150-3RC-M74), while antisera to a second WHcAg-based hybrid particle (HyW-M78) exhibited no inhibition. Therefore the use of WHcAg as a vaccine platform circumvents the problem of interference with the commercial anti-HBc assay.

EXAMPLE 7

WHcAg Effectiveness as a Vaccine Platform in HBV Chronic Carriers

Another problem with the use of HBcAg as a vaccine platform is the issue of immune tolerance that exists to HBcAg in chronic carriers of the HBV. The HBV is endemic in many parts of the world with an estimated 300-400 million HBV chronic carriers worldwide. The HBcAg-specific $CD4^+$ and $CD8^+$ T cell responses in HBV chronic carriers are severely depressed and usually undetectable (Ferrari et al., J Immnol, 145:3442-3449, 1990). As the WHV is not a human pathogen and because $CD4^+$ T cell recognition of WHcAg and HBcAg is mostly non-crossreactive, a vigorous WHcAg-specific Th cell repertoire is contemplated to be available in HBV chronic carriers. To explore this issue, an HBV-Tg mouse model of HBV chronic infection was used in the following studies. HBeAg-Tg mice produce the secreted form of the HBcAg and HBeAg-Tg mice on a $(B10.S \times Balb/c)_{F1}$ background are tolerant to the HBcAg at the Th cell level, mimicking the immune status of HBV chronic carriers (Milich et al., Proc. Natl. Acad. Sci. USA, 87:6599-6603, 1990).

Figure 12:
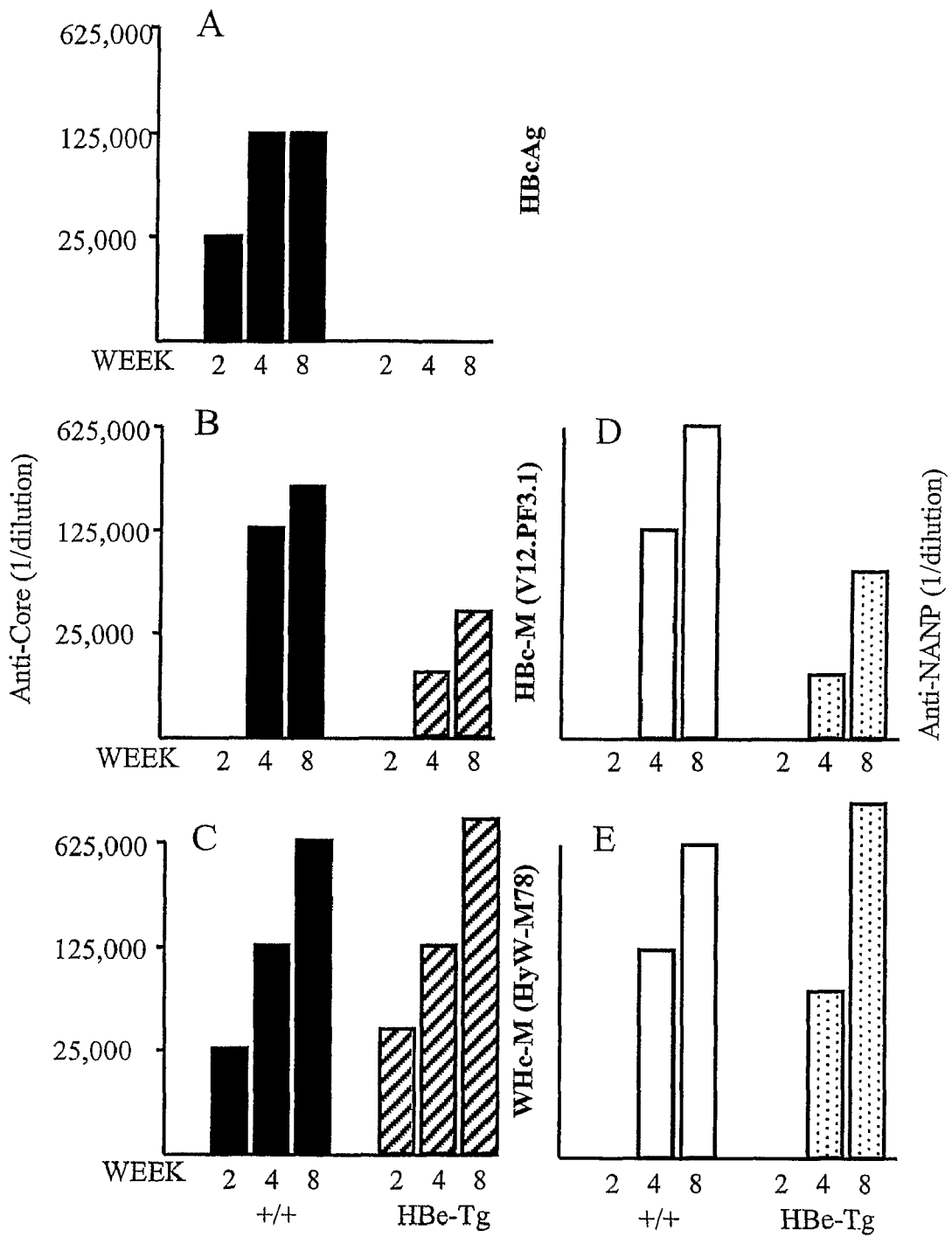

Wild-type (+/+) mice and HBeAg-Tg mice were immunized with either HBcAg, a HBcAg-based malaria vaccine candidate (HBc-M, V12.PF3.1) or a WHcAg-based malaria vaccine candidate (WHc-M, HyW-M78). Both vaccine candidates possess the same malaria CS-derived B cell epitope (i.e., NANPNVDP(NANP)$_3$, set forth as SEQ ID NO:75). The HBc-M vaccine candidate also possesses a heterologous malaria-specific Th cell epitope referred to as the malaria universal T cell site (Calvo-Calle et al., J Immunol, 159:1362-1373, 1997). As shown in FIG. 12 panel A, HBeAg-Tg mice are immune tolerant to the HBcAg and produce no anti-HBc antibody, whereas, the control (+/+) mice produce anti-HBc at weeks 2, 4 and 8 post immunization. Likewise, immunization with the HBc-based V12.PF3.1 vaccine candidate also elicits significantly less anti-HBc antibody production and less anti-NANP antibody production in HBeAg-Tg mice as compared to the control (+/+) mice (FIG. 12, panels B and D). Therefore, immune tolerance to the HBcAg was shown herein to adversely affect the ability of the HBcAg to perform as a vaccine platform for a malaria-specific B cell epitope. The low level of anti-core and anti-NANP antibodies that are produced may be due to the function of the heterologous universal T cell site or a novel Th cell epitope(s) created at the junction between the HBcAg and the inserted sequence. The (NANP)$_3$ sequence (SEQ ID NO:68) is not a T cell epitope in $(B10.S \times Balb/c)_{F1}$ mice. Importantly, the HBeAg-Tg mice demonstrated no diminished ability to produce anti-WHc or anti-NANP antibodies when the WHcAg-based malaria vaccine candidate (HyW-M78) was used (FIG. 12, panels C and E). Thus, the negative effects of immune tolerance to the HBcAg were circumvented by using the WHcAg as a vaccine platform for a malaria B cell epitope.

Figure 13:
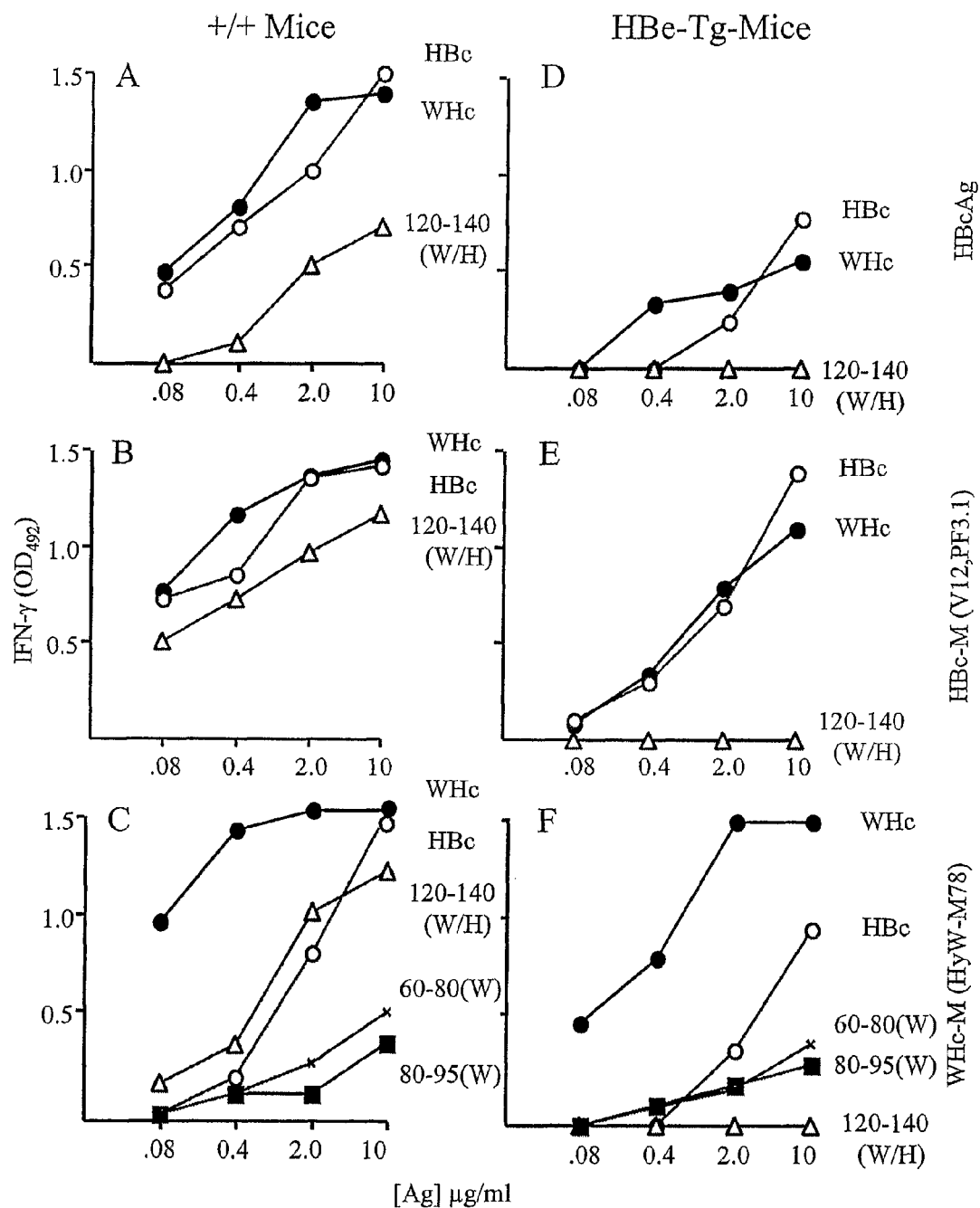

In additional studies, the HBcAg-primed T cells of $(B10.S \times Balb/c)_{F1}$ mice were found to predominantly recognize the p120-140 sequence. The p120-140 sequence is highly conserved between WHcAg and HBcAg, and all three antigens recall in vitro IFNγ production from HBcAg-primed T cells in +/+ mice (FIG. 13, panel A). However, p120-140-specific T cells are tolerized in HBeAg-Tg mice (i.e., no recall response with 120-140), which accounts for the poor in vitro recall responses elicited by both the HBcAg and the WHcAg compared to +/+ mice (FIG. 13, panel D). Similarly, the in vitro T cell responses to the HBcAg and the WHcAg are significantly reduced in HBeAg-Tg mice as compared to +/+ mice immunized with the HBcAg-based V12.PF3.1 vaccine candidate because 120-140-specific T cells are tolerized in HBeAg-Tg mice (FIG. 13, panels B and E). In contrast, an advantage to using the WHcAg as a carrier platform is the presence of T cell epitopes within the WHcAg that are unique to the WHcAg and not present on the HBcAg, for example, residues 60-80 (W) and 80-95 (W) (FIG. 13, panels C and F). Therefore, while the function of p120-140-specific T cells is lost in HBeAg-Tg mice immunized with the WHcAg-based vaccine (HyW-M78) due to the tolerizing effects of the presence of HBeAg, T cell recognition of the WHcAg-specific T cell epitopes (p60-80W and p80-95W) is identical in control (+/+) and HBeAg-Tg mice. The ability of the WHcAg to recall IFNγ production in HBeAg-Tg mice is marginally decreased as compared to the HBcAg due to the function of the p60-80 (W) and p80-95 (W) T cell sites, which are also sufficient to promote high levels of anti-WHc and anti-NANP antibody production in HBeAg-Tg mice as shown in FIG. 12. Thus, the WHcAg platform is contemplated to be significantly more effective in an HBV chronic carrier population than a vaccine based on the HBcAg platform.

EXAMPLE 8

Versatility of the WHcAg Combinatorial Technology

Although the HBcAg has been used as a carrier platform, less than 50% of selected foreign sequences can be successfully inserted into HBcAg (See, Jegerlehner et al, Vaccine, 20:3104, 2002; and International Application No. PCT/US01/25625, hereby incorporated by reference). This high failure rate is contemplated to be due to the destabilizing effects of inserting foreign sequences on particle assembly.

To circumvent this problem, others have chosen to chemically link foreign epitopes to wild-type particles, as opposed to trying to incorporate the epitopes into the particles by recombinant methods (Jegerlehner et al., supra, 2002, and Chackerian et al, J Clin Invest, 108:415-423, 2001). In contrast, the current invention was developed to accommodate a greater variety of foreign epitope insertions without destabilizing particle assembly. Specifically, successful direct insertions of epitopes have been reported for positions 77, 78, 81, 82 and the N- and C-termini of HBcAg (Pumpens and Grens, Intervirology, 44:98-114, 2001). On the other hand, using the WHcAg platform, in addition to positions 77, 78, 81, and 82 within the loop region and the N- and C-termini, a number of other internal insertion sites outside the loop region have been identified including positions 44, 71, 72, 73, 74, 75, 76, 83, 84, 85 and 92 (See, FIG. 3). Importantly, during development of the present invention, three HIV epitopes, which could not be expressed and/or assembled using the HBcAg platform, were successfully expressed and assembled in the context of the WHcAg platform. Specifically, the WHcAg platform rescued the HIV4.1, HIV5.1, and HIV6.1 epitopes (See, Table 10), for which failures using HBcAg were previously reported (International Application No. PCT/US01/25625). In short, a relatively large library of 17 competent insertion sites on the WHcAg platform have been identified during development of the present invention.

Importantly, this expansion of the number of positions available for insertion of foreign epitopes was made possible by the generation of a library of C-terminal modifications to the WHcAg which variably stabilize insertions at different positions. In fact, the C-terminal modifications of the WHcAg described herein comprise a very useful second library of 21 C-terminal modifications. Table 1 lists the sequences of the various modified C-termini. The C-terminal modifications were designed to eliminate RNA/DNA binding motifs, eliminate/substitute prolines, replace the last five C-terminal amino acids and to eliminate or conserve non-homologous regions between HBcAg and WHcAg. Wild type or full length WHcAg binds significant amounts of bacterial RNA/DNA, which is undesirable for a vaccine platform. During development of the present invention, RNA/DNA binding to the C-terminally modified WHcAg particles has largely been eliminated. In contrast, three different HBcAg C-termini have been previously described: full length; truncated at residue 149, and truncated plus an added cysteine at position 150.

The combined libraries of insertion sites and modified C-termini accumulated for the WHcAg have permitted the successful insertion of 22 of 24 attempted sequences (See, Table 9). Additionally, the sequence of the inserted epitope has been found to play a role in determining whether a given sequence can be inserted at a given position in the context of a given C-terminus. The sequence of selected inserts is provided in Table 10. Therefore, three variables must be considered in designing a WHcAg-hybrid particle: the insert position; the C-terminal sequence; and the epitope sequence. For this reason, a rapid screening method has been developed to examine efficacy of expression and assembly of hybrid-core particles at the early bacterial lysate step. This method makes feasible a combinatorial approach involving shuffling of the insert position, and the C-terminal modification for each epitope of interest. As shown in Table 11, a strong correlation between the relative lysate assembly scores and the ability to purify hybrid core particles in high yield has been observed.

TABLE 9

Summary of Insert Sites, Model Epitopes, and C-Termini Successfully Tested on the WHcAg Platform

| List of Insert Sites | List of Epitopes[1] | List of C-Termini |
|---|---|---|
| 44-45 | M | FL(188) |
| 71-72 | MV | 150C |
| 72-73 | IM2 | 150R |
| 73-74 | IM2(—) | 150-2RC |
| 74-75 | FV-1 | 150-3RC |
| 75-76 | FV-2 | 150-4RC |
| 77-78 | HV-1 | 150-3KC |
| 78-79 | HV-2 | 150-3AC |
| 81-82 | HV-3 | WT-R |
| 82-83 | HV-4 | WT-R1 |
| 83-84 | HV 4.1 | WT-R2 |
| 84-85 | HV 5.1 | WT-R3 |
| 85-86 | HV 6.1 | C-long |
| 92-93 | CETP | C-long(M1) |
| C-terminal | SEB | C-long(M2) |
| N-terminal | AZ | C-long(M3) |
|  | HCV-6 | HyW |
|  | HCV-10 | HyW-1 |
|  | HCV-17 | HyW-2 |
|  | HCV-18 | HyW-3 |
|  | HCV-24 | HyW-4 |
|  | EGFR VIII | HyW-5 |
|  | OMP-1 |  |
|  | OMP-2 |  |

[1]Abbreviations include: M, malarial CS repeat - *P. falciparum*; MV, malarial CS repeat type I - *P. vivax*; IM2, influenza A M2e extracellular domain; IM2(—), mutant influenza A M2e domain lacking two cysteine residues; FV, feline immunodeficiency virus-1 gp41, HV, human immunodeficiency virus gp120; CETP, cholesteryl ester transfer protein; SEB, *staphylococcus* enterotoxin B; AZ, β-amyloid; HCV, hepatitis C virus; EGFR VIII, epidermal growth factor receptor mutant VIII; and OMP, outer membrane protein. To date 22 out of 24 epitopes tested were accommodated by the WHcAg vaccine platform (92% success rate). This is in contrast to the less than 50% success rate seen when using the HBcAg platform (wild type, $I^{149}$ C-terminus and $C^{150}$ C-terminus) as determined through review of the literature and through development of the present invention.

TABLE 10

Primary Amino Acid Sequences of the Various Model Epitopes

| Designation[1] | Sequence | Identifier |
|---|---|---|
| HV-1 | GEIKNCSFNISTSIR-GKVQKEYAFF | SEQ ID NO: 70 |
| HV-2 | LTSCNTSVITQACPKVS-FEPIPIHYC | SEQ ID NO: 71 |
| HV-3 | PKVSFEPIPIHYCAPAG-FAILKCNN | SEQ ID NO: 72 |
| HV-4 | THGIRPVVSTQLLLNGSLAEEE | SEQ ID NO: 73 |
| MV | DRAAGQPAGDRADGQPAG | SEQ ID NO: 74 |
| M | NANPNVDPNANPNANPNANP | SEQ ID NO: 75 |
| IM2 | SLLTEVETPIRNEWGCRCNDSSD | SEQ ID NO: 76 |
| IM2(-) | SLLTEVETPIRNEWGARANDSSD | SEQ ID NO: 77 |
| SEB | KLKKVTAQELD | SEQ ID NO: 78 |
| CETP | FGFPEHLLVDFLQSLS | SEQ ID NO: 79 |
| FV-1 | FYEIIMDIEQNNVQGKQGLQKL | SEQ ID NO: 80 |
| FV-2 | MELRKNGRQCGMSEKEEE | SEQ ID NO: 81 |
| EGFR VIII | LEEKKGNYVVTDH | SEQ ID NO: 82 |

TABLE 10-continued

Primary Amino Acid Sequences of the
Various Model Epitopes

| Designation[1] | Sequence | Identifier |
|---|---|---|
| AZ-1 | DAEFRHDSGYEV | SEQ ID NO: 83 |
| AZ-2 | FRHDSGY | SEQ ID NO: 84 |
| HV 4.1 | RIKQIGMPGGK | SEQ ID NO: 85 |
| HV 5.1 | LLELDKWASL | SEQ ID NO: 86 |
| HV 6.1 | EQELLELDKWASLW | SEQ ID NO: 87 |
| HCV-6 | DTGFLAAL | SEQ ID NO: 88 |
| HCV-10 | YCFTPSPV | SEQ ID NO: 89 |
| HCV-17 | CFRKHPEA | SEQ ID NO: 90 |
| HCV-18 | EATYSRCG | SEQ ID NO: 91 |
| HCV-24 | HLHQMVD | SEQ ID NO: 92 |

[1]See footnote to Table 9 for a key to epitope abbreviations.

TABLE 11

Positive Correlation Between Expression and Assembly Scores
and Hybrid Particle Purification[1]

| Designation | Expression (anti-pWHc) | Assembly (anti-nWHc) | Accessability (anti-insert) | Particle Purification |
|---|---|---|---|---|
| 150-3KC-M74 | 3 | 4 | 4 | yes |
| 150-3AC-M74 | 4 | 3 | 4 | yes |
| c-long(M3)-M74 | 3 | 3 | 4 | yes |
| 150C-M75 | 4 | 4 | 5 | yes |
| 150C-M77 | 4 | 3 | 2 | yes |
| 150C-M78 | 5 | 4 | 3 | yes |
| C-long-M78 | 3 | 3 | 4 | yes |
| HyW-M78 | 3 | 4 | 4 | yes |
| HyW-M92 | 2 | 3 | 3 | yes |
| HyW-M(NH2) | 2 | 3 | 3 | yes |
| HyW-M(COOH) | 3 | 4 | 2 | yes |
| HyW-MV78 | 4 | 3 | 4 | yes |
| HyW-CE74 | 3 | 3 | 3 | yes |
| HyW-HV-4(74) | 2 | 2 | ND | yes |
| 150C-HV-4(78) | 3 | 2 | ND | yes |
| HyW-IM2(—)78 | 4 | 4 | 3 | yes |
| HyW2-K75 | 3 | 3 | ND | yes |
| average | 3.24 | 3.24 | 3.4 | n/a |
| 150C-IM2(74) | 3 | 2 | 3 | no |
| HyW-IM2(74) | 2 | 2 | 3 | no |
| WT-R-IM2(74) | 3 | 2 | 2 | no |
| HyW-K78 | 2 | 2 | ND | no |
| HyW-M74-CD40L(470) | 2 | 2 | 2 | no |
| average | 2.4 | 2.0 | 2.5 | n/a |

[1]The scores shown are relative and designate antibody binding normalized to wild type (WT) WHcAg or maximal (MAX) binding for the insert-specific mAbs: 5 = WT/MAX; 4 = 5X less than WT, 3 = 25X less than WT, and 2 = 125X less than WT.
ND = not determined.

EXAMPLE 9

Effect of Insert Position and C-Terminus on Particle Assembly

The position of the inserted epitope within the WHcAg has been shown herein to affect the ability of the hybrid WHcAg core to assemble as a particle. For example, the (M) epitope in the context of either HyW or HyW2 C-termini permitted assembly in most positions tested with the exception of positions 21, 91 and 96 (See, Table 12). Similarly, positions 75, 76, 77, 78, 81, 82, and 83 were permissive in the context of the 150-C C-terminus. Note that position 74 (bold-type) was not permissive in the context of the 150-C C-terminus, but this position is rescued in the context of HyW/HyW2 C-termini. Similarly, position 78 is not permissive for assembly in the context of the 188-C C-terminus, but is permissive in combination with HyW/HyW2 and 150-C. Thus, the position of the insert can affect assembly and non-permissive insert positions can be rescued through combination with an alternate C-terminus. This phenomenon was not unique to malaria inserts, as similar effects were observed with other heterologous sequences.

TABLE 12

Effect of Insert Position on Hybrid Particle Assembly[1]

| C-terminus | Epitope | Satisfactory Assembly | Poor/Non-Assembly |
|---|---|---|---|
| HyW/HyW2 | M | 44, 73, 74, 75, 78, 84, 85, 92, N, C | 21, 91, 96 |
| 150C | M | 75, 76, 77, 78, 81, 82, 83 | 66, 74, 79, 80, 86 |
| 188 | M | 74 | 78 |
| HyW/HyW2 | CE | 74 | 75, 78 |
| HyW2 | FV-1 | 75, 78 | 74 |
| HyW2 | FV-2 | 74, 75, 78 | — |
| 150C | FV-1 | 75, 78 | 74 |
| 150C | FV-2 | 74, 75, 78 | — |
| HyW/HyW2 | HV-4 | 74, 75 | — |
| 150C | HV-4 | 75, 78 | 74 |

[1]Numbers represent the amino acid position on WHcAg that precedes the inserted epitope. Assembly was assessed by ELISA using core assembly-dependent anti-Hc antibody. Bold numbers depict insert positions that can be rescued by altering the C-terminus.

A second variable influencing hybrid particle assembly is the C-terminus of the WHcAg protein (See, Table 13). For example, the (M) epitope inserted at position 74 results in hybrid core particle assembly in the context of ten different C-termini, however, five C-termini are non-permissive for assembly with (M) at position 74. The (M) epitope in position 78 appears less destabilizing since most C-termini are permissive including all five of the C-termini which were non-permissive for this epitope inserted at position 74. Therefore, non-permissive C-termini can be rescued by altering the insert position. Interestingly, the two non-permissive C-termini for (M) at 78 are both permissive for (M) at 74. Without intending to limit the invention to any mechanism, this reciprocal relationship indicates that the mechanisms of destabilization of the (M) insert at positions 74 and 78 are different and can be stabilized by different C-terminal sequences. Furthermore, the HyW and HyW2 C-termini appear to be significantly more permissive for a variety of inserted epitopes and positions than is the 150-C C-terminus. A summary of the combinatorial technology is depicted in Table 14. Ten of the heterologous model epitopes that have been used are listed together with the combination of C-terminus and insert position which resulted in an optimal platform. Note that for these ten heterologous epitopes, seven different combinations of C-terminus plus insert position are represented. In short as determined during development of the present invention, no one universal WHcAg platform suffices for all heterologous epitopes, and thus a combinatorial approach is necessary for the widest possible application of the WHcAg vaccine platform technology. During development of the present invention, various WHcAg C-termini (seven) were used in place of the wild type HBcAg C-terminus. Specifically, three epitopes were inserted into modified WHcAg and into modified HBcAg at five different positions. As shown in Table 15, in all but one instance, the model epitopes expressed as part of a hybrid HBcAg containing a WHcAg C-terminus were assembled as virus-like particles. Therefore, the C-terminal modifications developed for WHcAg are also useful in the context of the HBcAg N-terminus. Similarly, the same 3 epitopes were inserted into modified GSHcAg at four different positions using various WHcAg C-termini (five) in place of the wild-type GSHcAg C-terminus. As shown in Table 15, in all but one instance, the model epitopes expressed as part of a hybrid GSHcAg containing a WHcAg C-terminus were assembled as virus-like particles. Therefore, the C-terminal modifications developed for WHcAg are also useful in the context of the GSHcAg N-terminus.

TABLE 13

Effect of C-terminal Modification on Hybrid Particle Assembly[1]

| Epitope | Insert | Satisfactory Assembly | Poor/Non-Assembly |
|---|---|---|---|
| M | 74 | 188, 150R, 150-3RC, 150-4RC, 150-3KC, 150-3AC, C-long(M3), HyW HyW1, HyW2 | 150C, C-long, C-long(M1) C-long(M2), WT-R |
| M | 78 | 150C, HyW, 150-2RC, 150-3RC, C-long, C-long(M1), C-long(M2), C-long(M3), WT-R | 150R, 188 |
| CE | 74 | HyW | 150C |
| HV-2 | 75 | HyW2 | 150C |
| HV-3 | 74 | HyW2 | 150C |
| HV-3 | 75 | HyW2 | 150C |
| HV-4 | 74 | HyW | 150C |
| CD40L (470) | C | 188 | 150C, 150R |
| IM2(—) | 78 | HyW | 150C |

[1]Numbers represent the amino acid position on WHcAg that precedes the inserted epitope. Assembly was assessed by ELISA using core assembly-dependent anti-Hc antibody. Bold numbers depict C-termini that can be rescued by altering the insert position.

TABLE 14

Optimal C-Terminus and Insert Position Combinations for Model Epitopes[1]

| Epitope | C-Terminus | Insert Position |
|---|---|---|
| M | C-long | 78 |
| MV | HyW | 78 |
| CE | HyW | 74 |
| FV-1 | HyW2 | 75 |
| FV-2 | 150C | 74 |
| HV-2 | HyW2 | 75 |
| HV-3 | HyW2 | 75 |
| HV-4 | 150C | 75 |
| IM2 | WT-R | 74 |
| IM2(—) | HyW | 78 |

[1]The amino acid sequences of the WHcAg C-termini and of the model epitopes are provided in Tables 1 and 10, respectively. The optimal platform determination was based upon either the immunogenicity of the purified hybrid particles or upon their assembly score.

TABLE 15

Comparison of the WHcAg (W), GSHcAg (G) and HBcAg (H) Vaccine Platforms[1]

| Epitope | Position | C-Terminus | Platform | Assembly |
|---|---|---|---|---|
| M | 92 | HyW | W | + |
|   |   |   | H | + |
|   |   |   | G | + |
| M | 78 | HyW2 | W | + |
|   |   |   | H | + |
|   |   |   | G | + |
| M | 83 | 150C | W | + |
|   |   |   | H | + |
|   |   |   | G | + |

TABLE 15-continued

Comparison of the WHcAg (W), GSHcAg (G) and HBcAg (H) Vaccine Platforms[1]

| Epitope | Position | C-Terminus | Platform | Assembly |
|---|---|---|---|---|
| M | 78 | C-long | W | + |
|   |   |   | H | + |
|   |   |   | G | + |
| M | 78 | C-long (M3) | W | + |
|   |   |   | H | + |
| M | 78 | 150-3KC | W | + |
|   |   |   | H | + |
| M | 78 | WT-R | W | + |
|   |   |   | H | + |
|   |   |   | G | + |
| CETP | 74 | HyW2 | W | + |
|   |   |   | H | − |
|   |   |   | G | − |
| CETP | 75 | HyW2 | W | − |
|   |   |   | H | − |
| CETP | 78 | HyW2 | W | − |
|   |   |   | H | − |
| IM2(—) | 78 | HyW2 | W | + |
|   |   |   | H | + |
|   |   |   | G | + |
| IM2(—) | 78 | 150C | W | − |
|   |   |   | H | + |
|   |   |   | G | + |

[1]Bold type highlights differences observed between WHcAg, GSHcAg and HBcAg platform.

EXAMPLE 10

Immunogenicity of Hybrid Particles

Figure 14:
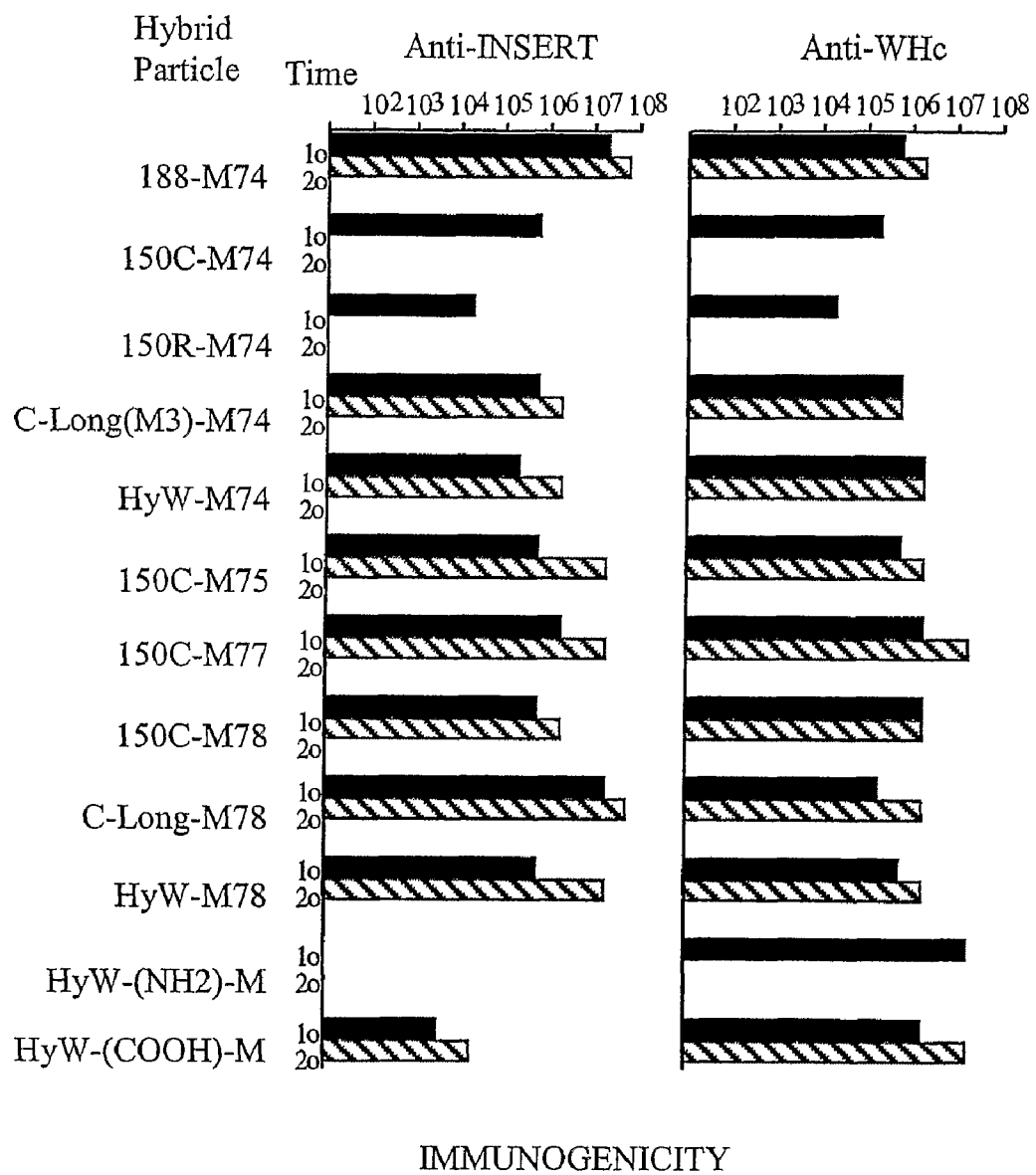
Figure 15:
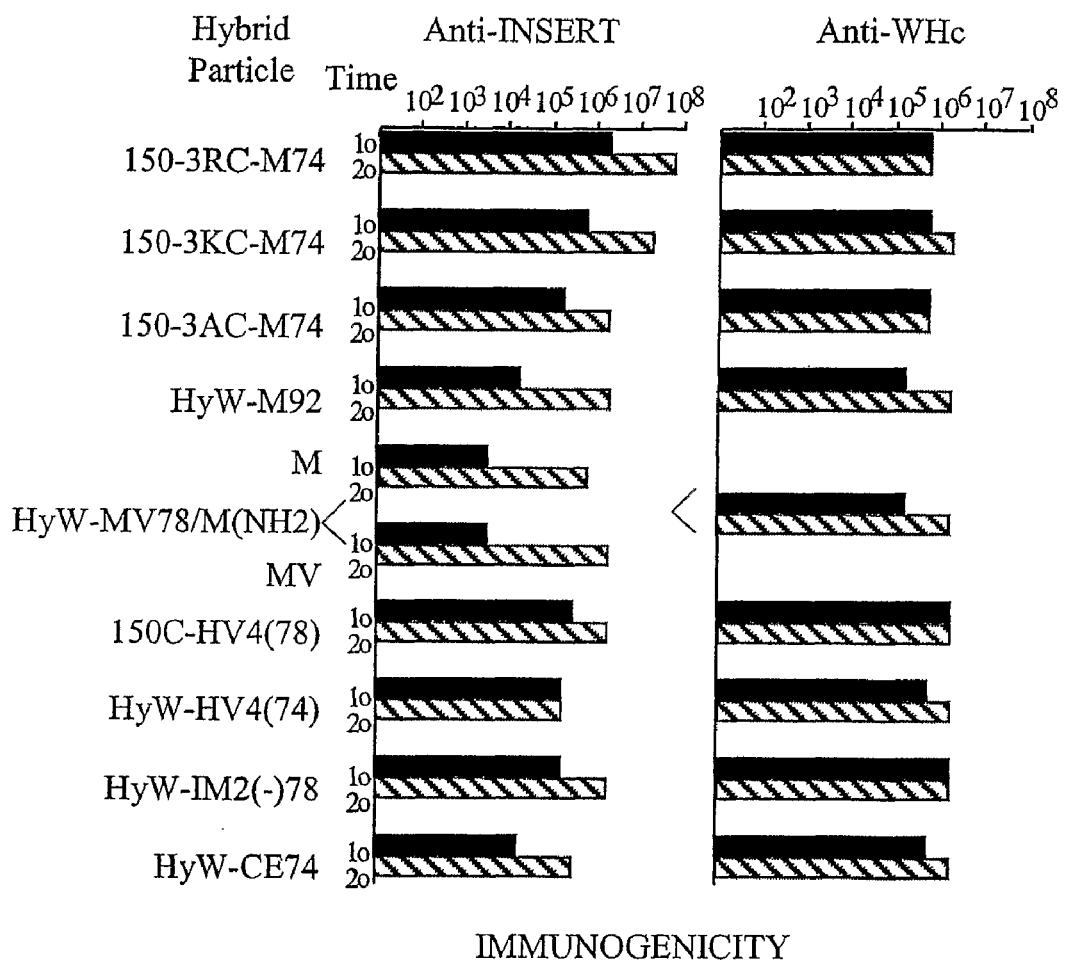

A number of hybrid core particles containing different epitopes inserted at different positions with varying C-termini have been produced and purified during the development of the present invention (See, Table 16). The in vivo humoral immune response to the inserted epitope, as well as the WHcAg carrier, was assessed for these particles. FIGS. 14 and 15 provide a summary of antibody production 8 weeks after a primary (20 µg), and 6 weeks after a secondary (10 µg) immunization with the various hybrid particles emulsified in IFA for both injections. Although a hierarchy of immunogenicity was observed, most hybrid core particles were quite immunogenic both in terms of anti-insert and anti-core antibody production. The primary anti-insert IgG serum titers ranged from 1:5000 to $15 \times 10^6$ and the secondary anti-insert IgG serum titers ranged from 1:25,000 to $1:75 \times 10^6$. These very high levels of anti-insert antibody production (particularly over such a wide variety of inserted epitopes) are unprecedented in the hybrid VLP literature, and thus the effectiveness of the WHcAg vaccine platform was not predictable.

Similarly, the GSHcAg can function as a carrier for inserted epitopes as demonstrated by immunization of mice with GS-150C-M83 hybrid particles that elicited an early (4 week) anti-insert titer of 1:5000.

TABLE 16

Exemplary Purified Hybrid WHcAg Particles

| Particle | Yield (mg/L) |
|---|---|
| 188-M74 | 30 |
| 150C-M74 | 2 |
| 150R-M74 | 16 |
| 150C-M77 | 12 |
| 150C-M78 | 18 |

TABLE 16-continued

Exemplary Purified Hybrid WHcAg Particles

| Particle | Yield (mg/L) |
|---|---|
| 150C-HV4(78) | 2 |
| HyW-HV4 (74) | 6 |
| 150C-3RC-M74 | 15 |
| 150C-3KC-M74 | 30 |
| 150C-3AC-M74 | 25 |
| 150C-M75 | 26 |
| C-long-M78 | 16 |
| HyW-M78 | 32 |
| HyW2-IM2(—)81 | 30 |
| 150C-IM2(—)82 | 35 |
| HyW2-SEB75 | 20 |
| C-long-M3-M74 | 18 |
| HyW-M74 | 21 |
| HyW-M(COOH) | 31 |
| HyW-M(NH2) | 16 |
| HyW2-M75 | 12 |
| HyW-IM2(—)78 | 10 |
| HyW-CE74 | 16 |
| HyW-K(COOH) | 28 |
| HyW2-LK75 | 26 |
| HyW-M92 | 21 |
| HyW-MV78 | 38 |
| HyW-MV78/MF(NH2) | 35 |
| HyW2-FV-1(75) | 22 |
| 188-CD40L | 2 |
| GS-150C-M78 | 40 |
| GS-150C-M83 | 30 |

EXAMPLE 11

Effect of Heterologous Insert Position on Immunogenicity

Figure 16:
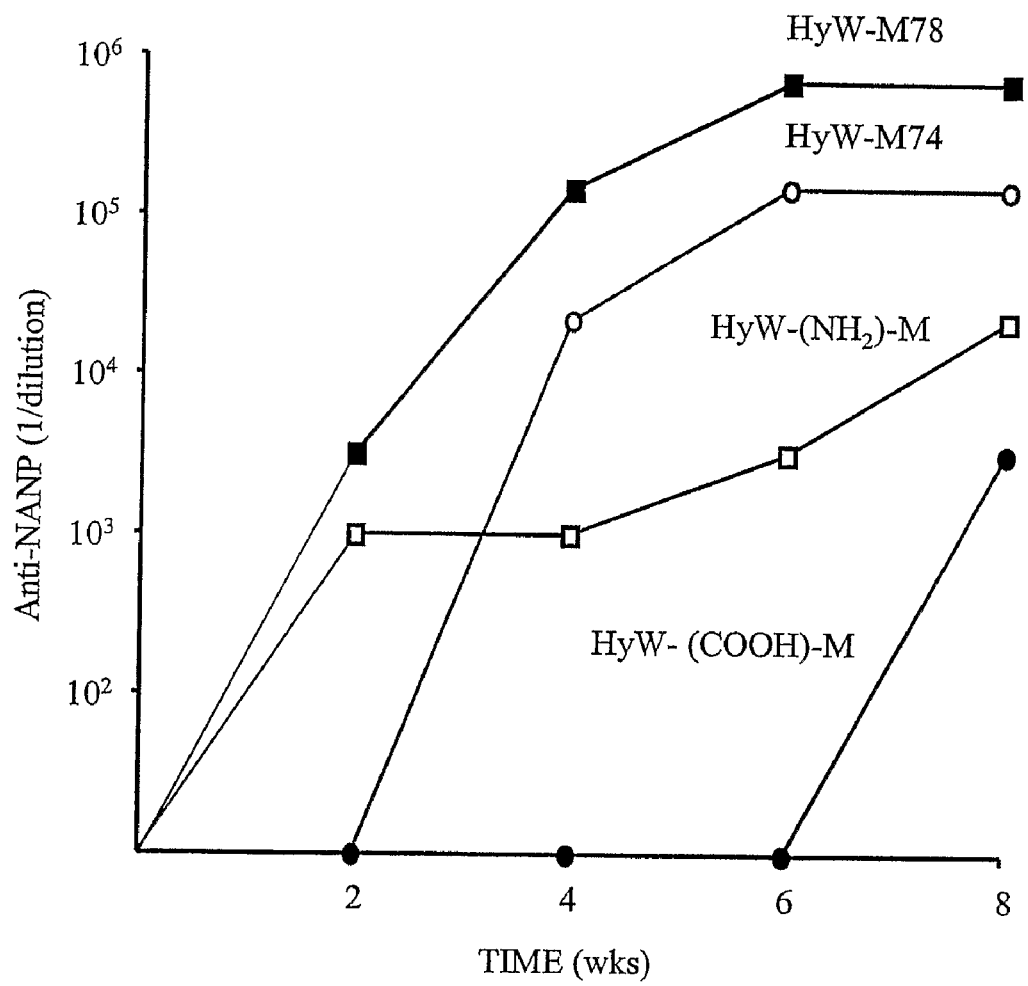

The immunogenicity of hybrid core particles composed of the same HyW-modified C-terminus and the same malaria repeat epitope was found to vary depending on where the epitope (M) was positioned (See, FIG. 16). Particles with insertions in (position 78) or near (position 74) the loop were more immunogenic in terms of the anti-insert response, than were particles with inserts fused to the N-terminus. Moreover, insert placement at the C-terminus was poorly immunogenic both in terms of end-point serum titer and delayed onset of antibody production. This correlation was not true for anti-carrier antibody production, which was greater or equal for the N- and C-terminal locations of the (M) epitope, as compared to the internal insertions. Therefore, the position of the epitope did not alter the overall immunogenicity of the particle and the positional effects are due to greater surface exposure and/or optimal spacing of the heterologous epitopes in or near the loop region. The high anti-carrier responses to the N- and C-terminally fused epitopes were contemplated to be due to conservation of the native loop structure and the endogenous WHcAg B cell epitopes on these hybrid core particles.

EXAMPLE 12

Effect of C-Terminus on Immunogenicity

Figure 17:
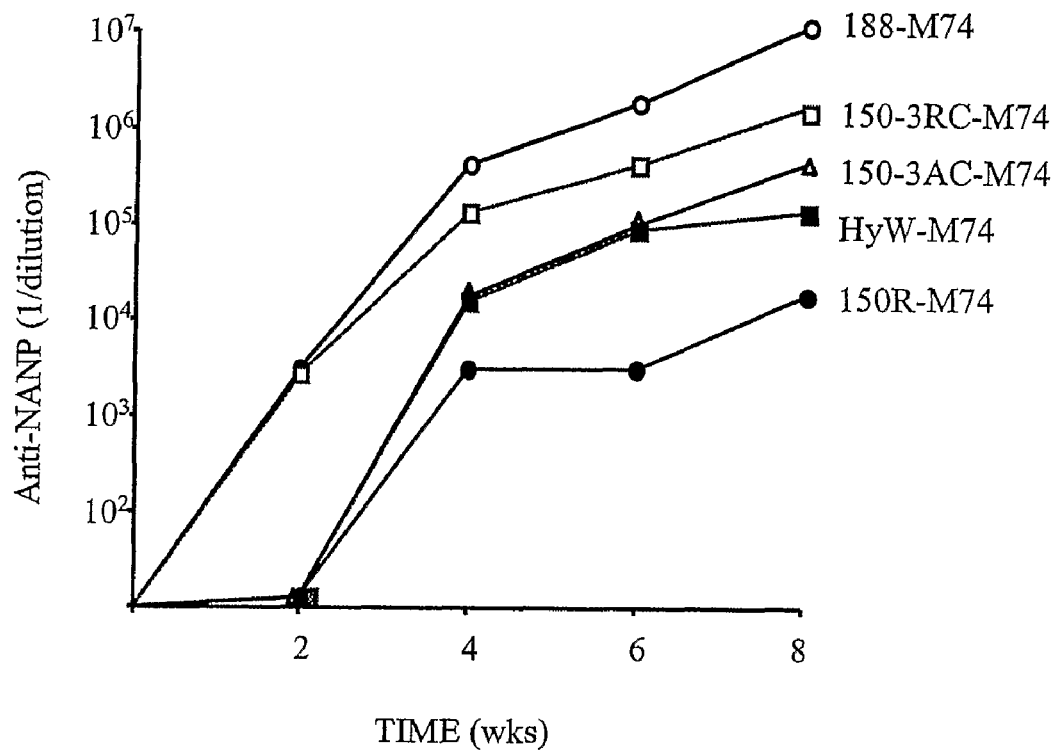

The immunogenicity of particles with the malaria (M) epitope inserted at position 74 but with varied C-termini were compared as shown in FIG. 17. Particles with the native full length (188-M74) or with the 150-3RC C-terminus were more immunogenic in terms of serum titers of anti-NANP antibody as well as a quicker onset (week 2) as compared to the 150 3AC and HyW C-termini. The particle comprised of the 150R C-terminus, which lacks a cysteine, was weakly immunogenic. The 150R-M74-hybrid particle was the least stable in vitro (and most likely in vivo), explaining the poorer immunogenicity results. The in vitro stability of the various other hybrid core particles is expected to correlate with immunogenicity in vivo.

Additionally, a bivalent hybrid core particle was constructed, containing the *Plasmodium falciparum* CS repeat epitope at the N-terminus and the *P. vivax* CS repeat (type 1) epitope in the loop position 78, HyW-MV78/M (NH$_2$). As shown in FIG. 15, during the primary response antibodies were produced to both inserts, although the serum titers were rather low (1:5000) as compared to most single inserts. However, after boosting, high titer antibodies were produced to both CS repeat sequences. Thus, the present invention provides bivalent hybrid core particles containing highly immunogenic epitopes at different positions on the same particle.

EXAMPLE 13

Effect of Genetics on Immunogenicity of a WHcAg-based Malaria Vaccine

Efforts to produce *P. falciparium* vaccine candidates based on the CS repeat sequences have been plagued by low immunogenicity and severe genetic restriction characterized by low responders in human clinical trials, and low or nonresponder murine MHC genotypes in mouse immunization studies. To address this issue, CS-derived CD4$^+$ T cell epitopes such as CS$_{326-345}$ were included (Calvo-Calle et al., J Immunol, 159: 1362-1373, 1997), although murine strains differ in responsiveness to CS$_{326-345}$. Therefore, for pathogen-specific B cell epitopes and in particular for malaria B cell epitopes, it is imperative that the carrier platform provide sufficient T cell helper function in the context of a wide variety of MHC haplotypes to eliminate genetic nonresponsiveness.

Figure 18:
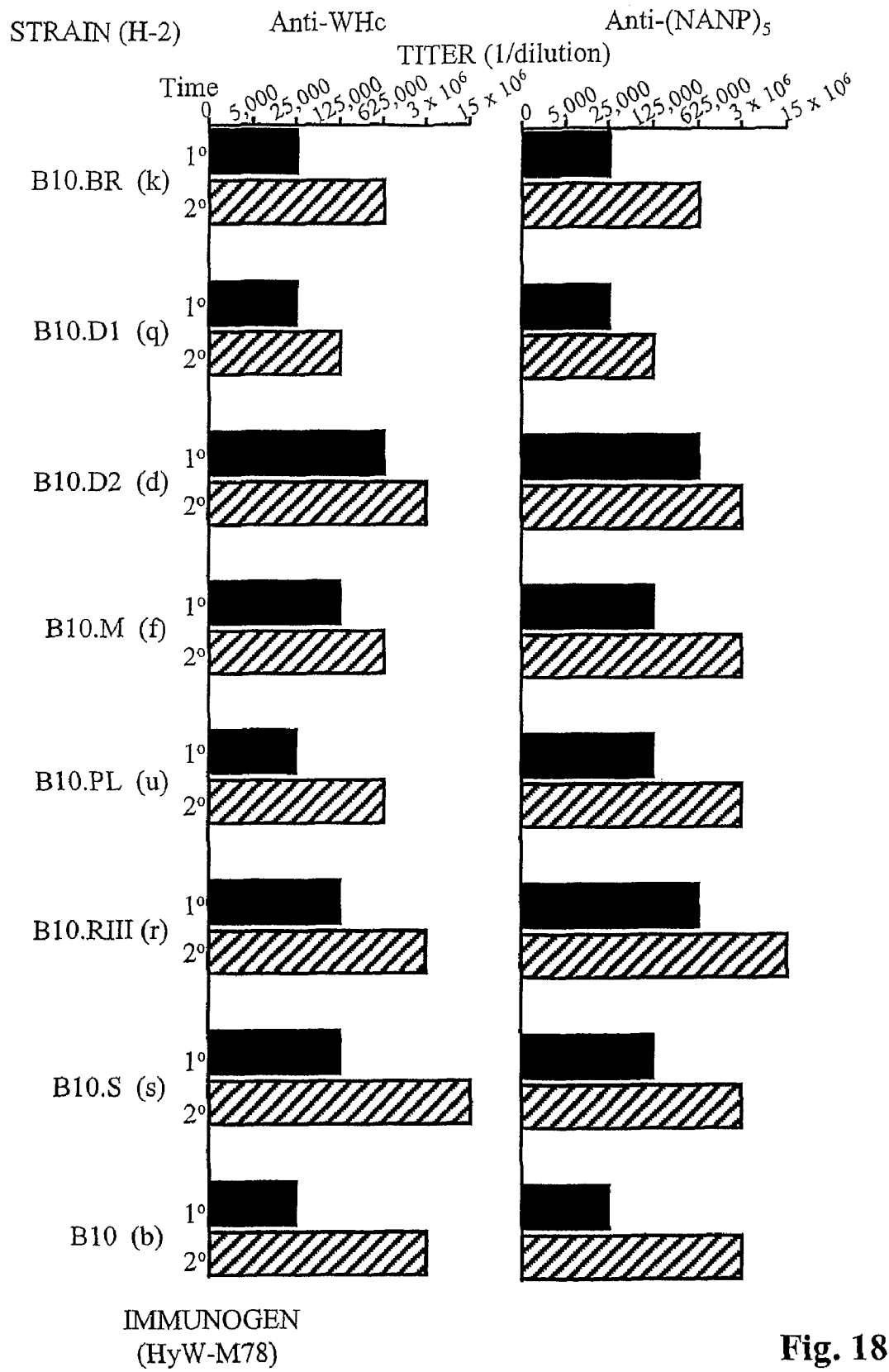

To directly examine the issue of MHC-linked restriction of the antibody response to a WHcAg-based vaccine, B10H-2 congenic murine strains expressing eight different H-2 haplotypes were immunized with a 10 μg dose of a WHcAg-malaria vaccine candidate (HyW-M78) in IFA. Both primary (1°, 6 weeks) and secondary (2°) anti-WHc and anti-NANP serum antibody titers were determined as shown in FIG. 18. First and importantly, all H-2 haplotypes responded and produced both anti-WHc and anti-NANP antibodies after a primary immunization with HyW-M78 (no nonresponder H-2 haplotypes were identified). Secondly, all strains at all time points produced an equal or greater antibody response to the insert (anti-NANP) as compared to anti-WHc, with the exception of the secondary antibody responses of the B10.S strain. The lack of genetic nonresponders to this experimental WHcAg-based vaccine is consistent with the absence of nonresponders to the WHcAg platform itself at the antibody (FIG. 5) and T cell (FIGS. 9 and 10) levels as determined during development of the present invention.

EXAMPLE 14

Complexity of T Cell Recognition of Hybrid Particles

Figure 19:
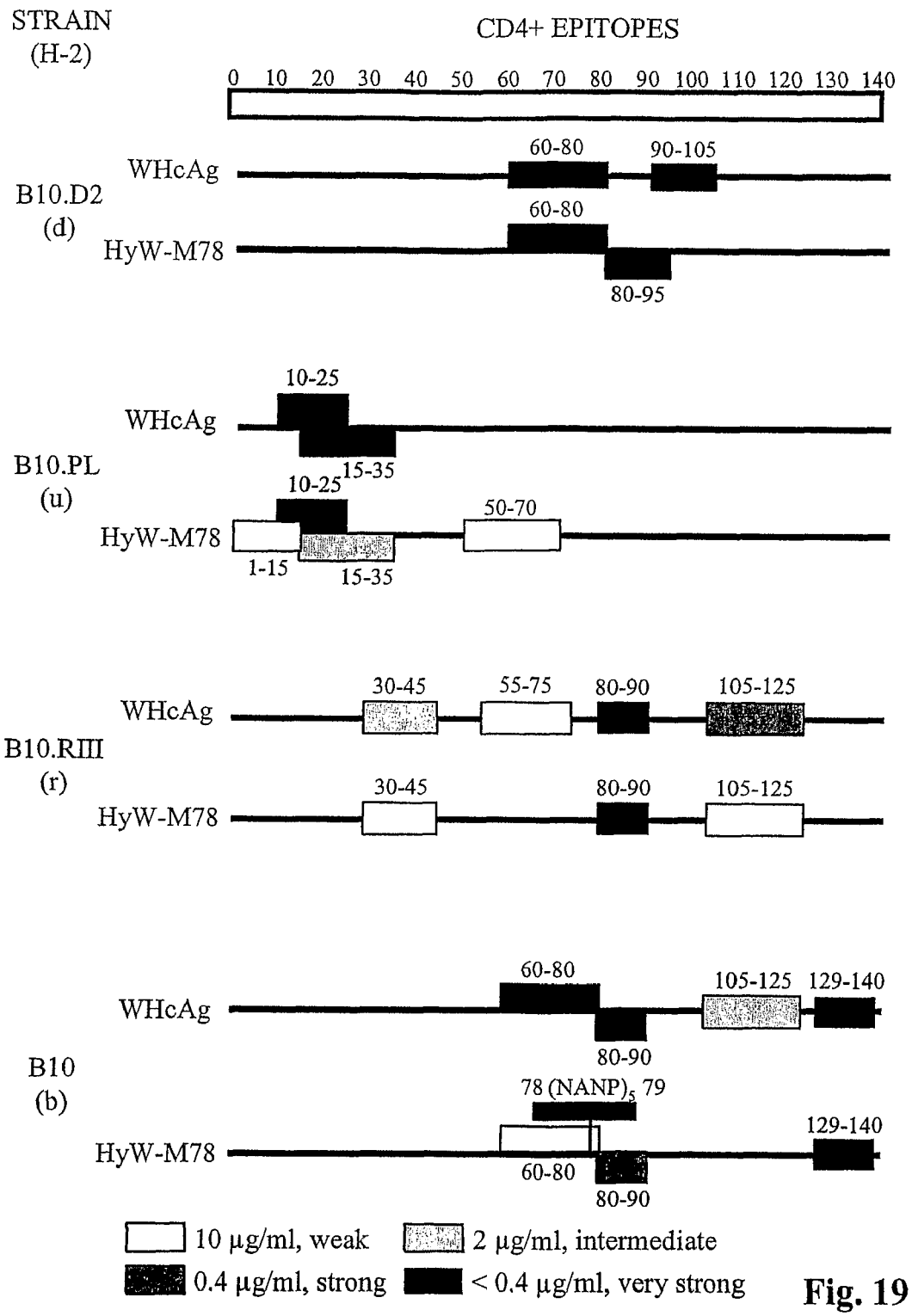

The insertion of a foreign B cell epitope is contemplated to at times itself either represent a novel T cell site or create a novel T cell site at the junction between the inserted sequence and the core sequence. Also, it is contemplated that an insertion at times disrupts an endogenous T cell site. Unexpectedly, inserting the NANPNVDP(NANP)₃ epitope (SEQ ID NO:75) into the WHcAg platform, has been observed to cause the loss and/or gain of novel WHcAg-specific T cell sites unrelated to interrupting an endogenous T cell site or creating a junctional T cell site, respectively. As shown in FIG. 19, pairs of H-2 congenic mice were immunized with wild-type WHcAg or the HyW-M78 hybrid particle containing the malaria CS repeat epitope. T cell fine specificity was mapped using a panel of WHcAg-derived synthetic peptides as antigens. Note that in B10.D2 mice, immunization with HyW-M78 caused a loss of one very strong T cell site (amino acids 90-105) and the gain of one very strong T cell site (amino acids 80-95) as compared to WHcAg immunization. The dominant T cell site at amino acids 60-80 was functional for both immunogens. The loss of the amino acid 90-105 site was not obvious because the insertion at amino acids 78-79 does not directly interrupt the amino acid 90-105 sequence. Similarly, the new T cell site at amino acids 80-95, was downstream of the inserted sequence.

Likewise, in the B10.PL strain, two new rather weak T cell sites were gained (amino acids 1-15 and amino acids 50-70) and a very strong T cell site (amino acids15-35) was converted into an intermediate T cell site by the insertion of a malaria B cell epitope. In the B10.RIII strain three of the four T cell sites recognized on native WHcAg were either lost or weakened when the HyW-M78 hybrid particle was used as the immunogen. Lastly, the B10 strain was found to recognize the (NANP)$_n$ sequence as a T cell site, as well as a B cell epitope. This insertion of a novel T cell site caused the loss of one T cell site (amino acids 105-125), and converted a very strong T cell site into a weak T cell site (amino acids 60-80). Thus, the variability of T cell recognition caused by the insertion of foreign sequences even at a distance from endogenous T cell sites emphasizes the necessity for a carrier platform to possess a multiplicity of T cell recognition sites relevant to any given MHC genotype. The WHcAg satisfies this requirement as demonstrated by the direct mapping of numerous T cell sites relevant for each of eight different MHC genotypes, and by the absence of nonresponder MHC haplotypes corresponding to the HyW-M78 candidate malaria vaccine. Additionally, the recognition of the (NANP)$_n$ sequence as a T cell site by B10 mice after immunization with HyW-M78, indicates that the WHcAg platform serves as a vaccine carrier for heterologous T cell (CD4+) epitopes, as well as B cell epitopes.

EXAMPLE 15

Effects of Insert pI and Linker Addition on the Assembly of Hybrid WHcAg, hybrid GSHcAg and hybrid HBeAg Particles During development of the present invention, the effect of insert isoelectric point (pI) on assembly of hybrid hepadna virus core particles was assessed. The predicted p1 shown below was calculated using the MacVector software program version 6.5.3, (Oxford Molecular Group, plc). The use of other programs, such as Protparam Tool and Compute pI/MW (available on the ExPASy proteomics server of the Swiss Institute of Bioinformatics), for predicting the pI of an insert peptide sequence was found to give slightly different pI values. However, as used herein, the predicted p1 calculated using MacVector is considered to be equivalent to the predicted p1 calculated using Protparam Tool, Compute pI/MW and any analogous algorithms.

As shown in Table 17, positively charged inserts (e.g., pI equal to or greater than 7.0) appear to adversely effected assembly of hybrid WHcAg or HBcAg particles. However, using the methods and compositions described herein, the addition of acidic substitutions or linker residues was found to be useful for neutralizing the apparent destabilizing effect of positively-charged inserts (high pI) on particle assembly. As shown in Table 18, the addition of acidic residues rescued hybrid-core particle assembly on WHcAg, the GSHcAg and HBcAg vaccine platforms. Nonetheless, an understanding of the mechanism(s) is not necessary in order to make and use the present invention.

Additionally, the rescue of a model positively-charged insert was made possible through the use of either flanking glutamic acid residues (EE-insert-EE), or flanking aspartic acid residues (DD-insert-DD). In contrast, neither flanking nonpolar residues (L-insert-L and P-insert-P), nor flanking uncharged polar residues (QQ-insert-QQ, TT-insert-TT, and YY-insert-YY) were able to convert an assembly-incompetent, positively-charged insert into an assembly-competent insert.

TABLE 17

Correlation Between Insert pI and Hybrid Particle Assembly[1]

| Epitope | Sequence | Identifier | pI | Particles |
|---|---|---|---|---|
| FMDV* | RYNRNAVPNLRGDLQVLAQKVARTLF | SEQ ID NO: 93 | 12.01 | − |
| HIV4.1* | RIKQIGMPGGK | SEQ ID NO: 85 | 11.30 | − |
| P. yoelii* | TAVVHQLKRKH | SEQ ID NO: 94 | 11.30 | − |
| HIV10.1* | HLLQLTVWGIKQLQAR | SEQ ID NO: 95 | 11.14 | |
| IgE$_{413-435}$* | GETYQSRVTHPHLPRALMRSTTK | SEQ ID NO: 96 | 11.13 | |
| P450-1A2* | GRERRPRLSDRPQLPYLEA | SEQ ID NO: 97 | 10.92 | − |
| HV-1 | GEIKNCSFNISTSIRGKVQKEYAFF | SEQ ID NO: 70 | 9.41 | − |
| HV-3 | PKVSFEPIPIHYCAPAGFAILKCNN | SEQ ID NO: 72 | 8.68 | |
| SEB | KKKVTAQELD | SEQ ID NO: 78 | 8.63 | +/− |
| HV-2 | LTSCNTSVITQACPKVSFEPIPIHYC | SEQ ID NO: 71 | 7.00 | − |

TABLE 17-continued

Correlation Between Insert pI and Hybrid Particle Assembly[1]

| Epitope | Sequence | Identifier | pI | Particles |
|---|---|---|---|---|
| AZ2 | FRHDSGY | SEQ ID NO: 84 | 7.00 | – |
| FV-2 | MELRKNGRQCGMSEKEEE | SEQ ID NO: 81 | 4.86 | + |
| HV-4 | THGIRPVVSTQLLLNGSLAEEE | SEQ ID NO: 73 | 4.55 | + |
| FV-1 | FYEIIMDIEQNNVQGKQGLQKL | SEQ ID NO: 80 | 4.46 | + |
| MV | DRAAGQPAGDRNDGQPAG | SEQ ID NO: 74 | 4.20 | + |
| CETP | FGFPEHLLVDFLQSL | SEQ ID NO: 79 | 4.11 | + |
| AZ1 | DAEFRHDSGYEV | SEQ ID NO: 83 | 4.08 | + |
| IM2(–) | SLLTEVETPIRNEWGARANDSSD | SEQ ID NO: 77 | 3.95 | |
| M | NANPNVDPNANANANPNANP | SEQ ID NO: 75 | 3.43 | + |
| MB | DPPPPNPNDPPPPNPN | SEQ ID NO: 98 | 3.22 | + |

[1]Asterisk denotes negative assembly on HBcAg as previously reported (PCT/US01/25625).

TABLE 18

Effect of Acidic Amino Acid Addition on Assembly of Hybrid Particles

| Epitope | Sequence[1] | Identifier | INSERT pI | ASSEMBLY |
|---|---|---|---|---|
| | | WHcAg Platform | | |
| SEB | KKKVTAQELD | SEQ ID NO: 78 | 8.63 | +/– |
| SEB2E | EEKKKVTAQELDEE | SEQ ID NO: 99 | 4.20 | + |
| AZ2 | FRHDSGY | SEQ ID NO: 84 | 7.00 | – |
| AZ2E | EEFRHDSGYEE | SEQ ID NO: 100 | 4.02 | + |
| HIV4.1 | RIKQIGMPGGK | SEQ ID NO: 85 | 11.3 | – |
| HIV4.1E | EERIKQIGMPGGKEE | SEQ ID NO: 101 | 4.74 | + |
| | | HBcAg Platform | | |
| AZ2 | FRHDSGY | SEQ ID NO: 84 | 7.00 | – |
| AZ2E | EEPRHDSGYEE | SEQ ID NO: 100 | 4.02 | + |

TABLE 18-continued

Effect of Acidic Amino Acid Addition on Assembly of Hybrid Particles

| Epitope | Sequence[1] | Identifier | INSERT pI | ASSEMBLY |
|---|---|---|---|---|
| HIV4.1* | RIKQIGMPGGK | SEQ ID NO: 85 | 11.3 | – |
| HIV4.1E | EERIKQIGMPGGKEE | SEQ ID NO: 101 | 4.74 | + |
| | | GSHcAg Platform | | |
| AZ2 | FRHDSGY | SEQ ID NO: 84 | 7.00 | + |
| AZ2E | EEFRHDSGYEE | SEQ ID NO: 100 | 4.02 | + |
| HIV4.1 | RIKQIGMPGGK | SEQ ID NO: 85 | 11.3 | – |
| HIV4.1E | EERIKQIGMPGGKEE | SEQ ID NO: 101 | 4.74 | + |

[1]Acidic substitutions or linker additions are shown in underlined, while asterisks denote negative assembly on HBcAg as previously reported (PCT/US01/25625).

TABLE 19

Antibody crossreactivity between the HBcAg, the WHcAg, the GSHcAg and the ArGSHcAg.

| | Antigens | | | | | |
|---|---|---|---|---|---|---|
| Antibodies | HBc | WHC | WHc (Δ loop) | GSHc | GSHc (Δ loop) | ArGSHc |
| α-HBc | | | | | | |
| (3105)Mab | ++ | 0 | 0 | 0 | 0 | 0 |
| (3120)Mab | ++ | 0 | 0 | 0 | 0 | 0 |
| α-WHc (poly) | 1,000 | $1.5 \times 10^7$ | 625,000 | 625,000 | | 50,000 |
| α-GSHc (poly) | 200 | 125,000 | 125,000 | $1.5 \times 10^7$ | | 50,000 |
| α-WHc (Δ loop) | | | | | | |
| #1 | | $3 \times 10^6$ | | $3 \times 10^6$ | | |
| #2 | | 25,000 | | 25,000 | | |
| #3 | | 125,000 | | 125,000 | | |

The indicated antigens (i.e., recombinant core particles) were examined for reactivity with the listed panel of antibodies. The anti-HBc antibodies consisted of monoclonal (Mab) and the remainder were polyclonal antibodies. (Δ loop) refers to alteration or disruption of the core loop antigenic region by insertion of a foreign B cell epitope sequence.

TABLE 20

Crossreactivity of GSHcAg-primed T cells for WhcAg and HBcAg.

| Strain | H-2 | IL-2 (U/ml) | | |
|---|---|---|---|---|
| | | GSHcAg | WHcAg | HBcAg |
| B10.BR | (k) | 2,500 | 450 | 0 |
| B10.D1 | (q) | 900 | 130 | 0 |
| B10.D2 | (d) | 1,200 | 320 | 0 |
| B10.M | (f) | 600 | 290 | 0 |
| B10.PL | (u) | 2,000 | 400 | 0 |
| B10.RIII | (r) | 2,400 | 750 | 0 |
| B10.S | (s) | 2,500 | 1,800 | 750 |
| B10 | (b) | 850 | 300 | 110 |

The indicated B10, H-2 congenic strains were immunized with GSHcAg (10 μg, IFA) and 4 weeks later spleen cells were incubated with GSHcAg, WHcAg or HBcAg (0.5 μg/ml) for 2 days and IL-2 in the culture media was measured by ELISA.

EXAMPLE 16

Avoiding the Problem of Pre-Existing Anti-HBe Antibodies by Using the WHcAg or GSHeAg Platforms Pre-existing anti-HBc antibodies are present in all chronic or acute HBV patients as well as persons previously exposed to HBV even though they have recovered. Pre-existing antibodies to a carrier protein may have negative effects on the primary response to a carrier-hapten complex because the carrier-hapten complex may be prematurely cleared from the circulation due to the presence of circulating anti-carrier antibodies. This is less of a concern after secondary boosting with the carrier-hapten complex because although anti-carrier antibodies may have been elicited by the primary immunization anti-hapten memory B cells are also present and require less antigen for the booster effect to occur. A way to avoid this problem of pre-existing anti-HBc antibodies is to use a carrier platform, which will not be recognized by natural anti-HBc antibodies. As shown in Table 21, HBcAg particles are recognized by anti-HBc antibodies present in the serum of chronic HBV patients and acute HBV patients. Similarly, hybrid-HBcAg particles are also recognized by chronic and acute HBV patient sera (data not shown).

We have previously reported that anti-HBc antibodies in the sera of chronic but not acute HBV-infected patients can recognize the WHcAg and in fact suggested that this WHcAg crossreactivity could be exploited as a diagnostic test for chronic as opposed to acute HBV infection (Maruyama, et al., Gastroenterol., 106:1006-1015, 1994). Indeed, as shown in Table 21, WHcAg is recognized by anti-HBc antibodies in chronic patient sera but not acute patient sera. This crossreactivity could compromise the efficacy of the WHcAg platform at least in chronic HBV patients just as the use of the HBcAg platform may be compromised in all HBV-exposed individuals with anti-HBc antibodies.

However, as shown in Table 21, hybrid-WHcAg particles, which would be used as a vaccine, are not recognized by chronic HBV patient serum anti-HBc antibodies. Regardless if the heterologous B cell epitope is inserted in the loop region, 76-82, outside the loop region (i.e., 74, 75, 92) or N- or C-terminally on WHcAg, the anti-HBc crossreactive determinant on WHcAg is destroyed on hybrid-WHcAg particles. Therefore, pre-existing anti-HBc antibodies in the sera of HBV-exposed individuals will not compromise the efficacy of the WHcAg platform.

TABLE 21

Problem of pre-existing anti-core antibodies in HBV-infected or previously infected patients.

| | Human Antisera | | |
|---|---|---|---|
| | Chronic HBV (n = 6) | Acute HBV (n = 6) | Normal human sera (n = 4) |
| Core Particles | | | |
| HBcAg | 2.8 ± 0.18 | 2.5 ± 0.18 | 0.3 ± 0.02 |
| WHcAg | 2.3 ± 0.41 | 0.3 ± 0.10 | 0.17 ± 0.03 |
| HYBRID-WHcAg | | | |
| 150-M74 | 0.21 ± 0.05 | 0.18 ± 0.05 | 0.17 ± 0.02 |
| 150C-M75 | 0.19 ± 0.06 | 0.16 ± 0.05 | 0.18 ± 0.01 |
| 150C-M77 | 0.37 ± 0.08 | 0.24 ± 0.04 | 0.24 ± 0.02 |
| 150C-M78 | 0.31 ± 0.06 | 0.28 ± 0.07 | 0.21 ± 0.02 |
| C-long-M78 | 0.32 ± 0.09 | 0.15 ± 0.02 | 0.20 ± 0.03 |
| HyW-M (COOH) | 0.25 ± 0.08 | 0.24 ± 0.09 | 0.23 ± 0.03 |
| HyW-M (NH2) | 0.30 ± 0.13 | 0.23 ± 0.07 | 0.23 ± 0.05 |
| HyW-M92 | 0.33 ± 0.10 | 0.26 ± 0.07 | 0.24 ± 0.04 |
| 150C-IM2(—)-82 | 0.26 ± 0.04 | 0.22 ± 0.08 | 0.20 ± 0.05 |
| HyW-SEB-75 | 0.29 ± 0.10 | 0.16 ± 0.04 | 0.25 ± 0.04 |

Human sera from chronic HBV patients (6), acute HBV patients (6) or normal non-infected blood donors (4) were diluted 1:500 and tested in ELISA using the indicated core particles as the solid-phase ligands (20 ng/well).
The data are presented as mean O.D.$_{492}$ values ± standard deviations.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, or related fields are intended to be within the scope of the following claims.

We claim:

1. A method for producing an immune response, comprising
a) providing:
a composition comprising one of:
1) a hybrid particle comprising a fusion protein comprising a rodent hepadnavirus core antigen and a heterologous antigen, wherein said hybrid particle is a hybrid ground squirrel hepadnavirus particle that assembles satisfactorily of Table 15, or woodchuck hepadnavirus particle that assembles satisfactorily of Table 11, Table 12, Table 13, Table 15, or Table 16, and
2) an expression vector encoding said fusion protein; and
b) administering said composition to an animal under conditions such that an immune response is generated to said heterologous antigen.

2. The method of claim 1, wherein said immune response comprises one or more of lymphocyte proliferative response, cytokine response and antibody response.

3. The method of claim 2, wherein said antibody response comprises production of IgG antibodies.

4. The method of claim 1, wherein said animal is a human having pre-existing antibodies to hepatitis B virus core antigen.

5. The method of claim 1, wherein said rodent hepadnavirus core antigen is a woodchuck hepadnavirus core antigen.

6. The method of claim 1, wherein said rodent hepadnavirus core antigen is a ground squirrel hepadnavirus core antigen.

* * * * *

SEQUENCE LISTING

<160> NUMBER OF SEQ ID NOS: 256

<210> SEQ ID NO 1
<211> LENGTH: 188
<212> TYPE: PRT
<213> ORGANISM: Woodchuck hepatitis virus

<400> SEQUENCE: 1

Met Asp Ile Asp Pro Tyr Lys Glu Phe Gly Ser Ser Tyr Gln Leu Leu

```
                1               5                   10                  15
Asn Phe Leu Pro Leu Asp Phe Phe Pro Asp Leu Asn Ala Leu Val Asp
                20                  25                  30

Thr Ala Thr Ala Leu Tyr Glu Glu Glu Leu Thr Gly Arg Glu His Cys
                35                  40                  45

Ser Pro His His Thr Ala Ile Arg Gln Ala Leu Val Cys Trp Asp Glu
                50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
                100                 105                 110

His Thr Val Gln Glu Phe Leu Val Ser Phe Gly Val Trp Ile Arg Thr
                115                 120                 125

Pro Ala Pro Tyr Arg Pro Pro Asn Ala Pro Ile Leu Ser Thr Leu Pro
                130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
                180                 185

<210> SEQ ID NO 2
<211> LENGTH: 39
<212> TYPE: PRT
<213> ORGANISM: Woodchuck hepatitis virus

<400> SEQUENCE: 2

Arg Arg Arg Gly Gly Ala Arg Ala Ser Arg Ser Pro Arg Arg Arg Thr
1               5                   10                  15

Pro Ser Pro Arg Arg Arg Ser Gln Ser Pro Arg Arg Arg Arg Ser
                20                  25                  30

Gln Ser Pro Ser Ala Asn Cys
        35

<210> SEQ ID NO 3
<211> LENGTH: 4
<212> TYPE: PRT
<213> ORGANISM: Woodchuck hepatitis virus

<400> SEQUENCE: 3

Arg Arg Arg Cys
1

<210> SEQ ID NO 4
<211> LENGTH: 5
<212> TYPE: PRT
<213> ORGANISM: Woodchuck hepatitis virus

<400> SEQUENCE: 4

Arg Arg Arg Arg Cys
1               5

<210> SEQ ID NO 5
<211> LENGTH: 4
<212> TYPE: PRT
<213> ORGANISM: Woodchuck hepatitis virus
```

```
<400> SEQUENCE: 5

Lys Lys Lys Cys
1

<210> SEQ ID NO 6
<211> LENGTH: 4
<212> TYPE: PRT
<213> ORGANISM: Woodchuck hepatitis virus

<400> SEQUENCE: 6

Ala Ala Ala Cys
1

<210> SEQ ID NO 7
<211> LENGTH: 23
<212> TYPE: PRT
<213> ORGANISM: Woodchuck hepatitis virus

<400> SEQUENCE: 7

Ala Ala Gly Gly Ala Arg Ala Ser Arg Ser Pro Ser Gln Ser Pro Ser
1               5                   10                  15

Gln Ser Pro Ser Ala Asn Cys
            20

<210> SEQ ID NO 8
<211> LENGTH: 21
<212> TYPE: PRT
<213> ORGANISM: Woodchuck hepatitis virus

<400> SEQUENCE: 8

Ala Ala Gly Gly Ala Arg Ala Ser Arg Ser Gln Ser Pro Ser Gln Ser
1               5                   10                  15

Pro Ser Ala Asn Cys
            20

<210> SEQ ID NO 9
<211> LENGTH: 20
<212> TYPE: PRT
<213> ORGANISM: Woodchuck hepatitis virus

<400> SEQUENCE: 9

Ala Ala Gly Gly Ala Arg Ala Ser Arg Ser Gln Ser Ser Gln Ser Pro
1               5                   10                  15

Ser Ala Asn Cys
            20

<210> SEQ ID NO 10
<211> LENGTH: 19
<212> TYPE: PRT
<213> ORGANISM: Woodchuck hepatitis virus

<400> SEQUENCE: 10

Ala Ala Gly Gly Ala Arg Ala Ser Arg Ser Gln Ser Ser Gln Ser Ser
1               5                   10                  15

Ala Asn Cys

<210> SEQ ID NO 11
<211> LENGTH: 13
<212> TYPE: PRT
<213> ORGANISM: Woodchuck hepatitis virus

<400> SEQUENCE: 11
```

```
Arg Arg Gly Gly Ala Arg Ala Ser Gln Ser Ala Asn Cys
1               5                   10

<210> SEQ ID NO 12
<211> LENGTH: 13
<212> TYPE: PRT
<213> ORGANISM: Woodchuck hepatitis virus

<400> SEQUENCE: 12

Ala Arg Gly Gly Ala Arg Ala Ser Gln Ser Ala Asn Cys
1               5                   10

<210> SEQ ID NO 13
<211> LENGTH: 13
<212> TYPE: PRT
<213> ORGANISM: Woodchuck hepatitis virus

<400> SEQUENCE: 13

Arg Ala Gly Gly Ala Arg Ala Ser Gln Ser Ala Asn Cys
1               5                   10

<210> SEQ ID NO 14
<211> LENGTH: 13
<212> TYPE: PRT
<213> ORGANISM: Woodchuck hepatitis virus

<400> SEQUENCE: 14

Ala Ala Gly Gly Ala Arg Ala Ser Gln Ser Ala Asn Cys
1               5                   10

<210> SEQ ID NO 15
<211> LENGTH: 18
<212> TYPE: PRT
<213> ORGANISM: Woodchuck hepatitis virus

<400> SEQUENCE: 15

Ala Ala Gly Arg Ser Pro Ser Gln Ser Pro Ser Gln Ser Arg Glu Ser
1               5                   10                  15

Gln Cys

<210> SEQ ID NO 16
<211> LENGTH: 18
<212> TYPE: PRT
<213> ORGANISM: Woodchuck hepatitis virus

<400> SEQUENCE: 16

Ala Ala Gly Arg Ser Pro Ser Gln Ser Pro Ser Gln Ser Pro Ser Ala
1               5                   10                  15

Asn Cys

<210> SEQ ID NO 17
<211> LENGTH: 17
<212> TYPE: PRT
<213> ORGANISM: Woodchuck hepatitis virus

<400> SEQUENCE: 17

Ala Ala Gly Arg Ser Pro Ser Gln Ser Pro Ser Gln Ser Ser Ala Asn
1               5                   10                  15

Cys

<210> SEQ ID NO 18
<211> LENGTH: 15
```

```
<212> TYPE: PRT
<213> ORGANISM: Woodchuck hepatitis virus

<400> SEQUENCE: 18

Ala Ala Gly Arg Ser Gln Ser Pro Ser Gln Ser Ser Ala Asn Cys
1               5                   10                  15

<210> SEQ ID NO 19
<211> LENGTH: 16
<212> TYPE: PRT
<213> ORGANISM: Woodchuck hepatitis virus

<400> SEQUENCE: 19

Ala Ala Gly Arg Ser Pro Ser Gln Ser Gln Ser Ser Ala Asn Cys
1               5                   10                  15

<210> SEQ ID NO 20
<211> LENGTH: 14
<212> TYPE: PRT
<213> ORGANISM: Woodchuck hepatitis virus

<400> SEQUENCE: 20

Ala Ala Gly Arg Ser Gln Ser Ser Gln Ser Ser Ala Asn Cys
1               5                   10

<210> SEQ ID NO 21
<211> LENGTH: 187
<212> TYPE: PRT
<213> ORGANISM: Ground squirrel hepatitis virus

<400> SEQUENCE: 21

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Ala Ala Leu Tyr Glu Glu Leu Thr Gly Arg Glu His Cys
        35                  40                  45

Ser Pro His His Thr Ala Ile Arg Gln Ala Leu Val Cys Trp Glu Glu
    50                  55                  60

Leu Thr Arg Leu Ile Thr Trp Met Ser Glu Asn Thr Thr Glu Val
65                  70                  75                  80

Arg Arg Ile Ile Val Asp His Val Asn Asn Thr Trp Gly Leu Lys Val
                85                  90                  95

Arg Gln Thr Leu Trp Phe His Leu Ser Cys Leu Thr Phe Gly Gln His
            100                 105                 110

Thr Val Gln Glu Phe Leu Val Ser Phe Gly Val Trp Ile Arg Thr Pro
        115                 120                 125

Ala Pro Tyr Arg Pro Pro Asn Ala Pro Ile Leu Ser Thr Leu Pro Glu
    130                 135                 140

His Thr Val Ile Arg Arg Gly Gly Ser Arg Ala Ala Arg Ser Pro
145                 150                 155                 160

Arg Arg Arg Thr Pro Ser Pro Arg Arg Arg Ser Gln Ser Pro Arg
                165                 170                 175

Arg Arg Arg Ser Gln Ser Pro Ala Ser Asn Cys
            180                 185

<210> SEQ ID NO 22
<211> LENGTH: 39
<212> TYPE: PRT
<213> ORGANISM: Ground squirrel hepatitis virus
```

```
<400> SEQUENCE: 22

Arg Arg Arg Gly Gly Ser Arg Ala Ala Arg Ser Pro Arg Arg Arg Thr
1               5                   10                  15

Pro Ser Pro Arg Arg Arg Ser Gln Ser Pro Arg Arg Arg Ser
            20                  25                  30

Gln Ser Pro Ala Ser Asn Cys
        35

<210> SEQ ID NO 23
<211> LENGTH: 23
<212> TYPE: PRT
<213> ORGANISM: Ground squirrel hepatitis virus

<400> SEQUENCE: 23

Ala Ala Gly Gly Ser Arg Ala Ala Arg Ser Pro Ser Gln Ser Pro Ser
1               5                   10                  15

Gln Ser Pro Ala Ser Asn Cys
            20

<210> SEQ ID NO 24
<211> LENGTH: 21
<212> TYPE: PRT
<213> ORGANISM: Ground squirrel hepatitis virus

<400> SEQUENCE: 24

Ala Ala Gly Gly Ser Arg Ala Ala Arg Ser Gln Ser Pro Ser Gln Ser
1               5                   10                  15

Pro Ala Ser Asn Cys
            20

<210> SEQ ID NO 25
<211> LENGTH: 20
<212> TYPE: PRT
<213> ORGANISM: Ground squirrel hepatitis virus

<400> SEQUENCE: 25

Ala Ala Gly Gly Ser Arg Ala Ala Arg Ser Gln Ser Ser Gln Ser Pro
1               5                   10                  15

Ala Ser Asn Cys
            20

<210> SEQ ID NO 26
<211> LENGTH: 19
<212> TYPE: PRT
<213> ORGANISM: Ground squirrel hepatitis virus

<400> SEQUENCE: 26

Ala Ala Gly Gly Ser Arg Ala Ala Arg Ser Gln Ser Ser Gln Ser Ala
1               5                   10                  15

Ser Asn Cys

<210> SEQ ID NO 27
<211> LENGTH: 14
<212> TYPE: PRT
<213> ORGANISM: Ground squirrel hepatitis virus

<400> SEQUENCE: 27

Arg Arg Gly Gly Ser Arg Ala Ala Ser Gln Ala Ser Asn Cys
1               5                   10
```

<210> SEQ ID NO 28
<211> LENGTH: 14
<212> TYPE: PRT
<213> ORGANISM: Ground squirrel hepatitis virus

<400> SEQUENCE: 28

Ala Arg Gly Gly Ser Arg Ala Ala Ser Gln Ala Ser Asn Cys
1               5                   10

<210> SEQ ID NO 29
<211> LENGTH: 14
<212> TYPE: PRT
<213> ORGANISM: Ground squirrel hepatitis virus

<400> SEQUENCE: 29

Arg Ala Gly Gly Ser Arg Ala Ala Ser Gln Ala Ser Asn Cys
1               5                   10

<210> SEQ ID NO 30
<211> LENGTH: 14
<212> TYPE: PRT
<213> ORGANISM: Ground squirrel hepatitis virus

<400> SEQUENCE: 30

Ala Ala Gly Gly Ser Arg Ala Ala Ser Gln Ala Ser Asn Cys
1               5                   10

<210> SEQ ID NO 31
<211> LENGTH: 18
<212> TYPE: PRT
<213> ORGANISM: Ground squirrel hepatitis virus

<400> SEQUENCE: 31

Ala Ala Gly Arg Ser Pro Ser Gln Ser Pro Ser Gln Ser Arg Glu Ser
1               5                   10                  15

Gln Cys

<210> SEQ ID NO 32
<211> LENGTH: 18
<212> TYPE: PRT
<213> ORGANISM: Ground squirrel hepatitis virus

<400> SEQUENCE: 32

Ala Ala Gly Arg Ser Pro Ser Gln Ser Pro Ser Gln Ser Pro Ala Ser
1               5                   10                  15

Asn Cys

<210> SEQ ID NO 33
<211> LENGTH: 17
<212> TYPE: PRT
<213> ORGANISM: Ground squirrel hepatitis virus

<400> SEQUENCE: 33

Ala Ala Gly Arg Ser Pro Ser Gln Ser Pro Ser Gln Ser Ala Ser Asn
1               5                   10                  15

Cys

<210> SEQ ID NO 34
<211> LENGTH: 15
<212> TYPE: PRT
<213> ORGANISM: Ground squirrel hepatitis virus

<400> SEQUENCE: 34

```
Ala Ala Gly Arg Ser Gln Ser Pro Ser Gln Ser Ala Ser Asn Cys
1               5                   10                  15

<210> SEQ ID NO 35
<211> LENGTH: 16
<212> TYPE: PRT
<213> ORGANISM: Ground squirrel hepatitis virus

<400> SEQUENCE: 35

Ala Ala Gly Arg Ser Pro Ser Gln Ser Gln Ser Ala Ser Asn Cys
1               5                   10                  15

<210> SEQ ID NO 36
<211> LENGTH: 14
<212> TYPE: PRT
<213> ORGANISM: Ground squirrel hepatitis virus

<400> SEQUENCE: 36

Ala Ala Gly Arg Ser Gln Ser Ser Gln Ser Ala Ser Asn Cys
1               5                   10

<210> SEQ ID NO 37
<211> LENGTH: 567
<212> TYPE: DNA
<213> ORGANISM: Woodchuck hepatitis virus

<400> SEQUENCE: 37
atggacatag atccctataa agaatttggt tcatcttatc agttgttgaa ttttcttcct      60
ttggacttct ttcctgacct taatgctttg gtggacactg ctactgcctt gtatgaagaa    120
gagctaacag gtagggaaca ttgctctccg caccatacag ctattagaca agctttagta    180
tgctgggatg aattaactaa attgatagct tggatgagct ctaacataac ttctgaacaa    240
gtaagaacaa tcattgtaaa tcatgtcaat gatacctggg gacttaaggt gagacaaagt    300
ttatggtttc atttgtcatg tctcactttc ggacaacata cagttcaaga ttttttagta    360
agttttggag tatggatcag gactccagct ccatatagac ctcctaatgc acccattctc    420
tcgactcttc cggaacatac agtcattagg agaagaggag gtgcaagagc ttctaggtcc    480
cccagaagac gcactccctc tcctcgcagg agaagatctc aatcaccgcg tcgcagacgc    540
tctcaatctc catctgccaa ctgctga                                        567

<210> SEQ ID NO 38
<211> LENGTH: 149
<212> TYPE: PRT
<213> ORGANISM: Woodchuck hepatitis virus

<400> SEQUENCE: 38

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95
```

```
Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
            115                 120                 125

Pro Ala Pro Tyr Arg Pro Pro Asn Ala Pro Ile Leu Ser Thr Leu Pro
        130                 135                 140

Glu His Thr Val Ile
145

<210> SEQ ID NO 39
<211> LENGTH: 564
<212> TYPE: DNA
<213> ORGANISM: Ground squirrel hepatitis virus

<400> SEQUENCE: 39
atggacatag atccctataa agaatttggt tcttcttatc agttgttgaa ttttcttcct      60
ttggactttt ttcctgatct caatgcattg gtggacactg ctgctgctct ttatgaagaa     120
gaattaacag gtagggagca ttgttctcct catcatactg ctattagaca ggccttagtg     180
tgttgggaag aattaactag attaattaca tggatgagtg aaaatacaac agaagaagtt     240
agaagaatta tgttgatca tgtcaataat acttggggac ttaaagtaag acagacttta     300
tggtttcatt tatcatgtct tacttttgga caacacacag ttcaagaatt tttggttagt     360
tttggagtat ggattagaac tccagctcct tatagaccac taatgcacc catttatca     420 actcttccgg aacatacagt cattaggaga agaggaggtt caagagctgc taggtccccc     480
cgaagacgca ctccctctcc tcgcaggaga aggtctcaat caccgcgtcg cagacgctct     540
caatctccag cttccaactg ctga                                           564

<210> SEQ ID NO 40
<211> LENGTH: 148
<212> TYPE: PRT
<213> ORGANISM: Ground squirrel hepatitis virus

<400> SEQUENCE: 40

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Ala Ala Leu Tyr Glu Glu Glu Leu Thr Gly Arg Glu His Cys
        35                  40                  45

Ser Pro His His Thr Ala Ile Arg Gln Ala Leu Val Cys Trp Glu Glu
    50                  55                  60

Leu Thr Arg Leu Ile Thr Trp Met Ser Glu Asn Thr Thr Glu Glu Val
65                  70                  75                  80

Arg Arg Ile Ile Val Asp His Val Asn Asn Thr Trp Gly Leu Lys Val
                85                  90                  95

Arg Gln Thr Leu Trp Phe His Leu Ser Cys Leu Thr Phe Gly Gln His
            100                 105                 110

Thr Val Gln Glu Phe Leu Val Ser Phe Gly Val Trp Ile Arg Thr Pro
            115                 120                 125

Ala Pro Tyr Arg Pro Pro Asn Ala Pro Ile Leu Ser Thr Leu Pro Glu
        130                 135                 140

His Thr Val Ile
145
```

```
<210> SEQ ID NO 41
<211> LENGTH: 183
<212> TYPE: PRT
<213> ORGANISM: Human hepatitis B virus

<400> SEQUENCE: 41

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 42
<211> LENGTH: 34
<212> TYPE: PRT
<213> ORGANISM: Human hepatitis B virus

<400> SEQUENCE: 42

Arg Arg Arg Gly Arg Ser Pro Arg Arg Arg Thr Pro Ser Pro Arg Arg
1               5                   10                  15

Arg Arg Ser Gln Ser Pro Arg Arg Arg Arg Ser Gln Ser Arg Glu Ser
            20                  25                  30

Gln Cys

<210> SEQ ID NO 43
<211> LENGTH: 18
<212> TYPE: PRT
<213> ORGANISM: Human hepatitis B virus

<400> SEQUENCE: 43

Ala Ala Gly Arg Ser Pro Ser Gln Ser Pro Ser Gln Ser Arg Glu Ser
1               5                   10                  15

Gln Cys

<210> SEQ ID NO 44
<211> LENGTH: 16
<212> TYPE: PRT
<213> ORGANISM: Human hepatitis B virus

<400> SEQUENCE: 44
```

Ala Ala Gly Arg Ser Gln Ser Pro Ser Gln Ser Arg Glu Ser Gln Cys
1               5                   10                  15

<210> SEQ ID NO 45
<211> LENGTH: 15
<212> TYPE: PRT
<213> ORGANISM: Human hepatitis B virus

<400> SEQUENCE: 45

Ala Ala Gly Arg Ser Gln Ser Ser Gln Ser Arg Glu Ser Gln Cys
1               5                   10                  15

<210> SEQ ID NO 46
<211> LENGTH: 14
<212> TYPE: PRT
<213> ORGANISM: Human hepatitis B virus

<400> SEQUENCE: 46

Ala Ala Gly Arg Ser Gln Ser Ser Gln Ser Glu Ser Gln Cys
1               5                   10

<210> SEQ ID NO 47
<211> LENGTH: 11
<212> TYPE: PRT
<213> ORGANISM: Human hepatitis B virus

<400> SEQUENCE: 47

Arg Arg Gly Ser Gln Ser Arg Glu Ser Gln Cys
1               5                   10

<210> SEQ ID NO 48
<211> LENGTH: 11
<212> TYPE: PRT
<213> ORGANISM: Human hepatitis B virus

<400> SEQUENCE: 48

Ala Arg Gly Ser Gln Ser Arg Glu Ser Gln Cys
1               5                   10

<210> SEQ ID NO 49
<211> LENGTH: 11
<212> TYPE: PRT
<213> ORGANISM: Human hepatitis B virus

<400> SEQUENCE: 49

Arg Ala Gly Ser Gln Ser Arg Glu Ser Gln Cys
1               5                   10

<210> SEQ ID NO 50
<211> LENGTH: 11
<212> TYPE: PRT
<213> ORGANISM: Human hepatitis B virus

<400> SEQUENCE: 50

Ala Ala Gly Ser Gln Ser Arg Glu Ser Gln Cys
1               5                   10

<210> SEQ ID NO 51
<211> LENGTH: 18
<212> TYPE: PRT
<213> ORGANISM: Human hepatitis B virus

<400> SEQUENCE: 51

Ala Ala Gly Arg Ser Pro Ser Gln Ser Pro Ser Gln Ser Pro Ser Ala

<210> SEQ ID NO 52
<211> LENGTH: 18
<212> TYPE: PRT
<213> ORGANISM: Human hepatitis B virus

<400> SEQUENCE: 52

Ala Ala Gly Arg Ser Pro Ser Gln Ser Pro Ser Gln Ser Arg Glu Ser
1               5                   10                  15

Gln Cys

<210> SEQ ID NO 53
<211> LENGTH: 17
<212> TYPE: PRT
<213> ORGANISM: Human hepatitis B virus

<400> SEQUENCE: 53

Ala Ala Gly Arg Ser Pro Ser Gln Ser Pro Ser Gln Ser Glu Ser Gln
1               5                   10                  15

Cys

<210> SEQ ID NO 54
<211> LENGTH: 15
<212> TYPE: PRT
<213> ORGANISM: Human hepatitis B virus

<400> SEQUENCE: 54

Ala Ala Gly Arg Ser Gln Ser Pro Ser Gln Ser Glu Ser Gln Cys
1               5                   10                  15

<210> SEQ ID NO 55
<211> LENGTH: 16
<212> TYPE: PRT
<213> ORGANISM: Human hepatitis B virus

<400> SEQUENCE: 55

Ala Ala Gly Arg Ser Pro Ser Gln Ser Ser Gln Ser Glu Ser Gln Cys
1               5                   10                  15

<210> SEQ ID NO 56
<211> LENGTH: 14
<212> TYPE: PRT
<213> ORGANISM: Human hepatitis B virus

<400> SEQUENCE: 56

Ala Ala Gly Arg Ser Gln Ser Ser Gln Ser Glu Ser Gln Cys
1               5                   10

<210> SEQ ID NO 57
<211> LENGTH: 552
<212> TYPE: DNA
<213> ORGANISM: Human hepatitis B virus

<400> SEQUENCE: 57
atggacatcg acccttataa agaatttgga gctactgtgg agttactctc gttttttgcct      60
tctgacttct ttccttcagt acgagatctt ctagataccg cctcagctct gtatcgggaa     120
gccttagagt ctcctgagca ttgttcacct caccatactg cactcaggca agcaattctt     180
tgctgggggg aactaatgac tctagctacc tgggtgggtg ttaatttgga agatccagca     240

```
tccagagacc tagtagtcag ttatgtcaac actaatatgg gcctaaagtt caggcaactc    300
ttgtggtttc acatttcttg tctcactttt ggaagagaaa ccgttataga gtatttggtg    360
tctttcggag tgtggattcg cactcctcca gcttatagac caccaaatgc ccctatccta    420
tcaacacttc cggaaactac tgttgttaga cgacgaggca ggtcccctag aagaagaact    480
ccctcgcctc gcagacgaag gtctcaatcg ccgcgtcgca aagatctca atctcgggaa    540 tctcaatgtt ga                                                       552
```

```
<210> SEQ ID NO 58
<211> LENGTH: 149
<212> TYPE: PRT
<213> ORGANISM: Human hepatitis B virus

<400> SEQUENCE: 58
```

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145
```

```
<210> SEQ ID NO 59
<211> LENGTH: 12
<212> TYPE: PRT
<213> ORGANISM: Artificial Sequence
<220> FEATURE:
<223> OTHER INFORMATION: Synthetic

<400> SEQUENCE: 59
```

```
Val Ser Phe Gly Val Trp Ile Arg Thr Pro Ala Pro
1               5                   10
```

```
<210> SEQ ID NO 60
<211> LENGTH: 12
<212> TYPE: PRT
<213> ORGANISM: Artificial Sequence
<220> FEATURE:
<223> OTHER INFORMATION: Synthetic

<400> SEQUENCE: 60
```

```
Val Ser Phe Gly Val Trp Ile Arg Thr Pro Pro Ala
1               5                   10
```

```
<210> SEQ ID NO 61
<211> LENGTH: 21
```

```
<212> TYPE: PRT
<213> ORGANISM: Artificial Sequence
<220> FEATURE:
<223> OTHER INFORMATION: Synthetic

<400> SEQUENCE: 61

Val Cys Trp Asp Glu Leu Thr Lys Leu Ile Ala Trp Met Ser Ser Asn
1               5                   10                  15

Ile Thr Ser Glu Gln
            20

<210> SEQ ID NO 62
<211> LENGTH: 21
<212> TYPE: PRT
<213> ORGANISM: Artificial Sequence
<220> FEATURE:
<223> OTHER INFORMATION: Synthetic

<400> SEQUENCE: 62

Leu Cys Trp Gly Glu Leu Met Thr Leu Ala Thr Trp Val Gly Gly Asn
1               5                   10                  15

Leu Glu Asp Pro Ile
            20

<210> SEQ ID NO 63
<211> LENGTH: 19
<212> TYPE: DNA
<213> ORGANISM: Artificial Sequence
<220> FEATURE:
<223> OTHER INFORMATION: Synthetic

<400> SEQUENCE: 63
ggaaattctt ctcctcgag                                              19

<210> SEQ ID NO 64
<211> LENGTH: 24
<212> TYPE: PRT
<213> ORGANISM: Artificial Sequence
<220> FEATURE:
<223> OTHER INFORMATION: Synthetic

<400> SEQUENCE: 64

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 65
<211> LENGTH: 18
<212> TYPE: PRT
<213> ORGANISM: Plasmodium vivax

<400> SEQUENCE: 65

Ala Asn Gly Ala Gly Asn Gln Pro Gly Ala Asn Gly Ala Gly Asp Gln
1               5                   10                  15

Pro Gly

<210> SEQ ID NO 66
<211> LENGTH: 18
<212> TYPE: PRT
<213> ORGANISM: Plasmodium vivax

<400> SEQUENCE: 66

Ala Asn Gly Ala Asp Asn Gln Pro Gly Ala Asn Gly Ala Asp Asp Gln
```

```
                1               5                  10                 15
Pro Gly

<210> SEQ ID NO 67
<211> LENGTH: 22
<212> TYPE: PRT
<213> ORGANISM: Plasmodium vivax

<400> SEQUENCE: 67

Ala Pro Gly Ala Asn Gln Glu Gly Gly Ala Ala Pro Gly Ala Asn
1               5                  10                 15

Gln Glu Gly Gly Ala Ala
            20

<210> SEQ ID NO 68
<211> LENGTH: 12
<212> TYPE: PRT
<213> ORGANISM: Artificial Sequence
<220> FEATURE:
<223> OTHER INFORMATION: Synthetic

<400> SEQUENCE: 68

Asn Ala Asn Pro Asn Ala Asn Pro Asn Ala Asn Pro
1               5                  10

<210> SEQ ID NO 69
<211> LENGTH: 260
<212> TYPE: PRT
<213> ORGANISM: Mus musculus

<400> SEQUENCE: 69

Met Ile Glu Thr Tyr Ser Gln Pro Ser Pro Arg Ser Val Ala Thr Gly
1               5                  10                 15

Leu Pro Ala Ser Met Lys Ile Phe Met Tyr Leu Leu Thr Val Phe Leu
            20                  25                 30

Ile Thr Gln Met Ile Gly Ser Val Leu Phe Ala Val Tyr Leu His Arg
        35                  40                 45

Arg Leu Asp Lys Val Glu Glu Val Asn Leu His Glu Asp Phe Val
    50                  55                 60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                 95

Asp Ile Thr Leu Asn Lys Glu Glu Lys Lys Glu Asn Ser Phe Glu Met
            100                 105                110

Gln Arg Gly Asp Glu Asp Pro Gln Ile Ala Ala His Val Val Ser Glu
        115                 120                125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                175

Cys Ser Asn Arg Glu Pro Ser Ser Gln Arg Pro Phe Ile Val Gly Leu
            180                 185                190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
```

```
                 210                 215                 220
Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
            245                 250                 255

Leu Leu Lys Leu
        260

<210> SEQ ID NO 70
<211> LENGTH: 25
<212> TYPE: PRT
<213> ORGANISM: Artificial Sequence
<220> FEATURE:
<223> OTHER INFORMATION: Synthetic

<400> SEQUENCE: 70

Gly Glu Ile Lys Asn Cys Ser Phe Asn Ile Ser Thr Ser Ile Arg Gly
1               5                   10                  15

Lys Val Gln Lys Glu Tyr Ala Phe Phe
            20                  25

<210> SEQ ID NO 71
<211> LENGTH: 26
<212> TYPE: PRT
<213> ORGANISM: Artificial Sequence
<220> FEATURE:
<223> OTHER INFORMATION: Synthetic

<400> SEQUENCE: 71

Leu Thr Ser Cys Asn Thr Ser Val Ile Thr Gln Ala Cys Pro Lys Val
1               5                   10                  15

Ser Phe Glu Pro Ile Pro Ile His Tyr Cys
            20                  25

<210> SEQ ID NO 72
<211> LENGTH: 25
<212> TYPE: PRT
<213> ORGANISM: Artificial Sequence
<220> FEATURE:
<223> OTHER INFORMATION: Synthetic

<400> SEQUENCE: 72

Pro Lys Val Ser Phe Glu Pro Ile Pro Ile His Tyr Cys Ala Pro Ala
1               5                   10                  15

Gly Phe Ala Ile Leu Lys Cys Asn Asn
            20                  25

<210> SEQ ID NO 73
<211> LENGTH: 22
<212> TYPE: PRT
<213> ORGANISM: Artificial Sequence
<220> FEATURE:
<223> OTHER INFORMATION: Synthetic

<400> SEQUENCE: 73

Thr His Gly Ile Arg Pro Val Val Ser Thr Gln Leu Leu Leu Asn Gly
1               5                   10                  15

Ser Leu Ala Glu Glu Glu
            20

<210> SEQ ID NO 74
<211> LENGTH: 18
<212> TYPE: PRT
```

```
<213> ORGANISM: Artificial Sequence
<220> FEATURE:
<223> OTHER INFORMATION: Synthetic

<400> SEQUENCE: 74

Asp Arg Ala Ala Gly Gln Pro Ala Gly Asp Arg Ala Asp Gly Gln Pro
1               5                   10                  15

Ala Gly

<210> SEQ ID NO 75
<211> LENGTH: 20
<212> TYPE: PRT
<213> ORGANISM: Artificial Sequence
<220> FEATURE:
<223> OTHER INFORMATION: Synthetic

<400> SEQUENCE: 75

Asn Ala Asn Pro Asn Val Asp Pro Asn Ala Asn Pro Asn Ala Asn Pro
1               5                   10                  15

Asn Ala Asn Pro
            20

<210> SEQ ID NO 76
<211> LENGTH: 23
<212> TYPE: PRT
<213> ORGANISM: Artificial Sequence
<220> FEATURE:
<223> OTHER INFORMATION: Synthetic

<400> SEQUENCE: 76

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 77
<211> LENGTH: 23
<212> TYPE: PRT
<213> ORGANISM: Artificial Sequence
<220> FEATURE:
<223> OTHER INFORMATION: Synthetic

<400> SEQUENCE: 77

Ser Leu Leu Thr Glu Val Glu Thr Pro Ile Arg Asn Glu Trp Gly Ala
1               5                   10                  15

Arg Ala Asn Asp Ser Ser Asp
            20

<210> SEQ ID NO 78
<211> LENGTH: 10
<212> TYPE: PRT
<213> ORGANISM: Artificial Sequence
<220> FEATURE:
<223> OTHER INFORMATION: Synthetic

<400> SEQUENCE: 78

Lys Lys Lys Val Thr Ala Gln Glu Leu Asp
1               5                   10

<210> SEQ ID NO 79
<211> LENGTH: 16
<212> TYPE: PRT
<213> ORGANISM: Artificial Sequence
<220> FEATURE:
<223> OTHER INFORMATION: Synthetic
```

```
<400> SEQUENCE: 79

Phe Gly Phe Pro Glu His Leu Leu Val Asp Phe Leu Gln Ser Leu Ser
1               5                   10                  15

<210> SEQ ID NO 80
<211> LENGTH: 22
<212> TYPE: PRT
<213> ORGANISM: Artificial Sequence
<220> FEATURE:
<223> OTHER INFORMATION: Synthetic

<400> SEQUENCE: 80

Phe Tyr Glu Ile Ile Met Asp Ile Glu Gln Asn Asn Val Gln Gly Lys
1               5                   10                  15

Gln Gly Leu Gln Lys Leu
            20

<210> SEQ ID NO 81
<211> LENGTH: 18
<212> TYPE: PRT
<213> ORGANISM: Artificial Sequence
<220> FEATURE:
<223> OTHER INFORMATION: Synthetic

<400> SEQUENCE: 81

Met Glu Leu Arg Lys Asn Gly Arg Gln Cys Gly Met Ser Glu Lys Glu
1               5                   10                  15

Glu Glu

<210> SEQ ID NO 82
<211> LENGTH: 13
<212> TYPE: PRT
<213> ORGANISM: Artificial Sequence
<220> FEATURE:
<223> OTHER INFORMATION: Synthetic

<400> SEQUENCE: 82

Leu Glu Glu Lys Lys Gly Asn Tyr Val Val Thr Asp His
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic

<400> SEQUENCE: 83

Asp Ala Glu Phe Arg His Asp Ser Gly Tyr Glu Val
1               5                   10

<210> SEQ ID NO 84
<211> LENGTH: 7
<212> TYPE: PRT
<213> ORGANISM: Artificial Sequence
<220> FEATURE:
<223> OTHER INFORMATION: Synthetic

<400> SEQUENCE: 84

Phe Arg His Asp Ser Gly Tyr
1               5

<210> SEQ ID NO 85
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 85

Arg Ile Lys Gln Ile Gly Met Pro Gly Gly Lys
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic

<400> SEQUENCE: 86

Leu Leu Glu Leu Asp Lys Trp Ala Ser Leu
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Synthetic

<400> SEQUENCE: 87

Glu Gln Glu Leu Leu Glu Leu Asp Lys Trp Ala Ser Leu Trp
1               5                   10

<210> SEQ ID NO 88
<211> LENGTH: 8
<212> TYPE: PRT
<213> ORGANISM: Artificial Sequence
<220> FEATURE:
<223> OTHER INFORMATION: Synthetic

<400> SEQUENCE: 88

Asp Thr Gly Phe Leu Ala Ala Leu
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic

<400> SEQUENCE: 89

Tyr Cys Phe Thr Pro Ser Pro Val
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic

<400> SEQUENCE: 90

Cys Phe Arg Lys His Pro Glu Ala
1               5

<210> SEQ ID NO 91
<211> LENGTH: 8
<212> TYPE: PRT
```

```
<213> ORGANISM: Artificial Sequence
<220> FEATURE:
<223> OTHER INFORMATION: Synthetic

<400> SEQUENCE: 91

Glu Ala Thr Tyr Ser Arg Cys Gly
1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic

<400> SEQUENCE: 92

His Leu His Gln Asn Ile Val Asp
1               5

<210> SEQ ID NO 93
<211> LENGTH: 26
<212> TYPE: PRT
<213> ORGANISM: Artificial Sequence
<220> FEATURE:
<223> OTHER INFORMATION: Synthetic

<400> SEQUENCE: 93

Arg Tyr Asn Arg Asn Ala Val Pro Asn Leu Arg Gly Asp Leu Gln Val
1               5                   10                  15

Leu Ala Gln Lys Val Ala Arg Thr Leu Phe
            20                  25

<210> SEQ ID NO 94
<211> LENGTH: 11
<212> TYPE: PRT
<213> ORGANISM: Artificial Sequence
<220> FEATURE:
<223> OTHER INFORMATION: Synthetic

<400> SEQUENCE: 94

Thr Ala Val Val His Gln Leu Lys Arg Lys His
1               5                   10

<210> SEQ ID NO 95
<211> LENGTH: 16
<212> TYPE: PRT
<213> ORGANISM: Artificial Sequence
<220> FEATURE:
<223> OTHER INFORMATION: Synthetic

<400> SEQUENCE: 95

His Leu Leu Gln Leu Thr Val Trp Gly Ile Lys Gln Leu Gln Ala Arg
1               5                   10                  15

<210> SEQ ID NO 96
<211> LENGTH: 23
<212> TYPE: PRT
<213> ORGANISM: Artificial Sequence
<220> FEATURE:
<223> OTHER INFORMATION: Synthetic

<400> SEQUENCE: 96

Gly Glu Thr Tyr Gln Ser Arg Val Thr His Pro His Leu Pro Arg Ala
1               5                   10                  15

Leu Met Arg Ser Thr Thr Lys
            20
```

```
<210> SEQ ID NO 97
<211> LENGTH: 19
<212> TYPE: PRT
<213> ORGANISM: Artificial Sequence
<220> FEATURE:
<223> OTHER INFORMATION: Synthetic

<400> SEQUENCE: 97

Gly Arg Glu Arg Arg Pro Arg Leu Ser Asp Arg Pro Gln Leu Pro Tyr
1               5                   10                  15

Leu Glu Ala

<210> SEQ ID NO 98
<211> LENGTH: 16
<212> TYPE: PRT
<213> ORGANISM: Artificial Sequence
<220> FEATURE:
<223> OTHER INFORMATION: Synthetic

<400> SEQUENCE: 98

Asp Pro Pro Pro Pro Asn Pro Asn Asp Pro Pro Pro Pro Asn Pro Asn
1               5                   10                  15

<210> SEQ ID NO 99
<211> LENGTH: 14
<212> TYPE: PRT
<213> ORGANISM: Artificial Sequence
<220> FEATURE:
<223> OTHER INFORMATION: Synthetic

<400> SEQUENCE: 99

Glu Glu Lys Lys Lys Val Thr Ala Gln Glu Leu Asp Glu Glu
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthetic

<400> SEQUENCE: 100

Glu Glu Phe Arg His Asp Ser Gly Tyr Glu Glu
1               5                   10

<210> SEQ ID NO 101
<211> LENGTH: 15
<212> TYPE: PRT
<213> ORGANISM: Artificial Sequence
<220> FEATURE:
<223> OTHER INFORMATION: Synthetic

<400> SEQUENCE: 101

Glu Glu Arg Ile Lys Gln Ile Gly Met Pro Gly Gly Lys Glu Glu
1               5                   10                  15

<210> SEQ ID NO 102
<211> LENGTH: 187
<212> TYPE: PRT
<213> ORGANISM: Arctic ground squirrel hepatitis virus

<400> SEQUENCE: 102

Met Asp Ile Asp Pro Tyr Lys Glu Phe Gly Ser Ser Tyr Gln Leu Leu
1               5                   10                  15
```

Asn Phe Leu Pro Leu Asp Phe Pro Glu Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Glu Glu
50                  55                  60

Leu Thr Arg Leu Ile Ala Trp Met Ser Ala Asn Ile Asn Ser Glu Glu
65                  70                  75                  80

Val Arg Arg Val Ile Val Ala His Val Asn Asp Thr Trp Gly Leu Lys
                85                  90                  95

Val Arg Gln Asn Leu Trp Phe His Leu Ser Cys Leu Thr Phe Gly Gln
            100                 105                 110

His Thr Val Gln Glu Phe Leu Val Ser Phe Gly Val Arg Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Gly Ser Ala Arg Val Val Arg Ser
145                 150                 155                 160

Pro Arg Arg Arg Thr Pro Ser Pro Arg Arg Arg Ser Gln Ser Pro
                165                 170                 175

Arg Arg Arg Pro Gln Ser Pro Ala Ser Asn Cys
            180                 185

<210> SEQ ID NO 103
<211> LENGTH: 188
<212> TYPE: PRT
<213> ORGANISM: Woodchuck hepatitis virus

<400> SEQUENCE: 103

Met Asp Ile Asp Pro Tyr Lys Glu Phe Gly Ser Ser Tyr Gln Leu Leu
1               5                   10                  15

Asn Phe Leu Pro Leu Asp Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
            180                 185

<210> SEQ ID NO 104

```
<211> LENGTH: 188
<212> TYPE: PRT
<213> ORGANISM: Woodchuck hepatitis virus

<400> SEQUENCE: 104

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Ala Asn Cys
            180                 185

<210> SEQ ID NO 105
<211> LENGTH: 187
<212> TYPE: PRT
<213> ORGANISM: Woodchuck hepatitis virus

<400> SEQUENCE: 105

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Val Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Gly Gly Ala Arg Ala Ser Arg Ser Pro
145                 150                 155                 160
```

```
Arg Arg Arg Thr Pro Ser Pro Arg Arg Arg Ser Gln Ser Pro Arg
                165                 170                 175

Arg Arg Arg Ser Gln Ser Pro Ser Ala Asn Cys
            180                 185

<210> SEQ ID NO 106
<211> LENGTH: 188
<212> TYPE: PRT
<213> ORGANISM: Woodchuck hepatitis virus

<400> SEQUENCE: 106

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Leu Thr Gly Arg Glu His Cys
            35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Ser Gln Ser Pro Ser Ala Asn Cys
            180                 185

<210> SEQ ID NO 107
<211> LENGTH: 188
<212> TYPE: PRT
<213> ORGANISM: Woodchuck hepatitis virus

<400> SEQUENCE: 107

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Leu Thr Gly Arg Glu His Cys
            35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110
```

```
His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Thr Asn Cys
            180                 185

<210> SEQ ID NO 108
<211> LENGTH: 187
<212> TYPE: PRT
<213> ORGANISM: Ground squirrel hepatitis virus

<400> SEQUENCE: 108

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Ala Leu Tyr Glu Glu Leu Thr Gly Arg Glu His Cys
        35                  40                  45

Ser Pro His His Thr Ala Ile Arg Gln Ala Leu Val Cys Trp Glu Glu
    50                  55                  60

Leu Thr Arg Leu Ile Thr Trp Met Ser Glu Asn Thr Thr Glu Glu Val
65              70                  75                  80

Arg Arg Ile Ile Val Asp His Val Asn Asn Thr Trp Gly Leu Lys Val
                85                  90                  95

Arg Gln Thr Leu Trp Phe His Leu Ser Cys Leu Thr Phe Gly Gln His
            100                 105                 110

Thr Val Gln Glu Phe Leu Val Ser Phe Gly Val Trp Ile Arg Thr Pro
        115                 120                 125

Ala Pro Tyr Arg Pro Pro Asn Ala Pro Ile Leu Ser Thr Leu Pro Glu
    130                 135                 140

His Thr Val Ile Arg Arg Gly Gly Ser Arg Ala Ala Arg Ser Pro
145                 150                 155                 160

Arg Arg Arg Thr Pro Ser Pro Arg Arg Arg Ser Gln Ser Pro Arg
                165                 170                 175

Arg Arg Arg Ser Gln Ser Pro Ala Ser Asn Cys
            180                 185

<210> SEQ ID NO 109
<211> LENGTH: 183
<212> TYPE: PRT
<213> ORGANISM: Human hepatitis B virus

<400> SEQUENCE: 109

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60
```

```
Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Ile Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180
```

<210> SEQ ID NO 110
<211> LENGTH: 185
<212> TYPE: PRT
<213> ORGANISM: Human hepatitis B virus

<400> SEQUENCE: 110

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Val Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Asp Arg Gly Arg Ser Pro Arg Arg
145                 150                 155                 160

Arg Thr Pro Ser Pro Arg Arg Arg Arg Ser Pro Ser Pro Arg Arg Arg
                165                 170                 175

Arg Ser Gln Ser Arg Glu Ser Gln Cys
            180                 185
```

<210> SEQ ID NO 111
<211> LENGTH: 183
<212> TYPE: PRT
<213> ORGANISM: Human hepatitis B virus

<400> SEQUENCE: 111

```
Met Asp Ile Asp Pro Tyr Lys Glu Phe Gly Ala Ser Val Glu Leu Leu
1               5                   10                  15
```

```
Ser Phe Leu Pro Ser Asp Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 112
<211> LENGTH: 183
<212> TYPE: PRT
<213> ORGANISM: Human hepatitis B virus

<400> SEQUENCE: 112

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

```
<210> SEQ ID NO 113
<211> LENGTH: 183
<212> TYPE: PRT
<213> ORGANISM: Human hepatitis B virus

<400> SEQUENCE: 113

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 114
<211> LENGTH: 183
<212> TYPE: PRT
<213> ORGANISM: Human hepatitis B virus

<400> SEQUENCE: 114

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
```

```
                    145                 150                 155                 160
Pro Ser Pro Arg Arg Arg Ser Gln Ser Pro Arg Arg Arg Ser
                165                 170                 175

Gln Ser Arg Glu Ser Gln Cys
            180

<210> SEQ ID NO 115
<211> LENGTH: 183
<212> TYPE: PRT
<213> ORGANISM: Chimpanzee hepatitis B virus

<400> SEQUENCE: 115

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro Asn His Thr Ala Leu Arg Gln Ala Ile Leu Cys Trp Gly Glu
        50                  55                  60

Leu Met Thr Leu Ala Ser Trp Val Gly Asn Asn Leu Glu Asp Pro Ala
65                  70                  75                  80

Ser Arg Glu Gln Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Pro Ala Ser Gln Cys
            180

<210> SEQ ID NO 116
<211> LENGTH: 183
<212> TYPE: PRT
<213> ORGANISM: Gibbon hepatitis B virus

<400> SEQUENCE: 116

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro Asn His Thr Ala Leu Arg Gln Ala Val Leu Cys Trp Gly Glu
        50                  55                  60

Leu Met Thr Leu Ala Ser Trp Val Gly Asn Asn Leu Glu Asp Pro Ala
65                  70                  75                  80

Ser Arg Glu Leu Val Val Ser Tyr Val Asn Asn Asn Met Gly Leu Lys
                85                  90                  95

Ile Arg Gln Leu Leu Trp Phe His Ile Ser Cys Leu Thr Phe Gly Arg
```

```
                100                 105                 110
Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Pro Ala Ser Gln Cys
            180

<210> SEQ ID NO 117
<211> LENGTH: 183
<212> TYPE: PRT
<213> ORGANISM: Orangutan hepatitis virus

<400> SEQUENCE: 117

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro Asn His Thr Ala Leu Arg Gln Ala Val Leu Cys Trp Gly Glu
    50                  55                  60

Leu Met Thr Leu Ala Ser Trp Val Gly Asn Asn Leu Glu Asp Pro Ala
65                  70                  75                  80

Ser Arg Glu Leu Val Val Asn Tyr Val Asn Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Pro Ala Ser Gln Cys
            180

<210> SEQ ID NO 118
<211> LENGTH: 182
<212> TYPE: PRT
<213> ORGANISM: Woolly monkey hepatitis virus

<400> SEQUENCE: 118

Met Asp Ile Asp Pro Tyr Lys Glu Phe Gly Ala Thr Val Glu Leu Leu
1               5                   10                  15

Ser Phe Leu Pro Ala Asp Phe Phe Pro Ser Val Arg Asp Leu Leu

```
                50                  55                  60
Leu Met Ser Leu Ala Ser Trp Val Gly Thr Asn Leu Glu Asp Pro Ala
 65                  70                  75                  80

Ala Arg Glu Leu Val Val Ser Tyr Val Asn Asp Asn Met Gly Leu Lys
                 85                  90                  95

Val Arg Gln Leu Leu Trp Phe His Ile Ser Cys Leu Thr Phe Gly Arg
                100                 105                 110

Glu Thr Val Leu Glu Tyr Leu Val Ser Phe Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Arg Arg Arg Pro Ser Gly Arg Arg Thr Pro
145                 150                 155                 160

Ser Pro Arg Arg Arg Ser Gln Ser Pro Arg Arg Arg Ser Gln
                165                 170                 175

Ser Pro Ala Ser Ser Cys
                180

<210> SEQ ID NO 119
<211> LENGTH: 262
<212> TYPE: PRT
<213> ORGANISM: Duck hepatitis virus

<400> SEQUENCE: 119

Met Asp Ile Asn Ala Ser Arg Ala Leu Ala Asn Val Tyr Asp Leu Pro
 1               5                  10                  15

Asp Asp Phe Phe Pro Lys Ile Asp Asp Leu Val Arg Asp Ala Lys Asp
                 20                  25                  30

Ala Leu Glu Pro Tyr Trp Lys Ser Asp Ser Ile Lys Lys His Val Leu
                 35                  40                  45

Ile Ala Thr His Phe Val Asp Leu Ile Glu Asp Phe Trp Gln Thr Thr
 50                  55                  60

Gln Gly Met His Glu Ile Ala Glu Ser Leu Arg Ala Val Ile Pro Pro
 65                  70                  75                  80

Thr Thr Ala Pro Val Pro Thr Gly Tyr Leu Ile Gln His Glu Glu Ala
                 85                  90                  95

Glu Glu Ile Pro Leu Gly Asp Leu Phe Lys His Gln Glu Glu Arg Ile
                100                 105                 110

Val Ser Phe Gln Pro Asp Tyr Pro Ile Thr Ala Arg Ile His Ala His
                115                 120                 125

Leu Lys Ala Tyr Ala Lys Ile Asn Glu Glu Ser Leu Asp Arg Ala Arg
                130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
                180                 185                 190

Ile Gln Val Ala Gln Gly Gly Arg Lys Thr Ser Ser Gly Thr Arg Lys
                195                 200                 205

Pro Arg Gly Leu Glu Pro Arg Arg Lys Val Lys Thr Thr Phe Val
                210                 215                 220

Tyr Gly Arg Arg Arg Ser Lys Ser Arg Glu Arg Arg Ala Pro Ser Pro
225                 230                 235                 240
```

-continued

```
Gln Arg Ala Gly Ser Pro Leu Pro Arg Ser Ser Ser His His Arg
            245                 250                 255

Ser Pro Ser Pro Arg Lys
            260

<210> SEQ ID NO 120
<211> LENGTH: 262
<212> TYPE: PRT
<213> ORGANISM: Duck hepatitis virus

<400> SEQUENCE: 120

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30

Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ser Leu Arg Ala Val Ile Pro Pro
65                  70                  75                  80

Thr Thr Thr Pro Val Pro Pro Gly Tyr Leu Ile Gln His Glu Glu Ala
                85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Gln
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Val Ala Gln Gly Gly Arg Lys Thr Thr Thr Gly Thr Arg Lys
        195                 200                 205

Pro Arg Gly Leu Glu Pro Arg Arg Lys Val Lys Thr Thr Val Val
    210                 215                 220

Tyr Gly Arg Arg Arg Ser Lys Ser Arg Glu Arg Ala Pro Thr Pro
225                 230                 235                 240

Gln Arg Ala Gly Ser Pro Leu Pro Arg Ser Ser Ser His His Arg
            245                 250                 255

Ser Pro Ser Pro Arg Lys
            260

<210> SEQ ID NO 121
<211> LENGTH: 262
<212> TYPE: PRT
<213> ORGANISM: Duck hepatitis virus

<400> SEQUENCE: 121

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30
```

```
Ala Leu Glu Pro Tyr Trp Lys Ser Asp Ser Ile Lys Lys His Val Leu
            35                  40                  45

Ile Ala Thr His Phe Val Asp Leu Ile Glu Asp Phe Trp Gln Thr Thr
 50                  55                  60

Gln Gly Met His Glu Ile Ala Glu Ser Leu Arg Ala Val Ile Pro Pro
 65                  70                  75                  80

Thr Thr Ala Pro Val Pro Thr Gly Tyr Leu Ile Gln His Glu Glu Ala
                 85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Val Ala Gln Gly Gly Arg Lys Thr Ser Ser Gly Thr Arg Lys
        195                 200                 205

Pro Arg Gly Leu Glu Pro Arg Arg Lys Val Lys Thr Thr Val Val
    210                 215                 220

Tyr Gly Arg Arg Arg Ser Lys Ser Arg Asp Arg Arg Ala Pro Ser Pro
225                 230                 235                 240

Gln Arg Ala Gly Ser Pro Leu Pro Arg Ser Ser Ser His His Arg
                245                 250                 255

Ser Pro Ser Pro Arg Lys
            260

<210> SEQ ID NO 122
<211> LENGTH: 262
<212> TYPE: PRT
<213> ORGANISM: Duck hepatitis virus

<400> SEQUENCE: 122

Met Asp Ile Asn Ala Ser Arg Ala Leu Ala Asn Val Tyr Asp Leu Pro
 1               5                  10                  15

Asp Asp Phe Phe Pro Lys Ile Asp Leu Val Arg Asp Ala Lys Asp
                 20                  25                  30

Ala Leu Glu Pro

```
Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Val Ala Gln Gly Gly Arg Lys Thr Ser Ser Gly Thr Arg Lys
            195                 200                 205

Pro Arg Gly Leu Glu Pro Arg Arg Arg Lys Val Lys Thr Thr Val Val
            210                 215                 220

Tyr Gly Arg Arg Arg Ser Lys Ser Arg Glu Arg Arg Ala Pro Ser Pro
225                 230                 235                 240

Gln Arg Ala Gly Ser Pro Leu Pro Arg Ser Ser Ser Ser His His Arg
                245                 250                 255

Ser Pro Ser Pro Arg Lys
            260

<210> SEQ ID NO 123
<211> LENGTH: 262
<212> TYPE: PRT
<213> ORGANISM: Duck hepatitis virus

<400> SEQUENCE: 123

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
                20                  25                  30

Ala Leu Glu Pro Tyr Trp Lys Ser Asp Ser Ile Lys Lys His Val Leu
            35                  40                  45

Ile Ala Thr His Phe Val Asp Leu Ile Glu Asp Phe Trp Gln Thr Thr
        50                  55                  60

Gln Gly Met His Glu Ile Ala Glu Ser Leu Arg Ala Val Ile Pro Pro
65                  70                  75                  80

Thr Thr Ala Pro Val Pro Thr Gly Tyr Leu Ile Gln His Glu Glu Ala
                85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Ala Ala Gln Gly Gly Arg Lys Thr Ser Ser Gly Thr Arg Lys
            195                 200                 205

Pro Arg Gly Leu Glu Pro Arg Arg Arg Lys Val Lys Thr Thr Val Val
            210                 215                 220

Tyr Gly Arg Arg Arg Ser Lys Ser Arg Glu Arg Arg Ala Pro Ser Pro
225                 230                 235                 240

Gln Arg Ala Gly Ser Pro Leu Pro Arg Ser Ser Ser Ser His His Arg
```

Ser Pro Ser Pro Arg Lys
            260

<210> SEQ ID NO 124
<211> LENGTH: 262
<212> TYPE: PRT
<213> ORGANISM: Duck hepatitis virus

<400> SEQUENCE: 124

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30

Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ser Leu Arg Ala Val Ile Pro Pro
65                  70                  75                  80

Thr Thr Ala Pro Val Pro Thr Gly Tyr Leu Ile Gln His Glu Glu Ala
                85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Ala Ala Gln Gly Gly Arg Lys Thr Ser Ser Gly Thr Arg Lys
        195                 200                 205

Pro Arg Gly Leu Glu Pro Arg Arg Lys Val Lys Thr Thr Val Val
    210                 215                 220

Tyr Gly Arg Arg Arg Ser Lys Ser Arg Glu Arg Arg Ala Pro Ser Pro
225                 230                 235                 240

Gln Arg Ala Gly Ser Pro Leu Pro Arg Ser Ser Ser His His Arg
                245                 250                 255

Ser Pro Ser Pro Arg Lys
            260

<210> SEQ ID NO 125
<211> LENGTH: 262
<212> TYPE: PRT
<213> ORGANISM: Ross' goose hepatitis virus

<400> SEQUENCE: 125

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30

Ala Leu Glu Pro Tyr Trp Arg Asn Asp Ser Ile Lys Lys His Val Leu

```
                35                  40                  45
Ile Ala Thr His Phe Val Asp Leu Ile Glu Asp Phe Trp Gln Thr Thr
 50                  55                  60
Gln Gly Met His Glu Ile Ala Glu Ala Leu Arg Ala Ile Ile Pro Ala
 65                  70                  75                  80
Thr Thr Ala Pro Val Pro Gln Gly Phe Leu Val Gln His Glu Glu Ala
                 85                  90                  95
Glu Glu Ile Pro Leu Gly Glu Leu Phe Arg Tyr Gln Glu Glu Arg Leu
                100                 105                 110
Thr Asn Phe Gln Pro Asp Tyr Pro Val Thr Ala Arg Ile His Ala His
            115                 120                 125
Leu Lys Ala Tyr Ala Lys Ile Asn Glu Glu Ser Leu Asp Arg Ala Arg
130                 135                 140
Arg Leu Leu Trp Trp His Tyr Asn Cys Leu Leu Trp Gly Glu Pro Asn
145                 150                 155                 160
Val Thr Asn Tyr Ile Ser Arg Leu Arg Thr Trp Leu Ser Thr Pro Glu
                165                 170                 175
Lys Tyr Arg Gly Lys Asp Ala Pro Thr Ile Glu Ala Ile Thr Arg Pro
            180                 185                 190
Ile Gln Val Ala Gln Gly Gly Arg Asn Lys Thr Gln Gly Val Arg Lys
        195                 200                 205
Ser Arg Gly Leu Glu Pro Arg Arg Arg Val Lys Thr Thr Ile Val
    210                 215                 220
Tyr Gly Arg Arg Ser Lys Ser Arg Glu Arg Ala Pro Thr Pro
225                 230                 235                 240
Gln Arg Ala Gly Ser Pro Leu Pro Arg Thr Ser Arg Asp His His Arg
                245                 250                 255
Ser Pro Ser Pro Arg Glu
                260

<210> SEQ ID NO 126
<211> LENGTH: 262
<212> TYPE: PRT
<213> ORGANISM: Heron hepatitis virus

<400> SEQUENCE: 126

Met Asp Val Asn Ala Ser Arg Ala Leu Ala Asn Val Tyr Asp Leu Pro
 1               5                  10                  15
Asp Asp Phe Phe Pro Gln Ile Asp Asp Leu Val Arg Asp Ala Lys Asp
                20                  25                  30
Ala Leu Glu Pro Tyr Trp Lys Ala Glu Thr Ile Lys Lys His Val Leu
            35                  40                  45
Ile Ala Thr His Phe Val Asp Leu Ile Glu Asp Phe Trp Gln Thr Thr
 50                  55                  60
Gln Gly Met Ser Gln Ile Ala Asp Ala Leu Arg Ala Val Ile Pro Pro
 65                  70                  75                  80
Thr Thr Val Pro Val Pro Glu Gly Phe Leu Ile Thr His Ser Glu Ala
                 85                  90                  95
Glu Glu Ile Pro Leu Asn Asp Leu Phe Ser Asn Gln Glu Glu Arg Ile
                100                 105                 110
Val Asn Phe Gln Pro Asp Tyr Pro Ile Thr Ala Arg Ile His Thr His
            115                 120                 125
Leu Arg Val Tyr Thr Lys Leu Asn Glu Gln Ala Leu Asp Lys Ala Arg
130                 135                 140
```

```
Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Lys Asp Ala Pro Thr Ile Glu Ala Ile Thr Arg Pro
            180                 185                 190

Ile Gln Val Ala Gln Gly Gly Arg Asn Gln Thr Lys Gly Thr Arg Lys
        195                 200                 205

Pro Arg Gly Leu Glu Pro Arg Arg Lys Val Lys Thr Thr Val Val
    210                 215                 220

Tyr Gly Arg Arg Ser Lys Ser Arg Gly Arg Ser Ser Pro Ser
225                 230                 235                 240

Gln Arg Ala Gly Ser Pro Leu Pro Arg Asn Arg Gly Asn Gln Thr Arg
                245                 250                 255

Ser Pro Ser Pro Arg Glu
            260

<210> SEQ ID NO 127
<211> LENGTH: 564
<212> TYPE: DNA
<213> ORGANISM: Arctic ground squirrel hepatitis virus

<400> SEQUENCE: 127
atggacatag atccctataa agaatttggt tcatcctacc agttgttgaa ttttcttcct    60
ttggacttct ttcctgaact caatgccttg gtggacactg ctactgctct ctatgaagaa   120
gaattaacag gtagggagca ctgctctcct catcacacag ctatcagaca gctttagtt    180 tgctgggaag aattaacaag attaattgcg tggatgagtg ctaacattaa ttcagaagaa   240
gtaagaagag ttatagttgc tcatgtcaat gacacttggg gacttaaagt taggcagaat   300
ttatggtttc acttatcctg tctgactttt gggcaacaca cagtgcagga attttagtc    360 agctttggag taaggatcag aactccggct ccttatagac ctcctaatgc acccattctc   420
tcaactcttc cggaacatac agtcattagg agaaggaggaa gtgcaagagt tgttaggtcc   480
cccagaagac gcactccctc tcctcgcagg agaagatctc aatcaccgcg tcgcaggcct   540
caatctccag cttccaactg ctga                                          564

<210> SEQ ID NO 128
<211> LENGTH: 564
<212> TYPE: DNA
<213> ORGANISM: Ground squirrel hepatitis virus

<400> SEQUENCE: 128
atggacatag atccctataa agaatttggt tcttcttatc agttgttgaa ttttcttcct    60
ttggactttt ttcctgatct caatgcattg gtggacactg ctgctgctct ttatgaagaa   120
gaattaacag gtagggagca ttgttctcct catcatactg ctattagaca ggccttagtg   180
tgttgggaag aattaactag attaattaca tggatgagtg aaaatacaac agaagaagtt   240
agaagaatta ttgttgatca tgtcaataat acttggggac ttaaagtaag acagacttta   300
tggtttcatt tatcatgtct tactttgga caacacacag ttcaagaatt tttggttagt   360 tttgagtat ggattagaac tccagctcct tatagaccac ctaatgcacc catttttatca   420 actcttccgg aacatacagt cattaggaga agaggaggtt caagagctgc taggtcccccc   480 cgaagacgca ctccctctcc tcgcaggaga aggtctcaat caccgcgtcg cagacgctct   540
caatctccag cttccaactg ctga                                          564
```

<210> SEQ ID NO 129
<211> LENGTH: 567
<212> TYPE: DNA
<213> ORGANISM: Woodchuck hepatitis virus

<400> SEQUENCE: 129

```
atggacatag atccttataa agaatttggt tcatcttatc agttgttgaa ttttcttcct    60
ttggactttt ttcctgacct taatgctttg gtggacactg ctactgcctt gtatgaagaa   120
gaactaacag gtagggaaca ttgctctccg caccatacag ctattagaca agctttagta   180
tgctgggatg aattaactaa attaatagct tggatgagct caacataac ttctgaacaa    240
gtaagaacaa tcattgtaaa tcatgtcaat gatacctggg gacttaaggt gagacaaagt   300
ttatggtttc atttgtcatg tctcactttc ggacaacata cagttcaaga attttagta    360
agttttggag tatggattag gactccagct ccatatagac ctcctaatgc acccattctc   420
tcgactcttc cggaacatac agtcattagg agaagaggag gtgcaagagc ttctaggtcc   480
cccagaagac gcactccctc tcctcgcagg agaagatctc aatcaccgcg tcgcagacgc   540
tctcaatctc catctaccaa ctgctga                                       567
```

<210> SEQ ID NO 130
<211> LENGTH: 567
<212> TYPE: DNA
<213> ORGANISM: Woodchuck hepatitis virus

<400> SEQUENCE: 130

```
atggacatag atccctataa agaatttggt tcatcttatc agttgttgaa ttttcttcct    60
ttggacttct ttcctgacct taatgctttg gtggacactg ctactgcctt gtatgaagaa   120
gagctaacag gtagggaaca ttgctctccg caccatacag ctattagaca agctttagta   180
tgctgggatg aattaactaa attgatagct tggatgagct caacataac ttctgaacaa    240
gtaagaacaa tcatagtaaa tcatgtcaat gatacctggg gacttaaggt gagacaaagt   300
ttatggtttc atttgtcatg tctcactttt ggacaacata cagttcaaga attttagta    360
agttttggag tatggatcag aactccagct ccatatagac ctcctaatgc acccattctc   420
tcgactcttc cggaacatac agtcattagg agaagaggag gtgcaagagc ttctaggtcc   480
cccagaagac gcactccctc tcctcgcagg agaagatctc aatcaccgcg tcgcagacgc   540
tctcaatctc catctgccaa ctgctga                                       567
```

<210> SEQ ID NO 131
<211> LENGTH: 564
<212> TYPE: DNA
<213> ORGANISM: Woodchuck hepatitis virus

<400> SEQUENCE: 131

```
atggacatag atccctataa agaatttggt tcatcttatc agttgttgaa ttttcttcct    60
ttggacttct ttcctgacct taatgctttg gtggacactg ctactgcctt gtatgaagaa   120
gagctaacag gtagggaaca ttgctctccg caccatacag ctattagaca agctttagta   180
tgctgggatg aattaactaa attgatagct tggatgagct caacataac ttctgaacaa    240
gtaagaacaa tcatagtaaa tcatgtcaat gatacctggg gacttaaggt gagacaaagt   300
ttatggtttc atttgtcatg tctcactttc ggacaacata cagttcaaga attttagta    360
agttttgtag tatggatcag aactccagct ccatatagac ctcctaatgc acccattctc   420
```

```
tcgactcttc cggaacatac agtcattaga agaggaggtg caagagcttc taggtccccc      480
agaagacgca ctccctctcc tcgcaggaga agatctcaat caccgcgtcg cagacgctct      540
caatctccat ctgccaactg ctga                                             564
```

<210> SEQ ID NO 132
<211> LENGTH: 567
<212> TYPE: DNA
<213> ORGANISM: Woodchuck hepatitis virus

<400> SEQUENCE: 132

```
atggacatag atccctataa agaatttggt tcatcttatc agttgttgaa ttttcttcct       60
ttggacttct ttcctgacct taatgctttg gtggacactg ctactgcctt gtatgaagaa      120
gagctaacag gtagggaaca ttgctctccg caccatacag ctattagaca agctttagta      180
tgctgggatg aattaactaa attgatagct tggatgagct caacataac ttctgaacaa       240 gtaagaacaa tcatagtaaa tcatgtcaat gatacctggg gacttaaggt gagacaaagt      300
ttatggtttc atttgtcatg tctcactttc ggacaacata cagttcaaga atttttagta      360
agttttggag tatggatcag aactccagct ccatatagac ctcctaatgc acccattctc      420
tcgactcttc cggaacatac agtcattagg agaagaggag gtgcaagagc ttctaggtcc      480
cccagaagac gcactccctc tcctcgcagg agaagatctc aatcaccgcg tcgcagacgc      540
tctcaatctc catctgccaa ctgctga                                          567
```

<210> SEQ ID NO 133
<211> LENGTH: 567
<212> TYPE: DNA
<213> ORGANISM: Woodchuck hepatitis virus

<400> SEQUENCE: 133

```
atggacatag atccttataa agaatttggt tcatcttatc agttgttgaa ttttcttcct       60
ttggacttct ttcctgatct taatgctttg gtggacactg ctactgcctt gtatgaagaa      120
gaactaacag gtagggaaca ttgctctccg caccatacag ctattagaca agctttagta      180
tgctgggatg aattaactaa attgatagct tggatgagct caacataac ttctgaacaa       240 gtaagaacaa tcattgtaaa tcatgtcaat gatacctggg gacttaaggt gagacaaagt      300
ttatggtttc atttgtcatg tctcactttc ggacaacata cagttcaaga atttttagta      360
agttttggag tatggatcag gactccagct ccatatagac ctcctaatgc acccattctc      420
tcgactcttc cggaacatac agtcattagg agaagaggag gtgcaagagc ttctaggtcc      480
cccagaagac gcactccctc tcctcgcagg agaagatctc aatcaccgcg tcgcagacgc      540
tctcaatctc catctgccaa ctgctga                                          567
```

<210> SEQ ID NO 134
<211> LENGTH: 552
<212> TYPE: DNA
<213> ORGANISM: Orangutan hepatitis virus

<400> SEQUENCE: 134

```
atggacattg acccttataa agaatttgga gctactgtgg agttactctc ttttttgcct       60
tcggatttct ttccgtctgt cagagatcta ctcgacaccg catcagccct gtatcgggaa      120
gccttagagt ctccagaaca ttgttcacct aaccacacag cactcaggca agcagttctg      180
tgctggggtg agttaatgac tctggcttcc tgggtgggta ataatttgga agacccagca      240
tctagggaac tggtagttaa ttatgtcaac aataatatgg ggctaaaaat cagacaacta      300
```

```
ctgtggtttc acatttcctg tcttactttt ggaagagaaa cagttttaga atatttggtg      360
tcttttggag tgtggattcg cactcctcct gcgtacagac caccaaatgc ccctatcttg      420
tcaacacttc cggaaactac tgttgttaga cgaagaggcg ggtcccctag aagaagaact      480
ccctcgcctc gcagacgaag gtctcaatca ccgcgtcgca gaagatctca atctccagct      540
tcccaatgtt ag                                                         552

<210> SEQ ID NO 135
<211> LENGTH: 549
<212> TYPE: DNA
<213> ORGANISM: Woolly monkey hepatitis virus

<400> SEQUENCE: 135
atggacattg atccttataa agaatttggc gctactgttg agttattgtc tttttttgcct     60 gctgacttct tccttccgt acgggatttg ctggacacag cttctgctct gtatagagaa      120
gccctggagt cttccgacca ctgttcaccg caccatactg ccttgaggca gacggtactg     180
tgctggggag aattaatgtc cttagcttct gggtgggaa ctaatttgga ggatcctgct      240
gctagagaat tagtggttag ctatgtcaat gacaacatgg gactgaaggt gagacaactc     300 cttttggttcc atatttcctg tctcactttt ggtaggaaa ctgttttgga atatctggtt    360 tcttttggg tgtggatacg cacacctcct gcatatagac cacccaatgc ccctatctta     420
tcaacacttc cggaaactac tgttgttaga cgaaggagac cctctggaag acgcactccc    480
tcgcctcgca gacgaagatc tcaatcgccg cgtcgcagaa ggtctcaatc tccagcatct     540
tcctgttag                                                            549

<210> SEQ ID NO 136
<211> LENGTH: 552
<212> TYPE: DNA
<213> ORGANISM: Gibbon hepatitis B virus

<400> SEQUENCE: 136
atggacattg acccttataa agaatttgga gctactgtgg agttactctc ttttttgcct      60
tctgacttct ttccgtcggt tagagatctc cttgacaccg cctcagctct atatcgggaa      120
gccctagagt ctcagaaca ttgttcacct aatcatacag cactcaggca agctgttttg     180
tgctggggtg agttgatgac tctggcttcc tgggtgggca ataatttgga agatccagca    240
tctagggaac tagtagtcag ttatgttaat aataacatgg gtctaaaaat caggcaacta     300
ttgtggtttc acatttcctg tcttactttt ggaagagaaa ctgtccttga gtatttagtg     360
tcttttggag tgtggattcg cactcctcca gcttacagac caccaaatgc ccctatctta     420
tccactcttc cggagactac tgttgttaga cgaagaggca ggtcccctag aagaagaact     480
ccctcgcctc gcagacgaag gtctcaatcg ccgcgtcgca gaagatctca atctccagct     540
tcccaatgtt ag                                                        552

<210> SEQ ID NO 137
<211> LENGTH: 552
<212> TYPE: DNA
<213> ORGANISM: Chimpanzee hepatitis B virus

<400> SEQUENCE: 137
atggacattg acccttataa agaatttgga gctacagtgg agttactctc ttttttgcct      60
tctgatttct ttccgtcggt ccgtgatctc ctcgacaccg cctcagctct gtaccgggaa     120
```

```
gccttagagt ctccagagca ctgttcacct aaccatacag cacttaggca agctatactg    180
tgctggggtg agttaatgac tctggcctcc tgggtgggca ataatttgga agatccagca    240
tccagggaac aagtagttaa ttatgtcaat accaatatgg gtttaaagat cagacaatta    300
ttgtggtttc atatttcctg tcttactttt ggaagagaaa ctgtccttga gtatttggtg    360
tcttttggag tgtggattcg cactcccccc gcttatagac caccaaatgc ccctatctta    420
tcaacacttc cggaaactac tgttgttaga cgacgaggca ggtcccctag aagaagaact    480
ccctcgcctc gcagacgaag gtctcaatcg ccgcgtcgca aagatctca atctccagct    540 tcccaatgtt ag                                                        552
```

<210> SEQ ID NO 138
<211> LENGTH: 552
<212> TYPE: DNA
<213> ORGANISM: Human hepatitis B virus

<400> SEQUENCE: 138

```
atggacattg accccttataa agaatttgga gctaccgtgg agttactctc gttttttgcct    60 tctgacttct ttccttcagt acgagatctt ctagataccg cctcagctct gtatcgggat    120
gccttagagt ctcctgagca ttgttcacct caccatactg cactcaggca agcaattctt    180 tgctggggg aactaatgac tctagctacc tgggtgggtg ttaatttgga agatccagca    240
tctagggacc tagtagtcag ttatgtcaac actaatatgg gcctaaagtt cagacaactc    300
ttgtggtttc acatttcttg tctcattttt ggaagagaaa cagttataga gtatttggtg    360
tctttcggag tgtggattcg cactcctcca gcttatagac caccaaatgc ccctatccta    420
tcaacacttc cggagactac tgttgttaga cgacgaggca ggtcccctag aagaagaact    480
ccctcgcctc gcagacgaag gtctcaatcg ccgcgtcgca aagatctca atctcgggaa    540 tctcaatgtt ag                                                        552
```

<210> SEQ ID NO 139
<211> LENGTH: 558
<212> TYPE: DNA
<213> ORGANISM: Human hepatitis B virus

<400> SEQUENCE: 139

```
atggacattg accccttataa agaatttgga gctactgtgg agttactctc gttttttgcct    60 tctgacttct ttccttccgt cagagatctc ctagacaccg cctcagctct gtatcgagaa    120
gccttagagt ctcctgagca ttgctcacct caccatactg cactcaggca agccattctc    180 tgctggggg aattgatgac tctagctacc tgggtgggta ataatttgga agatccagca    240
tctagggatc ttgtagtaaa ttatgttaat actaacgtgg gtttaaagat caggcaacta    300
ttgtggtttc atatatcttg ccttactttt ggaagagaga ctgtacttga atatttggtc    360
tctttcggag tgtggattcg cactcctcca gcttatagac caccaaatgc ccctatctta    420
tcaacacttc cggaaactac tgttgttaga cgacgggacc gaggcaggtc ccctagaaga    480
agaactccct cgcctcgcag acgcagatct ccatcgccgc gtcgcagaag atctcaatct    540
cgggaatctc aatgttag                                                  558
```

<210> SEQ ID NO 140
<211> LENGTH: 552
<212> TYPE: DNA
<213> ORGANISM: Human hepatitis B virus

<400> SEQUENCE: 140

```
atggacattg acccgtataa agaatttgga gcttctgtgg agttactctc ttttttgcct      60
tctgacttct ttccttctat tcgagatctc ctcgacaccg cctcagctct atatcgggag     120
gccttagagt ctccggaaca ttgttctcct catcatacag cactcaggca agctattctg     180
tgttggggtg agttgatgaa tctggccacc tgggtgggaa gtaatttgga agacccagca     240
tccagggaat tagtagtcag ctatgtcaat gttaatatgg gcctaaaaat cagacaacta     300
ctgtggtttc acatttcctg tcttactttt ggaagagaaa ctgttcttga gtatttggtg     360
tcttttggag tgtggattcg cactcctcct gcttacagac caccaaatgc ccctatctta     420
tcaacacttc cggaaactac tgttgttaga cgacgaggca ggtcccctag aagaagaact     480
ccctcgcctc gcagacgaag gtctcaatcg ccgcgtcgca gaagatctca atctcgggaa     540
tctcaatgtt ag                                                         552

<210> SEQ ID NO 141
<211> LENGTH: 552
<212> TYPE: DNA
<213> ORGANISM: Human hepatitis B virus

<400> SEQUENCE: 141
atggacattg acccttataa agaatttgga gctactgtgg agttactctc gttttttgcct    60 tctgacttct ttccttccgt acgagatctt ctagataccg ccgcagctct gtatcgggat    120
gccttagagt ctcctgagca ttgttcacct caccatactg cactcaggca agcaattctt    180
tgctggggag acttaatgac tctagctacc tgggtgggta ctaatttaga agatccagca    240
tctagggacc tagtagtcag ttatgtcaac actaatgtgg cctaaagtt cagacaatta    300 ttgtggtttc acatttcttg tctcactttt ggaagagaaa cggttctaga gtatttggtg    360
tcttttggag tgtggattcg cactcctcca gcttatagac caccaaatgc ccctatccta    420
tcaacgcttc cggagactac tgttgttaga cgacgaggca ggtcccctag aagaagaact    480
ccctcgcctc gcagacgaag atctcaatcg ccgcgtcgca gaagatctca atctcgggaa    540
tctcaatgtt ag                                                         552

<210> SEQ ID NO 142
<211> LENGTH: 552
<212> TYPE: DNA
<213> ORGANISM: Human hepatitis B virus

<400> SEQUENCE: 142
atggacattg acccgtataa agaatttgga gcttctgtgg agttactctc ttttttgcct     60
tctgacttct ttccttctat tcgagatctc ctcgacaccg cctctgctct gtatcgggag    120
gccttagagt ctccggaaca ttgttcacct caccatacag cactcaggca agctattctg    180
tgttggggtg agttgatgaa tttggccacc tgggtgggaa gtaatttgga agacccagca    240
tccagggaat tagtagtcag ctatgtcaat gttaatatgg gcctaaaaat cagacaacta    300
ttgtggtttc atatttcctg tcttactttt ggaagagaaa ctgttcttga gtatttggtg    360
tcttttggag tgtggattcg cactcctccc gcttacagac caccaaatgc ccctatctta    420
tcaacacttc cggaaactac tgttgttaga cgacgaggca ggtcccctag aagaagaact    480
ccctcgcctc gcagacgaag gtctcaatcg ccgcgtcgca gaagatctca atctcgggaa    540
tctcaatgtt ag                                                         552

<210> SEQ ID NO 143
```

-continued

<211> LENGTH: 786
<212> TYPE: DNA
<213> ORGANISM: Ross' goose hepatitis virus

<400> SEQUENCE: 143

```
atggatatca acgcttcaag agctttagct aatgtatatg atttgccaga tgatttcttt     60
ccaaagattg atgatttagt tagagatgct aaagatgctt tagagcctta ttggagaaat    120
gattcaataa agaaacatgt tttaattgca actcactttg tggatctcat tgaggatttc    180
tggcaaacca ctcagggtat gcatgaaata gcagaggcac tgagagctat aattcctgcc    240
actactgctc cagtacctca gggatttctg gtccaacacg aagaagctga agagatacct    300
ttgggtgaac tttttaggta tcaggaagaa agactaacta actttcaacc agattatcca    360
gttaccgcca gaattcatgc tcacctgaaa gcatatgcaa aaataaatga ggaatcttta    420
gatagagcta ggagattgct ttggtggcat tataactgtt tattgtgggg cgagcctaac    480
gttaccaact atatttcgag attaagaact tggttatcca cacctgaaaa atacagagga    540
aaagatgccc caaccattga agcaatcact agaccaatcc aagtggcgca gggaggcaga    600
aataagactc agggagttag aaaatctcgt ggactcgaac ctaggagaag aagagttaaa    660
accacaattg tctatgggag aagacgttca aagtccaggg aaaggagagc ccctacaccc    720
cagcgtgcgg gctcccctct cccgcgtact tctagggacc accacagatc tccctcgcct    780
agggaa                                                               786
```

<210> SEQ ID NO 144
<211> LENGTH: 789
<212> TYPE: DNA
<213> ORGANISM: Heron hepatitis virus

<400> SEQUENCE: 144

```
atggatgtca atgcttcaag agctttagca aatgtatatg atctgccaga tgatttcttt     60
cctcagattg atgatcttgt tagagatgct aaggatgctt tagaacctta ttggaaagcc    120
gaaacaataa agaaacatgt tttaattgct actcactttg tggatttgat tgaggacttc    180
tggcagacca ctcagggtat gagccaaatt gcagacgccc tccgagcagt aattccacct    240
actaccgtac cagtaccgga gggttttctc attactcata gtgaggcaga agagatcccc    300
ttgaacgatc tcttttcaaa tcaagaggag aggatagtca atttccaacc tgactatccc    360
attacagcta gaattcatac ccacttacgt gtttatacta aattgaatga acaagctttg    420
gacaaagctc gcagattgct ttggtggcat tacaattgcc tcctctgggg agaagccact    480
gttacaaatt atatttctcg cctccgtact tggctttcta ctcccgaaaa atatcgaggc    540
aaggatgccc caaccattga agcaatcact agaccaatcc aggtggctca aggaggcaga    600
aatcaaacta agggaactag aaaacctcgt ggactcgaac ctagaagacg aaaggttaaa    660
accacagttg tctatgggag aagacgttct aagtcccgag gcaggagatc ctctccatcc    720
caacgtgcgg gctcccctct cccacgtaat cggggaaacc agacacgatc cccctcacct    780
agggaatag                                                            789
```

<210> SEQ ID NO 145
<211> LENGTH: 786
<212> TYPE: DNA
<213> ORGANISM: Duck hepatitis virus

<400> SEQUENCE: 145

```
atggatatca atgcttctag agccttagca aatgtgtatg atctgcctga tgatttcttt     60
```

| | |
|---|---|
| ccaaaaatag atgatcttgt aagggatgct aaagacgctt tagaacctta ttggaaatct | 120 |
| gactcaataa agaaacatgt tttaattgca actcattttg tggatcttat tgaggatttt | 180 |
| tggcagacta cgcagggtat gcatgaaatc gctgaatcac taagagcagt aattccacct | 240 |
| accactgctc ctgttcctac tgggtatctc attcagcacg aagaggcaga agagatacca | 300 |
| ttaggtgatt tatttaaaca tcaagaagaa agaatagtca gtttccaacc tgactaccca | 360 |
| attacagcaa gaattcatgc acacctaaaa gcatatgcaa aaattaacga ggaatcattg | 420 |
| gatcgggcta ggagattgct ttggtggcat tataactgtt tactgtgggg agaagctaac | 480 |
| gttactaatt atatttctcg cctccgtact tggttgtcaa ctcctgaaaa gtacagaggt | 540 |
| cgagatgccc caaccattga agcaatcact agaccaatcc aagtggctca gggaggcaga | 600 |
| aaaacatctt cgggaactag aaaacctcgt ggactcgaac ctagaagaag aaaagttaaa | 660 |
| accacatttg tctatgggag aagacgttca agtccaggg aaaggagagc cccttcaccc | 720 |
| caacgtgcgg gctcccctct cccacgtagt tcgagcagcc accatagatc tccctcgcct | 780 |
| aggaaa | 786 |

<210> SEQ ID NO 146
<211> LENGTH: 789
<212> TYPE: DNA
<213> ORGANISM: Duck hepatitis virus

<400> SEQUENCE: 146

| | |
|---|---|
| atggatatca atgcttctag agccttagcc aatgtgtatg atctaccaga tgatttcttt | 60 |
| ccaaaaatag atgatcttgt tagagatgct aaagacgctt tagagcctta ttggaaatca | 120 |
| gattcaataa agaaacatgt tttgattgca actcactttg tggatcttat tgaagacttc | 180 |
| tggcagacta cacagggcat gcatgaaata gccgaatcct taagagctgt atacctccc | 240 |
| actactactc ctgttccacc gggttatctt attcagcacg aagaagctga agagatacct | 300 |
| ttgggagatt tatttaaaca ccaagaagaa aggatagtga gtttccaacc cgactatcca | 360 |
| attacggcta gaattcatgc tcatttgaaa gcttatgcaa aaattaacga ggaatcactg | 420 |
| gatagggcta ggagattgct ttggtggcat tacaattgtt tactgtgggg agaagctcaa | 480 |
| gttactaact atatttctcg cttgcgtact tggttgtcaa ctcctgagaa atatagaggt | 540 |
| agagatgccc cgaccattga agcaatcact agaccaatcc aagtggctca gggaggccga | 600 |
| aaaacaacta cgggtactag aaaacctcgt ggactcgaac ctagaagaag aaaagttaaa | 660 |
| accacagttg tctatgggag aagacgttca agtcccggg aaaggagagc cctacaccc | 720 |
| caacgtgcgg gctcccctct cccacgtagt tcgagcagcc accatagatc tccctcgcct | 780 |
| aggaaataa | 789 |

<210> SEQ ID NO 147
<211> LENGTH: 789
<212> TYPE: DNA
<213> ORGANISM: Duck hepatitis virus

<400> SEQUENCE: 147

| | |
|---|---|
| atggatatca atgcttctag agccttagcc aatgtgtatg atctgccaga tgatttcttc | 60 |
| cctaaaattg atgatcttgt aagggatgct aaagacgcat tagaacctta ttggaaatct | 120 |
| gattcaataa agaaacatgt tttaattgca actcactttg tggatcttat tgaagacttt | 180 |
| tggcagacta ctcagggtat gcatgaaatt gctgaatcct taagagctgt aataccacct | 240 |

```
acgactgctc ctgtacctac tgggtatctc attcaacacg aggaagctga agagatacct      300
ttaggtgatt tatttaaaca tcaggaagaa agaatagtca gtttccaacc tgactatcct      360
attacagcaa gaattcatgc acacctaaaa gcttatgcta aaattaatga ggaatcgttg      420
gatagggcta ggagattgct ttggtggcat tacaactgtt tactgtgggg agaagctaac      480
gttactaatt atatttctcg gctccgtact tggttgtcaa ctcctgaaaa gtacagaggc      540
cgtgatgccc caaccattga agcaatcact agaccaatcc aggtggctca gggaggcaga      600
aaaacatctt cgggaactag aaaacctcgt ggactcgaac ctagaagaag aaaagttaaa      660
accacagttg tctatgggag aagacgttca aagtccaggg ataggagagc ccttcacccc     720
caacgtgcgg gctcccctct cccacgtagt tcgagcagcc accatagatc tccctcgcct      780
aggaaataa                                                              789

<210> SEQ ID NO 148
<211> LENGTH: 789
<212> TYPE: DNA
<213> ORGANISM: Duck hepatitis virus

<400> SEQUENCE: 148
atggatatca atgcttctag agccttagcc aatgtatatg atctgccaga tgatttcttt        60
ccaaaaattg atgatcttgt aagggatgcg aaagatgctt tagaacctta ttggaaatct      120
gattcaataa agaaacatgt tttaattgca actcacttcg tggatcttat tgaagacttc      180
tggcagacta cacagggtat gcatgagata gctgaatcat taagagcagt aattccacct      240
accactgctc ctgtacctac ggggtatctc attcaacacg aagaggctga agagatacct      300
ttaggtgatc ttttcaaaca tcaggaagaa aggatagtta gtttccagcc agactatccg      360
attactgcta gaattcatgc acatctaaaa gcttatgcta aaattaatga ggaatcatta      420
gatcgggcta ggagattgct ttggtggcat tacaactgtt tactgtgggg agaagctaac      480
gttaccaact atatttctcg gctccgtact tggttgtcaa ctcctgaaaa gtaccgaggc      540
cgtgatgccc caaccattga agcaatcact agaccaatcc aagtggctca gggaggcaga      600
aaaacatctt cgggaactag aaaacctcgt ggactcgaac ctagaagaag aaaagttaaa      660
accacagttg tctatgggag aagacgttca aagtcccggg aaaggagagc ccttcacccc     720
caacgtgcgg gctcccctct cccacgtagt tcgagcagcc accatagatc tccctcgcct      780
aggaaataa                                                              789

<210> SEQ ID NO 149
<211> LENGTH: 789
<212> TYPE: DNA
<213> ORGANISM: Duck hepatitis virus

<400> SEQUENCE: 149
atggatatca atgcttctag agccttagcc aatgtatatg atctgccaga tgatttcttt        60
ccaaaaattg atgatcttgt aagggatgct aaagacgctt tagaacctta ctggaaatct      120
gattcaataa agaaacatgt tttgattgca actcactttg tggatcttat tgaagacttc      180
tggcagacta ctcagggtat gcatgaaatt gctgaatcct taagagcagt aataccacct      240
accactgctc ctgtacctac tggatatctc attcaacacg aggaggctga agagataccc      300
ttaggtgatt tatttaaaca tcaggaagaa agaatagtca gttttcaacc agactatcct      360
attacagcaa gaattcatgc acacctaaaa gcttatgcaa aaattaatga ggaatctttg      420
gatagggcta ggagattgct ttggtggcat tacaactgtt tactgtgggg agaagctaac      480
```

```
gttactaatt acatttctcg gctccgtact tggttgtcaa ctccggaaaa gtaccgaggc    540
cgtgatgccc caaccattga agcaatcact agaccaatcc aagcggctca gggaggcaga    600
aaaacatctt cgggaactag aaaacctcgt ggactcgaac ctagaagaag aaaagttaaa    660
accacagttg tctatgggag aagacgttca aagtccaggg aaaggagagc cccttcaccc    720
caacgtgcgg gctcccctct cccacgtagt tcgagcagcc accatagatc tccctcgcct    780
aggaaataa                                                            789

<210> SEQ ID NO 150
<211> LENGTH: 789
<212> TYPE: DNA
<213> ORGANISM: Duck hepatitis virus

<400> SEQUENCE: 150
atggatatca atgcttctag agccttagcc aatgtatatg atctgccaga tgatttcttt     60
ccaaaaattg atgatcttgt aagggatgct aaagacgctt tagaacctta ctggaaatct    120
gattcaataa agaaacatgt tttgattgca actcactttg tggatcttat tgaagcttc     180 tggcagacta ctcagggtat gcatgaaatt gctgaatcct aagagcagt aataccacct     240 accactgctc ctgtacctac tggatatctc attcaacacg aggaggctga agagataccc    300
ttaggtgatt tatttaaaca tcaggaagaa agaatagtca gttttcaacc agactatcct    360
attacagcaa gaattcatgc cacctaaaa gcttatgcaa aaattaatga ggaatctttg     420
gatagggcta ggagattgct ttggtggcat tacaactgtt tactgtgggg agaagctaac    480
gttactaatt acatttctcg gctccgtact tggttgtcaa ctccggaaaa gtaccgaggc    540
cgtgatgccc caaccattga agcaatcact agaccaatcc aagcggctca gggaggcaga    600
aaaacatctt cgggaactag aaaacctcgt ggactcgaac ctagaagaag aaaagttaaa    660
accacagttg tctatgggag aagacgttca aagtccaggg aaaggagagc cccttcaccc    720
caacgtgcgg gctcccctct cccacgtagt tcgagcagcc accatagatc tccctcgcct    780
aggaaataa                                                            789

<210> SEQ ID NO 151
<211> LENGTH: 262
<212> TYPE: PRT
<213> ORGANISM: Sheldgoose hepatitis virus

<400> SEQUENCE: 151

Met Asp Val Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30

Ala Leu Glu Pro Tyr Trp Arg Ser Glu Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ala Leu Arg Ala Val Ile Pro Pro
65                  70                  75                  80

Thr Thr Thr Pro Val Pro Pro Gly Tyr Leu Ile Gln His Glu Glu Ala
                85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
```

```
                115                 120                 125
Leu Lys Ala Tyr Ala Lys Ile Asn Glu Glu Ser Leu Asp Lys Ala Arg
        130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Arg Tyr Arg Gly Arg Asp Ala Pro Thr Ile Glu Ala Ile Thr Arg Pro
            180                 185                 190

Ile Gln Val Ala Gln Gly Gly Arg Asn Lys Thr Gln Gly Ser Arg Lys
        195                 200                 205

Pro Arg Gly Leu Gln Pro Arg Arg Arg Lys Val Lys Thr Thr Val Val
    210                 215                 220

Tyr Gly Arg Arg Arg Ser Lys Ser Arg Asp Arg Arg Ala Pro Ser Pro
225                 230                 235                 240

Gln Arg Ala Gly Ser Pro Leu Pro Arg Pro Ser Thr Ser His His Arg
                245                 250                 255

Ser Pro Ser Pro Arg Lys
            260

<210> SEQ ID NO 152
<211> LENGTH: 262
<212> TYPE: PRT
<213> ORGANISM: Stork hepatitis virus

<400> SEQUENCE: 152

Met Asp Val Asn Ala Ser Arg Ala Leu Ala Asn Val Tyr Asp Leu Pro
1               5                   10                  15

Asp Asp Phe Phe Pro Gln Ile Asp Leu Val Arg Asp Ala Lys Asp
                20                  25                  30

Ala Leu Glu Pro Tyr Trp Lys Ala Glu Thr Ile Lys Lys His Val Leu
            35                  40                  45

Ile Ala Thr His Phe Val Asp Leu Ile Glu Asp Phe Trp Gln Thr Thr
        50                  55                  60

Gln Gly Met Ser Gln Ile Ala Asp Ala Leu Arg Ala Val Ile Pro Pro
65                  70                  75                  80

Thr Thr Thr Pro Val Pro Asp Gly Tyr Leu Ile Ser His Asn Glu Ala
                85                  90                  95

Gln Glu Leu Pro Leu Asn Asp Leu Phe Val Asn Gln Glu Glu Arg Ile
            100                 105                 110

Val Asn Phe Gln Pro Asp Tyr Pro Ile Thr Ala Arg Ile His Thr His
        115                 120                 125

Leu Arg Val Tyr Thr Lys Leu Asn Glu Gln Ala Leu Asp Lys Ala Arg
        130                 135                 140

Arg Leu Leu Trp Trp His Tyr Asn Cys Leu Leu Trp Gly Glu Ser Asn
145                 150                 155                 160

Val Thr Asn Tyr Ile Ser Arg Leu Arg Thr Trp Leu Ser Thr Pro Glu
                165                 170                 175

Lys Tyr Arg Gly Lys Asp Ala Pro Thr Ile Glu Ala Ile Thr Arg Pro
            180                 185                 190

Ile Gln Val Ala Gln Gly Ser Arg Asn Gln Thr Lys Gly Val Arg Lys
        195                 200                 205

Pro Arg Gly Leu Glu Pro Arg Arg Arg Lys Val Lys Thr Thr Val Val
    210                 215                 220
```

-continued

```
Tyr Gly Arg Arg Arg Ser Lys Ser Arg Gly Arg Arg Ser Ser Pro Ser
225                 230                 235                 240

Gln Arg Ala Gly Ser Pro Ile Pro Arg Asn Arg Glu Asn Gln Ser Arg
                245                 250                 255

Ser Ser Ser Pro Arg Glu
            260

<210> SEQ ID NO 153
<211> LENGTH: 38
<212> TYPE: PRT
<213> ORGANISM: Arctic ground squirrel hepatitis virus

<400> SEQUENCE: 153

Arg Arg Arg Gly Ser Ala Arg Val Val Arg Ser Pro Arg Arg Arg Thr
1               5                   10                  15

Pro Ser Pro Arg Arg Arg Arg Ser Gln Ser Pro Arg Arg Arg Pro Gln
            20                  25                  30

Ser Pro Ala Ser Asn Cys
        35

<210> SEQ ID NO 154
<211> LENGTH: 149
<212> TYPE: PRT
<213> ORGANISM: Arctic ground squirrel hepatitis virus

<400> SEQUENCE: 154

Met Asp Ile Asp Pro Tyr Lys Glu Phe Gly Ser Ser Tyr Gln Leu Leu
1               5                   10                  15

Asn Phe Leu Pro Leu Asp Phe Phe Pro Glu Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Glu Glu
    50                  55                  60

Leu Thr Arg Leu Ile Ala Trp Met Ser Ala Asn Ile Asn Ser Glu Glu
65                  70                  75                  80

Val Arg Arg Val Ile Val Ala His Val Asn Asp Thr Trp Gly Leu Lys
                85                  90                  95

Val Arg Gln Asn Leu Trp Phe His Leu Ser Cys Leu Thr Phe Gly Gln
            100                 105                 110

His Thr Val Gln Glu Phe Leu Val Ser Phe Gly Val Arg Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile
145

<210> SEQ ID NO 155
<211> LENGTH: 33
<212> TYPE: PRT
<213> ORGANISM: Woolly monkey hepatitis virus

<400> SEQUENCE: 155

Arg Arg Arg Arg Pro Ser Gly Arg Arg Thr Pro Ser Pro Arg Arg Arg
1               5                   10                  15

Arg Ser Gln Ser Pro Arg Arg Arg Arg Ser Gln Ser Pro Ala Ser Ser
            20                  25                  30

Cys
```

<210> SEQ ID NO 156
<211> LENGTH: 149
<212> TYPE: PRT
<213> ORGANISM: Woolly monkey hepatitis virus

<400> SEQUENCE: 156

```
Met Asp Ile Asp Pro Tyr Lys Glu Phe Gly Ala Thr Val Glu Leu Leu
1               5                   10                  15

Ser Phe Leu Pro Ala Asp Phe Phe Pro Ser Val Arg Asp Leu Leu Asp
            20                  25                  30

Thr Ala Ser Ala Leu Tyr Arg Glu Ala Leu Glu Ser Ser Asp His Cys
        35                  40                  45

Ser Pro His His Thr Ala Leu Arg Gln Thr Val Leu Cys Trp Gly Glu
    50                  55                  60

Leu Met Ser Leu Ala Ser Trp Val Gly Thr Asn Leu Glu Asp Pro Ala
65                  70                  75                  80

Ala Arg Glu Leu Val Val Ser Tyr Val Asn Asp Asn Met Gly Leu Lys
                85                  90                  95

Val Arg Gln Leu Leu Trp Phe His Ile Ser Cys Leu Thr Phe Gly Arg
            100                 105                 110

Glu Thr Val Leu Glu Tyr Leu Val Ser Phe Trp Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145
```

<210> SEQ ID NO 157
<211> LENGTH: 34
<212> TYPE: PRT
<213> ORGANISM: Orangutan hepatitis virus

<400> SEQUENCE: 157

```
Arg Arg Arg Gly Arg Ser Pro Arg Arg Thr Pro Ser Pro Arg Arg
1               5                   10                  15

Arg Arg Ser Gln Ser Pro Arg Arg Arg Ser Gln Ser Pro Ala Ser
            20                  25                  30

Gln Cys
```

<210> SEQ ID NO 158
<211> LENGTH: 149
<212> TYPE: PRT
<213> ORGANISM: Orangutan hepatitis virus

<400> SEQUENCE: 158

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro Asn His Thr Ala Leu Arg Gln Ala Val Leu Cys Trp Gly Glu
    50                  55                  60

Leu Met Thr Leu Ala Ser Trp Val Gly Asn Asn Leu Glu Asp Pro Ala
65                  70                  75                  80

Ser Arg Glu Leu Val Val Asn Tyr Val Asn Asn Asn Met Gly Leu Lys
```

-continued

```
                    85                  90                  95
Ile Arg Gln Leu Leu Trp Phe His Ile Ser Cys Leu Thr Phe Gly Arg
            100                 105                 110
Glu Thr Val Leu Glu Tyr Leu Val Ser Phe Gly Val Trp Ile Arg Thr
        115                 120                 125
Pro Pro Ala Tyr Arg Pro Pro Asn Ala Pro Ile Leu Ser Thr Leu Pro
    130                 135                 140
Glu Thr Thr Val Val
145

<210> SEQ ID NO 159
<211> LENGTH: 34
<212> TYPE: PRT
<213> ORGANISM: Gibbon hepatitis B virus

<400> SEQUENCE: 159

Arg Arg Arg Gly Arg Ser Pro Arg Arg Thr Pro Ser Pro Arg Arg
1               5                   10                  15
Arg Arg Ser Gln Ser Pro Arg Arg Arg Ser Gln Ser Pro Ala Ser
            20                  25                  30
Gln Cys

<210> SEQ ID NO 160
<211> LENGTH: 149
<212> TYPE: PRT
<213> ORGANISM: Gibbon hepatitis B virus

<400> SEQUENCE: 160

Met Asp Ile Asp Pro Tyr Lys Glu Phe Gly Ala Thr Val Glu Leu Leu
1               5                   10                  15
Ser Phe Leu Pro Ser Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro Asn His Thr Ala Leu Arg Gln Ala Val Leu Cys Trp Gly Glu
    50                  55                  60
Leu Met Thr Leu Ala Ser Trp Val Gly Asn Asn Leu Glu Asp Pro Ala
65                  70                  75                  80
Ser Arg Glu Leu Val Val Ser Tyr Val Asn Asn Met Gly Leu Lys
            85                  90                  95
Ile Arg Gln Leu Leu Trp Phe His Ile Ser Cys Leu Thr Phe Gly Arg
            100                 105                 110
Glu Thr Val Leu Glu Tyr Leu Val Ser Phe Gly Val Trp Ile Arg Thr
        115                 120                 125
Pro Pro Ala Tyr Arg Pro Pro Asn Ala Pro Ile Leu Ser Thr Leu Pro
    130                 135                 140
Glu Thr Thr Val Val
145

<210> SEQ ID NO 161
<211> LENGTH: 34
<212> TYPE: PRT
<213> ORGANISM: Chimpanzee hepatitis B virus

<400> SEQUENCE: 161

Arg Arg Arg Gly Arg Ser Pro Arg Arg Arg Thr Pro Ser Pro Arg Arg
1               5                   10                  15
```

```
Arg Arg Ser Gln Ser Pro Arg Arg Arg Ser Gln Ser Pro Ala Ser
            20                  25                  30

Gln Cys

<210> SEQ ID NO 162
<211> LENGTH: 149
<212> TYPE: PRT
<213> ORGANISM: Chimpanzee hepatitis B virus

<400> SEQUENCE: 162

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro Asn His Thr Ala Leu Arg Gln Ala Ile Leu Cys Trp Gly Glu
    50                  55                  60

Leu Met Thr Leu Ala Ser Trp Val Gly Asn Asn Leu Glu Asp Pro Ala
65                  70                  75                  80

Ser Arg Glu Gln Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 163
<211> LENGTH: 67
<212> TYPE: PRT
<213> ORGANISM: Duck hepatitis virus

<400> SEQUENCE: 163

Ala Gln Gly Gly Arg Lys Thr Ser Ser Gly Thr Arg Lys Pro Arg Gly
1               5                   10                  15

Leu Glu Pro Arg Arg Arg Lys Val Lys Thr Thr Phe Val Tyr Gly Arg
            20                  25                  30

Arg Arg Ser Lys Ser Arg Glu Arg Arg Ala Pro Ser Pro Gln Arg Ala
        35                  40                  45

Gly Ser Pro Leu Pro Arg Ser Ser Ser His His Arg Ser Pro Ser
    50                  55                  60

Pro Arg Lys
65

<210> SEQ ID NO 164
<211> LENGTH: 195
<212> TYPE: PRT
<213> ORGANISM: Duck hepatitis virus

<400> SEQUENCE: 164

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30
```

```
Ala Leu Glu Pro Tyr Trp Lys Ser Asp Ser Ile Lys Lys His Val Leu
            35                  40                  45

Ile Ala Thr His Phe Val Asp Leu Ile Glu Asp Phe Trp Gln Thr Thr
 50                  55                  60

Gln Gly Met His Glu Ile Ala Glu Ser Leu Arg Ala Val Ile Pro Pro
 65                  70                  75                  80

Thr Thr Ala Pro Val Pro Thr Gly Tyr Leu Ile Gln His Glu Ala
                 85                  90                  95

Glu Glu Ile Pro Leu Gly Asp Leu Phe Lys His Gln Glu Arg Ile
                100                 105                 110

Val Ser Phe Gln Pro Asp Tyr Pro Ile Thr Ala Arg Ile His Ala His
            115                 120                 125

Leu Lys Ala Tyr Ala Lys Ile Asn Glu Glu Ser Leu Asp Arg Ala Arg
            130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
                180                 185                 190

Ile Gln Val
        195

<210> SEQ ID NO 165
<211> LENGTH: 67
<212> TYPE: PRT
<213> ORGANISM: Duck hepatitis virus

<400> SEQUENCE: 165

Ala Gln Gly Gly Arg Lys Thr Thr Thr Gly Thr Arg Lys Pro Arg Gly
1               5                   10                  15

Leu Glu Pro Arg Arg Arg Lys Val Lys Thr Thr Val Val Tyr Gly Arg
                20                  25                  30

Arg Arg Ser Lys Ser Arg Glu Arg Ala Pro Thr Pro Gln Arg Ala
            35                  40                  45

Gly Ser Pro Leu Pro Arg Ser Ser Ser His His Arg Ser Pro Ser
 50                  55                  60

Pro Arg Lys
 65

<210> SEQ ID NO 166
<211> LENGTH: 195
<212> TYPE: PRT
<213> ORGANISM: Duck hepatitis virus

<400> SEQUENCE: 166

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
                20                  25                  30

Ala Leu Glu Pro Tyr Trp Lys Ser Asp Ser Ile Lys Lys His Val Leu
            35                  40                  45

Ile Ala Thr His Phe Val Asp Leu Ile Glu Asp Phe Trp Gln Thr Thr
 50                  55                  60

Gln Gly Met His Glu Ile Ala Glu Ser Leu Arg Ala Val Ile Pro Pro
 65                  70                  75                  80
```

```
Thr Thr Thr Pro Val Pro Gly Tyr Leu Ile Gln His Glu Glu Ala
             85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
            115                 120                 125

Leu Lys Ala Tyr Ala Lys Ile Asn Glu Glu Ser Leu Asp Arg Ala Arg
        130                 135                 140

Arg Leu Leu Trp Trp His Tyr Asn Cys Leu Leu Trp Gly Glu Ala Gln
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Val
        195

<210> SEQ ID NO 167
<211> LENGTH: 67
<212> TYPE: PRT
<213> ORGANISM: Duck hepatitis virus

<400> SEQUENCE: 167

Ala Gln Gly Gly Arg Lys Thr Ser Ser Gly Thr Arg Lys Pro Arg Gly
1               5                   10                  15

Leu Glu Pro Arg Arg Lys Val Lys Thr Thr Val Val Tyr Gly Arg
            20                  25                  30

Arg Arg Ser Lys Ser Arg Asp Arg Arg Ala Pro Ser Pro Gln Arg Ala
        35                  40                  45

Gly Ser Pro Leu Pro Arg Ser Ser Ser His His Arg Ser Pro Ser
    50                  55                  60

Pro Arg Lys
65

<210> SEQ ID NO 168
<211> LENGTH: 195
<212> TYPE: PRT
<213> ORGANISM: Duck hepatitis virus

<400> SEQUENCE: 168

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30

Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ser Leu Arg Ala Val Ile Pro Pro
65                  70                  75                  80

Thr Thr Ala Pro Val Pro Thr Gly Tyr Leu Ile Gln His Glu Glu Ala
            85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
            115                 120                 125
```

```
Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Val
        195

<210> SEQ ID NO 169
<211> LENGTH: 67
<212> TYPE: PRT
<213> ORGANISM: Duck hepatitis virus

<400> SEQUENCE: 169

Ala Gln Gly Gly Arg Lys Thr Ser Ser Gly Thr Arg Lys Pro Arg Gly
1               5                   10                  15

Leu Glu Pro Arg Arg Arg Lys Val Lys Thr Thr Val Val Tyr Gly Arg
            20                  25                  30

Arg Arg Ser Lys Ser Arg Glu Arg Arg Ala Pro Ser Pro Gln Arg Ala
        35                  40                  45

Gly Ser Pro Leu Pro Arg Ser Ser Ser His His Arg Ser Pro Ser
    50                  55                  60

Pro Arg Lys
65

<210> SEQ ID NO 170
<211> LENGTH: 195
<212> TYPE: PRT
<213> ORGANISM: Duck hepatitis virus

<400> SEQUENCE: 170

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30

Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ser Leu Arg Ala Val Ile Pro Pro
65                  70                  75                  80

Thr Thr Ala Pro Val Pro Thr Gly Tyr Leu Ile Gln His Glu Glu Ala
                85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175
```

```
Lys Tyr Arg Gly Arg Asp Ala Pro Thr Ile Glu Ala Ile Thr Arg Pro
            180                 185                 190

Ile Gln Val
        195

<210> SEQ ID NO 171
<211> LENGTH: 67
<212> TYPE: PRT
<213> ORGANISM: Duck hepatitis virus

<400> SEQUENCE: 171

Ala Gln Gly Gly Arg Lys Thr Ser Ser Gly Thr Arg Lys Pro Arg Gly
1               5                   10                  15

Leu Glu Pro Arg Arg Lys Val Lys Thr Thr Val Val Tyr Gly Arg
            20                  25                  30

Arg Arg Ser Lys Ser Arg Glu Arg Ala Pro Ser Pro Gln Arg Ala
        35                  40                  45

Gly Ser Pro Leu Pro Arg Ser Ser Ser His His Arg Ser Pro Ser
    50                  55                  60

Pro Arg Lys
65

<210> SEQ ID NO 172
<211> LENGTH: 195
<212> TYPE: PRT
<213> ORGANISM: Duck hepatitis virus

<400> SEQUENCE: 172

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30

Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ser Leu Arg Ala Val Ile Pro Pro
65                  70                  75                  80

Thr Thr Ala Pro Val Pro Thr Gly Tyr Leu Ile Gln His Glu Glu Ala
                85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Ala
        195

<210> SEQ ID NO 173
```

```
<211> LENGTH: 67
<212> TYPE: PRT
<213> ORGANISM: Duck hepatitis virus

<400> SEQUENCE: 173

Ala Gln Gly Gly Arg Lys Thr Ser Ser Gly Thr Arg Lys Pro Arg Gly
1               5                   10                  15

Leu Glu Pro Arg Arg Arg Lys Val Lys Thr Thr Val Val Tyr Gly Arg
            20                  25                  30

Arg Arg Ser Lys Ser Arg Glu Arg Arg Ala Pro Ser Pro Gln Arg Ala
        35                  40                  45

Gly Ser Pro Leu Pro Arg Ser Ser Ser His His Arg Ser Pro Ser
    50                  55                  60

Pro Arg Lys
65

<210> SEQ ID NO 174
<211> LENGTH: 195
<212> TYPE: PRT
<213> ORGANISM: Duck hepatitis virus

<400> SEQUENCE: 174

Met Asp Ile Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30

Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ser Leu Arg Ala Val Ile Pro Pro
65              70                  75                  80

Thr Thr Ala Pro Val Pro Thr Gly Tyr Leu Ile Gln His Glu Glu Ala
            85                  90                  95

Glu Glu Ile Pro Leu Gly Asp Leu Phe Lys His Gln Glu Glu Arg Ile
        100                 105                 110

Val Ser Phe Gln Pro Asp Tyr Pro Ile Thr Ala Arg Ile His Ala His
    115                 120                 125

Leu Lys Ala Tyr Ala Lys Ile Asn Glu Glu Ser Leu Asp Arg Ala Arg
130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
            180                 185                 190

Ile Gln Ala
        195

<210> SEQ ID NO 175
<211> LENGTH: 67
<212> TYPE: PRT
<213> ORGANISM: Ross' goose hepatitis virus

<400> SEQUENCE: 175

Ala Gln Gly Gly Arg Asn Lys Thr Gln Gly Val Arg Lys Ser Arg Gly
1               5                   10                  15
```

```
Leu Glu Pro Arg Arg Arg Val Lys Thr Thr Ile Val Tyr Gly Arg
        20                  25                  30

Arg Arg Ser Lys Ser Arg Glu Arg Ala Pro Thr Pro Gln Arg Ala
        35                  40                  45

Gly Ser Pro Leu Pro Arg Thr Ser Arg Asp His His Arg Ser Pro Ser
        50                  55                      60

Pro Arg Glu
65

<210> SEQ ID NO 176
<211> LENGTH: 195
<212> TYPE: PRT
<213> ORGANISM: Ross' goose hepatitis virus

<400> SEQUENCE: 176

Met Asp Ile Asn Ala Ser Arg Ala Leu Ala Asn Val Tyr Asp Leu Pro
1               5                   10                  15

Asp Asp Phe Phe Pro Lys Ile Asp Leu Val Arg Asp Ala Lys Asp
            20                  25                  30

Ala Leu Glu Pro Tyr Trp Arg Asn Asp Ser Ile Lys Lys His Val Leu
            35                  40                  45

Ile Ala Thr His Phe Val Asp Leu Ile Glu Asp Phe Trp Gln Thr Thr
    50                  55                  60

Gln Gly Met His Glu Ile Ala Glu Ala Leu Arg Ala Ile Ile Pro Ala
65                  70                  75                  80

Thr Thr Ala Pro Val Pro Gln Gly Phe Leu Val Gln His Glu Glu Ala
                85                  90                  95

Glu Glu Ile Pro Leu Gly Glu Leu Phe Arg Tyr Gln Glu Glu Arg Leu
            100                 105                 110

Thr Asn Phe Gln Pro Asp Tyr Pro Val Thr Ala Arg Ile His Ala His
            115                 120                 125

Leu Lys Ala Tyr Ala Lys Ile Asn Glu Glu Ser Leu Asp Arg Ala Arg
    130                 135                 140

Arg Leu Leu Trp Trp His Tyr Asn Cys Leu Leu Trp Gly Glu Pro Asn
145                 150                 155                 160

Val Thr Asn Tyr Ile Ser Arg Leu Arg Thr Trp Leu Ser Thr Pro Glu
                165                 170                 175

Lys Tyr Arg Gly Lys Asp Ala Pro Thr Ile Glu Ala Ile Thr Arg Pro
            180                 185                 190

Ile Gln Val
    195

<210> SEQ ID NO 177
<211> LENGTH: 67
<212> TYPE: PRT
<213> ORGANISM: Sheldgoose hepatitis virus

<400> SEQUENCE: 177

Ala Gln Gly Gly Arg Asn Lys Thr Gln Gly Ser Arg Lys Pro Arg Gly
1               5                   10                  15

Leu Gln Pro Arg Arg Arg Lys Val Lys Thr Thr Val Val Tyr Gly Arg
            20                  25                  30

Arg Arg Ser Lys Ser Arg Asp Arg Ala Pro Ser Pro Gln Arg Ala
        35                  40                  45

Gly Ser Pro Leu Pro Arg Pro Ser Thr Ser His His Arg Ser Pro Ser
        50                  55                      60
```

```
Pro Arg Lys
65

<210> SEQ ID NO 178
<211> LENGTH: 195
<212> TYPE: PRT
<213> ORGANISM: Sheldgoose hepatitis virus

<400> SEQUENCE: 178

Met Asp Val Asn Ala Ser Arg Ala Leu Ala Asn Val Tyr Asp Leu Pro
1               5                   10                  15

Asp Asp Phe Phe Pro Lys Ile Asp Asp Leu Val Arg Asp Ala Lys Asp
            20                  25                  30

Ala Leu Glu Pro Tyr Trp Arg Ser Glu Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ala Leu Arg Ala Val Ile Pro Pro
65                  70                  75                  80

Thr Thr Thr Pro Val Pro Pro Gly Tyr Leu Ile Gln His Glu Glu Ala
                85                  90                  95

Glu Glu Ile Pro Leu Gly Asp Leu Phe Lys His Gln Glu Glu Arg Ile
            100                 105                 110

Val Ser Phe Gln Pro Asp Tyr Pro Ile Thr Ala Arg Ile His Ala His
        115                 120                 125

Leu Lys Ala Tyr Ala Lys Ile Asn Glu Glu Ser Leu Asp Lys Ala Arg
    130                 135                 140

Arg Leu Leu Trp Trp His Tyr Asn Cys Leu Leu Trp Gly Glu Ala Asn
145                 150                 155                 160

Val Thr Asn Tyr Ile Ser Arg Leu Arg Thr Trp Leu Ser Thr Pro Glu
                165                 170                 175

Arg Tyr Arg Gly Arg Asp Ala Pro Thr Ile Glu Ala Ile Thr Arg Pro
            180                 185                 190

Ile Gln Val
        195

<210> SEQ ID NO 179
<211> LENGTH: 67
<212> TYPE: PRT
<213> ORGANISM: Heron hepatitis virus

<400> SEQUENCE: 179

Ala Gln Gly Gly Arg Asn Gln Thr Lys Gly Thr Arg Lys Pro Arg Gly
1               5                   10                  15

Leu Glu Pro Arg Arg Lys Val Lys Thr Thr Val Val Tyr Gly Arg
            20                  25                  30

Arg Arg Ser Lys Ser Arg Gly Arg Arg Ser Ser Pro Ser Gln Arg Ala
            35                  40                  45

Gly Ser Pro Leu Pro Arg Asn Arg Gly Asn Gln Thr Arg Ser Pro Ser
        50                  55                  60

Pro Arg Glu
65

<210> SEQ ID NO 180
<211> LENGTH: 195
<212> TYPE: PRT
<213> ORGANISM: Heron hepatitis virus
```

```
<400> SEQUENCE: 180

Met Asp Val Asn Ala Ser Arg Ala Leu Ala Asn Val Tyr Asp Leu Pro
1               5                   10                  15

Asp Asp Phe Phe Pro Gln Ile Asp Asp Leu Val Arg Asp Ala Lys Asp
            20                  25                  30

Ala Leu Glu Pro Tyr Trp Lys Ala Glu Thr Ile Lys Lys His Val Leu
        35                  40                  45

Ile Ala Thr His Phe Val Asp Leu Ile Glu Asp Phe Trp Gln Thr Thr
    50                  55                  60

Gln Gly Met Ser Gln Ile Ala Asp Ala Leu Arg Ala Val Ile Pro Pro
65                  70                  75                  80

Thr Thr Val Pro Val Pro Glu Gly Phe Leu Ile Thr His Ser Glu Ala
                85                  90                  95

Glu Glu Ile Pro Leu Asn Asp Leu Phe Ser Asn Gln Glu Glu Arg Ile
            100                 105                 110

Val Asn Phe Gln Pro Asp Tyr Pro Ile Thr Ala Arg Ile His Thr His
            115                 120                 125

Leu Arg Val Tyr Thr Lys Leu Asn Glu Gln Ala Leu Asp Lys Ala Arg
        130                 135                 140

Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Lys Asp Ala Pro Thr Ile Glu Ala Ile Thr Arg Pro
            180                 185                 190

Ile Gln Val
        195

<210> SEQ ID NO 181
<211> LENGTH: 67
<212> TYPE: PRT
<213> ORGANISM: Stork hepatitis virus

<400> SEQUENCE: 181

Ala Gln Gly Ser Arg Asn Gln Thr Lys Gly Val Arg Lys Pro Arg Gly
1               5                   10                  15

Leu Glu Pro Arg Arg Arg Lys Val Lys Thr Thr Val Val Tyr Gly Arg
            20                  25                  30

Arg Arg Ser Lys Ser Arg Gly Arg Arg Ser Ser Pro Ser Gln Arg Ala
        35                  40                  45

Gly Ser Pro Ile Pro Arg Asn Arg Glu Asn Gln Ser Arg Ser Ser Ser
    50                  55                  60

Pro Arg Glu
65

<210> SEQ ID NO 182
<211> LENGTH: 195
<212> TYPE: PRT
<213> ORGANISM: Stork hepatitis virus

<400> SEQUENCE: 182

Met Asp Val Asn Ala Ser Arg Ala Leu Ala Asn Val Tyr Asp Leu Pro
1               5                   10                  15

Asp Asp Phe Phe Pro Gln Ile Asp Asp Leu Val Arg Asp Ala Lys Asp
            20                  25                  30

Ala Leu Glu Pro Tyr Trp Lys Ala Glu Thr Ile Lys Lys His Val Leu
```

```
                35                  40                  45
Ile Ala Thr His Phe Val Asp Leu Ile Glu Asp Phe Trp Gln Thr Thr
        50                  55                  60
Gln Gly Met Ser Gln Ile Ala Asp Ala Leu Arg Ala Val Ile Pro Pro
 65                  70                  75                  80
Thr Thr Thr Pro Val Pro Asp Gly Tyr Leu Ile Ser His Asn Glu Ala
                85                  90                  95
Gln Glu Leu Pro Leu Asn Asp Leu Phe Val Asn Gln Glu Glu Arg Ile
            100                 105                 110
Val Asn Phe Gln Pro Asp Tyr Pro Ile Thr Ala Arg Ile His Thr His
        115                 120                 125
Leu Arg Val Tyr Thr Lys Leu Asn Glu Gln Ala Leu Asp Lys Ala Arg
    130                 135                 140
Arg Leu Leu Trp Trp His Tyr Asn Cys Leu Leu Trp Gly Glu Ser Asn
145                 150                 155                 160
Val Thr Asn Tyr Ile Ser Arg Leu Arg Thr Trp Leu Ser Thr Pro Glu
                165                 170                 175
Lys Tyr Arg Gly Lys Asp Ala Pro Thr Ile Glu Ala Ile Thr Arg Pro
            180                 185                 190
Ile Gln Val
        195

<210> SEQ ID NO 183
<211> LENGTH: 22
<212> TYPE: PRT
<213> ORGANISM: Arctic ground squirrel hepatitis virus

<400> SEQUENCE: 183

Ala Ala Gly Ser Ala Arg Val Val Arg Ser Pro Ser Gln Ser Pro Gln
1               5                   10                  15

Ser Pro Ala Ser Asn Cys
            20

<210> SEQ ID NO 184
<211> LENGTH: 21
<212> TYPE: PRT
<213> ORGANISM: Arctic ground squirrel hepatitis virus

<400> SEQUENCE: 184

Ala Ala Gly Ser Ala Arg Val Val Arg Ser Ser Gln Ser Pro Gln Ser
1               5                   10                  15

Pro Ala Ser Asn Cys
            20

<210> SEQ ID NO 185
<211> LENGTH: 20
<212> TYPE: PRT
<213> ORGANISM: Arctic ground squirrel hepatitis virus

<400> SEQUENCE: 185

Ala Ala Gly Ser Ala Arg Val Val Arg Ser Ser Gln Ser Gln Ser Pro
1               5                   10                  15

Ala Ser Asn Cys
        20

<210> SEQ ID NO 186
<211> LENGTH: 19
<212> TYPE: PRT
<213> ORGANISM: Arctic ground squirrel hepatitis virus
```

```
<400> SEQUENCE: 186

Ala Ala Gly Ser Ala Arg Val Val Arg Ser Ser Gln Ser Gln Ser Ala
1               5                   10                  15

Ser Asn Cys

<210> SEQ ID NO 187
<211> LENGTH: 14
<212> TYPE: PRT
<213> ORGANISM: Arctic ground squirrel hepatitis virus

<400> SEQUENCE: 187

Arg Arg Gly Ser Ala Arg Val Val Ser Gln Ala Ser Asn Cys
1               5                   10

<210> SEQ ID NO 188
<211> LENGTH: 14
<212> TYPE: PRT
<213> ORGANISM: Arctic ground squirrel hepatitis virus

<400> SEQUENCE: 188

Ala Arg Gly Ser Ala Arg Val Val Ser Gln Ala Ser Asn Cys
1               5                   10

<210> SEQ ID NO 189
<211> LENGTH: 14
<212> TYPE: PRT
<213> ORGANISM: Arctic ground squirrel hepatitis virus

<400> SEQUENCE: 189

Arg Ala Gly Ser Ala Arg Val Val Ser Gln Ala Ser Asn Cys
1               5                   10

<210> SEQ ID NO 190
<211> LENGTH: 14
<212> TYPE: PRT
<213> ORGANISM: Arctic ground squirrel hepatitis virus

<400> SEQUENCE: 190

Ala Ala Gly Ser Ala Arg Val Val Ser Gln Ala Ser Asn Cys
1               5                   10

<210> SEQ ID NO 191
<211> LENGTH: 17
<212> TYPE: PRT
<213> ORGANISM: Arctic ground squirrel hepatitis virus

<400> SEQUENCE: 191

Ala Ala Gly Arg Ser Pro Ser Gln Ser Pro Gln Ser Arg Glu Ser Gln
1               5                   10                  15

Cys

<210> SEQ ID NO 192
<211> LENGTH: 17
<212> TYPE: PRT
<213> ORGANISM: Arctic ground squirrel hepatitis virus

<400> SEQUENCE: 192

Ala Ala Gly Arg Ser Pro Ser Gln Ser Pro Gln Ser Pro Ala Ser Asn
1               5                   10                  15

Cys
```

```
<210> SEQ ID NO 193
<211> LENGTH: 16
<212> TYPE: PRT
<213> ORGANISM: Arctic ground squirrel hepatitis virus

<400> SEQUENCE: 193

Ala Ala Gly Arg Ser Pro Ser Gln Ser Pro Gln Ser Ala Ser Asn Cys
1               5                   10                  15

<210> SEQ ID NO 194
<211> LENGTH: 14
<212> TYPE: PRT
<213> ORGANISM: Arctic ground squirrel hepatitis virus

<400> SEQUENCE: 194

Ala Ala Gly Arg Ser Gln Ser Pro Gln Ser Ala Ser Asn Cys
1               5                   10

<210> SEQ ID NO 195
<211> LENGTH: 15
<212> TYPE: PRT
<213> ORGANISM: Arctic ground squirrel hepatitis virus

<400> SEQUENCE: 195

Ala Ala Gly Arg Ser Pro Ser Gln Ser Gln Ser Ala Ser Asn Cys
1               5                   10                  15

<210> SEQ ID NO 196
<211> LENGTH: 13
<212> TYPE: PRT
<213> ORGANISM: Arctic ground squirrel hepatitis virus

<400> SEQUENCE: 196

Ala Ala Gly Arg Ser Gln Ser Gln Ser Ala Ser Asn Cys
1               5                   10

<210> SEQ ID NO 197
<211> LENGTH: 18
<212> TYPE: PRT
<213> ORGANISM: Woolly monkey hepatitis virus

<400> SEQUENCE: 197

Ala Ala Arg Pro Ser Pro Ser Gln Ser Pro Gln Ser Pro Ala Ser
1               5                   10                  15

Ser Cys

<210> SEQ ID NO 198
<211> LENGTH: 16
<212> TYPE: PRT
<213> ORGANISM: Woolly monkey hepatitis virus

<400> SEQUENCE: 198

Ala Ala Arg Pro Ser Gln Ser Pro Ser Gln Ser Pro Ala Ser Ser Cys
1               5                   10                  15

<210> SEQ ID NO 199
<211> LENGTH: 15
<212> TYPE: PRT
<213> ORGANISM: Woolly monkey hepatitis virus

<400> SEQUENCE: 199

Ala Ala Arg Pro Ser Gln Ser Ser Gln Ser Pro Ala Ser Ser Cys
1               5                   10                  15
```

```
<210> SEQ ID NO 200
<211> LENGTH: 14
<212> TYPE: PRT
<213> ORGANISM: Woolly monkey hepatitis virus

<400> SEQUENCE: 200

Ala Ala Arg Pro Ser Gln Ser Ser Gln Ser Ala Ser Ser Cys
1               5                   10

<210> SEQ ID NO 201
<211> LENGTH: 13
<212> TYPE: PRT
<213> ORGANISM: Woolly monkey hepatitis virus

<400> SEQUENCE: 201

Arg Arg Gly Ser Gln Ser Arg Arg Ser Gln Ser Ser Cys
1               5                   10

<210> SEQ ID NO 202
<211> LENGTH: 13
<212> TYPE: PRT
<213> ORGANISM: Woolly monkey hepatitis virus

<400> SEQUENCE: 202

Ala Arg Gly Ser Gln Ser Arg Arg Ser Gln Ser Ser Cys
1               5                   10

<210> SEQ ID NO 203
<211> LENGTH: 13
<212> TYPE: PRT
<213> ORGANISM: Woolly monkey hepatitis virus

<400> SEQUENCE: 203

Arg Ala Gly Ser Gln Ser Arg Arg Ser Gln Ser Ser Cys
1               5                   10

<210> SEQ ID NO 204
<211> LENGTH: 13
<212> TYPE: PRT
<213> ORGANISM: Woolly monkey hepatitis virus

<400> SEQUENCE: 204

Ala Ala Gly Ser Gln Ser Arg Arg Ser Gln Ser Ser Cys
1               5                   10

<210> SEQ ID NO 205
<211> LENGTH: 18
<212> TYPE: PRT
<213> ORGANISM: Woolly monkey hepatitis virus

<400> SEQUENCE: 205

Ala Ala Arg Arg Arg Pro Ser Gln Ser Pro Gln Ser Pro Ala Ser
1               5                   10                  15

Ser Cys

<210> SEQ ID NO 206
<211> LENGTH: 17
<212> TYPE: PRT
<213> ORGANISM: Woolly monkey hepatitis virus

<400> SEQUENCE: 206

Ala Ala Arg Arg Arg Pro Ser Gln Ser Pro Gln Ser Ala Ser Ser
1               5                   10                  15

Cys
```

```
<210> SEQ ID NO 207
<211> LENGTH: 16
<212> TYPE: PRT
<213> ORGANISM: Woolly monkey hepatitis virus

<400> SEQUENCE: 207

Ala Ala Arg Arg Arg Pro Ser Gln Ser Pro Ser Gln Ser Ser Ser Cys
1               5                   10                  15

<210> SEQ ID NO 208
<211> LENGTH: 14
<212> TYPE: PRT
<213> ORGANISM: Woolly monkey hepatitis virus

<400> SEQUENCE: 208

Ala Ala Arg Arg Ser Gln Ser Pro Ser Gln Ser Ser Ser Cys
1               5                   10

<210> SEQ ID NO 209
<211> LENGTH: 15
<212> TYPE: PRT
<213> ORGANISM: Woolly monkey hepatitis virus

<400> SEQUENCE: 209

Ala Ala Arg Arg Ser Pro Ser Gln Ser Ser Gln Ser Ser Ser Cys
1               5                   10                  15

<210> SEQ ID NO 210
<211> LENGTH: 13
<212> TYPE: PRT
<213> ORGANISM: Woolly monkey hepatitis virus

<400> SEQUENCE: 210

Ala Ala Arg Arg Ser Gln Ser Ser Gln Ser Ser Ser Cys
1               5                   10

<210> SEQ ID NO 211
<211> LENGTH: 18
<212> TYPE: PRT
<213> ORGANISM: Orangutan hepatitis virus

<400> SEQUENCE: 211

Ala Ala Gly Arg Ser Pro Ser Gln Ser Pro Ser Gln Ser Pro Ala Ser
1               5                   10                  15

Gln Cys

<210> SEQ ID NO 212
<211> LENGTH: 16
<212> TYPE: PRT
<213> ORGANISM: Orangutan hepatitis virus

<400> SEQUENCE: 212

Ala Ala Gly Arg Ser Gln Ser Pro Ser Gln Ser Pro Ala Ser Gln Cys
1               5                   10                  15

<210> SEQ ID NO 213
<211> LENGTH: 15
<212> TYPE: PRT
<213> ORGANISM: Orangutan hepatitis virus

<400> SEQUENCE: 213

Ala Ala Gly Arg Ser Gln Ser Ser Gln Ser Pro Ala Ser Gln Cys
1               5                   10                  15
```

<210> SEQ ID NO 214
<211> LENGTH: 14
<212> TYPE: PRT
<213> ORGANISM: Orangutan hepatitis virus

<400> SEQUENCE: 214

Ala Ala Gly Arg Ser Gln Ser Ser Gln Ser Ala Ser Gln Cys
1               5                   10

<210> SEQ ID NO 215
<211> LENGTH: 11
<212> TYPE: PRT
<213> ORGANISM: Orangutan hepatitis virus

<400> SEQUENCE: 215

Arg Arg Gly Ser Gln Ser Pro Ala Ser Gln Cys
1               5                   10

<210> SEQ ID NO 216
<211> LENGTH: 11
<212> TYPE: PRT
<213> ORGANISM: Orangutan hepatitis virus

<400> SEQUENCE: 216

Ala Arg Gly Ser Gln Ser Pro Ala Ser Gln Cys
1               5                   10

<210> SEQ ID NO 217
<211> LENGTH: 11
<212> TYPE: PRT
<213> ORGANISM: Orangutan hepatitis virus

<400> SEQUENCE: 217

Arg Ala Gly Ser Gln Ser Pro Ala Ser Gln Cys
1               5                   10

<210> SEQ ID NO 218
<211> LENGTH: 11
<212> TYPE: PRT
<213> ORGANISM: Orangutan hepatitis virus

<400> SEQUENCE: 218

Ala Ala Gly Ser Gln Ser Pro Ala Ser Gln Cys
1               5                   10

<210> SEQ ID NO 219
<211> LENGTH: 18
<212> TYPE: PRT
<213> ORGANISM: Orangutan hepatitis virus

<400> SEQUENCE: 219

Ala Ala Gly Arg Ser Pro Ser Gln Ser Pro Gln Ser Pro Ala Ser
1               5                   10                  15

Gln Cys

<210> SEQ ID NO 220
<211> LENGTH: 17
<212> TYPE: PRT
<213> ORGANISM: Orangutan hepatitis virus

<400> SEQUENCE: 220

Ala Ala Gly Arg Ser Pro Ser Gln Ser Pro Ser Gln Ser Ala Ser Gln
1               5                   10                  15

```
<210> SEQ ID NO 221
<211> LENGTH: 16
<212> TYPE: PRT
<213> ORGANISM: Orangutan hepatitis virus

<400> SEQUENCE: 221

Ala Ala Gly Arg Ser Pro Ser Gln Ser Pro Ser Gln Ser Gln Cys
1               5                   10                  15

<210> SEQ ID NO 222
<211> LENGTH: 15
<212> TYPE: PRT
<213> ORGANISM: Orangutan hepatitis virus

<400> SEQUENCE: 222

Ala Ala Gly Arg Ser Gln Ser Pro Ser Gln Ser Ala Ser Gln Cys
1               5                   10                  15

<210> SEQ ID NO 223
<211> LENGTH: 16
<212> TYPE: PRT
<213> ORGANISM: Orangutan hepatitis virus

<400> SEQUENCE: 223

Ala Ala Gly Arg Ser Pro Ser Gln Ser Ser Gln Ser Ala Ser Gln Cys
1               5                   10                  15

<210> SEQ ID NO 224
<211> LENGTH: 14
<212> TYPE: PRT
<213> ORGANISM: Orangutan hepatitis virus

<400> SEQUENCE: 224

Ala Ala Gly Arg Ser Gln Ser Ser Gln Ser Ala Ser Gln Cys
1               5                   10

<210> SEQ ID NO 225
<211> LENGTH: 23
<212> TYPE: PRT
<213> ORGANISM: Duck hepatitis virus

<400> SEQUENCE: 225

Ala Ala Gly Gly Glu Arg Gly Val Arg Ser Pro Ser Gln Ser Pro Ser
1               5                   10                  15

Arg Ser Pro Ser Pro Arg Lys
            20

<210> SEQ ID NO 226
<211> LENGTH: 21
<212> TYPE: PRT
<213> ORGANISM: Duck hepatitis virus

<400> SEQUENCE: 226

Ala Ala Gly Gly Glu Arg Gly Val Arg Ser Gln Ser Pro Ser Arg Ser
1               5                   10                  15

Pro Ser Pro Arg Lys
            20

<210> SEQ ID NO 227
<211> LENGTH: 20
<212> TYPE: PRT
```

-continued

<213> ORGANISM: Duck hepatitis virus

<400> SEQUENCE: 227

Ala Ala Gly Gly Glu Arg Gly Val Arg Ser Gln Ser Ser Arg Ser Pro
1               5                   10                  15

Ser Pro Arg Lys
            20

<210> SEQ ID NO 228
<211> LENGTH: 19
<212> TYPE: PRT
<213> ORGANISM: Duck hepatitis virus

<400> SEQUENCE: 228

Ala Ala Gly Gly Glu Arg Gly Val Arg Ser Gln Ser Ser Arg Ser Ser
1               5                   10                  15

Pro Arg Lys

<210> SEQ ID NO 229
<211> LENGTH: 15
<212> TYPE: PRT
<213> ORGANISM: Duck hepatitis virus

<400> SEQUENCE: 229

Arg Arg Gly Gly Ala Arg Ala Ser Arg Ser Pro Ser Pro Arg Lys
1               5                   10                  15

<210> SEQ ID NO 230
<211> LENGTH: 15
<212> TYPE: PRT
<213> ORGANISM: Duck hepatitis virus

<400> SEQUENCE: 230

Ala Arg Gly Gly Ala Arg Ala Ser Arg Ser Pro Ser Pro Arg Lys
1               5                   10                  15

<210> SEQ ID NO 231
<211> LENGTH: 15
<212> TYPE: PRT
<213> ORGANISM: Duck hepatitis virus

<400> SEQUENCE: 231

Arg Ala Gly Gly Ala Arg Ala Ser Arg Ser Pro Ser Pro Arg Lys
1               5                   10                  15

<210> SEQ ID NO 232
<211> LENGTH: 15
<212> TYPE: PRT
<213> ORGANISM: Duck hepatitis virus

<400> SEQUENCE: 232

Ala Ala Gly Gly Ala Arg Ala Ser Arg Ser Pro Ser Pro Arg Lys
1               5                   10                  15

<210> SEQ ID NO 233
<211> LENGTH: 19
<212> TYPE: PRT
<213> ORGANISM: Duck hepatitis virus

<400> SEQUENCE: 233

Ala Ala Gly Arg Ser Pro Ser Gln Ser Pro Ser Ser Arg Ser Pro Ser
1               5                   10                  15

Pro Arg Lys

<210> SEQ ID NO 234
<211> LENGTH: 19
<212> TYPE: PRT
<213> ORGANISM: Duck hepatitis virus

<400> SEQUENCE: 234

Ala Ala Gly Arg Ser Pro Ser Gln Ser Pro Ser Ser Arg Ser Pro Ser
1               5                   10                  15

Pro Arg Glu

<210> SEQ ID NO 235
<211> LENGTH: 18
<212> TYPE: PRT
<213> ORGANISM: Duck hepatitis virus

<400> SEQUENCE: 235

Ala Ala Gly Arg Ser Pro Ser Gln Ser Pro Ser Ser Arg Ser Ser Pro
1               5                   10                  15

Arg Glu

<210> SEQ ID NO 236
<211> LENGTH: 16
<212> TYPE: PRT
<213> ORGANISM: Duck hepatitis virus

<400> SEQUENCE: 236

Ala Ala Gly Arg Ser Gln Ser Pro Ser Ser Arg Ser Ser Pro Arg Glu
1 5 10 15

<210> SEQ ID NO 237
<211> LENGTH: 16
<212> TYPE: PRT
<213> ORGANISM: Duck hepatitis virus

<400> SEQUENCE: 237

Ala Ala Gly Arg Ser Pro Ser Gln Ser Ser Arg Ser Ser Pro Arg Glu
1 5 10 15

<210> SEQ ID NO 238
<211> LENGTH: 14
<212> TYPE: PRT
<213> ORGANISM: Duck hepatitis virus

<400> SEQUENCE: 238

Ala Ala Gly Arg Ser Gln Ser Ser Arg Ser Ser Pro Arg Glu
1 5 10

<210> SEQ ID NO 239
<211> LENGTH: 20
<212> TYPE: PRT
<213> ORGANISM: Tetanus toxin

<400> SEQUENCE: 239

Ile Asp Lys Ile Ser Asp Val Ser Thr Ile Val Pro Tyr Ile Gly Pro
1 5 10 15

Ala Leu Asn Ile
20

<210> SEQ ID NO 240
<211> LENGTH: 21
<212> TYPE: PRT
<213> ORGANISM: Tetanus toxin

```
<400> SEQUENCE: 240

Asn Asn Phe Thr Val Ser Phe Trp Leu Arg Val Pro Lys Val Ser Ala
1               5                   10                  15

Ser His Leu Glu Gln
            20

<210> SEQ ID NO 241
<211> LENGTH: 21
<212> TYPE: PRT
<213> ORGANISM: Tetanus toxin

<400> SEQUENCE: 241

Phe Asn Asn Phe Thr Val Ser Phe Trp Leu Arg Val Pro Lys Val Ser
1               5                   10                  15

Ala Ser His Leu Glu
            20

<210> SEQ ID NO 242
<211> LENGTH: 14
<212> TYPE: PRT
<213> ORGANISM: Tetanus toxin

<400> SEQUENCE: 242

Gln Tyr Ile Lys Ala Asn Ser Lys Phe Ile Gly Ile Thr Glu
1               5                   10

<210> SEQ ID NO 243
<211> LENGTH: 16
<212> TYPE: PRT
<213> ORGANISM: Tetanus toxin

<400> SEQUENCE: 243

Val Ser Ile Asp Lys Phe Arg Ile Phe Cys Lys Ala Leu Asn Pro Lys
1               5                   10                  15

<210> SEQ ID NO 244
<211> LENGTH: 16
<212> TYPE: PRT
<213> ORGANISM: Tetanus toxin

<400> SEQUENCE: 244

Leu Lys Phe Ile Ile Lys Arg Tyr Thr Pro Asn Asn Glu Ile Asp Ser
1               5                   10                  15

<210> SEQ ID NO 245
<211> LENGTH: 19
<212> TYPE: PRT
<213> ORGANISM: Diptheria toxin

<400> SEQUENCE: 245

Pro Leu Phe Ala Gly Ala Asn Tyr Ala Ala Trp Ala Val Asn Val Ala
1               5                   10                  15

Gln Val Ile

<210> SEQ ID NO 246
<211> LENGTH: 20
<212> TYPE: PRT
<213> ORGANISM: Diptheria toxin

<400> SEQUENCE: 246

Val His His Asn Thr Glu Glu Ile Val Ala Gln Ser Ile Ala Leu Ser
1               5                   10                  15
```

```
Ser Leu Met Val
            20

<210> SEQ ID NO 247
<211> LENGTH: 20
<212> TYPE: PRT
<213> ORGANISM: Diptheria toxin

<400> SEQUENCE: 247

Gln Ser Ile Ala Leu Ser Ser Leu Met Val Ala Gln Ala Ile Pro Leu
1               5                   10                  15

Val Gly Glu Leu
            20

<210> SEQ ID NO 248
<211> LENGTH: 20
<212> TYPE: PRT
<213> ORGANISM: Diptheria toxin

<400> SEQUENCE: 248

Gln Gly Glu Ser Gly His Asp Ile Lys Ile Thr Ala Glu Asn Thr Pro
1               5                   10                  15

Leu Pro Ile Ala
            20

<210> SEQ ID NO 249
<211> LENGTH: 20
<212> TYPE: PRT
<213> ORGANISM: Diptheria toxin

<400> SEQUENCE: 249

Val Asp Ile Gly Phe Ala Ala Tyr Asn Phe Val Glu Ser Ile Ile Asn
1               5                   10                  15

Leu Phe Gln Val
            20

<210> SEQ ID NO 250
<211> LENGTH: 20
<212> TYPE: PRT
<213> ORGANISM: Diptheria toxin

<400> SEQUENCE: 250

Gly Val Leu Leu Pro Thr Ile Pro Gly Lys Leu Asp Val Asn Lys Ser
1               5                   10                  15

Lys Thr His Ile
            20

<210> SEQ ID NO 251
<211> LENGTH: 20
<212> TYPE: PRT
<213> ORGANISM: Plasmodium falciparum

<400> SEQUENCE: 251

Glu Tyr Leu Asn Lys Ile Gln Asn Ser Leu Ser Thr Glu Trp Ser Pro
1               5                   10                  15

Cys Ser Val Thr
            20

<210> SEQ ID NO 252
<211> LENGTH: 20
<212> TYPE: PRT
<213> ORGANISM: Plasmodium falciparum
```

```
<400> SEQUENCE: 252

Asp Ile Glu Lys Lys Ile Cys Lys Met Glu Lys Cys Ser Ser Val Phe
1               5                   10                  15

Asn Val Val Asn
            20

<210> SEQ ID NO 253
<211> LENGTH: 15
<212> TYPE: PRT
<213> ORGANISM: Hepatitis B virus

<400> SEQUENCE: 253

Phe Phe Leu Leu Thr Arg Ile Leu Thr Ile Pro Gln Ser Leu Asp
1               5                   10                  15

<210> SEQ ID NO 254
<211> LENGTH: 13
<212> TYPE: PRT
<213> ORGANISM: Influenza virus

<400> SEQUENCE: 254

Pro Lys Tyr Val Lys Gln Asn Thr Leu Lys Leu Ala Thr
1               5                   10

<210> SEQ ID NO 255
<211> LENGTH: 16
<212> TYPE: PRT
<213> ORGANISM: Influenza virus

<400> SEQUENCE: 255

Tyr Ser Gly Pro Leu Lys Ala Glu Ile Ala Gln Arg Leu Glu Asp Val
1               5                   10                  15

<210> SEQ ID NO 256
<211> LENGTH: 18
<212> TYPE: PRT
<213> ORGANISM: Measles virus

<400> SEQUENCE: 256

Lys Leu Leu Ser Leu Ile Lys Gly Val Ile Val His Arg Leu Glu Gly
1               5                   10                  15

Val Glu
```